US012573507B1

(12) United States Patent
Christopherson et al.

(10) Patent No.: US 12,573,507 B1
(45) Date of Patent: Mar. 10, 2026

(54) SYSTEM AND METHOD FOR EMOTIONALLY INTELLIGENT, PERSONALIZED AI AVATAR-BASED HEALTH COACHING USING MULTI-DOMAIN DATA AND ADAPTIVE BEHAVIORAL INTELLIGENCE

(71) Applicant: Gold AI, LLC, Wilmington, DE (US)

(72) Inventors: Sky Christopherson, Mesa, AZ (US); David Christopherson, Tucson, AZ (US)

(73) Assignee: Gold Inc., Palo Alto, CA (US)

( * ) Notice: Subject to any disclaimer, the term of this patent is extended or adjusted under 35 U.S.C. 154(b) by 7 days.

(21) Appl. No.: 19/189,025

(22) Filed: Apr. 24, 2025

(51) Int. Cl.
*G16H 50/20* (2018.01)
*A61B 5/00* (2006.01)
(Continued)

(52) U.S. Cl.
CPC ............. *G16H 50/20* (2018.01); *A61B 5/165* (2013.01); *A61B 5/4815* (2013.01); *A61B 5/486* (2013.01);
(Continued)

(58) Field of Classification Search
CPC ........ G16H 50/20; G16H 20/30; G16H 20/60; G16H 20/70; A61B 5/165; A61B 5/4815; A61B 5/486; A61B 5/4866; A61B 5/744
See application file for complete search history.

(56) References Cited

U.S. PATENT DOCUMENTS

| | | | |
|---|---|---|---|
| 10,783,800 B1 * | 9/2020 | Dieker | ................... G06T 15/005 |
| 2017/0147775 A1 * | 5/2017 | Ohnemus | ............... G16H 50/50 |

(Continued)

*Primary Examiner* — Kambiz Abdi
*Assistant Examiner* — Tran N Nguyen
(74) *Attorney, Agent, or Firm* — PatentPC PowerPatent; Bao Tran

(57) ABSTRACT

A programmatically generated AI avatar includes a customizable personality module, acting as the embodied interface for a powerful AI "mind" that delivers personalized coaching to improve user health, well-being, and longevity. The system uses machine learning, large language models, and biometric modeling to synthesize real-time, multi-modal health data—including sleep, nutrition, glucose, mood, and activity—and generate forward-prescribed KHAs. Unlike human coaches, it continuously adapts based on context and behavior, targeting the root cause: metabolic dysfunction—namely by restoring healthy, sustainable body composition through the preservation or building of lean muscle mass and reduction of excess fat. KHAs can also be shared with friends or programmatically generated AI avatars, allowing for coordinated action, emotional support, and accountability through social connection—further reinforcing positive behavior and adherence. The system's reinforcement learning engine incorporates both individual response data and anonymized population-level insights to optimize recommendations over time, learning which interventions are most effective for users with similar physiological and behavioral profiles. First validated with Olympic athletes—resulting in measurable improvements and medal-winning outcomes—this system offers a scalable, emotionally intelligent coaching enginethat exceeds human capability, designed for the ultimate purpose of supporting sustainable health, resilience, and human thriving.

20 Claims, 73 Drawing Sheets

(51) Int. Cl.
   *A61B 5/16*          (2006.01)
   *G16H 20/30*        (2018.01)
   *G16H 20/60*        (2018.01)
   *G16H 20/70*        (2018.01)

(52) U.S. Cl.
   CPC ............ *A61B 5/4866* (2013.01); *A61B 5/744*
               (2013.01); *G16H 20/30* (2018.01); *G16H*
               *20/60* (2018.01); *G16H 20/70* (2018.01)

(56)                  References Cited

U.S. PATENT DOCUMENTS

2021/0295579 A1*   9/2021  Davis ...................... G06F 30/20
2022/0199254 A1*   6/2022  Tuysuzoglu ........... G16H 15/00

* cited by examiner

System Overview of AI Avatar Coaching Platform

Detailed System Architecture of
AI Avatar Coach

System Architecture for Culturally Adaptive AI
Coaching Avatars with Biomatric, Relational
Data Integration and Reinforcement Learning
for Health Optimization

1. INPUT

Working

Input to mobile app
OR for direct user
question (ask coach)
skip to ②

- Reinforcement learning uses correlation
  to reinforce advice based on results.
- It will draw upon the LLM to analyze the data
  sets and return correlation coeffecients
  by sending prompt to ②

USER MODEL

| User inputs/interaction data |
| Device, data platform API |
| Socially provided data from other users |
| Cultural and emotional preferences |

ADVICE ALGOS

REINFORCEMENT LEARNING

ADVICE

RESULTS

Formulas

Example: Today's
recommendation
is to brisk walk
after largest
meals

Feel great

KNOWLEDGE MODEL

| Primary source | Peer reviewed |
| Tier 1 scientific Literature | |
| Hard Data | Cultural |
| Olympic medal-winning health + fitness + wellness data | |

If/then rules

Example: Get
sunlight upon
walking and eat
slow digesting
high protein
breakfast Lean body
weight UP Generaliztion
to constraint
satisfaction Body fat
% DOWN Assignment of
weights Conversational
advice/insight
from AI Coach +100's of
markers
improved

| Pull relevant user variables |
| Request for language in user's setting |
| Emotional tone + Avatar's affect |

②PROMPT

Finalized
Prompt

Advice based on time
context + priority

⑪ Final Avatar result
is played in-app

Final result video +
audio + music file -
View Samples (A)

Fig. 1B

VECTOR DATA PLATFORM

Method Flow for Personalized AI
Avatar Response to Video Content

Method Flow for Personalized Video Content as AI Avatar Response

Method Flow for Personalized AI Generated Workout

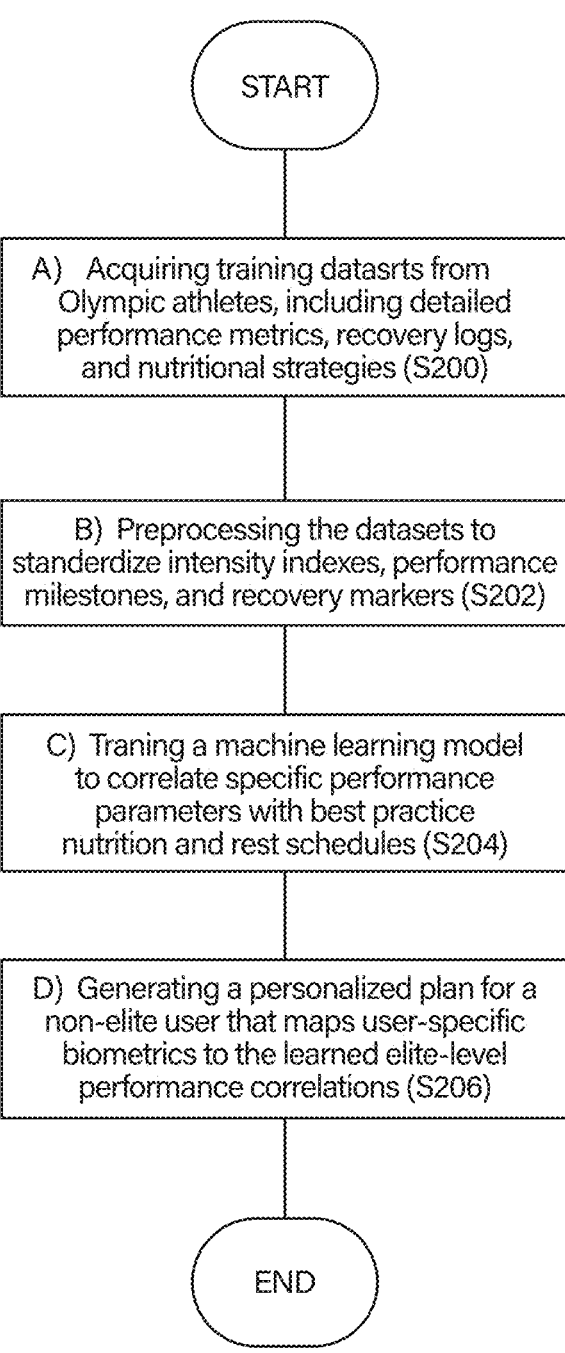

START

A) Acquiring training datasrts from Olympic athletes, including detailed performance metrics, recovery logs, and nutritional strategies (S200)

B) Preprocessing the datasets to standerdize intensity indexes, performance milestones, and recovery markers (S202)

C) Traning a machine learning model to correlate specific performance parameters with best practice nutrition and rest schedules (S204)

D) Generating a personalized plan for a non-elite user that maps user-specific biometrics to the learned elite-level performance correlations (S206)

END

Fig. 3

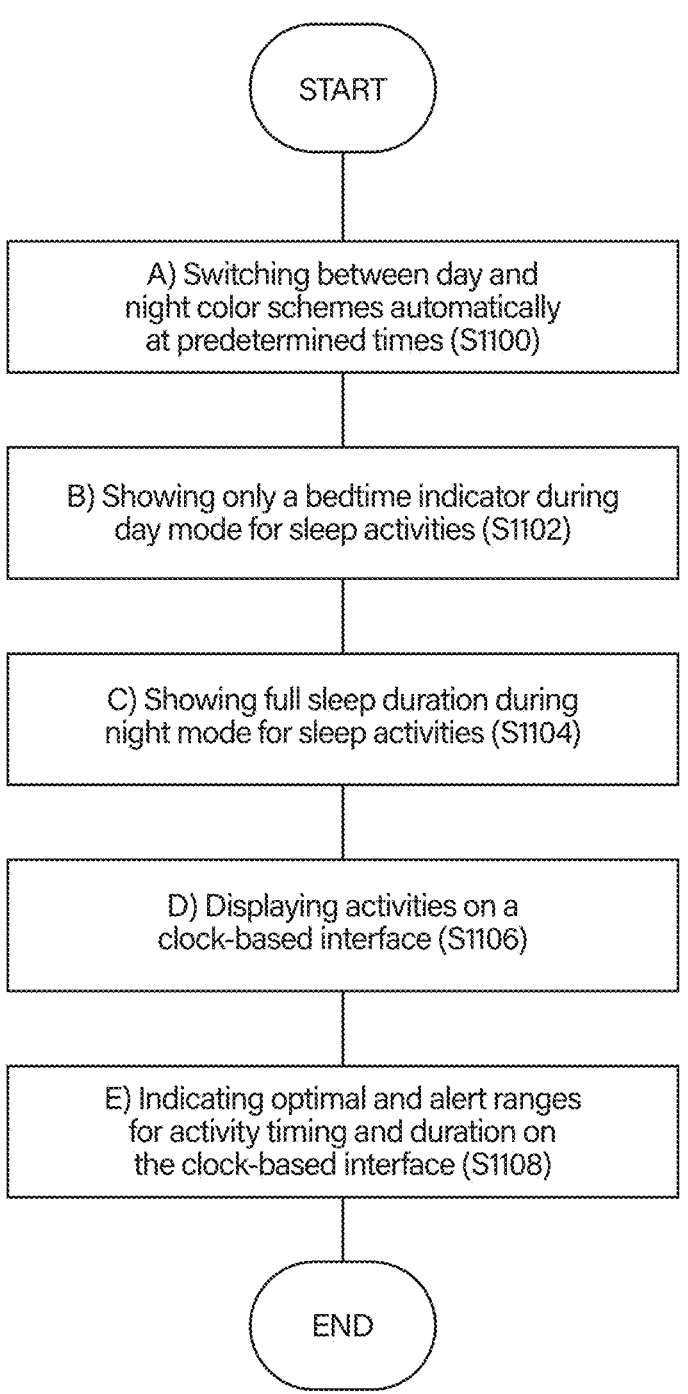

START

A) Switching between day and
night color schemes automatically
at predetermined times (S1100)

B) Showing only a bedtime indicator during
day mode for sleep activities (S1102)

C) Showing full sleep duration during
night mode for sleep activities (S1104)

D) Displaying activities on a
clock-based interface (S1106)

E) Indicating optimal and alert ranges
for activity timing and duration on
the clock-based interface (S1108)

END

Fig. 12

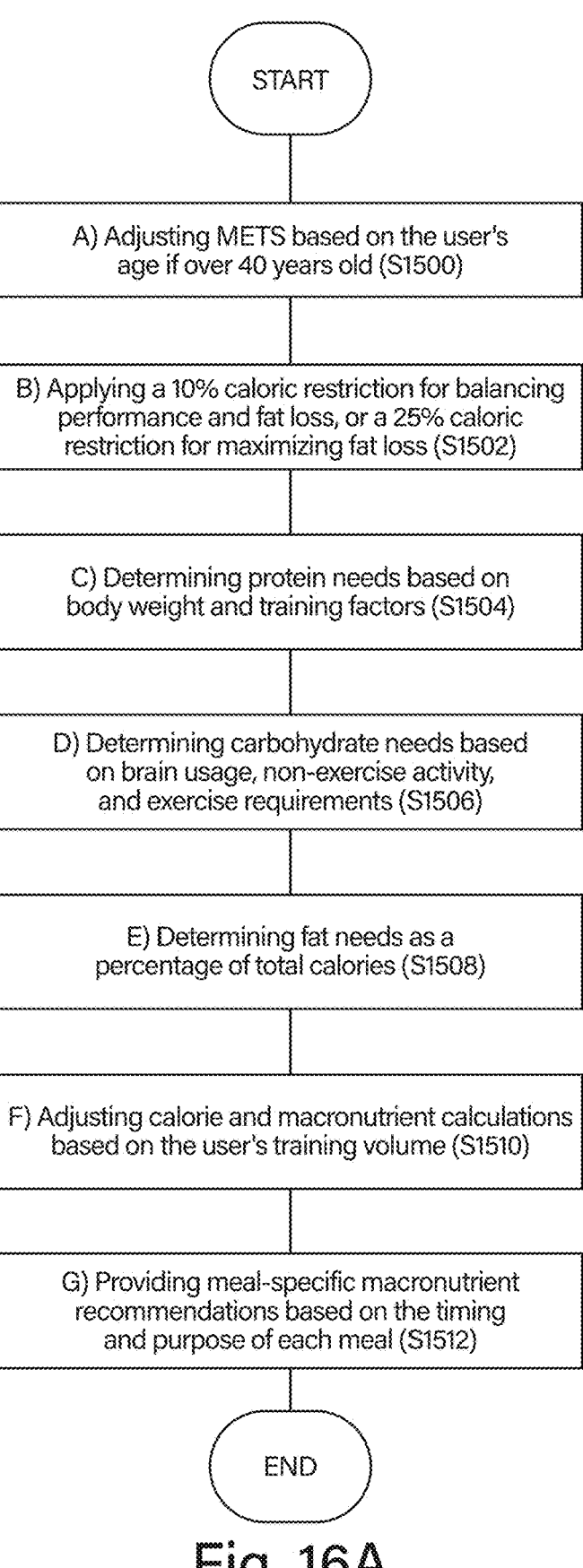

START

A) Adjusting METS based on the user's
age if over 40 years old (S1500)

B) Applying a 10% caloric restriction for balancing
performance and fat loss, or a 25% caloric
restriction for maximizing fat loss (S1502)

C) Determining protein needs based on
body weight and training factors (S1504)

D) Determining carbohydrate needs based
on brain usage, non-exercise activity,
and exercise requirements (S1506)

E) Determining fat needs as a
percentage of total calories (S1508)

F) Adjusting calorie and macronutrient calculations
based on the user's training volume (S1510)

G) Providing meal-specific macronutrient
recommendations based on the timing
and purpose of each meal (S1512)

END

Fig. 16A

Flow Chart: AI Body Composition Visualization & Goal Tracking System

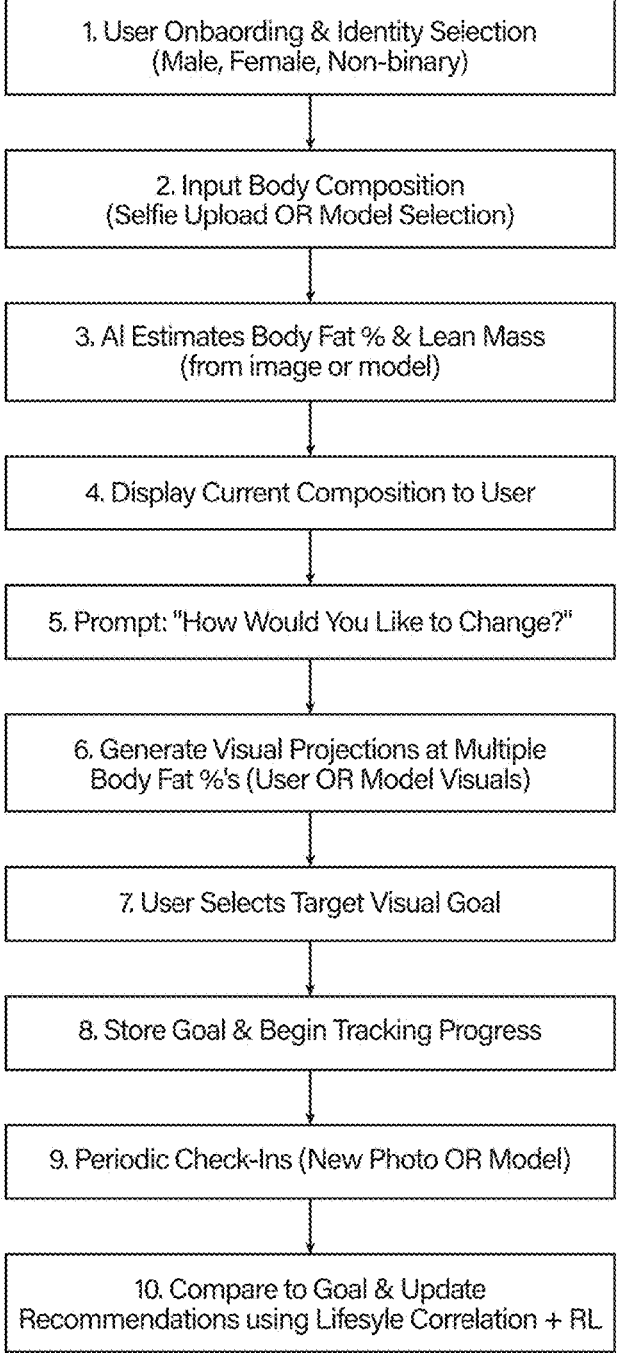

1. User Onbaording & Identity Selection
(Male, Female, Non-binary)

2. Input Body Composition
(Selfie Upload OR Model Selection)

3. AI Estimates Body Fat % & Lean Mass
(from image or model)

4. Display Current Composition to User

5. Prompt: "How Would You Like to Change?"

6. Generate Visual Projections at Multiple
Body Fat %'s (User OR Model Visuals)

7. User Selects Target Visual Goal

8. Store Goal & Begin Tracking Progress

9. Periodic Check-Ins (New Photo OR Model)

10. Compare to Goal & Update
Recommendations using Lifesyle Correlation + RL

Fig. 16B

System Data Model

System Architecture for Scale Integration

System User Flow

System Live Coach Flow

| Glossary | SParent | Start time of Parent Activity | | | | | |
|---|---|---|---|---|---|---|---|
| | Spreceding | Start time of Preceding Activity | | | | | |
| Parent activity | Type | Notification exists | Window start | Window start parameter (minutes) | Window end | Window end parameter (minutes) | Triggers iOS (local notification, only if app in BG) |
| Wake up | Now-window | Yes | SParent | 0 | SParent+45m | 45 | Yes |
| Wake up | Prepare window | No | Wake up | 0 | Wake up | 0 | n/a |
| Wake up | Upcoming window | Yes | SPreceding | 0 | SParent | 0 | No |
| Breakfast | Now window | Yes | SParent | 0 | SParent+45m | 45 | Yes |
| Breakfast | Prepare window | No | n/a | n/a | n/a | n/a | n/a |
| Breakfast | Upcoming window | Yes | SPreceding | 0 | SParent | 0 | No |
| Pre-train meal | Now-window | Yes | SParent | 0 | SParent+45m | 45 | Yes |
| Pre-train meal | Prepare window | No | n/a | n/a | n/a | n/a | n/a |
| Pre-train meal | Upcming window | Yes | SPreceding | 0 | SParent | 0 | No |
| Training | Now-window | Yes | SParent | 0 | SParent+45m | 45 | No |
| Training | Prepare window | Yes | SParent-30m | -30 | SParent | 0 | Yes |
| Training | Upcming window | Yes | SPreceding | 0 | SParent | 0 | No |
| Post-train meal | Now-window | Yes | SParent | 0 | SParent+45m | 45 | Yes |
| Post-train meal | Prepare window | No | n/a | n/a | n/a | n/a | n/a |
| Post-train meal | Upcoming window | Yes | SPreceding | 0 | SParent | 0 | No |
| Post-train meal | Now-window | Yes | SParent | 0 | SParent+45m | 45 | No |
| Floating meal | Prepare window | No | n/a | n/a | n/a | n/a | n/a |
| Floating meal | Upcoming window | Yes | SPreceding | 0 | SParent | 0 | No |
| Nap | Now window | Yes | SParent | 0 | SParent+25m | 25 | No |
| Nap | Prepare window | Yes | SParent-10m | -10 | SParent | 0 | Yes |
| Nap | Upcoming window | Yes | SPreceding | 0 | SParent | 0 | No |
| Bedtime | Now-window | Yes | SParent | 0 | SParent+45m | 45 | No |
| Bedtime | Prepare window | Yes | SParent-120m | -120 | SParent | 0 | Yes |
| Bedtime | Upcoming window | Yes | SPreceding | 0 | SParent | 0 | c |

Fig. 22

Retrival-Augmented Generation Based Custom LLM for Modules

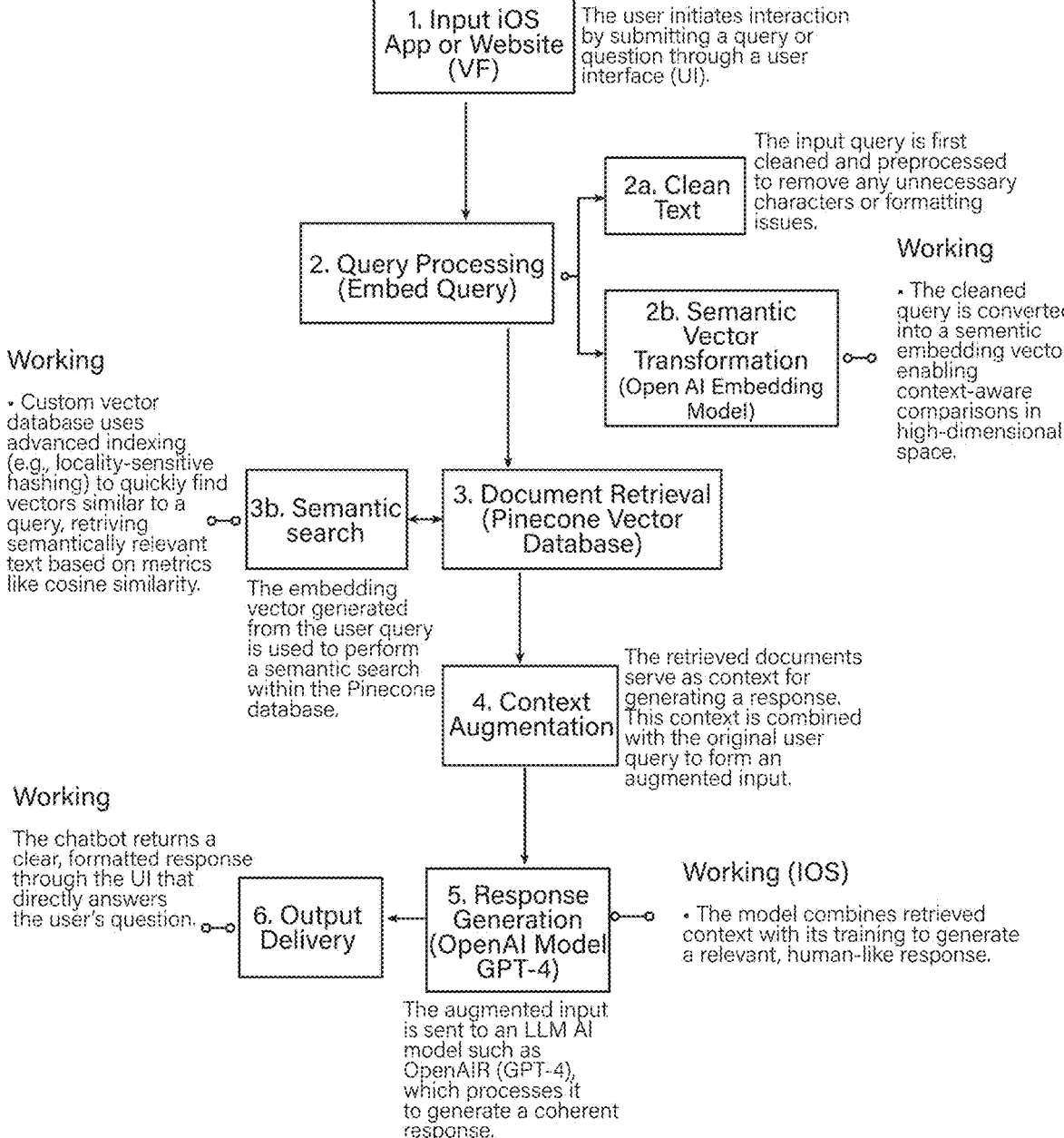

1. Input iOS App or Website (VF) — The user initiates interaction by submitting a query or question through a user interface (UI).

2a. Clean Text — The input query is first cleaned and preprocessed to remove any unnecessary characters or formatting issues.

2. Query Processing (Embed Query)

2b. Semantic Vector Transformation (Open AI Embedding Model)

Working

• The cleaned query is converted into a sementic embedding vector, enabling context-aware comparisons in high-dimensional space.

Working

• Custom vector database uses advanced indexing (e.g., locality-sensitive hashing) to quickly find vectors similar to a query, retriving semantically relevant text based on metrics like cosine similarity.

3b. Semantic search

3. Document Retrieval (Pinecone Vector Database)

The embedding vector generated from the user query is used to perform a semantic search within the Pinecone database.

The retrieved documents serve as context for generating a response. This context is combined with the original user query to form an augmented input.

4. Context Augmentation

Working

The chatbot returns a clear, formatted response through the UI that directly answers the user's question.

6. Output Delivery

5. Response Generation (OpenAI Model GPT-4)

Working (IOS)

• The model combines retrieved context with its training to generate a relevant, human-like response.

The augmented input is sent to an LLM AI model such as OpenAIR (GPT-4), which processes it to generate a coherent response.

Fig. 23

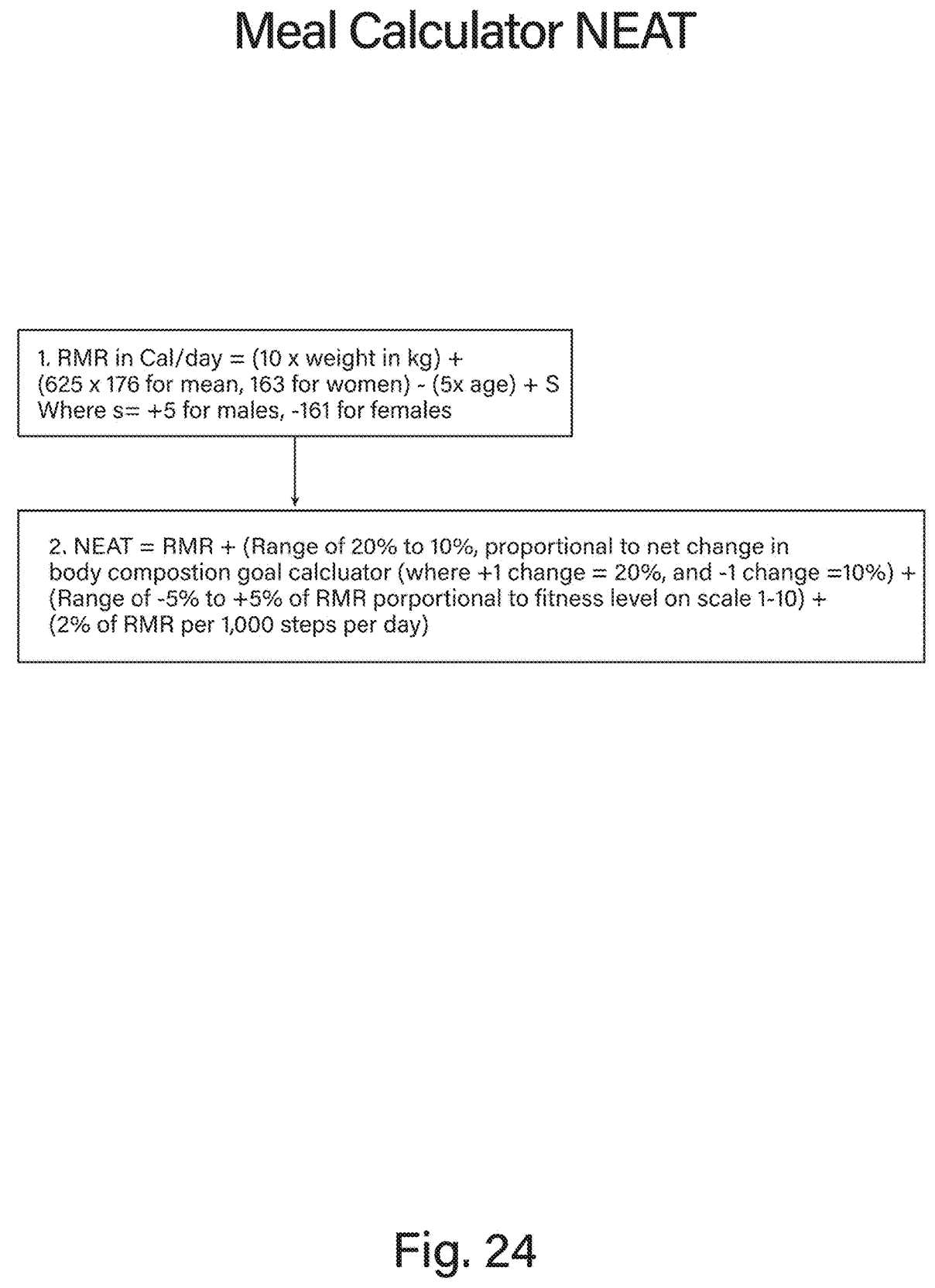

Meal Calculator NEAT

1. RMR in Cal/day = (10 x weight in kg) +
(625 x 176 for mean, 163 for women) - (5x age) + S
Where s= +5 for males, -161 for females 2. NEAT = RMR + (Range of 20% to 10%, proportional to net change in
body compostion goal calcluator (where +1 change = 20%, and -1 change =10%) +
(Range of -5% to +5% of RMR porportional to fitness level on scale 1-10) +
(2% of RMR per 1,000 steps per day)

Fig. 24

Meal Calculator PROTEIN

1. For daily Protein, first find the Training Volume factor using this:

Training volume algorithm to estimate refuel, protein & overreaching/training        DrClyde

| Pace | | Standardized | HR zone | Overreaching Xover |
|------|--|--------------|---------|--------------------|
| T1 | Ultra-endurance > triathlon | > 16 hours | 1 | 1-3 days |
| T1' | ½ to full triathlon 6-16 hours | >> 3 hours | 1 | 12-36 hours |
| T1" | century ride range 3-6 hours | 3 hours | 1 | 6-18 hours |
| T1'" | ½ to full marathon 1-4 hours | 2 hours | 2 | 4-12+ hours |
| T2 | threshold / LT / tempo 30-60 min | 1 hour | 3 | 4-10 hours |
| T2' | Sub-VO2 10-30 min | 30 min | 4 | 3-6 hours |
| VO2 | "long intervals" 6-12 min | 10 min | 5 | 90-180 min |
| Intervals | 1-3 min | 1 min | 6 | 30-60 min |
| Bursts | 10-60 sec | < 1 min | 6+ | 20-30 min |
| High rep | > 10 rep/set | - | - | 4-10 hours |
| Low rep | ≤ 10 rep/set | - | - | 4-10 hours |
| Power | ≤ 20 rep/set plyometric pace | - | - | 4-10 hours |

Overreaching Crossover depends on overall workout intensity: low, medium, high, very high

| 5 tier app | Intensity LOW | MEDIUM | HIGH | VERY HIGH |
|------------|---------------|--------|------|-----------|
| Aerobic | T1 | T1' | T1" | T1'" |
| Threshold | T1'"-T2 @60-90' | T2 @50-60' pace | T2 @40-50' pace | T2' @30-40' pace |
| VO2 | VO2 @12' pace | VO2 @10' pace | VO2 @8' pace | VO2 @6' pace |
| Intervals | Intervals 2-3 m | Intervals 1-1.5 m | Bursts 30-50 s | Bursts 10-30 s |
| Strength/Power | Max workout 2 h | Max workout 1.5 | Max workout 1 h | Max workout 0.5 |

A 5-tier approach consolidates 12+ training-type intensities
* Aerobic: Integrates T1-T1'" as the light, medium, high, and very high aerobic intensities
* Threshold: not combined with anything but instead covers the full pacing range of LT
* VO2: Combines slightly sub-threshold (T1'") with the full VO2max range into one category
* Intervals: Combines intervals of 1-3 min to deplete ATP with bursts (sub-minute intervals) for power
* Strength/Power: Integrates light and heavy strengthening with power work into one combined category

Fig. 25

Meal Calculator PROTEIN cont..

Training volume elements: user hours per week ($\Omega$) multiplied by year-round training limits

| Training type | Low | Medium | High | Very High |
|---|---|---|---|---|
| T1: Aerobic | Ultra $\Omega$ / 32 hours max | Triathlon $\Omega$ / 24 hours max | Century $\Omega$ / 16 hours max | Marathon $\Omega$ / 8 hours max |
| T2: Threshold | 90 min pace $\Omega$ / 7 hours | 60 min pace $\Omega$ / 6 hours | 45 min pace $\Omega$ / 5 hours | 30 m pace $\Omega$ / 4 hours |
| VO2max | 12 min pace $\Omega$ / 180 min | 10 min pace $\Omega$ / 150 min | 8 min pace $\Omega$ / 120 min | 6 min pace $\Omega$ / 90 min |
| Int: Intervals | 1.5-3 min pace $\Omega$ / 60 min | 1 min pace $\Omega$ / 30 min | 80-50 sec pace $\Omega$ / 25 min | 10-30 sec pace $\Omega$ / 20 min |
| Strength/Power If 1:1 work-rest | 120 min max $\Omega$ / 10 hours | 100 min max $\Omega$ / 8 hours | 80 min max $\Omega$ / 6 hours | 60 min max $\Omega$ / 4 hours |

Algorithm for Training Volume Factor (TF)

Sum of EACH matric term = TF = $\sum$ ($\Omega$ / training limit) for T1 + T2 + VO2 + Intervals + Strength TF = 1.0 corresponds to 100% of year-round limit before overreaching risk Overreaching Factor (OF) = training volume beyond maximum year-round capacity = (TF - 1) = OF
Months before overreaching likely = 1 / OF = 1 / (TF - 1.0)
Overreaching factor ranging from 0.1 to 1.0 therefore results in overreaching within 1-10 months
Overreaching months X 10 = overtraining risk being unrecoverable within career PROTEIN NEEDS TF max 1.0 = (0.6 to 0.8 g/day/kg) X (kg body weight) X [1 + (Training Factor X 2)]

2. Protein Need TF max 1.0= (.6 to .8 g/day/kg) x (kg body weight) X
   [1 + (Training Factor x 2)]

3. Divide (Daily) Protein needs by 20

4. Multiply by number of hours until the next meal x Meal Modifier (ex
   1.2, etc assigned by rules engine and modified by RL - Reinforcement
   learning) = Protein need for that meal.

Fig. 25 (Continued)

Meal Calculator PROTIEN (Basic)

Meal Calculator CARBOHYDRATES

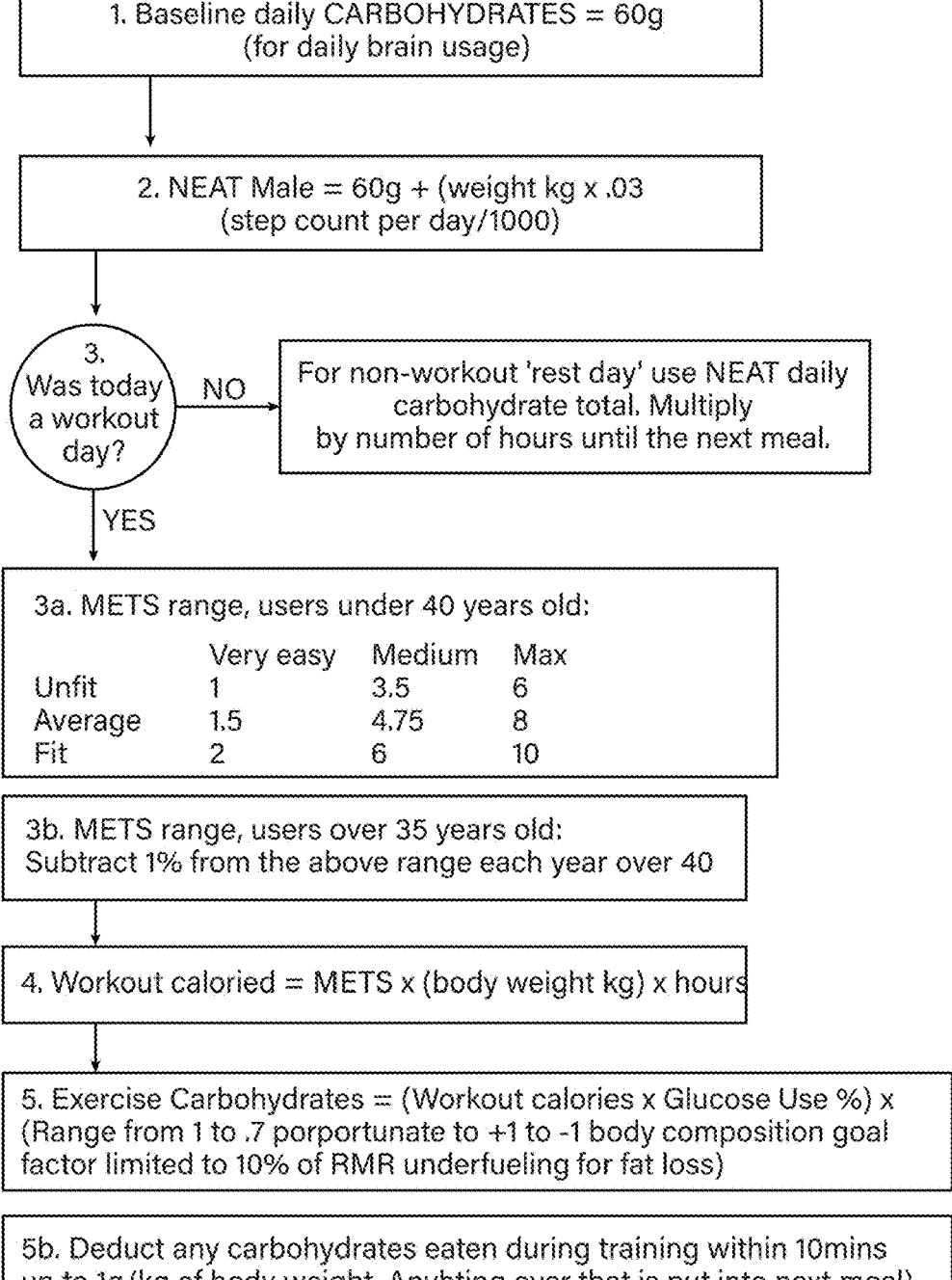

1. Baseline daily CARBOHYDRATES = 60g
(for daily brain usage)

2. NEAT Male = 60g + (weight kg x .03
(step count per day/1000)

3.
Was today
a workout
day?

NO

For non-workout 'rest day' use NEAT daily
carbohydrate total. Multiply
by number of hours until the next meal.

YES

3a. METS range, users under 40 years old:

|          | Very easy | Medium | Max |
|----------|-----------|--------|-----|
| Unfit    | 1         | 3.5    | 6   |
| Average  | 1.5       | 4.75   | 8   |
| Fit      | 2         | 6      | 10  |

3b. METS range, users over 35 years old:
Subtract 1% from the above range each year over 40

4. Workout caloried = METS x (body weight kg) x hours

5. Exercise Carbohydrates = (Workout calories x Glucose Use %) x
(Range from 1 to .7 porportunate to +1 to -1 body composition goal
factor limited to 10% of RMR underfueling for fat loss)

5b. Deduct any carbohydrates eaten during training within 10mins
up to 1g/kg of body weight. Anyhting over that is put into next meal)

6. Multiply by number of hours until the next meal x Meal Modifier
(ex 1.2, etc assigned by rules engine and modified by RL-
Reinforcement learning)

Fig. 25C

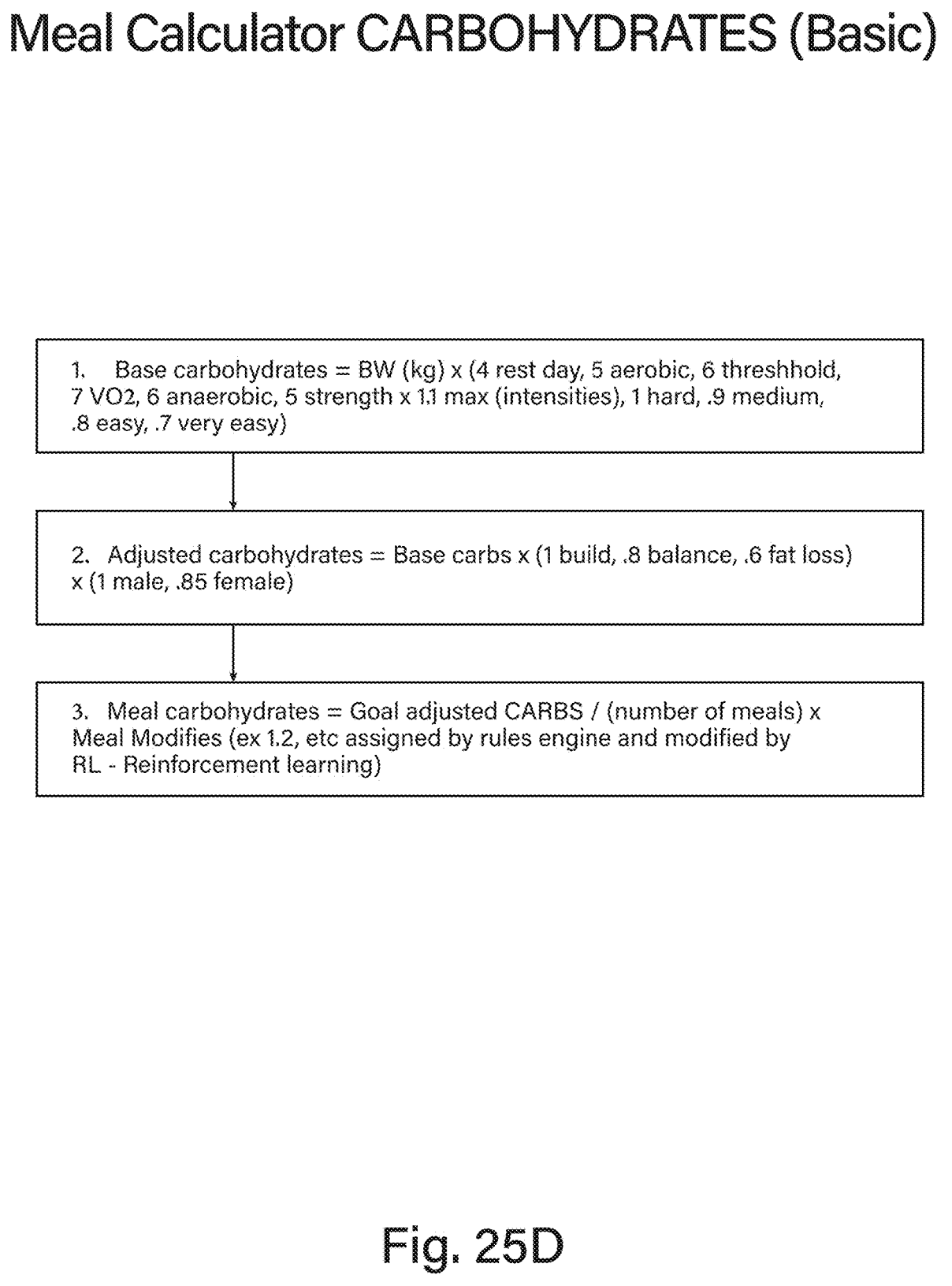

Meal Calculator CARBOHYDRATES (Basic)

1. Base carbohydrates = BW (kg) x (4 rest day, 5 aerobic, 6 threshhold, 7 VO2, 6 anaerobic, 5 strength x 1.1 max (intensities), 1 hard, .9 medium, .8 easy, .7 very easy)

2. Adjusted carbohydrates = Base carbs x (1 build, .8 balance, .6 fat loss) x (1 male, .85 female)

3. Meal carbohydrates = Goal adjusted CARBS / (number of meals) x Meal Modifies (ex 1.2, etc assigned by rules engine and modified by RL - Reinforcement learning)

Fig. 25D

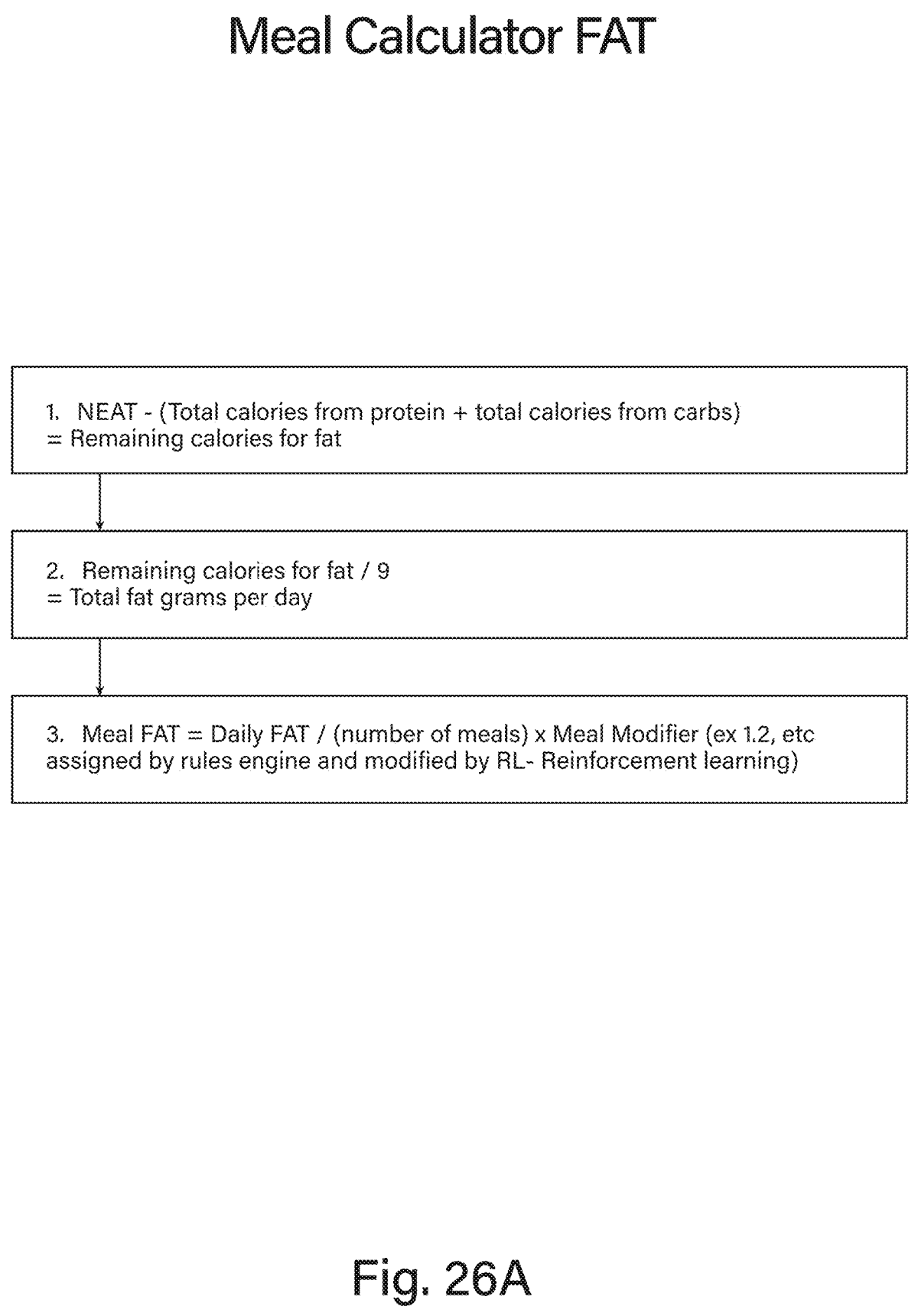

Meal Calculator FAT

1.  NEAT - (Total calories from protein + total calories from carbs)
    = Remaining calories for fat 2.  Remaining calories for fat / 9
    = Total fat grams per day 3.  Meal FAT = Daily FAT / (number of meals) x Meal Modifier (ex 1.2, etc
    assigned by rules engine and modified by RL- Reinforcement learning)

Fig. 26A

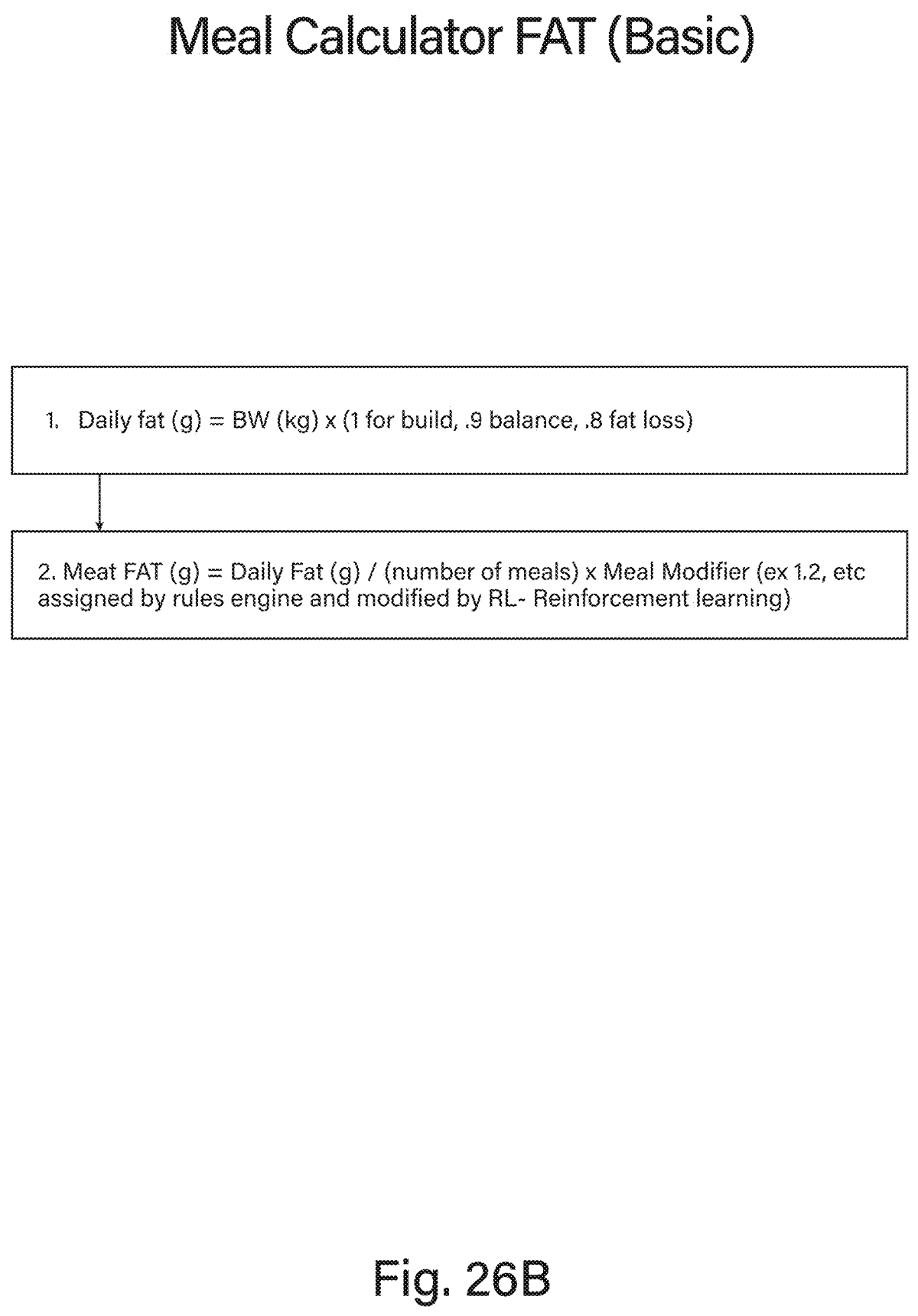

Meal Calculator FAT (Basic)

1. Daily fat (g) = BW (kg) x (1 for build, .9 balance, .8 fat loss)

2. Meat FAT (g) = Daily Fat (g) / (number of meals) x Meal Modifier (ex 1.2, etc assigned by rules engine and modified by RL- Reinforcement learning)

Fig. 26B

SLEEP (CONT.)

MEAL FLOATING

BREAKFAST

USER
INTERACTION

James, feel your pulse
and every time your
heart beats tap the heart

S

Resting heart rate          →

Count number of taps over 15 seconds
starting with the first tap and ending at 15
seconds then times the number of taps by
4 and display value under.

And then: 0-60 RHE is experienced user type
61+ is less experienced user type

Live Score Biological Regression Weighting

Influence past days have on current state

Programmatically generated AI meal recommendation

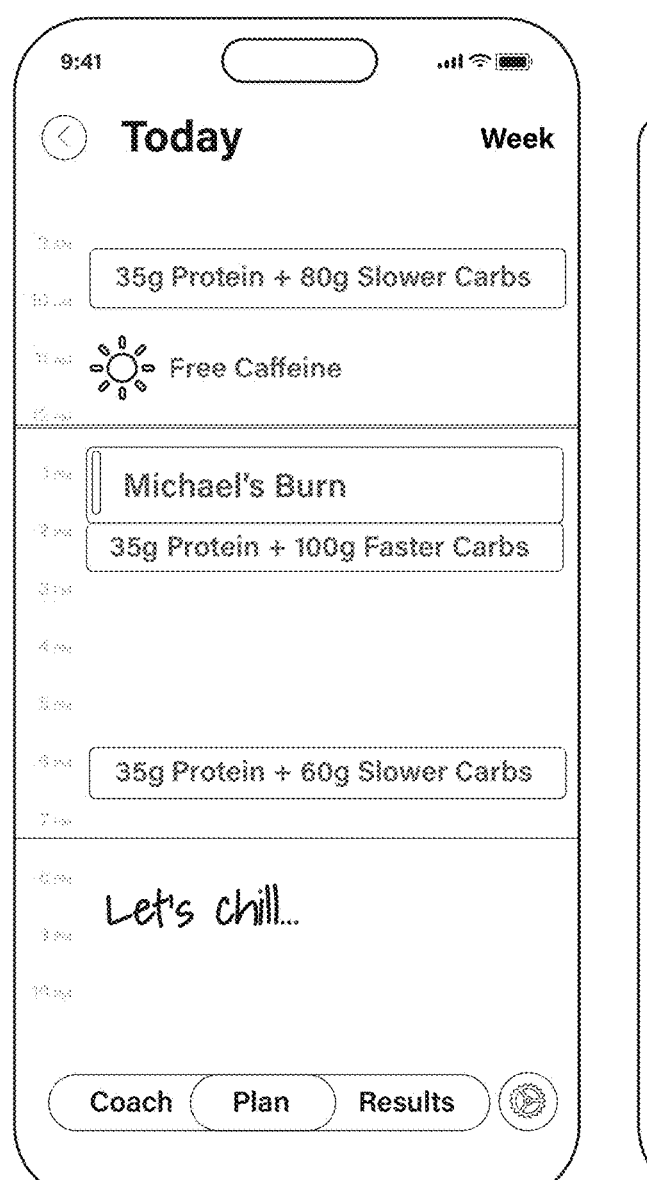
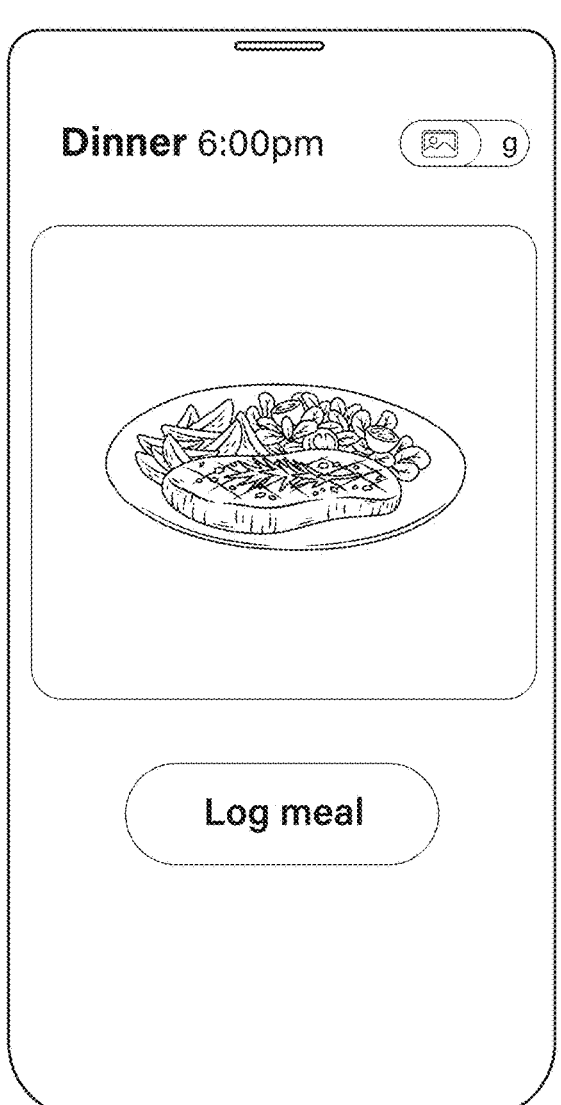
Fig. 38B

Live Score Biological Regression Weighting

SYSTEM AND METHOD FOR EMOTIONALLY INTELLIGENT, PERSONALIZED AI AVATAR-BASED HEALTH COACHING USING MULTI-DOMAIN DATA AND ADAPTIVE BEHAVIORAL INTELLIGENCE

BACKGROUND OF THE SYSTEM

Human coaching—when combined with social support and real-time, data-driven insights—remains the most effective method for achieving lasting health, fitness, and wellness outcomes. However, human coaches cannot be scaled to deliver personalized, daily guidance to millions of users. Current digital health and fitness platforms attempt to fill this gap but often fall short in replicating the responsiveness, insight, and emotional connection of a trusted coach. These systems typically rely on static, non-personalized advice and content such as instructional videos and cannot adapt meaningfully to a user's evolving goals, emotional state, schedule, or physiological condition. While some incorporate AI or multimedia, they remain disconnected from a holistic wellness model and lack the ability to integrate human-like empathy with computational precision. Even the most experienced human coaches are unable to synthesize complex biometrics, behavioral patterns, and health algorithms in real time. Most digital platforms also lack the infrastructure for continuous feedback, adaptive avatar expression, and personalized delivery across voice, visuals, and timing—creating a critical gap between what users need and what existing systems provide to sustain motivation, engagement, and meaningful results.—looking guidance and fails to address the dynamic, hour-to-hour behaviors that drive meaningful change.

SUMMARY OF THE SYSTEM

This invention provides a comprehensive digital health coaching system that delivers emotionally intelligent, real-time guidancethrough an AI-powered platform. At its core is a programmatically generated AI human avatar that serves as the user-facing interface for an adaptive coaching engine, supported by integrated modules for scheduling, progress tracking, and social coordination. The system continuously synthesizes biometric, behavioral, and contextual data—including sleep, nutrition, glucose, activity, and mood—to generate forward-prescribed Key Health Actions (KHAs) that evolve with the user's needs. These KHAs may be shared with peers or AI avatars via a social invitation feature, enabling collaborative participation and accountability. Another capability of the platform is the dynamic generation of personalized instructional video content using a combination of pre-recorded assets and AI-generated audio-visual segments, tailored to each user's context, preferences, and coaching goals. Reinforcement learning algorithms refine recommendations over time based on individual outcomes and anonymized trends across the user base. Additional features include dynamic workout programming, meal timing visualization, adaptive music integration, and privacy-controlled shared interfaces—together forming a scalable, holistic coaching experience that bridges the precision of AI with the relational effectiveness of human guidance.

In one aspect, a computer-implemented system provides personalized health coaching through a generative AI avatar interface that builds emotional rapport and adapts to coaching style preferences. The system includes a user onboarding module that collects high-level purpose, lifestyle goals, and physiological metrics while gathering preferences such as name, tone, personality, and language. It further incorporates API connectors for ingesting real-time biometric data from sensor devices and health data platforms.

In another aspect, a coaching recommendation engine generates and dynamically adjusts a schedule of Key Health Actions (KHAs) based on scientific literature, athlete data, and the user's context. A real-time adjustment engine reschedules future KHAs in response to missed actions or updated user availability. The system leverages a reinforcement learning model to analyze user outcome data alongside recent KHA history to rank and prioritize KHAs contributing to desired results. It also employs a biologically weighted regression model to determine the time-weighted influence of recent KH In one aspect, the system includes a content generation engine that creates initial scripts by inserting these variables into predetermined message templates. In one aspect, a voice synthesis module is configured to generate audio files from the produced scripts. In one aspect, a video generation module constructs avatar videos by utilizing AI-generated audio files along with visual animation libraries. In one aspect, a server-based storage system manages and serves personalized avatar content. The content generation engine creates initial scripts by inserting user variables into message templates, which are then transformed into audio files via a voice synthesis module and into avatar videos using a video generation module that integrates AI-generated audio with visual animation libraries. Lastly, a server-based storage system manages and serves the personalized avatar content.

In a further aspect, a computer-implemented system for delivering health coaching is provided that includes a social linking module enabling users to designate interpersonal relationships in the app. In another aspect, the system further comprises a structured feedback interface that allows users to submit emotional reflections, requests, or well-being impacts related to those linked users. In yet another aspect, an emotional analysis engine is included that processes the submitted feedback using techniques such as sentiment analysis, role classification, well-being scoring, and behavioral context evaluation. In an additional aspect, the system offers an avatar coaching module that provides personalized support, mediation, and relational advice based on best practices in therapy and cognitive behavior techniques.

In another aspect, the method includes collecting user data such as exercise metrics, sleep data, and dietary intake. In one aspect, the method analyzes the collected data using a multi-layered algorithm that correlates physical activity duration, intensity, and meal timing with metabolic responses. In one aspect, the method generates personalized recommendations, including an optimal nutrient intake time window tailored to the user's exercise intensity and recovery needs. In one aspect, the method implements a day-night mode interface by determining the current time, switching between day and night color schemes, adjusting sleep activity displays based on the current mode, and temporarily overriding the mode when editing specific activities.

In another aspect, the system includes a module that collects real-time or near-real-time biometric data. In another aspect, a learning engine weights each biometric stream based on user-specific and population-derived thresholds. In another aspect, a recommendation generator outputs personalized workout and nutrition protocols when threshold events occur, iteratively refining the protocols based on user adherence and performance outcomes. In another aspect, the system features a knowledge base that stores best practices from professional athletic coaches alongside performance metrics from Olympic-level trials. In another aspect, a decision module employs a neural network or ensemble learning architecture to compare user inputs against the stored knowledge base. In another aspect, an output interface delivers context-aware, dynamically adapted training session progressions based on daily feedback received from the user's wearable devices.

In a further aspect, the method involves determining a user's resting metabolic rate based on their characteristics. The method further calculates a non-exercise activity thermogenesis value and adjusts it according to the user's goals and fitness level. It then generates a total daily calorie need based on the adjusted NEAT value and calculates exercise-related calories using metabolic equivalents. The total daily calorie need is further adjusted in accordance with a user-defined goal, and finally, macronutrient ratios are determined based on this total daily calorie need.

In another aspect, the method determines a user's baseline protein requirement by using their body weight as a reference. It also analyzes a range of user data—including fitness goals, onboarding details, activity levels, training history, and psychometric trends—to develop a detailed profile. Based on the profile, the method generates a personalized AI coach persona with a selected communication style and behavioral tendencies that can deliver content through text and AI video messages. Additionally, it produces nutrition recommendations with meal-specific macronutrient targets derived from optimized caloric intake, food-derived GLP-1 levels, and digestion rates. The method further creates a custom fitness regimen incorporating various workout videos, audio cues, video instructions, and music, along with tailored movement sets and training styles. It then delivers the customized fitness and nutrition plan via a mobile application, offering ongoing monitoring and adjustments based on real-time physiological and performance metrics. Finally, the method generates and displays AI video messages featuring the personalized persona, which address specific user needs, goals, and trends by calling variable-based text-to-voice APIs and utilizing generative video AI platforms, while also analyzing and responding to user psychometric data, including humor and video content.

Other aspects that stand alone or combinable with the other aspects include:

Aspect 1. A computer-implemented system for delivering personalized health coaching comprising:

a generative AI avatar interface that builds emotional rapport with the user and adapts based on coaching style preferences;

a user onboarding module configured to collect high-level purpose, lifestyle goals, and physiological metrics, including preferences such as name, goals, tone, personality, and language;

API connectors for ingesting real-time biometric data from sensor devices and health data platforms;

a relational mapping engine to classify user relationships and quantify social influence factors;

a coaching recommendation engine that generates and dynamically adjusts a schedule of KHAs based on scientific literature, athlete data, and user context;

a real-time adjustment engine for rescheduling future KHAs in response to missed actions or updated user availability;

4 a reinforcement learning model for analyzing user outcome data in conjunction with recent KHA history to rank and prioritize KHAs contributing to desired outcomes;

a regression model for determining time-weighted influence of recent KHAs on user outcomes;

a knowledge model prioritizing high-level, functional scientific fields for long-term, drug-free optimization of metabolic health, skeletal muscle preservation, blood sugar regulation, inflammation reduction, and sleep quality;

a content generation engine that creates initial scripts using user variables inserted into message templates;

a voice synthesis module configured to generate audio files from said scripts;

a video generation module that constructs avatar videos using AI-generated audio files and visual animation libraries; and a server-based storage system for managing and serving personalized avatar content.

2. The system of aspect 1, wherein the avatar interface is customizable by the user in terms of voice, personality traits, coaching tone, and interaction frequency, and provides encouragement, troubleshooting, and adaptive guidance based on real-time context.

3. The system of aspect 1, wherein the avatar interface includes cultural localization of spoken language, gestural mannerisms, and affective vocal tones tailored to user-specific cultural segments to enhance comprehension and emotional engagement.

4. The system of aspect 1, wherein reinforcement learning is used to analyze performance outcomes such as body fat percentage, wellness scores, and other physiological metrics in conjunction with recent KHAs to refine future coaching recommendations.

5. The system of aspect 1, wherein the coaching engine flags KHAs with strong negative correlation to desired outcomes for user review, behavioral correction, or de-prioritization.

6. The system of aspect 1, wherein nutritional recommendations are calculated based on per-meal macronutrient needs derived from prior muscle damage, circadian phase, digestive efficiency, and the interrelationship of surrounding KHAs.

7. The system of aspect 1, wherein well-being is tracked through a multidimensional scoring system including physiological, psychological, and relational axes.

8. The system of aspect 1, wherein the coaching recommendation engine continuously re-optimizes the user's short-term and multi-day schedule of KHAs to reflect evolving goals, missed actions, and real-time updates in biometric and contextual inputs.

9. The system of aspect 1, wherein the vector database used for knowledge training incorporates continually updated Olympic medal-winning strategies, real-world athlete data, and peer-reviewed scientific literature prioritized toward functional, sustainable health models.

10. The system of aspect 9 wherein the content generation engine selects and sequences clips from the human-recorded content library based on user goals, time-of-day, and behavioral patterns.

11. The system of aspect 9 wherein the content generation engine retrieves pre-recorded AI video clips and selects transitions from a curated AI media database.

12. The system of aspect 9 wherein real-time text content is generated using a large language model based on recent user activity, biometric data, or health goals.

13. The system of aspect 1, wherein avatar coaching outputs include emotional reinforcement, praise, or habit correction suggestions based on both real-time events and long-term progress alignment.

14. The system of aspect 1 further comprising a real-time event monitoring engine that uses sensor and in-app data to determine when new coaching content should be generated.

15. The system of aspect 1 further comprising a human-recorded content library containing labeled video and audio clips from actors or coaches, stored and categorized by situation, tone, or topic.

16. The system of aspect 1 further comprising a timeline-based video assembly engine that sequences actor-recorded, pre-generated, and real-time generated clips using a rule-based engine or AI sequencing agent.

17. The system of aspect 1 further comprising a delivery engine that embeds the final coaching video into the app interface for user playback on demand or via notifications.

18. The system of aspect 1 wherein all personalization data and content generation parameters are transmitted between modules using internal RESTful APIs.

19. The system of aspect 1 wherein avatar customization settings modify tone, coaching frequency, animation expressions, and language across all generated outputs.

20. The system of aspect 1 wherein user feedback and interaction data are logged and used to refine future video generation through a reinforcement learning model.

21. The system of aspect 1 wherein avatar interactions include mood-based adaptation, where voice tone and language style adjust in real-time to biometric and behavioral trends.

22. The system of aspect 21, wherein avatars are capable of delivering praise or constructive feedback based on how the user is contributing to another's well-being.

23. The system of aspect 21, wherein the avatar offers scripts or phrases to help users communicate difficult emotional content with their linked user.

24. The system of aspect 21, further comprising a shared activity recommendation engine that schedules KHAs for both users to complete together as a means of emotional bonding.

25. The system of aspect 21, wherein user feedback is submitted via an interface including emotion tags, numerical sliders, multidimensional well-being scores, and optional journal-style entries.

26. The system of aspect 21, wherein emotional analysis uses a reinforcement learning model to detect evolving patterns in emotional state, relational satisfaction, or conflict resolution over time.

27. The system of aspect 21, wherein avatars adapt communication style, tone, and language based on the cultural segment and emotional preferences of the user.

28. The system of aspect 21, wherein feedback data is encrypted and stored in compliance with privacy regulations, with anonymization of shared insights between linked users where appropriate.

29. The system of aspect 21, wherein avatar-delivered coaching includes techniques derived from emotional intelligence research, family counseling protocols, and evidence-based communication strategies.

30. The system of aspect 21, wherein avatars initiate check-ins and offer empathy-driven coaching during emotionally sensitive timeframes (e.g., post-conflict, menstrual phases, recovery periods).

31. The system of aspect 21, wherein users can opt to share menstrual cycle data and receive avatar-led guidance tailored to their physiological phase, including recommendations for partners.

32. The system of aspect 21, wherein linked avatars coordinate to facilitate dialogue and mutual understanding between users using mirrored coaching strategies personalized to each user's role and goals.

33. The system of aspect 21, further comprising integration with future biosensors that detect physiological markers of emotional state, such as cortisol or endorphins, to enhance the emotional insight model through objective data inputs.

34. The system of aspect 1 wherein the content engine uses a hybrid decision system incorporating deterministic rule trees and AI models to compose timeline-based avatar videos from the three content types.

35. A computer-implemented system for delivering health coaching comprising:

A social linking module that enables users to designate interpersonal relationships in the app;

A structured feedback interface allowing users to submit emotional reflections, requests, or well-being impacts related to linked users;

26. An emotional analysis engine that processes said feedback using sentiment analysis, role classification, well-being scoring, and behavioral context; and An avatar coaching module that provides personalized support, mediation, and relational advice using best practices in therapy and cognitive behavior techniques.

Aspect 36. A method of optimizing a user's daily routine, comprising:

generating an optimal plan for a user's activities based on prioritized activity categories;

displaying the optimal plan on a clock-based user interface;

receiving user modifications to the optimal plan;

dynamically adjusting lower priority activities in response to user modifications of higher priority activities.

37. The method of aspect 36, wherein the prioritized activity categories include sleep, training, pre-training meal, post-training meal, breakfast, nap, and floating meals.

38. The method of aspect 36, wherein generating the optimal plan comprises assigning optimal, alert, and block ranges for each activity's timing and duration.

39. The method of aspect 36, wherein displaying the optimal plan comprises showing visual indicators for optimal and alert ranges on the clock-based interface.

40. The method of aspect 36, further comprising categorizing activities as either dot activities or interval activities.

41. The method of aspect 40, wherein dot activities are single time-point events and interval activities have a configurable duration.

42. The method of aspect 36, further comprising providing in-app notifications for upcoming activities.

43. The method of aspect 42, wherein the in-app notifications include now-notifications, prepare-notifications, and upcoming-notifications.

44. The method of aspect 36, further comprising generating local device notifications when the application is not in use.

45. The method of aspect 36, further comprising displaying contextual notifications with additional information when an activity is selected.

46. The method of aspect 36, wherein the clock-based user interface includes day and night modes.

47. The method of aspect 46, further comprising automatically switching between day and night color schemes based on the current time.

48. The method of aspect 36, further comprising hiding lower priority activities during modification of a higher priority activity.

49. The method of aspect 36, further comprising recalculating and redisplaying affected activities after a modification is complete.

50. The method of aspect 36, further comprising collecting user information during an onboarding process to generate initial activity schedules.

51. The method of aspect 50, wherein the user information includes training frequency and preferred wake-up time.

52. The method of aspect 36, further comprising learning from user modifications to improve future activity recommendations.

53. The method of aspect 36, wherein dynamically adjusting lower priority activities comprises rescheduling meals and naps based on changes to sleep and training times.

54. The method of aspect 36, further comprising allowing modification of past activities and recalculating future activities accordingly.

55. The method of aspect 36, further comprising rounding modified activity times to values divisible by 5 minutes.

Aspect 56. A method of managing sleep recommendations in a daily routine optimization application, comprising:
determining a default sleep duration and start time;
displaying the sleep recommendation on a clock interface;
allowing user modification of sleep duration and start time within predefined ranges;
automatically adjusting subsequent activities based on changes to the sleep recommendation.

57. The method of aspect 56, wherein the default sleep duration is 8.5 hours.

58. The method of aspect 56, wherein the predefined ranges include an optimal range of 7.5-9.5 hours and an alert range of 4.5-7.5 hours and 9.5-12.5 hours.

59. The method of aspect 56, further comprising blocking sleep durations less than 4.5 hours or greater than 12.5 hours.

60. The method of aspect 56, wherein automatically adjusting subsequent activities comprises rescheduling training, meals, and naps.

61. The method of aspect 56, further comprising displaying a visual indicator for optimal and alert sleep ranges on the clock interface.

62. The method of aspect 56, further comprising providing an in-app notification for upcoming bedtime.

63. The method of aspect 62, wherein the in-app notification for bedtime is triggered 120 minutes before the recommended bedtime.

64. The method of aspect 56, further comprising generating a local device notification for bedtime when the application is not in use.

65. The method of aspect 56, further comprising displaying a wake-up time notification minutes after the recommended wake-up time.

66. The method of aspect 56, wherein allowing user modification includes constraining the next sleep's bedtime to be after the last sleep's wake time.

67. The method of aspect 56, wherein allowing user modification includes constraining the previous sleep's wake time to be before the last sleep's bedtime.

68. The method of aspect 56, further comprising switching to a night mode display when editing sleep times.

69. The method of aspect 56, further comprising providing contextual notifications with sleep quality information when sleep activity is selected.

70. The method of aspect 56, wherein automatically adjusting subsequent activities includes maintaining a minimum gap between sleep and training activities.

71. The method of aspect 56, further comprising learning from user modifications to sleep times to improve future sleep recommendations.

72. The method of aspect 56, further comprising allowing modification of past wake times and recalculating the day's schedule accordingly.

73. The method of aspect 56, wherein displaying the sleep recommendation includes showing only a bedtime indicator during day mode.

74. The method of aspect 56, further comprising providing alert notifications when sleep duration or timing falls outside the optimal range.

75. The method of aspect 56, wherein automatically adjusting subsequent activities includes redistributing floating meals based on new wake and sleep times.

Aspect 76. A method of scheduling training activities in a daily routine optimization application, comprising:
determining if a current day is a training day based on user preferences;
calculating an optimal training duration and start time;
adjusting the training schedule to avoid conflicts with sleep periods;
inserting pre-training and post-training meals at optimal times relative to the training activity.

77. The method of aspect 76, wherein the optimal training duration is between 60 minutes and 2 hours.

78. The method of aspect 76, further comprising setting an alert for training durations exceeding 2 hours.

79. The method of aspect 76, further comprising blocking training durations less than 60 minutes or greater than 5 hours.

80. The method of aspect 76, wherein calculating the optimal training start time comprises setting it 100 minutes after wake time by default.

81. The method of aspect 76, further comprising adjusting the training start time if it conflicts with sleep, maintaining at least 120 minutes between training and sleep.

82. The method of aspect 76, wherein inserting the pre-training meal comprises placing it 80-110 minutes before training start.

83. The method of aspect 76, wherein inserting the post-training meal comprises placing it 0-30 minutes after training end.

84. The method of aspect 76, further comprising providing an in-app notification 30 minutes before training start.

85. The method of aspect 76, further comprising generating a local device notification for training when the application is not in use.

86. The method of aspect 76, further comprising displaying a visual indicator for optimal and alert training duration ranges on a clock interface.

87. The method of aspect 76, further comprising allowing user modification of training duration and start time within predefined ranges.

88. The method of aspect 87, wherein allowing user modification includes constraining training to avoid overlap with sleep periods.

89. The method of aspect 76, further comprising automatically adjusting floating meal times based on changes to the training schedule.

90. The method of aspect 76, further comprising providing contextual notifications with training preparation information when the training activity is selected.

91. The method of aspect 76, wherein determining if a current day is a training day is based on user-selected training frequency during an onboarding process.

92. The method of aspect 76, further comprising learning from user modifications to training times to improve future training recommendations.

93. The method of aspect 76, further comprising adjusting nap placement based on the training schedule.

94. The method of aspect 76, wherein inserting pre-training and post-training meals includes providing alert notifications if meal timing falls outside optimal ranges.

95. The method of aspect 76, further comprising rounding modified training times to values divisible by 5 minutes.

Aspect 96. A method of managing meal schedules in a daily routine optimization application, comprising:

identifying gaps between fixed activities in a user's daily plan;

calculating optimal positions for floating meals within the identified gaps;

distributing a variable number of meals based on gap duration;

adjusting meal positions in response to user modifications of other activities.

97. The method of aspect 96, wherein the fixed activities include sleep, training, and breakfast.

98. The method of aspect 96, wherein calculating optimal positions for floating meals comprises equally distributing meals within each gap.

99. The method of aspect 96, wherein distributing a variable number of meals comprises adding one meal for gaps of 5 hours or more, and an additional meal for every 2 hours thereafter.

100. The method of aspect 96, further comprising inserting a pre-training meal-110 minutes before training start.

101. The method of aspect 96, further comprising inserting a post-training meal-30 minutes after training end.

102. The method of aspect 96, further comprising inserting breakfast-90 minutes after wake time.

103. The method of aspect 96, further comprising providing in-app notifications for upcoming meals.

104. The method of aspect 96, further comprising generating local device notifications for meals when the application is not in use.

105. The method of aspect 96, wherein adjusting meal positions includes maintaining at least 120 minutes between meals and surrounding activities.

106. The method of aspect 96, further comprising displaying visual indicators for optimal and alert meal timing ranges on a clock interface.

107. The method of aspect 96, further comprising allowing user modification of meal times within predefined ranges.

108. The method of aspect 107, wherein allowing user modification includes constraining meals to avoid overlap with sleep and training periods.

109. The method of aspect 96, further comprising providing contextual notifications with meal preparation information when a meal activity is selected.

110. The method of aspect 96, wherein distributing meals includes adjusting the first meal after post-training to be closer to the gap start.

111. The method of aspect 96, further comprising learning from user modifications to meal times to improve future meal recommendations.

112. The method of aspect 96, further comprising adjusting meal schedules when a nap is inserted into the daily plan.

113. The method of aspect 96, wherein adjusting meal positions includes providing alert notifications if meal timing falls outside optimal ranges.

114. The method of aspect 96, further comprising rounding modified meal times to values divisible by 5 minutes.

115. The method of aspect 96, wherein identifying gaps includes considering the time between the last meal of the day and the next day's breakfast.

Aspect 116. A method of handling user interactions with a schedule interface in a daily routine optimization application, comprising:

detecting user selection of an activity on a clock-based interface;

allowing modification of the selected activity's timing or duration;

hiding lower priority activities during the modification process;

recalculating and redisplaying affected activities after the modification is complete.

117. The method of aspect 116, further comprising constraining modifications to prevent overlap with higher priority activities.

118. The method of aspect 116, wherein allowing modification includes displaying optimal and alert ranges for the selected activity.

119. The method of aspect 116, further comprising providing haptic feedback during activity modification.

120. The method of aspect 116, wherein recalculating affected activities includes adjusting meal and nap schedules.

121. The method of aspect 116, further comprising displaying contextual information about the selected activity during modification.

122. The method of aspect 116, wherein hiding lower priority activities includes fading them out gradually.

123. The method of aspect 116, further comprising animating the transition of activities to new positions after recalculation.

124. The method of aspect 116, wherein allowing modification includes enabling drag-and-drop functionality on the clock interface.

125. The method of aspect 116, further comprising providing undo and redo options for activity modifications.

126. The method of aspect 116, wherein recalculating activities includes maintaining minimum time gaps between activities.

127. The method of aspect 116, further comprising providing visual feedback during activity modification to indicate optimal and alert ranges.

128. The method of aspect 116, wherein allowing modification includes enabling pinch-to-zoom functionality to adjust activity duration.

129. The method of aspect 116, further comprising displaying a summary of changes after modification is complete.

130. The method of aspect 116, wherein hiding lower priority activities includes gradually fading them out based on their priority level.

131. The method of aspect 116, further comprising providing audio feedback to indicate when an activity enters or exits optimal ranges during modification.

132. The method of aspect 116, wherein recalculating and redisplaying affected activities includes adjusting the day-night mode display if necessary.

133. The method of aspect 116, further comprising allowing users to set custom constraints for specific activities.

134. The method of aspect 116, wherein detecting user selection includes recognizing long-press gestures to initiate activity modification.

135. The method of aspect 116, further comprising synchronizing modified schedules across multiple devices associated with the user's account.

Aspect 136. A method of implementing a day-night mode interface in a daily routine optimization application, comprising:

determining the current time;

switching between day and night color schemes based on the current time;

adjusting the display of sleep activities based on the current mode;

temporarily overriding the current mode when editing specific activities.

137. The method of aspect 136, wherein switching between day and night color schemes occurs automatically at predetermined times.

138. The method of aspect 136, wherein adjusting the display of sleep activities comprises showing only a bedtime indicator during day mode.

139. The method of aspect 136, wherein adjusting the display of sleep activities comprises showing full sleep duration during night mode.

140. The method of aspect 136, further comprising displaying activities on a clock-based interface.

141. The method of aspect 140, further comprising indicating optimal and alert ranges for activity timing and duration on the clock-based interface.

142. The method of aspect 136, wherein temporarily overriding the current mode includes switching to night mode when editing sleep activities.

143. The method of aspect 136, further comprising updating visual indicators in real-time as users modify activities.

144. The method of aspect 136, further comprising providing immediate feedback on the impact of modifications to the overall schedule.

145. The method of aspect 136, further comprising displaying in-app notifications below the clock interface.

146. The method of aspect 136, wherein determining the current time includes considering the user's time zone.

147. The method of aspect 136, further comprising adjusting the brightness of the interface based on the current mode.

148. The method of aspect 136, further comprising providing a manual override option for users to switch between day and night modes.

149. The method of aspect 136, wherein adjusting the display includes changing icon designs for day and night modes.

150. The method of aspect 136, further comprising animating transitions between day and night modes.

151. The method of aspect 136, further comprising adjusting text contrast to ensure readability in both modes.

152. The method of aspect 136, wherein temporarily overriding the current mode includes reverting to the appropriate mode after exiting edit state.

153. The method of aspect 136, further comprising displaying a visual indicator of the current mode.

154. The method of aspect 136, wherein adjusting the display includes modifying the appearance of activity trackers in different modes.

155. The method of aspect 136, further comprising synchronizing the day-night mode with the device's system-wide dark mode settings.

Aspect 156. A method of providing adaptive notifications in a daily routine optimization application, comprising:

generating in-app notifications for upcoming activities;

creating local device notifications for activities when the application is not in use;

displaying contextual notifications with additional information when an activity is selected; dynamically updating notification content based on activity state changes.

157. The method of aspect 156, wherein generating in-app notifications comprises creating now-notifications, prepare-notifications, and upcoming-notifications.

158. The method of aspect 157, wherein now-notifications are displayed from the activity start time to 45 minutes after start.

159. The method of aspect 157, wherein prepare-notifications are displayed for a specified time before the activity start.

160. The method of aspect 157, wherein upcoming-notifications are displayed from the preceding activity start to the current activity start.

161. The method of aspect 156, wherein creating local device notifications includes triggering notifications for sleep, training, and meal activities.

162. The method of aspect 156, wherein displaying contextual notifications includes showing different content for optimal and alert states of an activity.

163. The method of aspect 156, further comprising hiding notifications during activity modification.

164. The method of aspect 156, further comprising recalculating and refreshing notifications after user exits edit mode.

165. The method of aspect 156, wherein dynamically updating notification content includes changing notification state when an activity moves between optimal and alert ranges.

166. The method of aspect 156, further comprising providing expandable views for in-app and contextual notifications.

167. The method of aspect 166, wherein expanded notifications remain static until manually collapsed by the user.

168. The method of aspect 156, further comprising customizing notification icons for day and night modes.

169. The method of aspect 156, wherein generating in-app notifications includes prioritizing notifications when multiple activities overlap.

170. The method of aspect 156, further comprising integrating with a remote configuration service to update notification content and timing.

171. The method of aspect 156, wherein creating local device notifications includes ensuring notifications work even when the application is not running in the background.

172. The method of aspect 156, further comprising animating transitions between different notification states.

173. The method of aspect 156, wherein displaying contextual notifications includes showing different content for "too early," "too late," "too long," and "too short" states.

174. The method of aspect 156, further comprising collapsing expanded notifications when navigating to another screen or putting the app in the background.

175. The method of aspect 156, wherein dynamically updating notification content includes adjusting notifications based on real-time changes to the user's schedule.

Aspect 176. A method of personalizing a daily routine optimization application, comprising: collecting user information during an onboarding process;

determining initial activity schedules based on the collected information;

generating default sleep and training recommendations;

creating an initial optimized daily plan based on the user information and default recommendations.

177. The method of aspect 176, wherein collecting user information includes obtaining the user's preferred wake-up time.

178. The method of aspect 176, wherein collecting user information includes determining the user's training frequency.

179. The method of aspect 178, wherein the training frequency options include training every weekday for Olympic/Pro athletes and Amateur athletes.

180. The method of aspect 176, wherein determining initial activity schedules includes calculating an initial sleep schedule based on the user's preferred wake-up time.

181. The method of aspect 180, wherein calculating the initial sleep schedule uses a default sleep duration of 8.5 hours.

182. The method of aspect 176, further comprising allowing users to modify the initial optimized daily plan.

183. The method of aspect 176, further comprising providing explanations for each step of the onboarding process.

184. The method of aspect 176, wherein generating default sleep recommendations includes setting optimal and alert ranges for sleep duration.

185. The method of aspect 176, wherein generating default training recommendations includes setting optimal and alert ranges for training duration.

186. The method of aspect 176, further comprising adapting the onboarding process based on the user's athlete category.

187. The method of aspect 176, further comprising allowing users to skip certain onboarding steps and use default values.

188. The method of aspect 176, further comprising providing visual representations of how user inputs affect the daily plan during onboarding.

189. The method of aspect 176, further comprising offering a guided tour of the application's features after completing the onboarding process.

190. The method of aspect 176, wherein creating the initial optimized daily plan includes scheduling meals at recommended intervals.

191. The method of aspect 176, further comprising allowing users to import data from other fitness or health applications during onboarding.

192. The method of aspect 176, further comprising providing personalized tips based on the collected user information.

193. The method of aspect 176, wherein determining initial activity schedules includes considering the user's time zone.

194. The method of aspect 176, further comprising allowing users to set initial goals during the onboarding process.

195. The method of aspect 176, further comprising providing an option to reset the onboarding process and start over if desired.

Aspect 196. A method of calculating daily calorie needs for a user, comprising:

determining a resting metabolic rate (RMR) based on user characteristics;

calculating a non-exercise activity thermogenesis (NEAT) value;

adjusting the NEAT value based on user goals and fitness level;

generating a total daily calorie need based on the adjusted NEAT value.

197. The method of aspect 196, wherein determining the RMR comprises using the Mifflin-St. Jeor equation.

198. The method of aspect 196, wherein calculating the NEAT value comprises adding a percentage of the RMR based on the user's goal.

199. The method of aspect 198, wherein the percentage is 20% for a build goal, 15% for a balance goal, and 10% for a fat loss goal.

200. The method of aspect 196, further comprising adjusting the NEAT value based on the user's fitness level.

201. The method of aspect 200, wherein the adjustment is −5% of RMR for unfit users and +5% of RMR for fit users.

202. The method of aspect 196, further comprising adjusting the NEAT value based on the user's daily step count.

203. The method of aspect 202, wherein the adjustment is 2% of RMR per 1,000 steps per day.

204. The method of aspect 196, further comprising calculating exercise calories based on metabolic equivalents (METs).

205. The method of aspect 204, wherein the METs are adjusted based on the user's age if over 40 years old.

206. The method of aspect 196, further comprising adjusting the total daily calorie need based on a user-defined goal.

207. The method of aspect 206, wherein the adjustment is a 10% caloric restriction for balancing performance and fat loss.

208. The method of aspect 206, wherein the adjustment is a 25% caloric restriction for maximizing fat loss.

209. The method of aspect 196, further comprising calculating macronutrient ratios based on the total daily calorie need.

210. The method of aspect 209, wherein calculating macronutrient ratios comprises determining protein needs based on body weight and training factors.

211. The method of aspect 209, wherein calculating macronutrient ratios comprises determining carbohydrate needs based on brain usage, non-exercise activity, and exercise requirements.

212. The method of aspect 209, wherein calculating macronutrient ratios comprises determining fat needs as a percentage of total calories.

213. The method of aspect 196, further comprising adjusting calorie and macronutrient calculations based on the user's training volume.

214. The method of aspect 213, wherein the training volume is calculated using a training volume factor (TF) based on different types and intensities of exercise.

215. The method of aspect 196, further comprising providing meal-specific macronutrient recommendations based on the timing and purpose of each meal.

Aspect 216. A method of calculating protein needs for a user in a nutrition planning application, comprising:

determining a baseline protein requirement based on the user's body weight;

calculating a training volume factor based on the user's exercise intensity and duration;

adjusting the baseline protein requirement using the training volume factor;

generating protein recommendations for individual meals based on the adjusted protein requirement.

217. The method of aspect 216, wherein determining the baseline protein requirement comprises multiplying the user's body weight in kilograms by 0.6 grams.

218. The method of aspect 216, wherein calculating the training volume factor comprises categorizing exercises into aerobic, threshold, VO2 max, interval, and strength/power types.

219. The method of aspect 218, further comprising assigning intensity levels of low, medium, high, and very high to each exercise type.

220. The method of aspect 216, wherein calculating the training volume factor comprises dividing the user's training hours by a maximum training limit for each exercise type and intensity.

221. The method of aspect 216, wherein adjusting the baseline protein requirement comprises multiplying the baseline by $[1+(\text{Training Factor} \times 2)]$.

222. The method of aspect 216, further comprising calculating an overreaching factor based on the training volume factor.

223. The method of aspect 222, wherein the overreaching factor is calculated as $(TF-1)$, where TF is the training volume factor.

224. The method of aspect 216, further comprising estimating the time before overreaching is likely based on the overreaching factor.

225. The method of aspect 216, wherein generating protein recommendations for individual meals comprises dividing the daily protein need by 20 to determine hourly protein needs.

226. The method of aspect 225, further comprising multiplying the hourly protein need by the number of hours until the next meal to determine the protein content for a specific meal.

227. The method of aspect 216, further comprising adjusting protein recommendations based on the user's goal of building muscle, maintaining balance, or losing fat.

228. The method of aspect 216, further comprising calculating inherent protein in meals from non-protein food sources.

229. The method of aspect 228, wherein calculating inherent protein comprises estimating 10% of the calorie count of all feedings as usable protein.

230. The method of aspect 216, further comprising adjusting protein recommendations based on the timing of meals relative to training sessions.

231. The method of aspect 230, wherein protein recommendations are increased for pre-training and post-training meals.

232. The method of aspect 216, further comprising providing recommendations for protein food sources based on the digestion time needed until the next meal.

233. The method of aspect 216, further comprising adjusting protein recommendations based on the user's age, with increased recommendations for users over 40 years old.

234. The method of aspect 216, further comprising calculating and displaying the caloric contribution of protein to the total daily calorie intake.

235. The method of aspect 216, further comprising integrating the protein calculations with carbohydrate and fat calculations to provide a comprehensive macronutrient plan.

Aspect 236. A method of calculating carbohydrate needs for a user in a nutrition planning application, comprising:

determining a baseline carbohydrate requirement for brain function;

calculating non-exercise activity thermogenesis (NEAT) carbohydrate needs;

estimating exercise-induced carbohydrate requirements based on workout intensity and duration; generating carbohydrate recommendations for individual meals based on the calculated needs.

237. The method of aspect 236, wherein determining the baseline carbohydrate requirement comprises setting a minimum of 60 grams per day for brain function.

238. The method of aspect 236, wherein calculating NEAT carbohydrate needs comprises considering the user's weight and daily step count.

239. The method of aspect 238, wherein nEAT carbohydrate needs are calculated as $60 \text{ g}+(\text{weight in kg} \times 0.03 \times (\text{step count per day}/1,000))$.

240. The method of aspect 236, wherein estimating exercise-induced carbohydrate requirements comprises using metabolic equivalents (METs) based on the user's fitness level and exercise intensity.

241. The method of aspect 240, further comprising adjusting MET values for users over 40 years old by subtracting 1% for each year over 40.

242. The method of aspect 236, wherein estimating exercise-induced carbohydrate requirements comprises calculating workout calories as $(\text{METs} \times \text{body weight in kg} \times \text{exercise duration in hours})$.

243. The method of aspect 242, further comprising determining the percentage of workout calories derived from glucose based on the type of exercise.

244. The method of aspect 236, further comprising adjusting carbohydrate recommendations based on the user's goal of building muscle, maintaining balance, or losing fat.

245. The method of aspect 244, wherein the adjustment is 100% of calculated needs for building, 85% for balance, and 70% for fat loss.

246. The method of aspect 236, further comprising limiting carbohydrate under-fueling to 10% of RMR for fat loss goals.

247. The method of aspect 236, further comprising deducting carbohydrates consumed during training from post-exercise carbohydrate recommendations.

248. The method of aspect 247, wherein carbohydrates consumed during training are limited to 1 g per kg of body weight within 10 minutes of exercise completion.

249. The method of aspect 236, further comprising providing recommendations for carbohydrate timing and sources based on the glycemic index.

250. The method of aspect 236, further comprising adjusting carbohydrate recommendations based on the timing of meals relative to training sessions.

251. The method of aspect 250, wherein carbohydrate recommendations are increased for pre-training and post-training meals.

252. The method of aspect 236, further comprising calculating and displaying the caloric contribution of carbohydrates to the total daily calorie intake.

253. The method of aspect 236, further comprising integrating carbohydrate calculations with protein and fat calculations to provide a comprehensive macronutrient plan.

254. The method of aspect 236, further comprising adjusting carbohydrate recommendations based on the user's training volume factor.

255. The method of aspect 236, wherein generating carbohydrate recommendations for individual meals comprises considering the number of hours until the next meal and the meal's purpose (e.g., pre-training, post-training, or general sustenance).

Aspect 256. A method of calculating fat needs for a user in a nutrition planning application, comprising:

determining total daily calorie needs;

subtracting calories allocated to protein and carbohydrates;

calculating remaining calories for fat consumption;

converting remaining calories to fat grams;

distributing fat recommendations across individual meals.

257. The method of aspect 256, wherein determining total daily calorie needs comprises using the previously calculated NEAT (Non-Exercise Activity Thermogenesis) value.

258. The method of aspect 256, wherein subtracting calories allocated to protein comprises multiplying total protein grams by 4 calories per gram.

259. The method of aspect 256, wherein subtracting calories allocated to carbohydrates comprises multiplying total carbohydrate grams by 4 calories per gram.

260. The method of aspect 256, wherein converting remaining calories to fat grams comprises dividing the remaining calories by 9 calories per gram of fat.

261. The method of aspect 256, wherein distributing fat recommendations across individual meals comprises dividing the total fat grams by the number of meals.

262. The method of aspect 261, further comprising applying a meal modifier to adjust fat content for specific meals.

263. The method of aspect 256, further comprising adjusting fat recommendations based on the user's goal of building muscle, maintaining balance, or losing fat.

264. The method of aspect 263, wherein the adjustment is 0% reduction for building, 15% reduction for balance, and 30% reduction for fat loss.

265. The method of aspect 256, further comprising ensuring a minimum intake of essential fatty acids, including omega-3, omega-6, and omega-9.

266. The method of aspect 256, further comprising adjusting fat recommendations based on the timing of meals relative to training sessions.

267. The method of aspect 266, wherein fat recommendations are decreased for pre-training meals and increased for post-training meals.

268. The method of aspect 256, further comprising providing recommendations for fat sources based on the meal's purpose and timing.

269. The method of aspect 256, further comprising calculating and displaying the caloric contribution of fat to the total daily calorie intake.

270. The method of aspect 256, further comprising integrating fat calculations with protein and carbohydrate calculations to provide a comprehensive macronutrient plan.

271. The method of aspect 256, further comprising adjusting fat recommendations based on the user's training volume factor.

272. The method of aspect 256, wherein distributing fat recommendations across individual meals comprises considering the number of hours until the next meal.

273. The method of aspect 256, further comprising providing recommendations for the ratio of saturated, monounsaturated, and polyunsaturated fats.

274. The method of aspect 256, further comprising adjusting fat recommendations based on the user's age and gender.

275. The method of aspect 256, further comprising allowing manual adjustments to fat intake within predetermined safe ranges based on the user's preferences and tolerances.

Aspect 276. A method of calculating meal-specific macronutrient recommendations in a nutrition planning application, comprising:

determining the timing and purpose of each meal;

calculating base macronutrient needs for the meal; and;

applying meal-specific modifiers to the base macronutrient needs;

adjusting recommendations based on the time until the next meal;

generating final macronutrient recommendations for the meal.

277. The method of aspect 276, wherein determining the timing and purpose of each meal comprises categorizing meals as breakfast, pre-training, post-training, or general sustenance.

278. The method of aspect 276, wherein calculating base macronutrient needs comprises dividing daily protein, carbohydrate, and fat requirements by the number of planned meals.

279. The method of aspect 276, wherein applying meal-specific modifiers for protein comprises increasing protein for pre-training and post-training meals.

280. The method of aspect 276, wherein applying meal-specific modifiers for carbohydrates comprises increasing carbohydrates for pre-training meals and post-training meals.

281. The method of aspect 276, wherein applying meal-specific modifiers for fats comprises decreasing fats for pre-training meals and increasing fats for general sustenance meals.

282. The method of aspect 276, wherein adjusting recommendations based on the time until the next meal comprises increasing protein and fat for meals that need to sustain the user for longer periods.

283. The method of aspect 276, further comprising recommending the inclusion of coarse vegetables in meals to slow digestion when appropriate.

Aspect 284. A method of calculating training volume for a user in a fitness and nutrition planning application, comprising:

categorizing exercises into types including aerobic, threshold, VO2max, intervals, and strength/power;

assigning intensity levels to each exercise type;

determining training hours for each exercise type and intensity;

calculating a training volume factor based on the ratio of training hours to maximum training limits;

using the training volume factor to adjust nutrition and recovery recommendations.

285. The method of aspect 284, wherein categorizing exercises comprises defining aerobic exercises as those lasting more than 2 hours.

286. The method of aspect 284, wherein categorizing exercises comprises defining threshold exercises as those performed at lactate threshold pace for 30-90 minutes.

287. The method of aspect 284, wherein categorizing exercises comprises defining VO2max exercises as those performed at or near maximum oxygen uptake for 6-12 minutes.

288. The method of aspect 284, wherein categorizing exercises comprises defining interval exercises as those lasting 1-3 minutes at high intensity.

289. The method of aspect 284, wherein categorizing exercises comprises defining strength/power exercises as resistance training or plyometric movements.

290. The method of aspect 284, wherein assigning intensity levels comprises using categories of low, medium, high, and very high for each exercise type.

291. The method of aspect 284, wherein determining training hours comprises recording the duration of each exercise session performed by the user.

292. The method of aspect 284, wherein calculating the training volume factor comprises dividing the user's training hours by a predefined maximum training limit for each exercise type and intensity.

293. The method of aspect 292, wherein the maximum training limits are based on research-backed guidelines for preventing overtraining.

294. The method of aspect 284, further comprising calculating an overreaching factor by subtracting 1 from the training volume factor.

295. The method of aspect 294, further comprising estimating the time before overreaching is likely based on the overreaching factor.

296. The method of aspect 284, wherein using the training volume factor to adjust nutrition recommendations comprises increasing protein intake as the factor increases.

297. The method of aspect 284, wherein using the training volume factor to adjust nutrition recommendations comprises increasing carbohydrate intake as the factor increases.

298. The method of aspect 284, wherein using the training volume factor to adjust recovery recommendations comprises suggesting longer rest periods as the factor increases.

299. The method of aspect 284, further comprising adjusting the training volume calculations based on the user's age, with reduced capacities for users over 40 years old.

300. The method of aspect 284, further comprising providing warnings to the user when the training volume factor approaches or exceeds 1.0, indicating increased risk of overtraining.

301. The method of aspect 284, further comprising using the training volume factor to adjust the distribution of macronutrients in meal recommendations.

302. The method of aspect 284, further comprising integrating the training volume calculations with sleep quality and duration data to provide comprehensive recovery recommendations.

303. The method of aspect 284, further comprising allowing manual adjustments to the training volume factor based on the user's perceived exertion and recovery status.

Aspect 304. A method for calculating macronutrient requirements using biological temporal regression weight comprising acquiring data related to past biological stressor events identifying the magnitude and timing of each stressor event applying a biological temporal regression weight to each stressor event based on its recency adjusting macronutrient calculations according to the weighted stressor events primarily altering protein requirements to optimize healing and recovery.

270. The method of aspect 269 wherein the biological stressor event includes; physical activities such as exercise.

271. The method of aspect 269 comprising overlaying multiple regression weights for different types of stressors.

272. The method of aspect 269 wherein; the regression weight decreases as the stressor event recedes further into the past.

273. The method of aspect 269 wherein; the meal calculator updates macronutrient requirements daily.

274. The method of aspect 269 further comprising; displaying suggested meal plans based on calculated macronutrient requirements.

275. The method of aspect 269 wherein; data related to stressor events is input via a user interface;

276. The method of aspect 269 wherein; macronutrient calculations are adjusted automatically without user intervention.

277. The method of aspect 269 further comprising; storing historical data on stressor events and associated regression weights.

278. The method of aspect 269 wherein; the system provides feedback on macronutrient adjustments to the user.

279. The method of aspect 269 wherein; machine learning algorithms are employed to refine regression.

Advantages of one implementation may include one or more of the following:

Enhanced Personalization: By gathering detailed user profiles—including lifestyle goals, physiological metrics, and personal preferences—the system tailors health coaching content and strategies to individual needs, resulting in a more meaningful and engaging experience.

Dynamic Adaptability: The use of a real-time adjustment engine, supported by reinforcement learning and biologically weighted regression models, allows the system to continuously refine and reschedule KHAs based on user progress, missed actions, updated availability, and changing biometric data.

Data-Driven Decision Making: The integration of API connectors to collect real-time inputs from various sensor devices and health data platforms, coupled with advanced analytics from a relational mapping engine, ensures that coaching recommendations are supported by the most current, comprehensive, and meaningful data.

Scientifically Informed Coaching: By incorporating scientific literature, athlete data, and recognized best practices in therapy and cognitive behavior techniques, the system leverages validated methodologies to optimize metabolic health, skeletal muscle preservation, blood sugar regulation, inflammation reduction, and sleep quality.

Engaging Avatars with Emotional Rapport: The generative AI avatar interface not only delivers personalized coaching content but also builds an emotional connection with users, potentially increasing adherence to health recommendations while offering a supportive virtual presence.

Integrated Multimedia Experience: Automation across content generation—including the transformation of text scripts into synthesized audio and visually engaging avatar videos—ensures a coherent and multi-sensory coaching experience that can resonate with a wide range of users.

Social Connectivity and Emotional Support: The inclusion of a social linking module and structured feedback interface enables users to designate significant interpersonal relationships. With the assistance of an emotional analysis engine that processes sentiment and behavioral context, the system can provide relational advice, emotional support, and mediation in line with cognitive behavior techniques.

Scalability and Flexibility: A server-based storage system that manages and serves personalized content, along with modular system components (e.g., distinct engines for recommendation, feedback, and emotional analysis), facilitates scalability for broader health and wellness applications across diverse populations.

Outcome-Driven Optimization: The coupling of user outcome data with recent KHA history via reinforcement learning promotes continuous improvement of the coaching regimen, ensuring that interventions are progressively optimized for effectiveness overtime.

Dynamic adaptability by integrating day-night mode user interfaces and real-time biometric analyses, allowing the system to adjust recommendations based on current conditions and user feedback.

Improved user engagement via an intuitive, user-centric design that dynamically shifts with daily routines, thereby addressing variations in circadian rhythms and personal activity levels.

Increased accuracy in caloric and macronutrient guidance by employing precise calculations including resting metabolic rate, non-exercise activity thermogenesis adjustments, and metabolic equivalent assessments.

Seamless scalability and compatibility with diverse data sources and sensor technologies, allowing for future integration and refinement as digital and wearable technology evolves.

Professional-grade insights by leveraging a knowledge base that draws on best practices from elite athletic coaching and verified performance metrics, enabling users to receive guidance reflective of high-level expertise.

Cost and efficiency benefits by automating aspects of personalized wellness, reducing reliance on one-on-one human coaching, and delivering timely, context-aware advice directly through a mobile platform.

These advantages, taken together, provide a comprehensive and adaptive platform for personalized health coaching that not only meets the evolving needs of users but also leverages state-of-the-art technology and scientific methodologies to improve overall health outcomes.

BRIEF DESCRIPTION OF DRAWINGS

FIG. 1A, FIG. 1B1, FIG. 1B2, FIG. 1B3, and FIGS. 1C-1E show exemplary illustrations of the system architectures for various health generative AI avatar.

FIG. 2 shows an exemplary flowchart that describes a process for collecting user data (exercise, sleep, and diet), analyzing it to generate personalized recommendations.

FIG. 3 shows flowchart illustrating a process for acquiring and processing athlete data to generate personalized fitness plans.

FIG. 8 shows an exemplary flow chart

FIG. 12 shows an exemplary flowchart illustrating a process for managing activity visualization on a clock-based interface.

FIG. 16A-16B show flowchart for personalized nutrition and fitness optimization process.

FIG. 22 discloses the priority-ordered notification schema.

FIG. 23 shows an exemplary flowchart illustrating an AI coaching system, which utilizes Retrieval-Augmented Generation (RAG) techniques to provide personalized and context-aware coaching.

FIG. 24 shows a non-exercise activity thermogenesis (NEAT) calculation method.

FIG. 25A-25D detail the protein requirement calculation method.

FIG. 26A-26B reveals the fat intake algorithm which provides a structured method for determining the appropriate amount of fat for each meal based on individual daily calorie needs and dietary goals.

DETAILED DESCRIPTION OF THE SYSTEM

Figure 1A:
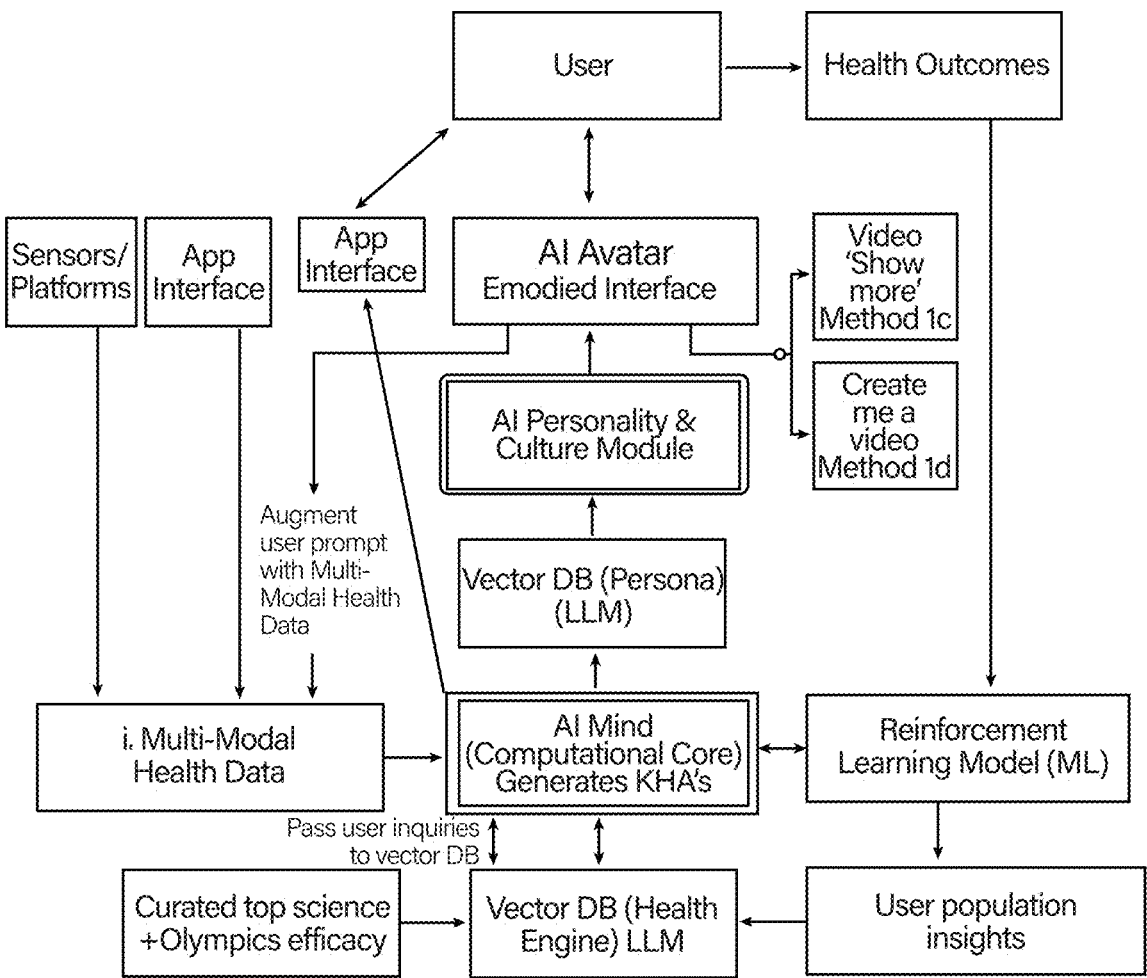

FIG. 1A-1E show exemplary illustrations of the system architectures for various health generative AI avatar. FIG. 1A illustrates a comprehensive AI-powered health coaching system. At the top, the User (1) interacts with the system and receives personalized health coaching, ultimately leading to improved Health Outcomes (i). The user engages with the system through App Interfaces (2 and 5), which serve as digital touchpoints. The system collects Multi-Modal Health Data (3), including metrics such as sleep, nutrition, emotional state, glucose patterns, activity, and social dynamics. This data is processed by the AI Mind (Computational Core) (4), which acts as the central processing unit. The AI Mind synthesizes data and makes decisions using machine learning, large language models, and biometric modeling. The Vector DB (Persona) (LLM) (5) contains personality training data for the avatar, generating scripts for the AI Personality & Culture Module (6). This module processes personality aspects and cultural adaptations for the avatar's interactions. The AI Avatar Embodied Interface (7) serves as a programmatically generated, human-like guide that builds trust and emotional connection with the user. A Reinforcement Learning Model (ii) creates a closed feedback loop, allowing the system to evolve based on user responses and progress. The Vector DB (Health Engine) LLM (4b) is trained in top scientific recommendations across relevant health fields, further informing the AI Mind's decision-making process. This architecture enables the delivery of context-aware, behaviorally prioritized KHAs that can identify and correct underlying metabolic dysfunction. The system's ability to process and act on real-time inputs in ways that human coaches cannot match due to cognitive and logistical limitations makes it a unique and powerful tool for guiding human health and well-being. This system features a programmatically generated AI avatar that serves as the embodied interface between the user and a highly advanced health optimization engine, providing users with a trusted, human-like guide that delivers personalized coaching to improve their health, well-being, and longevity. Each avatar includes a customizable personality and appearance module, allowing for coaching personas—ranging from archetypal roles to branded or celebrity-style guides. This embodiment builds trust, emotional connection, and long-term engagement. Functionally, the avatar is powered by a dynamic computational "mind": an AI system that delivers forward-prescribed KHAs based on continuously updated, multi-modal health data. These KHAs are synthesized using machine learning (ML), large language models (LLMs), and biometric modeling to process and act on real-time inputs such as sleep, nutrition, emotional state, glucose patterns, activity, and social dynamics. At its core, the system is designed to identify and correct underlying metabolic dysfunction—the root cause of many modern chronic conditions—by guiding behavior in precise, timely, and personalized ways. Unlike human coaches—who cannot cognitively or logistically integrate and respond to these data streams in real time—this system provides context-aware, behaviorally prioritized, and dynamically rescheduled actions, creating a closed feedback loop that evolves with the user. First validated in Olympic athletes, it contributed directly to improvements in metabolic function, glucose regulation, sleep quality, and performance readiness, leading to medal-winning outcomes. Far more than a digital assistant, this system constitutes a scalable, emotionally intelligent decision engine, uniquely positioned to guide human health in ways no human or conventional system can match.

The system supports sustainable fat loss rather than simple weight loss, with a primary focus on helping users achieve long-term fat reduction while preserving lean muscle mass and maintaining a high metabolic rate. This is especially important because many interventions, such as GLP-1 drugs, can inadvertently threaten muscle retention and metabolic health. Every dynamic aspect of the system— from meal calculations, timing, and digestion speed to the integration of strength training elements—is engineered to promote this sustainable fat loss outcome. The approach is never about calorie restriction; in fact, the system encourages users to avoid focusing on calories altogether, using calorie data only for backend calculations. Instead, users are guided to follow prescribed macronutrient targets at optimal times, particularly emphasizing proper breakfast composition and strategic fueling around workouts, as well as tailoring digestion speeds to individual needs. This methodology is designed to help users retain or build muscle, which in turn keeps metabolism elevated and supports long-term fat burning. The unique interface provides real-time feedback as users set their goals, reinforcing these principles. The system prioritizes slow-digesting, nutrient-dense meals with sufficient protein to ensure users feel satiated, avoid hunger battles, and preserve muscle mass. In contrast, traditional systems that focus on calorie restriction often reduce protein intake, leading to muscle loss, decreased metabolism, and ultimately making fat loss more difficult.

The system enables users to obtain their resting heart rate (RHR) directly within the app by tapping a button, even if they do not have external sensors or if sensor data is not available in their device's health kit. This is achieved using the phone's camera and a guided on-screen process, where the user places their finger over the camera and receives a real-time RHR measurement, leveraging validated smartphone-based photoplethysmography techniques. Once the RHR is captured, the system incorporates this data into the body composition goal calculator, using established associations between RHR, cardiorespiratory fitness, and body fat percentage. The RHR value helps inform the user's baseline fitness level and is factored into predictive models that estimate the time required to achieve specific body composition goals, such as muscle gain or fat loss. By integrating RHR data, the system personalizes recommendations and goal timelines, making them more accurate and actionable. This approach democratizes fitness tracking, allowing users without wearables to benefit from advanced health insights and progress monitoring. The RHR measurement is also used to dynamically adjust other aspects of the system, such as recommended workout intensity, recovery needs, and nutrition planning, ensuring that each user's plan is tailored to their current physiological state and long-term objectives.

This system features a programmatically generated AI avatar that acts as the primary interface between the user and a sophisticated health optimization engine. The user interacts with the system through various app interfaces, which serve as the main digital touchpoints for engaging with the AI coach and receiving personalized guidance. The AI avatar is not only visually embodied but also includes a customizable personality and appearance module, allowing users to select from a range of coaching personas, such as archetypal roles or branded and celebrity-style guides. This embodiment is designed to foster trust, emotional connection, and long-term engagement, making the avatar a relatable and motivating presence in the user's health journey. Functionally, the avatar is powered by a dynamic computational "mind"—an AI system that synthesizes multi-modal health data, including inputs related to sleep, nutrition, emotional state, glucose patterns, physical activity, and social dynamics. This data is continuously updated and processed by the AI Mind (Computational Core), which draws on a health engine vector database trained in leading scientific recommendations, as well as a persona vector database that informs the avatar's personality and communication style. The AI Personality & Culture Module further adapts the avatar's language and approach to fit the user's preferences and cultural context. The system's core function is to deliver forward-prescribed KHAs that are personalized, timely, and context-aware. These actions are generated using advanced machine learning, large language models, and biometric modeling, enabling the system to identify and address underlying metabolic dysfunction—the root cause of many chronic health conditions. Unlike human coaches, who cannot integrate and respond to these complex data streams in real time, this AI-driven system provides behaviorally prioritized and dynamically rescheduled actions, creating a closed feedback loop that evolves with the user through reinforcement learning.

Validated initially in Olympic athletes, the system has demonstrated measurable improvements in metabolic function, glucose regulation, sleep quality, and performance readiness, contributing to medal-winning outcomes. Ultimately, this system goes far beyond a digital assistant; it is a scalable, emotionally intelligent decision engine uniquely positioned to guide human health, well-being, and longevity in ways that no human or conventional system can match.

The system is an advanced, AI-powered health coaching platform designed to deliver personalized, emotionally intelligent guidance to users through a dynamic, embodied interface. At its core, the system begins with the user, who interacts via app interfaces that serve as the primary digital touchpoints. The user's multi-modal health data—including metrics such as sleep, nutrition, emotional state, glucose patterns, activity, and social dynamics—is continuously collected and fed into the AI Mind, the computational core of the system. This core processes the data using sophisticated machine learning models and is further informed by a health engine vector database trained on leading scientific recommendations.

For a deeply personalized experience, the AI Mind also accesses a separate vector database dedicated to the avatar's personality, which generates scripts tailored to the user's needs. These scripts are processed by the AI Personality & Culture Module, ensuring that the avatar's communication style and cultural context are finely tuned. The AI Avatar, serving as the system's embodied interface, delivers this tailored coaching directly to the user, fostering trust, emotional connection, and long-term engagement. The entire process is governed by a reinforcement learning model that creates a closed feedback loop, allowing the system to adapt and evolve based on user responses and health outcomes. This architecture enables the delivery of forward-prescribed, context-aware KHAs that are prioritized and dynamically rescheduled in response to real-time user data. Validated in high-performance contexts such as Olympic athletes, the system has demonstrated the ability to improve metabolic function, glucose regulation, sleep quality, and performance readiness. Ultimately, GOLDAI offers a scalable, emotionally intelligent decision enginethat guides users toward optimal health, well-being, and longevity in ways unmatched by human coaches or traditional digital assistants.

Human health isn't just individual—it's deeply relational. We are social animals, and our well-being is influenced by the people we live, love, and work alongside every day. This fitness and health app system recognizes that truth by creating shared health journeys. Through friend and partner connections, shared routines, and avatars that act as intelligent mediators and coaches, users experience emotional and physical support that mirrors real life. Whether it's syncing meals, modifying workouts based on a partner's energy, or navigating sensitive conversations, the app creates a networked ecosystem of wellness—making health not just personal, but communal, intuitive, and emotionally intelligent.

Users can add each other as friends

They can designate what type of relation they have to that person

Such as significant other living together, seeing occasionally, workout buddy etc They can set how much time they spend together (app can detect this in future)

They can input wellbeing attributes based on how the other is contributing to their wellbeing, or challenging it They can make requests to the other person for things they want but are hard to say.

Avatar will act as a relationship coach as well, a mediator, faciliator

Avatar can also offer proactive advice to the other based on wellbeing attributes that are coming from the other partner Avatar can praise the user for contributing to the well-being of the other Applies for workouts, meals, sleep, etc as well Applies to families, extended families, work groups, relatives, friend groups, etc Users can add each other into meals so that they plan to eat together App will suggest meal that meets both users macro requirements Female user can share menstrual cycle data Avatar can also offer tips to the female depending on part of monthly cycle Avatar can give tips to male or partners depending on this cycle as well System can adjust training, meals, etc based on female cycle Users can input sex info Avatar can recommend sex as healthy activity Will optimize based on time of day, energy of both users (if connected in app)

Behavioral & Emotional Sync:

Mood Syncing: Users can track mood and see patterns based on time spent with others or shared activities.

Emotional Check-ins: Avatar prompts gentle emotional reflections, offering partner-specific suggestions.

Empathy Score: AI generates insights about emotional balance within relationships, reinforcing shared awareness.

Gamified Support:

Relationship Health Score: Based on communication, support, shared meals, workouts, etc.

Shared Streaks: Points or badges for doing wellness activities together—sleep sync, walks, healthy meals, digital detox.

Network Effect:

Group Challenges: Work groups, families, or friend clusters can enter joint wellness challenges—ex: "Sleep 7 h avg for 7 days."

Inner Circle Insights: See how your core relationships are influencing your habits—both positively and negatively.

Advanced Biological Sync:

Hormonal Sync Tracking: Sync training and stress-reduction routines with hormonal phases, not just cycle days.

Couples Recovery Mode: Suggests lower-intensity days, recovery-focused meals, or "connection time" based on joint fatigue levels.

Communication Facilitation:

Soft Voice Requests: Avatars deliver sensitive asks on behalf of users—e.g., "Jamie's feeling low energy today. Maybe suggest a cozy night in?"

Conflict Cooldown Tool: When tension rises, avatar offers breathwork, grounding exercises, or guides a short empathy dialogue.

II. Primal Features to Add in App

Evolutionary biology, tribal dynamics, and deep subconscious archetypes offer powerful frameworks for designing a truly transformative health and fitness app. As social, ritual-driven beings, our behaviors are shaped not just by logic, but by primal instincts hardwired over millennia—the drive to compete, to belong, to protect, to attract, and to earn status within a group. By weaving these ancient patterns into modern app experiences, we can tap into the emotional and psychological levers that actually drive behavior change. Think: rallying a "tribe" for support during a health challenge, activating the warrior archetype before a tough workout, or creating digital rituals that mirror the communal fireside bonding our ancestors relied on. Features rooted in these dynamics not only boost engagement—they speak directly to the subconscious mind, creating a sense of meaning, connection, and identity that makes healthy behavior feel natural, even inevitable. This isn't just gamification—it's human nature, fully activated.

Testosterone levels can be influenced by deep evolutionary aspects of social order, etc. the app can simulate dynamics that stimulate these hormones.

Other Primal Features:

Primal Instinct-Based Feature Ideas for a Health & Fitness App

Warrior Instinct (Fight, Challenge, Power)

Challenge Arena: Users can "enter battle" by accepting a 7-day or 30-day challenge. They can rally their tribe to support them as they "go to war" with an old habit.

Battle Flags: Users can plant a digital flag declaring a personal mission (e.g. "Reclaim my energy") that others can rally behind.

Victory Rituals: When a user hits a milestone, the tribe gets notified and can perform a digital "ritual" (e.g. clapping emojis, video shoutouts, or chants).

Enemy Identifier: Users can name their "enemy" (e.g. stress, sugar, fatigue), and the app frames goals as battles against these.

Nurturing Instinct (Care, Protection, Bonding)

Care Loops: Users can mark others as those they "watch over"—offering gentle nudges, encouragement, or guided care routines.

Rest Day Guardian: Loved ones can ensure someone takes a rest day, hydrated, or gets sunlight, and receive praise from the avatar.

Digital Campfire: End-of-day reflection or breathwork that users can share together as a group, reinforcing the family bond.

Tribal Belonging & Status Dynamics
  Tribe Hierarchies: Each tribe (family, friend group, gym crew) has rotating roles—Warrior of the Week, Healer, Scout (explores new wellness ideas), Elder (wisdom sharer).
  Tribal Scoreboard: Displays health wins not as individual glory, but as contributions to tribe's wellness score.
  Initiation Ceremonies: New users are "welcomed into the tribe" through a special ritual— making them feel honored and seen.
Rallying in Times of Battle
  Distress Signal: A user feeling emotionally or physically low can send a "tribal signal"— rallying friends or family to reach out or show up.
  Shield Wall: When a user is in relapse, illness, or heartbreak, their tribe is prompted to provide a 3-day shield of care (texts, meals, co-workouts).
  Warrior Watch: Others are notified when someone is training especially hard or pushing themselves—they become part of a motivational watch party.
Shame & Accountability
  Shadow Tracking: The avatar gently mirrors back behaviors the user might hide (e.g. skipped meals, poor sleep), using nonjudgmental prompts rooted in curiosity.
  Witness Mode: User can request someone they trust to "witness" their week—increasing compliance through gentle, consensual social visibility.
  Rituals of Redemption: Missed goals can be reframed through redemptive rituals (e.g., extra act of service, community support post).
Jealousy & Competition
  Status Sparks: When a friend hits a milestone, others are shown the "spark"—not to induce shame, but to awaken their own drive.
  Peer Ranking (Opt-in): Compare your progress to others in your tribe with "Challenge Mode" enabled. Can be turned off for non-competitive types.
  Crush List: Users can select a small list of people whose progress inspires (or provokes) them—harnessing admiration and subtle rivalry.
Cultural & Ritual Tools
  Totem Creation: Tribes can create a shared symbol representing their mission—a badge they carry through the app.
  Weekly Tribal Council: Brief check-in moment where everyone reflects on what went well, what they're working on, and tribal goals for the week.
  The system features a sophisticated educational content bridge that seamlessly connects in-app educational videos with personalized avatar-based learning experiences. As users view masterclass mini-sessions within the application, the system's AI engine automatically transcribes and indexes all content, creating a searchable database paired with precise video timecodes. When a user encounters information they want to explore further or implement in their daily routine, they can simply tap a dedicated button indicating "I want to know more about this" or "I want to incorporate this in my life/lifestyle." The system immediately identifies the exact portion of the transcript corresponding to that moment in the video and forwards this segment to its large language model. The LLM then generates a comprehensive, personalized script for the AI avatar, drawing from an extensive knowledge base that includes long-form interviews, detailed written materials, and expert content specifically created for the avatar's educational repository. This script is further enhanced by incorporating the avatar's defined personality characteristics, coaching style preferences, and linguistic patterns, while simultaneously integrating the user's current biometric data, recent KHAs, and contextual information to create truly personalized implementation advice. The system then generates a realistic voice based on this tailored script and creates a video of the avatar delivering the personalized educational content. While future iterations will enable real-time avatar interaction, the current version supplements these video responses with an interactive chat window, allowing users to ask follow-up questions and receive immediate guidance as they implement new health practices.

In one embodiment, a system and method is disclosed for tracking user body composition without the need for any external scales, devices, etc. enabling users to estimate, visualize, and track body composition goals through AI-generated images and adaptive health optimization. The system allows users to either take a photo of themselves (shirtless or in jog bra, depending on gender identity) or select from a rendered library of body types that represent different body fat percentages. The system then either analyzes the photo or uses the selected model to estimate the user's current body fat percentage and lean body mass, which is then displayed to the user. Following this, the user is asked how they want to change their body composition, such as reducing body fat or increasing lean mass. Based on their selection, the system presents a series of AI-generated visual progressions-either of the user's own image rendered at projected body fat percentages, or a model representation. These visuals allow users to see what they would look like at different stages toward their goal.

The system stores these goals and tracks progress through follow-up inputs (selfies, model re-selection, or body comp device data). It uses reinforcement learning to correlate changes in composition with behavioral inputs like meals, workouts, and sleep, then adjusts personalized coaching, including meal plans via the AI meal image generation system.

1. Initial Assessment Module:
  Upon onboarding, user chooses between:
  Uploading a selfie (shirtless/jog bra, per gender selection), or
  Selecting from a set of rendered body models labeled by body fat percentage and gender.
  If using a selfie, the system uses a trained AI image model to estimate body fat % and lean body mass using the user's inputted weight.
  If using a rendered model, the associated % is applied directly.
2. Goal Visualization Engine:
  After showing current values, the system prompts the user:
  "how would You Like to Change Your Body?"
  Based on input (e.g., "lose fat," "gain lean mass"), the system:
  Generates a visual progression path using AI-generated images of the user's body at various body fat % s, OR
  Shows a gallery of default model bodies at the same ranges.
  The user selects a target visual which becomes their body composition goal.
3. Progress Check-Ins:
  Periodically, the system prompts the user to:
  Upload another selfie, OR
  Select an updated visual from the rendered gallery
  Or sync a connected body composition device (e.g., InBody)

System calculates new body fat %, lean mass, and compares against baseline and goals.

4. Behavioral Correlation Engine:

The system aggregates:

Meals (manual macros or photo-logged)

Sleep (duration, quality)

Workouts

Subjective well-being inputs

Reinforcement learning algorithm looks for correlations between improved body composition and lifestyle behaviors.

5. Recommendation System Integration:

Based on findings, the system adjusts:

Meal plans and visuals (via AI meal rendering engine)

Training suggestions

Behavioral tips

If user makes progress despite deviations, system adapts future plans.

If not, system reaffirms optimal strategies.

In another embodiment, a system and method is provided for delivering visually engaging and personalized meal recommendations by generating AI images based on calculated macronutrient targets. The system prompts the AI image generation based on system default or user preferred food items that correspond to the type of recombination the system is making for each macronutrient, specially protein amount and source (animal vs plant ratio %), carbohydrate amount and digestion speed (slower or faster and can be ranked with scores as well for non-binary ranking) wether coarse veggies should be added or not to slow digestion or speed digestion of meal depending on functional need, fat, water, etc. It allows users to adjust food preferences, and dietary parameters through a settings interface, which then dynamically informs the generation of example meal images using generative AI platforms (e.g., Runway API). These images serve to visually guide users on what their meals should look like in terms of macronutrient balance-protein, carbohydrates, fat, water, and more. The user can log actual meals through manual macronutrient entry or by uploading a photo, which is processed by an AI image recognition system to estimate nutrient content. The user is then asked to verify the estimated macronutrients, and the system logs both the actual and recommended meal data. Discrepancies between recommended and actual meals are tracked and used in reinforcement learning algorithms that adapt future meal recommendations based on progress toward user-defined outcomes, such as changes in body composition or well-being scores. This feedback loop enables a self-optimizing, goal-driven nutrition system supported by generative visuals and intelligent coaching.

1. Meal Panel Photo Mode:

The system presents meal recommendations in a photo mode—a visual depiction of what a meal with the user's current macro targets could look like.

Images are generated via an AI image generation API (e.g., Runway) using a prompt informed by the user's current macro targets and preferences.

2. User Settings Interface:

Users access a Settings menu to personalize meal generation inputs:

Protein source slider: e.g., from animal-based to plant-based

Favorite food checkboxes categorized by function (e.g., slow vs. fast carbs)

Dietary restrictions and visual presentation preferences

3. Meal Logging:

Users can:

Manually enter macronutrient totals for protein, carbs, fat, water, etc.

Or upload a photo of their meal, which is analyzed using AI image recognition

The system estimates macronutrients from the image and prompts the user to confirm or edit the result before logging.

4. Comparison and Discrepancy Tracking:

The system compares the recommended meal macros to the actual logged values

Logs daily totals, tracks discrepancies, and builds a history of user behavior.

5. Outcome Feedback Loop:

Uses reinforcement learning informed by:

Changes in body fat %, lean mass, subjective well-being, etc.

If the user consistently eats differently than recommended but shows progress, the system adapts recommendations.

If results do not improve and correlation to eating patterns is found, the system maintains original recommendations and encourages compliance.

In one aspect, a method of delivering personalized health coaching through an AI avatar system, includes generating the AI avatar with customizable personality and appearance characteristics; collecting multi-domain user data including sleep patterns, nutritional behavior, physical activity, emotional state, and social dynamics; processing the collected data through a contextual health engine to generate personalized coaching decisions; determining prioritized KHAs based on the processed data; delivering the KHAs to the user through the avatar using photo-realistic video and voice interaction; and adapting coaching strategies over time using reinforcement learning based on user responses and progress metrics.

In implementations, the system includes evaluating user progress through a Thriving Index derived from proxy data including estimated changes in body composition, sleep quality, nutritional patterns, emotional well-being, and social support metrics. The KHAs include glucose-stabilizing walks, heart rate variability-adjusted exercise routines, and timed nutrient intake for recovery or performance. Social KHAs coordinate health actions between the user and other individuals or instances of HERA acting as supportive peers. The HERA avatar's appearance, communication style, and cultural adaptation can be based on user preferences. The method detects user-specific metabolic dysfunction using contextual biometric and behavioral patterns and delivering precision interventions prioritizing sleep enhancement, nutrient timing, physical activity, and stress regulation. The coaching strategies includes analyzing correlations between specific interventions and changes in the user's composite health metrics. The method generates AI-customized workout content that adapts in real-time to accommodate user constraints and pairing it with personalized AI-generated music that aligns with the energy and tempo of the session. Neighboring contacts can contribute data about one another through mutual consent, including emotional impressions, mood check-ins, or expression of emotional needs. The HERA avatar leverages archetypal roles including warrior, nurturer, mentor, or guide to create coaching interactions that resonate with innate human relational patterns and emotional memory.

HERA—the Health-Enhancing Relational Avatar. HERA is a programmatically generated, AI-powered avatar designed to deliver culturally adaptive, emotionally intelligent health and wellness coaching across digital platforms including mobile, TV, VR, AR, and future interfaces. Functioning as the user-facing embodiment of the system's contextual intelligence and reinforcement learning, HERA engages users via photo-realistic video, voice, and multi-modal interaction. It simulates human-like presence and builds rapport, trust, and accountability over time. By integrating real-time physiological, behavioral, and psychosocial data, HERA delivers personalized guidance through coaching sessions, adaptive KHAs, reflective prompts, and social co-regulation. Its design enables scalable, deeply personalized coaching experiences across diverse populations, grounded in scientific rigor and adaptive human-like relational dynamics.

The system integrates multi-domain, interconnected inputs including sleep, nutrition, exercise, recovery, emotional state, and relational context. These inputs feed into a continuously updating contextual health engine, which serves as the personalized "mind" of HERA. The platform is built upon holistic, interconnected data models that incorporate the highest-efficacy insights from relevant interdisciplinary scientific domains—including physiology, behavioral science, nutrition, chronobiology, psychology, and social dynamics. These models are not only theoretically grounded but have also been validated through implementation across real-world use cases—ranging from Olympic-level athletes to non-athletes in diverse life contexts—demonstrating broad adaptability and utility.

This health-aware model enables HERA to engage with the user on a daily basis through a variety of interaction formats, including coaching sessions, nudges, reflective conversations, and motivational prompts. Through this ongoing engagement, HERA builds trust, rapport, and a strong sense of accountability. This design leverages the natural human tendency to connect more deeply with human-like personas than with abstract or transactional interfaces, resulting in a more motivating, trusted, and behaviorally effective experience.

Each instance of HERA includes an independent personality and appearance module, enabling any coaching persona—such as motivational styles, tones, or visual identities—to be "embodied" within the core coaching model. This allows for fully customizable coaching experiences, including branded, thematic, or celebrity-style avatars that reflect specific user preferences or licensing agreements. For example, a user may select a calming wellness guide, a high-energy athletic trainer, or a well-known celebrity persona to serve as their interactive AI coach and accountability partner.

A core biological aim of the system is to identify and correct metabolic dysfunction by detecting a user's top metabolic bottlenecks and delivering precise, personalized interventions across sleep, exercise, nutrition, and emotional well-being. A central mechanism is the preservation or development of lean muscle mass, which is fundamental to restoring and maintaining metabolic function. This biologically informed approach supports long-term fat loss and metabolic resilience—without reliance on pharmaceutical agents such as GLP-1 agonists.

The system uses reinforcement learning to refine its coaching strategies and communication over time, adapting to each user's responses and progress. It continuously evolves to become more effective and personalized. In addition to behavioral feedback, it evaluates physiological and psychosocial progress using proxy signals such as estimated changes in body composition (lean mass and body fat), sleep quality, nutritional responses, emotional state, and relational dynamics—even without external devices. These inputs are synthesized into a composite "Thriving" index, reflecting the user's holistic health and functional state. Machine learning models track correlations between interventions and Thriving scores, feeding insights back into the reinforcement learning loop. This results in an increasingly intelligent system whose optimized coaching is embodied by HERA for aligned, intuitive guidance.

A central feature of the system's behavior-shaping capabilities is the generation of KHAs—specific, timely, and prioritized interventions that guide users toward the next most impactful health behavior. KHAs are scheduled to fit seamlessly into a user's daily routine and recalculated in real time if missed or modified. Examples include walking to stabilize glucose, shifting workouts based on heart rate variability, or timing protein intake for optimal recovery. All workouts are AI-generated and adaptable, capable of instant regeneration to accommodate user constraints, and paired with personalized AI-generated music that aligns with the energy and tempo of the session.

The system also supports Social KHAs—coordinated actions shared with friends, partners, or instances of HERA acting as peer guides. These include joint workouts, synchronized meals, or co-regulated mindfulness practices. Social KHAs foster emotional support and accountability through collective action, whether with real people or intelligent avatars. When HERA is invited to participate in a KHA, it can provide pre-activity guidance, emotional encouragement, and reflective debriefing—emulating the behaviors of a skilled human coach or trusted companion.

Recognizing that psychosocial and emotional dynamics are critical to human well-being, the system also enables close contacts to contribute data about one another through mutual consent. This may include emotional impressions ("how the other makes me feel"), mood check-ins, menstrual cycle updates, or open expression of emotional needs. HERA integrates this data and may suggest communication strategies, conflict resolution techniques, or well-being prompts such as breathwork or guided reflection—fostering trust, empathy, and deeper relational health. These social dynamics may also incorporate primal or archetypal roles—such as the warrior, nurturer, mentor, or guide-drawing on anthropological insights to create coaching interactions that resonate with innate human relational patterns and emotional memory.

In summary, this system offers a next-generation AI coaching platform built around HERA to deliver real-time, emotionally adaptive, and culturally attuned health guidance. By synthesizing biometric, behavioral, and social data—and applying reinforcement learning, KHAs, and psychosocial co-regulation—the system enables scalable, personalized, and sustainable support for health, fitness, and human thriving.

HERA serves as the user-facing embodiment of the system's contextual intelligence and reinforcement learning engine, engaging users via photo-realistic video, voice, and multimodal digital platforms including mobile, TV, VR, AR, and other future environments. HERA simulates human-like emotional awareness, trust-building, and accountability, enabling scalable delivery of personalized guidance through structured interactions. The system receives, aggregates, and continuously updates multi-domain user data, including but not limited to: sleep and circadian patterns, nutritional behavior and responses, Physical activity and recovery, emotional state and psychological patterns, and Relational and social dynamics. These inputs feed a contextual health engine which computes real-time coaching decisions and behavioral prompts issued through HERA. The system employs a reinforcement learning (RL) model to adapt coaching strategies based on user interaction, engagement, and biometric/behavioral outcomes. User progress is evaluated through a dynamic metric called the Thriving Index, derived from proxy data including: Estimated changes in body composition (lean mass/fat %), sleep quality, nutritional patterns, emotional well-being, social support metrics, and Thriving Index which serves as a performance signal for the RL engine, continuously improving HERA's guidance strategy over time. The system generates and prioritizes KHAs—context-aware, time-sensitive behavioral prompts selected to optimize health outcomes. KHAs are scheduled into the user's day and are dynamically updated if missed or altered. Examples include:Glucose-stabilizing walks, HRV-adjusted exercise routines, timed nutrient intake for recovery or performance. HERA delivers and explains each KHA, providing supportive coaching before, during, and after the action. The system supports Social KHAs, which are behavior-change actions performed in coordination with: friends or family members, other users within the ecosystem, instances of HERA acting as a supportive peer or guide. Social KHAs include joint workouts, shared meals, or synchronized wellness practices. HERA leverages archetypal roles (e.g., nurturer, warrior, mentor) to guide emotional and behavioral interaction in culturally resonant ways. Each instance of HERA includes an independent personality and appearance module. This module allows HERA to adopt any coaching persona based on user preferences or brand licenses, including: communication style (e.g., gentle, assertive), visual identity (e.g., calm guide, energetic trainer), cultural adaptation (e.g., language, tone, gestures). The user can optionally select from predefined avatars or dynamically adjust persona traits over time. The system performs Metabolic Optimization via Non-Pharmaceutical Intervention. The system detects user-specific metabolic dysfunction using contextual biometric and behavioral patterns. HERA delivers precision interventions that prioritize: Sleep enhancement, Nutrient timing, Physical activity and recovery, and Stress regulation. One objective is the preservation and/or development of lean muscle mass, promoting long-term fat loss and metabolic stability-without the use of pharmaceutical aids such as GLP-1 receptor agonists.

Figure 1B:
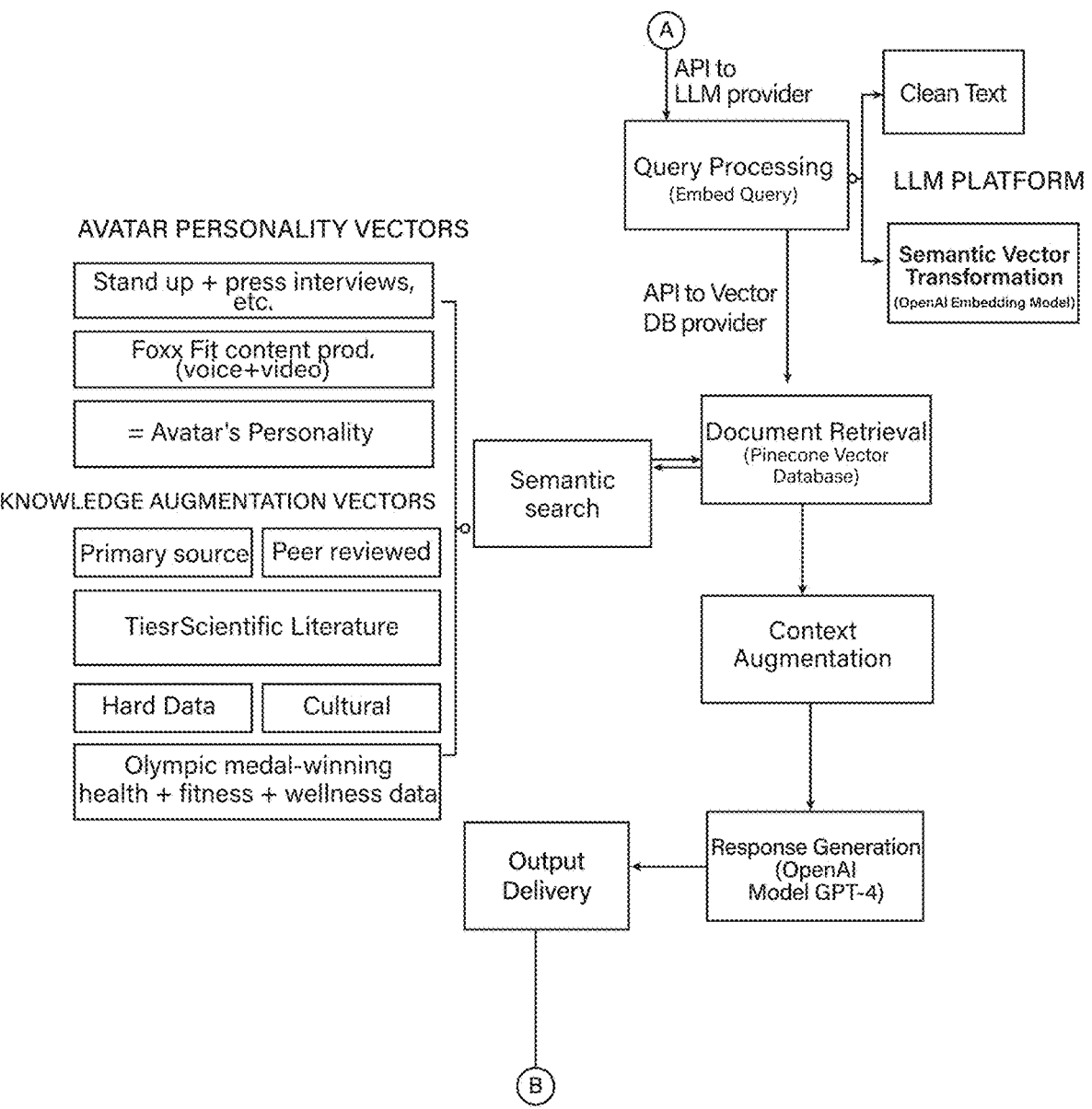
Figure 1B:
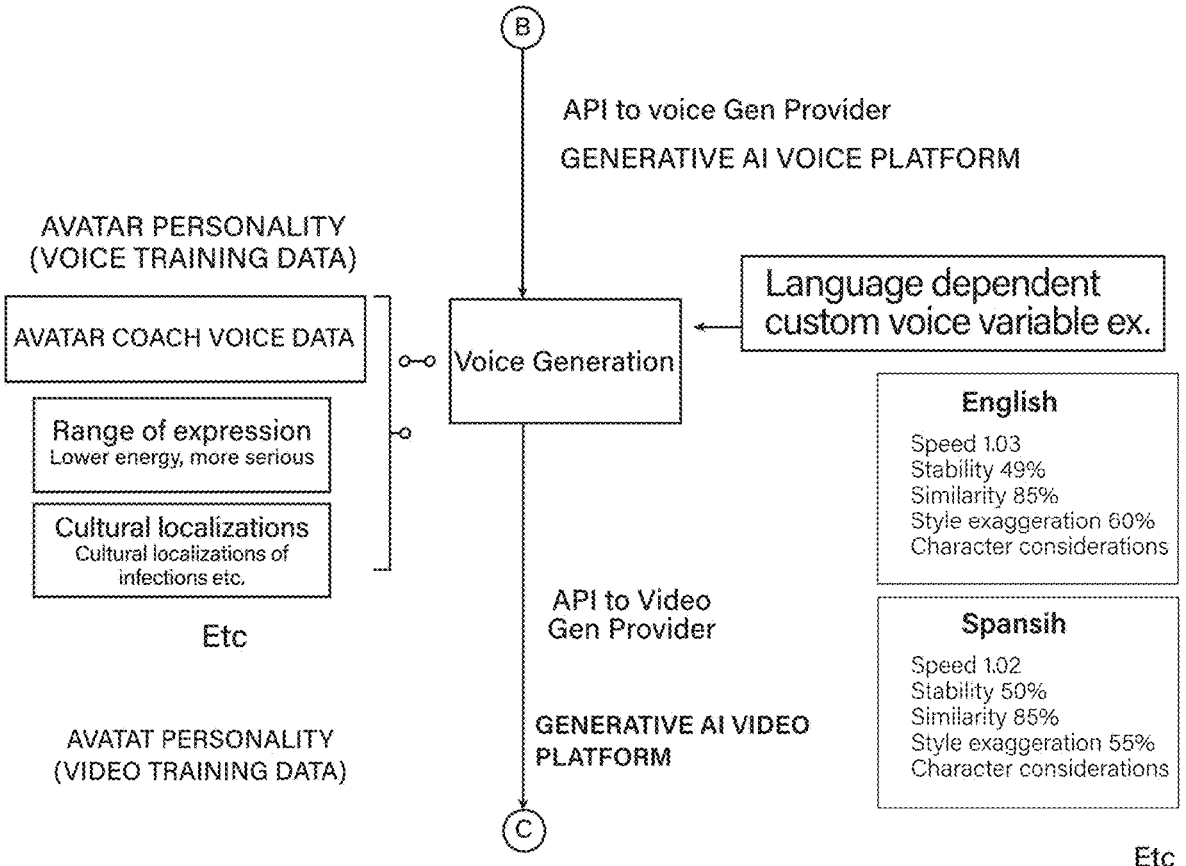
Figure 1B:
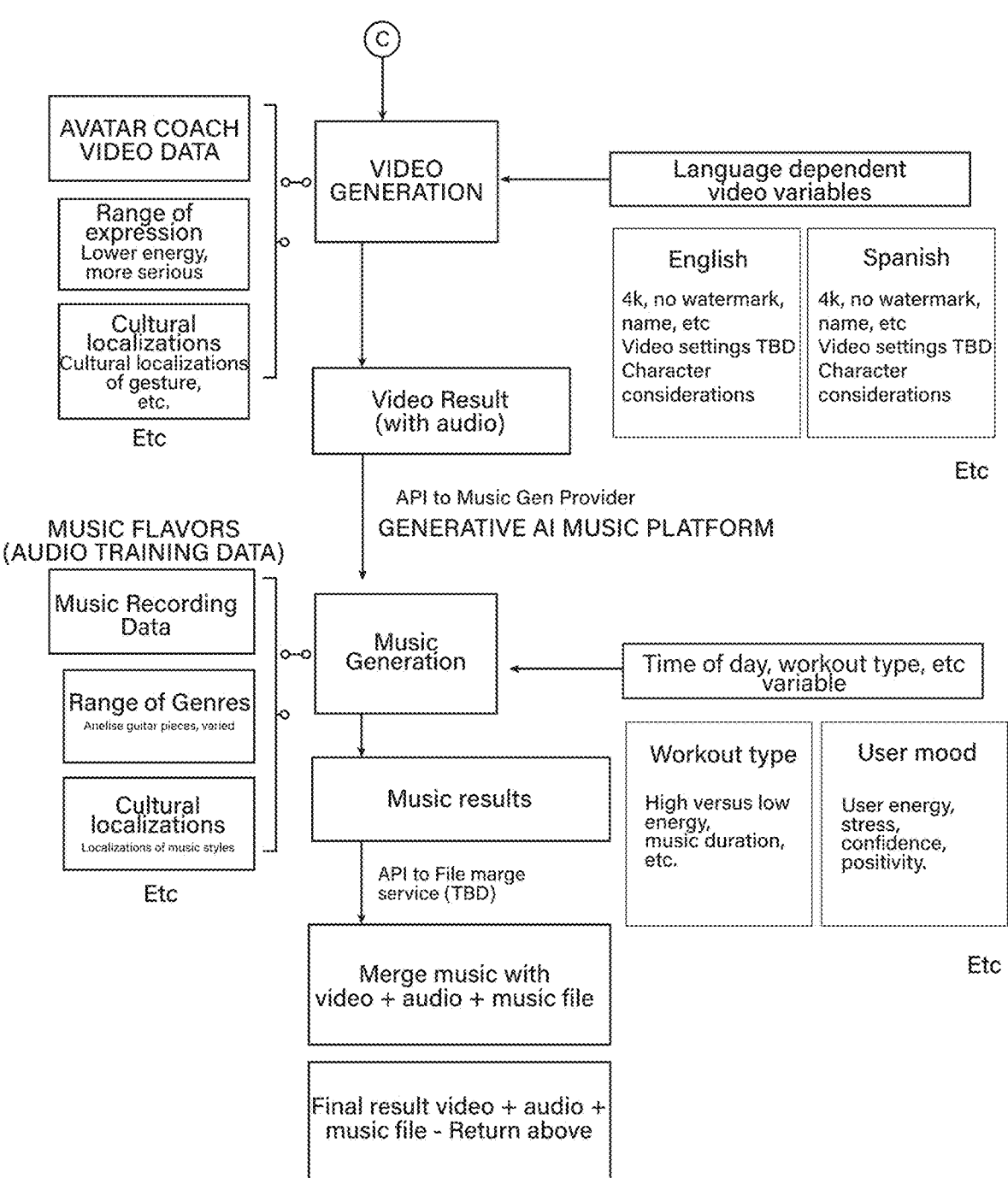

FIG. 1B shows another illustration of the system architecture for a generative AI avatar interface. Input 1 represents the initial data acquisition component where user-provided information is gathered and set as the baseline for the entire coaching framework. This foundational input is essential in enabling subsequent modules—from advice algorithms to avatar training modules across text, voice, and video—to deliver context-aware, avatar-driven lifestyle guidance that continuously evolves based on user interactions and outcomes.

In embodiments of one implementation, the system generates avatar coaching outputs that include emotional reinforcement, praise, or habit correction suggestions based on both immediate events and progress alignment over extended periods. The system monitors incoming user inputs through the input module 1 to capture instantaneous contextual data, such as behavioral cues, emotional expressions, and other relevant stimuli. This immediate information is processed in conjunction with advice algorithms 2 to assess the user's current state and determine appropriate coaching responses. Simultaneously, the system maintains a historical profile of user activities and interactions, which is used to assess progress and behavioral trends over time. The analysis of this historical data allows the system to align its coaching outputs with sustained behavioral objectives and personalized user goals.

The model exhibits a strong preference for drug-free and sustainable strategies designed for enduring skeletal muscle maintenance or growth, reduction of visceral and intra-organ fat, mitigation of chronic inflammation, and lowering of elevated cortisol levels. Interventions selected by this knowledge model foster stable blood sugar levels, promote better insulin responsiveness, and yield an extended duration of deep sleep accompanied by superior sleep quality. By integrating these sophisticated analytical methods, the system ultimately produces avatar-driven, context-aware lifestyle guidance that aspires to yield more favorable user outcomes in a sustainable and emotionally intelligent manner.

Reference label prompt 3 represents the component of this system that receives and processes user directives. It functions as the input interface whereby user instructions and preferences for coaching are captured, enabling the subsequent generation of context-aware, avatar-driven lifestyle guidance.

Reference label "response generation 4" is used to designate the component of the system responsible for synthesizing coherent, context-aware outputs by integrating processed input data and the results from various advice algorithms. In this context, "response generation 4" encapsulates the final stage of the algorithmic process that generates personalized health and wellness recommendations, ensuring that the output is both relevant and dynamically adjusted based on the latest user data and behavioral insights.

The reference label "output delivery 5" designates the module responsible for providing the final coaching and guidance output to the user. This module consolidates processed data derived from various analytical engines, including the coaching recommendation engine and reinforcement learning models, to generate a comprehensive, contextually relevant response delivered through the avatar interface. It ensures that the insights and instructions are presented in a user-friendly, accessible manner while maintaining the overall system's ability to adapt to real-time updates and user feedback.

The reference label "avatar personality (text training) 6" relates to the methodology by which the avatar is imparted with a sophisticated, emotionally intelligent conversational style through extensive training using textual data. The text training process is designed to enhance the avatar's ability to generate contextually relevant and engaging responses that reflect established coaching philosophies while sustaining consistency in tone, style, and empathy throughout interactions with users. This training methodology ensures that the avatar not only supports personalized coaching recommendations but also fosters a reliable and supportive user experience that promotes sustainable outcomes without reliance on pharmaceutical interventions.

The reference label "avatar personality (voice training data) 7" specifically identifies the collection of voice training datasets used to develop the generative avatar's vocal characteristics. This label encompasses audio recordings, intonation patterns, and speaking style parameters that are integrated into the system to produce a natural, engaging voice for the avatar. The datasets under this reference ensure that the avatar's voice is aligned with the overall coaching personality, thereby enhancing the user experience by delivering emotionally intelligent and contextually appropriate guidance.

The system continuously refines its coaching recommendations by utilizing vector databases informed by updated Olympic medal-winning strategies and supported by peer-reviewed scientific literature. It integrates a proprietary knowledge model that emphasizes functional scientific fields such as evolutionary biology, integrative physiology, and functional health. This model specifically prioritizes strategies designed to promote metabolic health, maintain skeletal muscle, stabilize blood sugar levels, and enhance deep sleep quality in a sustainable, drug-free manner. The training data for the avatar personality includes text, voice, and video components. The video training dataset, designated as avatar personality (video training data) 8, consists of imagery with refined resolution and motion capture details. This information is employed to imbue the generative AI avatar with dynamic, realistic, and culturally sensitive facial expressions and gestures, ensuring that its visual communication effectively reinforces the emotionally intelligent and empathetic interactions intended by the coaching system.

The reference label "music flavors (audio training data) 9" refers to a specific dataset used to train the avatar's auditory personality. This dataset consists of a variety of musical styles and audio cues that enhance the system's ability to deliver an engaging and emotionally intelligent coaching experience through voice-based interactions.

The realized embodiment described as the final avatar result 10 is a culmination of extensive training across multiple data types including text, voice, video, and music audio, integrating advanced reinforcement learning and regression methodologies with proprietary algorithms. This final avatar result 10 represents an emotionally intelligent and context-aware coaching entity that effectively delivers personalized, scientifically optimized lifestyle guidance to users and dynamically adapts its recommendations to improve overall outcomes in health and wellbeing.

Figure 1C:
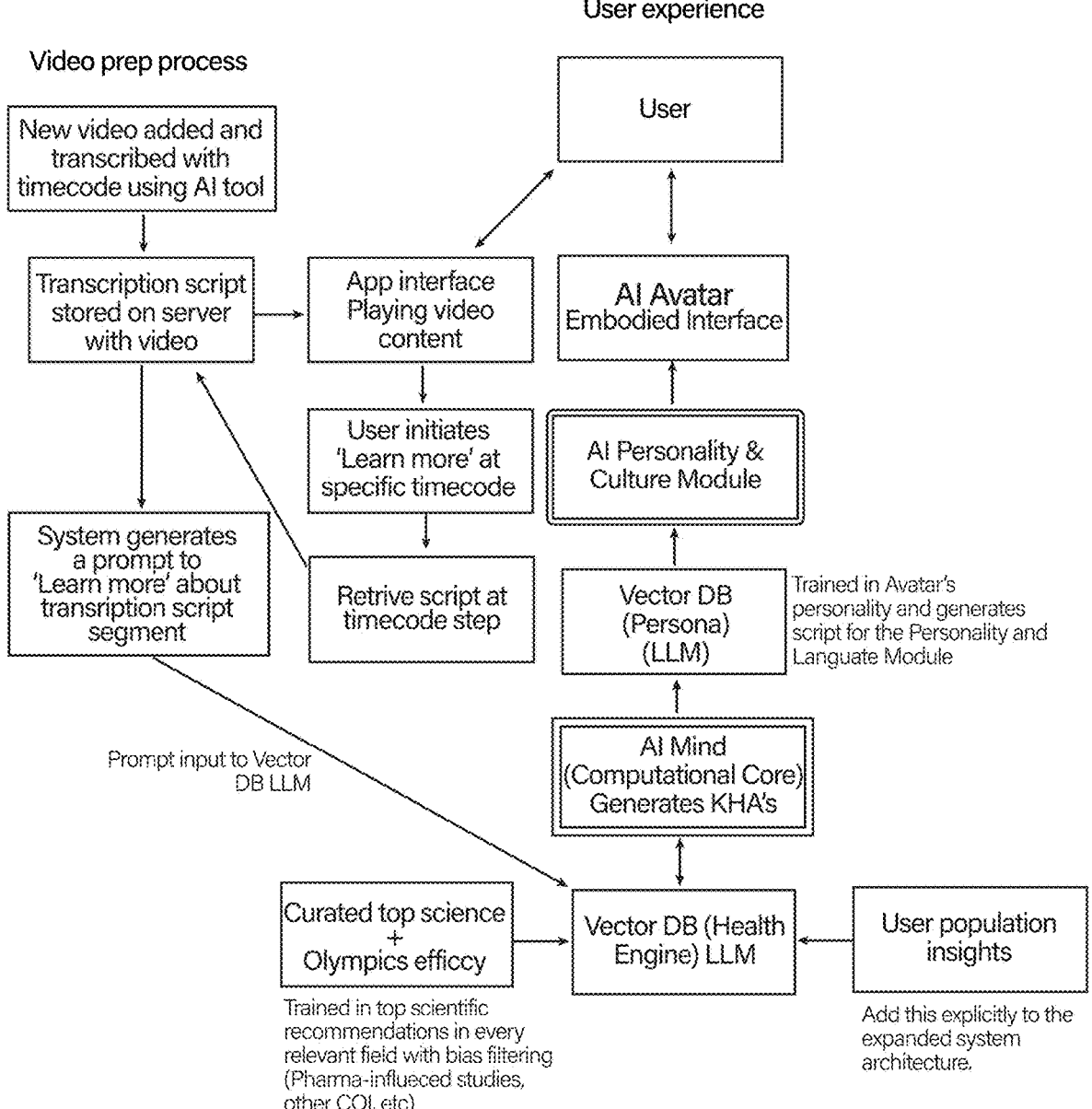

FIG. 1C illustrates a detailed method flow for enabling personalized AI avatar responses during video content playback. The process begins when a new video is added to the system and transcribed with timecodes using an AI tool. This transcription script is then stored on the server alongside the video. The system analyzes the script and generates prompts to "Learn more" about specific segments, preparing the content for interactive engagement. During playback, the user interacts with the app interface, which allows them to initiate a "Learn more" request at any specific timecode of interest. When such a request is made, the system retrieves the corresponding segment of the transcription script. This segment is then sent as input to the AI processing pipeline, starting with the AI Mind (Computational Core), which generates Knowledge and Health Answers (KHAs) by leveraging both the Vector DB (Persona) LLM and the Vector DB (Health Engine) LLM. The Vector DB (Persona) LLM is trained in the avatar's unique personality and is responsible for generating responses that match the avatar's persona and communication style. The AI Personality & Culture Module further tailors these responses to ensure they are consistent with the avatar's defined character. Simultaneously, the Vector DB (Health Engine) LLM draws from curated scientific recommendations, filtered to remove bias from sources such as pharma-influenced studies and other conflicts of interest, and incorporates user population insights to enhance personalization. The result is a real-time, contextual, and scientifically accurate explanation delivered by the AI avatar, providing users with a personalized and engaging learning experience directly within the video content.

Figure 1D:
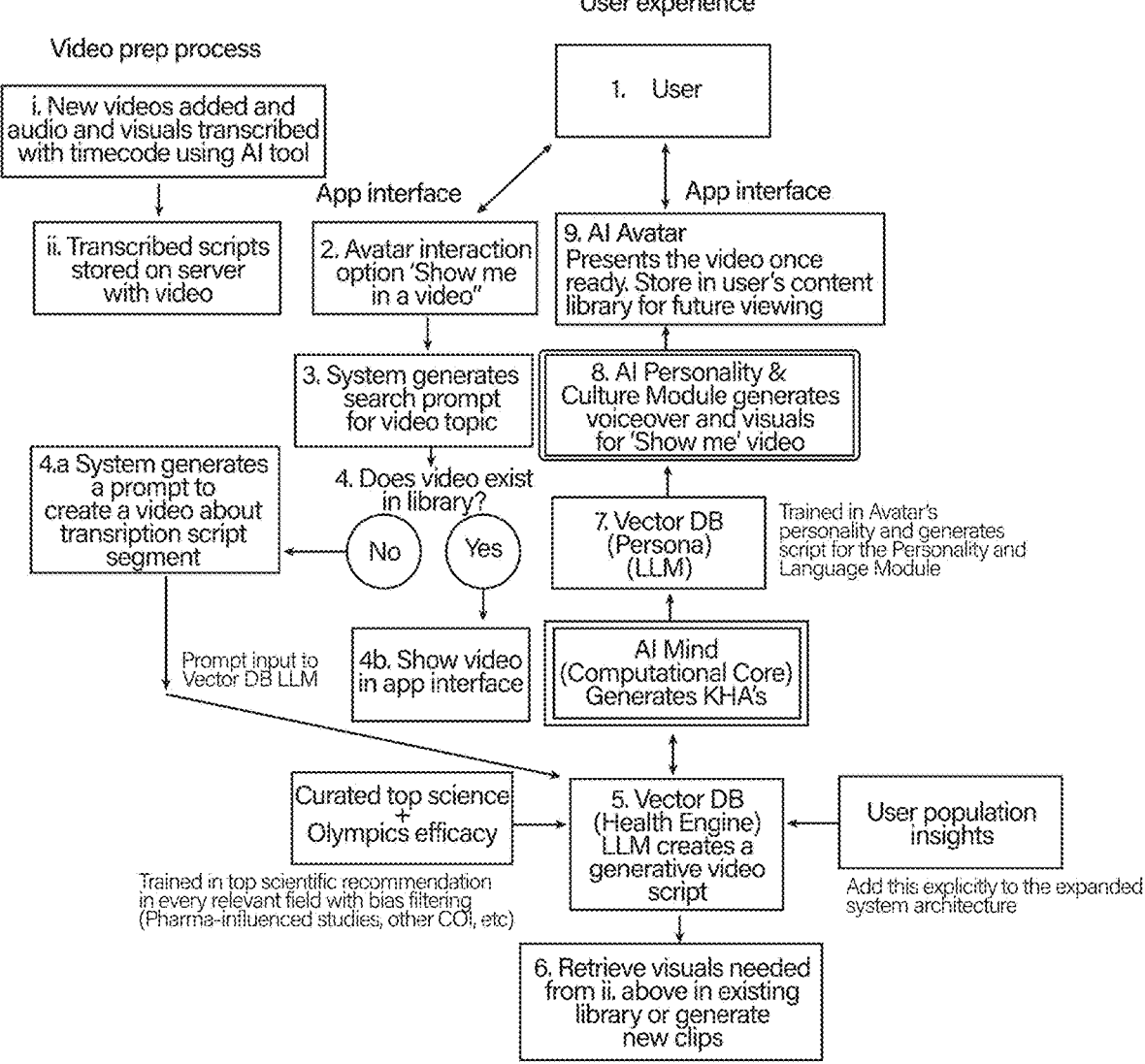

FIG. 1D expands upon the personalized AI avatar response system, illustrating the method flow for creating and delivering video content tailored to user requests. The diagram begins with the video preparation process, where new videos are added and their audio and visuals are transcribed with timecodes using AI tools, with these transcription scripts then stored on the server alongside the videos. When a user engages with the app interface, they can select the "Show me in a video" interaction option, prompting the system to generate a search for the requested video topic. The system then checks if the video already exists in the library. If it does, the video is immediately displayed in the app interface. If not, the system generates a prompt to create a new video based on the transcription script segment, which serves as input to the Vector DB LLM. This prompt travels to the Vector DB (Health Engine) LLM, which creates a generative video script by incorporating curated top scientific recommendations and Olympics efficacy data, with bias filtering to remove pharmaceutical-influenced studies and other conflicts of interest. The system then retrieves necessary visuals from the existing library or generates new clips as needed. The AI Mind (Computational Core) generates Knowledge and Health Answers (KHAs) that feed into the Vector DB (Persona) LLM, which is trained in the avatar's personality and generates the script for the Personality and Language Module. The AI Personality & Culture Module then generates the voiceover and visuals for the requested "Show me" video. Finally, the AI Avatar presents the completed video to the user and stores it in their content library for future viewing, with the entire process enhanced by user population insights explicitly added to the expanded system architecture.

Figure 1E:
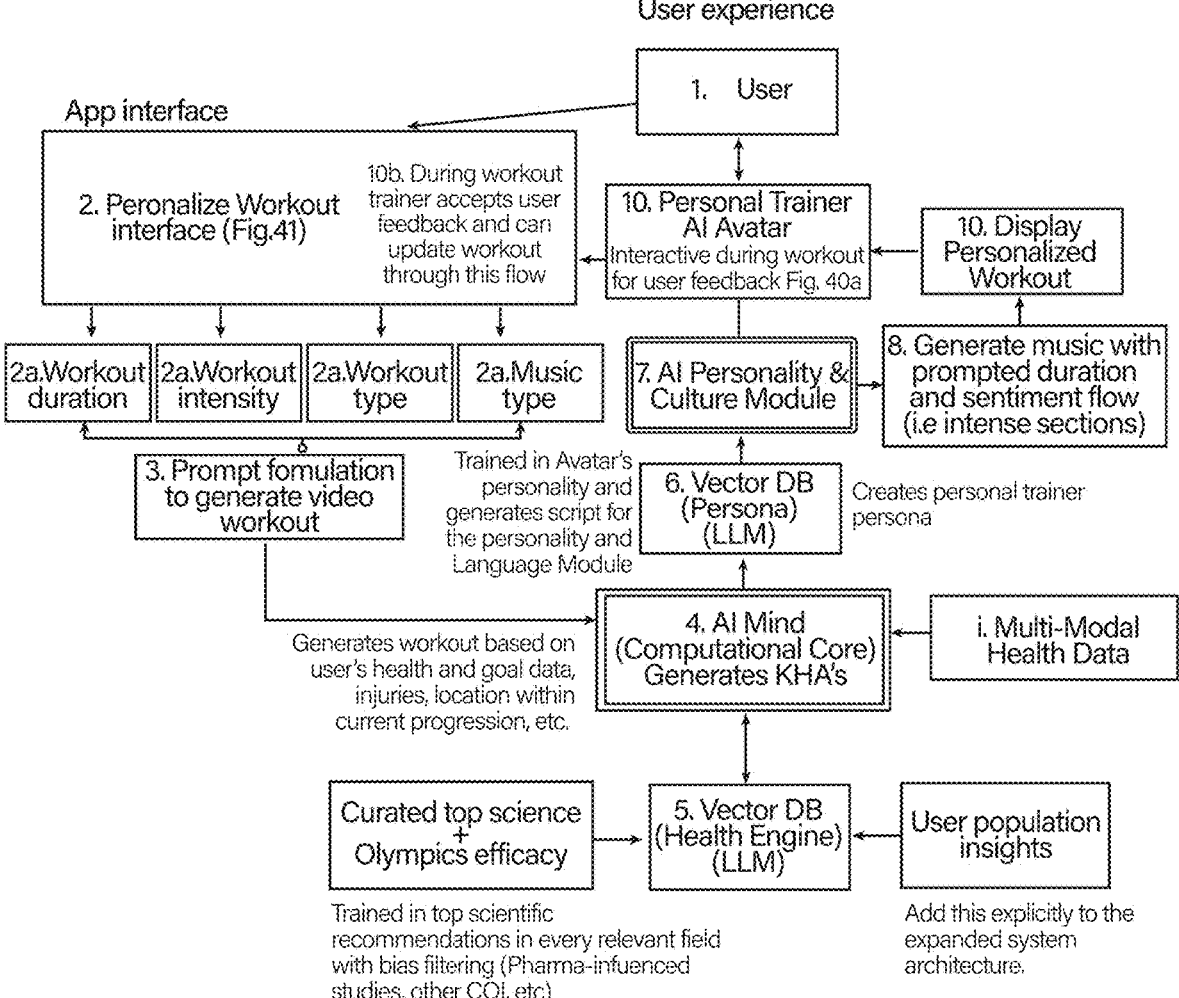

FIG. 1E details the method flow for a personalized AI-generated workout. The process begins with the user interacting with the Personalize Workout Interface in the app, where they can input workout duration, intensity, type, and preferred music. These preferences are used in Prompt Formulation to generate a video workout tailored to the user's needs. The prompt, along with Multi-M odal Health Data, is fed into the AI Mind (Computational Core), which generates Knowledge and Health Answers (KHAs) to create a workout based on the user's health and goal data, injuries, location, and current progression. The AI Mind also incorporates curated top science and Olympics efficacy data from the Vector DB (Health Engine) LLM, ensuring the workout is grounded in scientific recommendations and bias-filtered for conflicts of interest. The Vector DB (Persona) LLM, trained in the avatar's personality, uses these KHAs to create a personal trainer persona and generates a script for the Personality and Language Module. The AI Personality & Culture Module then takes this script and generates the AI Avatar's behavior and dialogue. The system also generates music with prompted duration and sentiment flow, and during the workout, the Personal Trainer AI Avatar interacts with the user, accepting feedback and updating the workout. Finally, the personalized workout is displayed to the user. User population insights are explicitly added to the expanded system architecture, further enhancing the personalization of the workout.

Figure 2:
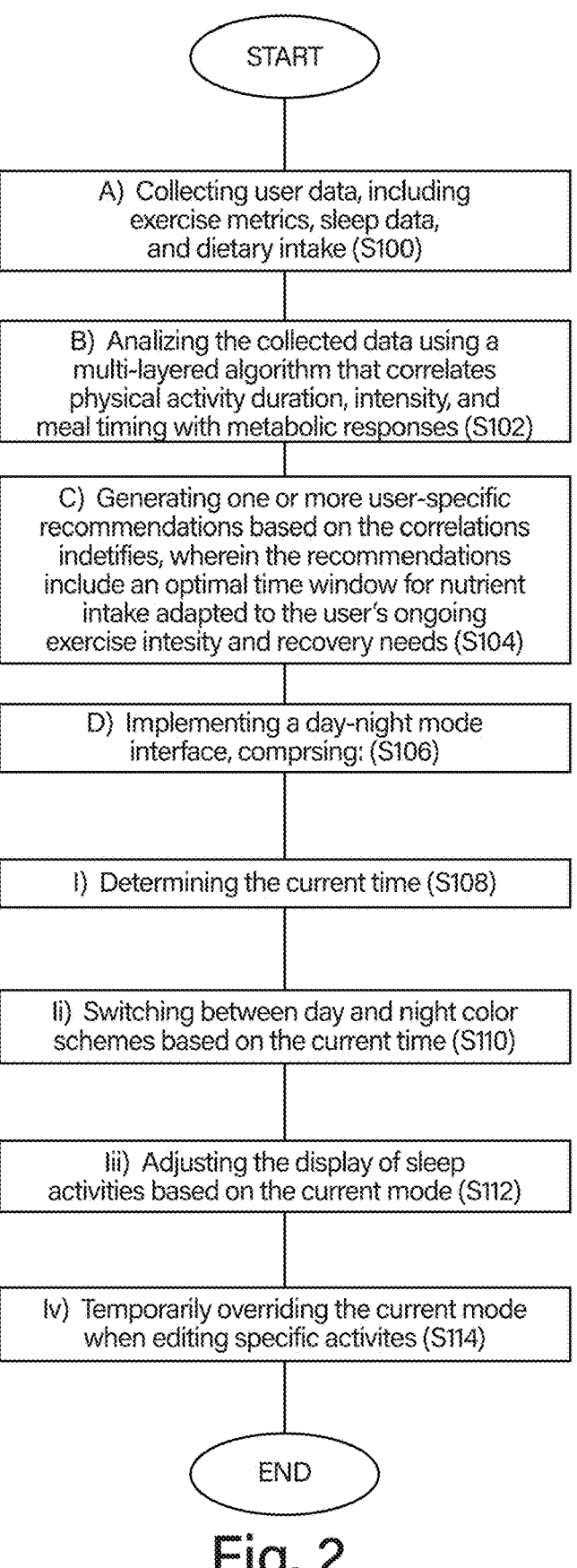

FIG. 2 shows an exemplary flow chart for collecting user data to generate recommendations. In one aspect of one implementation, a data collection module is configured to collect diverse user data S100. This component gathers exercise metrics, sleep data, and dietary intake that serve as essential inputs for the system's multi-layered analysis. By capturing this comprehensive set of data, the system ensures that subsequent analyses and personalized recommendations are precisely attuned to the user's unique physiological and behavioral patterns, thus forming a robust basis for the entire personalized training and nutrition guidance system.

The system analyzes collected user data to determine correlations between physical activity parameters, such as exercise intensity and duration, and corresponding metabolic responses S102. Based on these correlations, it generates one or more personalized recommendations, including the determination of an optimal time window for nutrient intake. This optimal window is dynamically tailored in accordance with the user's ongoing exercise intensity and recovery needs, ensuring that nutritional support is provided at the moment most conducive to promoting efficient recovery and metabolic balance S104.

One embodiment provides a day-night mode interface that automatically adjusts the visual presentation based on the time of day S106. In one implementation, the system determines the current time and then selects an appropriate color scheme to correspond to either a day mode or a night mode. Accordingly, sleep activity displays appear differently depending on whether the system is in day or night mode, thereby furnishing the user with information in the most legible and contextually relevant format. In addition, the interface allows for a temporary override of the selected mode when a user is engaged in editing specific activities, ensuring that modifications can be performed with optimal clarity irrespective of the underlying mode. This dynamic adjustment, as disclosed under reference label S106, facilitates an intuitive and adaptive user experience by seamlessly interfacing with the operational environment.

The embodiment determines the current time by accessing the device's system clock and processing the resulting time data according to predetermined criteria S108. This step, identified by reference label S108, is fundamental in establishing the appropriate mode for the user interface. By accurately determining the current time, the system can distinguish between day and night periods, thereby enabling the interface to adapt its visual presentation appropriately. The real-time acquisition of the current time ensures that the system provides a suitable display environment corresponding to ambient lighting conditions, ultimately enhancing the user experience.

According to reference label S110, the system automatically adjusts its display by selecting a day or night color scheme based on the current time. When the current time is determined to fall within typical daylight hours, the user interface adopts a brighter color palette intended to enhance visibility and readability. Conversely, when the current time suggests nighttime conditions, the system switches to a darker color scheme designed to reduce eye strain. This dynamic adjustment supports a more comfortable viewing experience in varying ambient lighting conditions without requiring manual intervention from the user.

FIG. 3 illustrates an exemplary flowchart outlining a process for acquiring and processing athlete data that is subsequently used to generate personalized fitness plans. The process involves collecting extensive training datasets from Olympic-level sportspeople S200. This dataset incorporates precise performance metrics that log a wide range of measurements related to athletic effort and advancements. It also includes comprehensive recovery documentation elucidating the athletes' biological rest intervals and corresponding recuperation strategies. The dataset integrates nutritional strategies as well, presenting the food intake patterns and meal preparations employed by these top-tier athletes. Such detailed datasets form the foundation for correlating elite performance parameters with effective physical training and dietary protocols, thus equipping the system with the capability to optimize personalized fitness plans for ordinary users by harnessing insights from peak athletic performance.

The datasets are then preprocessed to ensure that key performance metrics are consistent and directly comparable S202. In this step, intensity indexes obtained from various training sessions are normalized, allowing differences in measurement methods or units to be mitigated. Performance milestones, which indicate significant achievements or thresholds, are aligned across datasets so that they reflect a uniform scale. Recovery markers, used to assess the athlete's recuperative state, are similarly standardized to confirm that variations in monitoring techniques do not affect overall analysis. This preprocessing ensures that all subsequent modeling and analysis are based on data that have been uniformly calibrated and are reliable for making personalized fitness recommendations.

A machine learning model is trained to identify and correlate specific performance parameters with established best practices for nutrition and rest S204. In this embodiment, a training dataset that includes detailed records of exercise intensity, performance milestones, recovery metrics, and related biometric data is employed to instruct the model. This process allows the system to discover patterns between the athlete's performance and optimal nutritional intake as well as rest schedules that support recovery. The trained model subsequently serves as the basis for generating tailored recommendations that align with proven methods for enhancing athletic performance and recovery.

The system proposes a customized plan designed for a non-professional user, associating the user's distinct biometrics with learned elite-level performance patterns S206. In doing so, the system initially gathers a range of performance metrics and physical data from the non-professional user. This input is then benchmarked against a knowledge base obtained from premier athlete training schedules and performance results. Through this comparison, the system pinpoints key disparities and parallels between the user's present abilities and the optimal metrics noted in top-tier athletes. The resulting scheme is specifically crafted based on the user's biometric attributes, guaranteeing that suggested methods for exercise, nutrition, and recuperation are both realistic and in line with demonstrated superior performance benchmarks.

Figure 4:
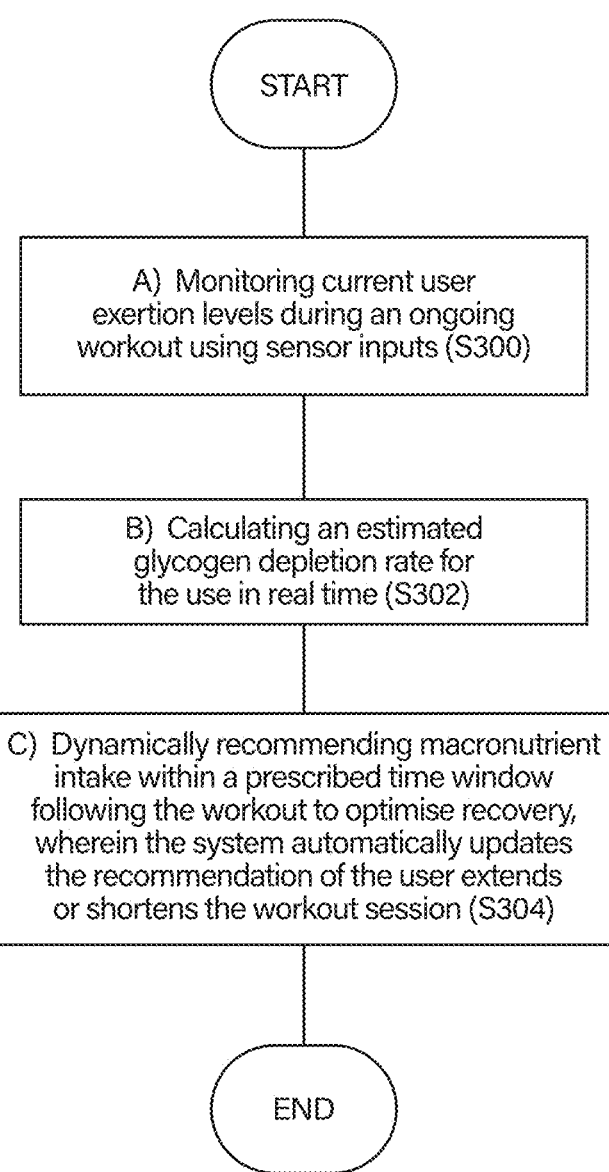
FIG. 4 shows flowchart displaying steps for monitoring exertion, calculating glycogen depletion, and recommending macronutrient intake during a workout.

FIG. 4 illustrates an exemplary flowchart displaying steps for monitoring exertion, calculating glycogen depletion, and recommending macronutrient intake during a workout.

The system monitors user exertion levels during a workout by leveraging sensor inputs that continuously capture physiological data S300. This approach allows the system to obtain precise, real-time measurements of the user's physical effort as the workout progresses. The collected sensor data is then used to evaluate the intensity of the exercise, ensuring that the monitoring accurately reflects the current state of exertion.

The system determines an estimated glycogen depletion rate for the user in real time S302. In one embodiment, sensor inputs and biometric metrics corresponding to physical exertion are continuously analyzed to dynamically estimate the rate at which the user's glycogen reserves are being exhausted. This calculation incorporates data reflective of instantaneous workload and historical activity patterns to yield a calibrated and responsive measure. The methodology enables the system to modify nutritional and training recommendations based on an assessment of energy expenditure during an ongoing workout session, ensuring that the adjustments accurately reflect the user's physiological state.

One implementation includes a feature for dynamically recommending macronutrient intake within a prescribed time window following a workout to optimize recovery S304. In this embodiment, the system monitors the user's exertion levels and calculates estimated glycogen depletion in real time during the exercise session. Following the workout, the system generates a tailored nutritional recommendation that specifies the optimal proportions of macronutrients needed to enhance recovery. The system continuously tracks the duration of the workout so that if the session is extended or shortened, the recommendation is automatically updated to reflect the revised timing and ensure that the nutrient intake remains suitably aligned with the user's recovery needs.

Figure 5:
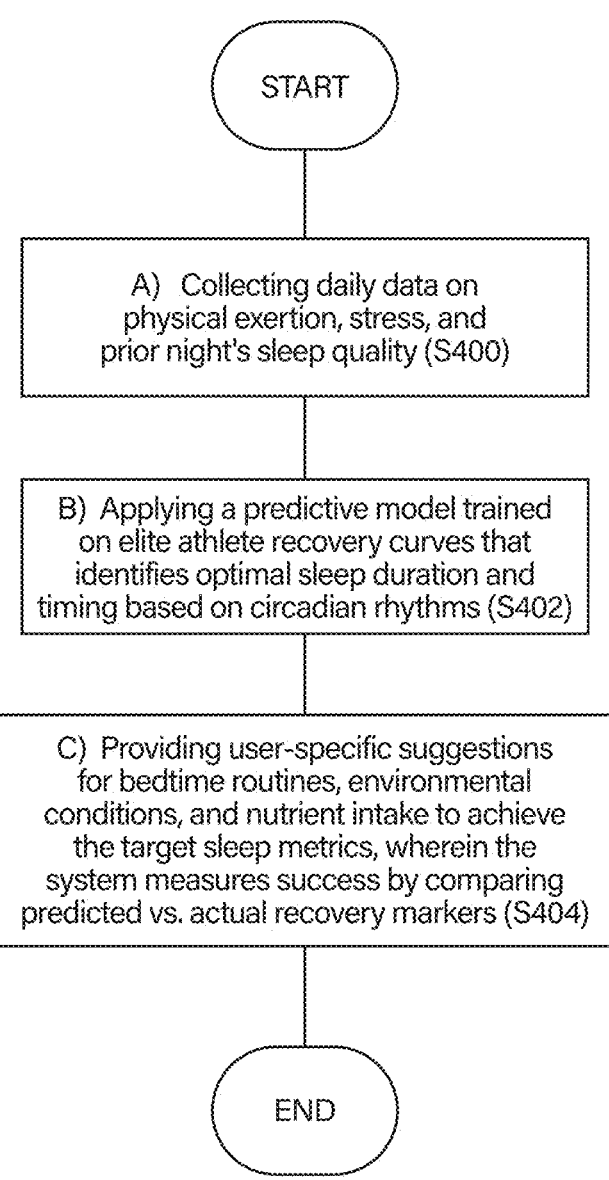
FIG. 5 shows flowchart for an AI-driven system optimizing health and sleep through data collection and predictive modeling.

FIG. 5 illustrates an exemplary flowchart for an AI-driven system optimizing health and sleep through data collection and predictive modeling.

Collecting daily data on physical exertion, stress, and prior night's sleep quality S400 refers to the process of gathering user-specific input concerning their daily physical activities, levels of stress experienced, and the quality of sleep achieved the previous night. This step is integral to understanding the user's physiological state and contributing factors impacting their overall well-being. By systematically recording this data, the system can better analyze and tailor health and fitness recommendations to improve user outcomes.

A predictive model, trained using recovery curves from elite athletes is then applied S402. This model identifies the optimal duration and timing for sleep based on circadian rhythms, focusing on maximizing recovery and performance outcomes.

The system generates personalized recommendations for bedtime routines, environmental conditions, and nutrient intake to help achieve target sleep metrics S404. These guidelines are tailored to enhance sleep quality by considering individual needs. Success is evaluated by comparing predicted recovery markers with actual outcomes, allowing the system to measure the effectiveness of its suggestions. This process ensures user-specific adjustments that optimize rest and recovery based on detailed analysis and feedback.

Figure 6:
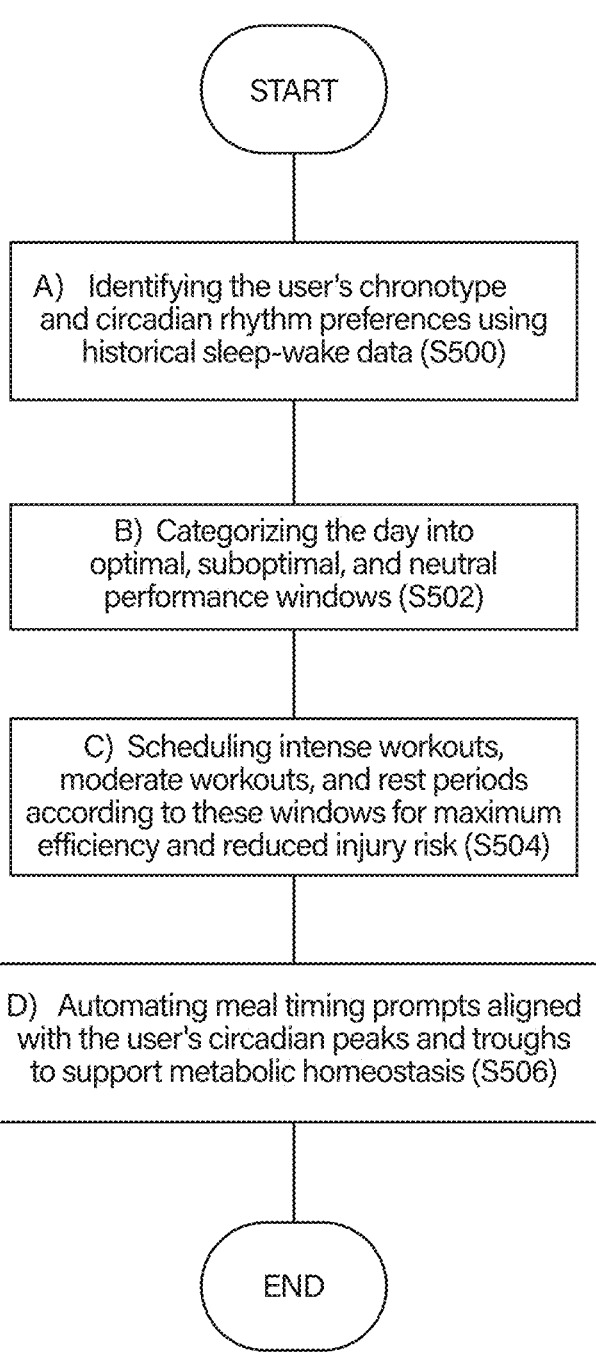
FIG. 6 shows an exemplary flowchart that outlines a process for optimizing daily performance.

FIG. 6 illustrates an exemplary flow chart outlining a process to optimize daily activities based on the user's circadian rhythm.

The process involves determining the user's chronotype and circadian rhythm preferences by analyzing historical sleep-wake data S500. This step aims to understand the user's natural sleep patterns and energy fluctuations throughout the day. By doing so, it allows for the optimization of activity schedules according to the user's biological clock, enhancing performance and well-being.

The process involves categorizing the day into distinct performance windows labeled as optimal, suboptimal, and neutral S502. This categorization is based on the user's historical sleep-wake data and circadian rhythm preferences. The aim is to identify specific times when the user can perform at their best, average, or least effectively, thereby allowing for an efficient scheduling of activities to align with these natural performance cycles.

A scheduling of workout sessions and rest periods occurs. This step involves assigning intense and moderate workout routines, as well as rest intervals, to specific times during the day based on predefined performance windows. The goal is to optimize efficiency and minimize the risk of injury by aligning physical activities with the user's optimal, suboptimal, or neutral performance periods. The reference sign for this step is S504.

Automating meal timing prompts aligned with the user's circadian peaks and troughs to support metabolic homeostasis S506 involves scheduling meal notifications to coincide with the user's natural biological rhythms. By understanding the user's circadian patterns, the system optimizes the timing of nutritional intake to enhance metabolic balance and overall health. This ensures that meal times are in harmony with periods of peak efficiency and rest, promoting optimal physiological functioning.

Figure 7:
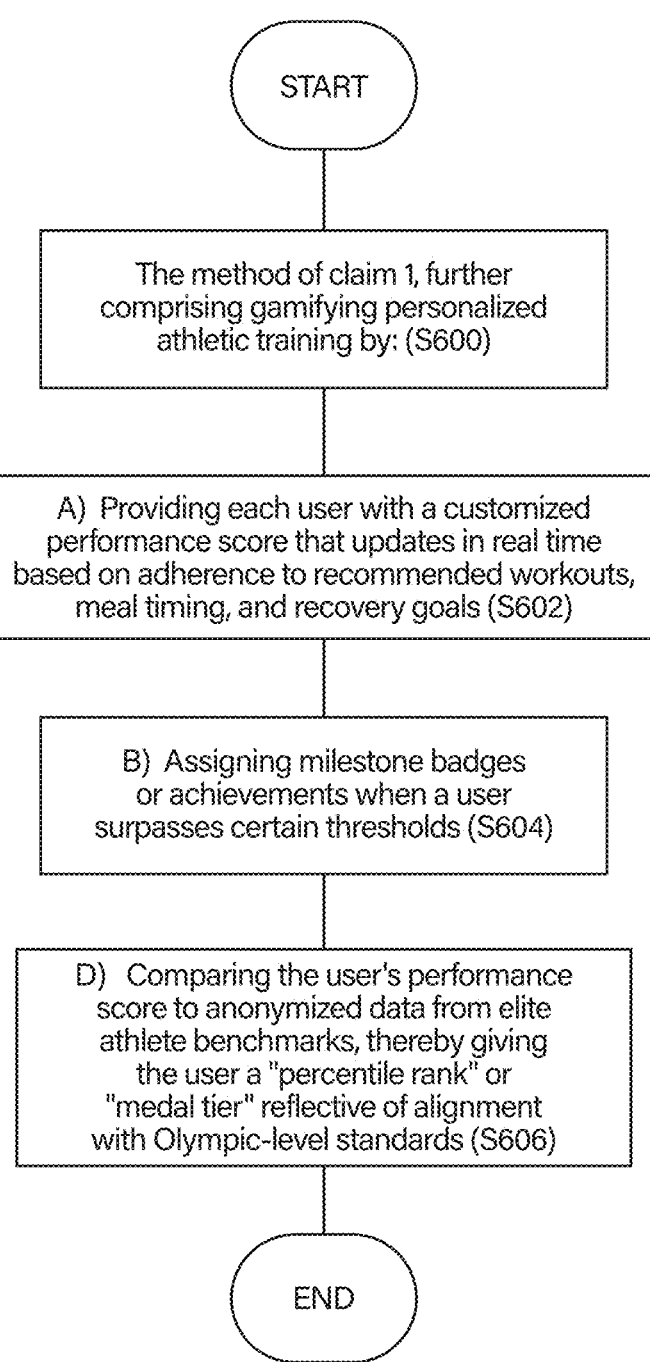
FIG. 7 shows an exemplary flow chart outlining a method for gamifying personalized athletic training with steps including performance scoring, milestone achievements, and benchmarking against elite athletes.

FIG. 7 illustrates an exemplary flowchart outlining a method for gamifying personalized athletic training by including steps such as performance scoring, milestone achievements, and benchmarking against elite athletes.

The method is further enhanced by gamifying personalized athletic training. In an embodiment, each user is provided with a customized performance score that is updated in real time based on how closely the user follows recommended workouts, meal timing, and recovery goals S600. Milestone badges or achievements are assigned automatically when a user exceeds predetermined performance thresholds. In addition, this approach includes comparing the user's performance score with anonymized data derived from elite athlete benchmarks, yielding a percentile rank or medal tier that reflects the user's alignment with Olympic-level performance standards.

In one embodiment, one implementation further enhances user engagement by providing each user with a customized performance score that updates in real time based on adherence to recommended workouts, meal timing, and recovery goals S602. This performance score reflects continuous monitoring and analysis of user compliance with the prescribed training and nutritional protocols, thereby offering immediate feedback and facilitating a transparent, motivational progress metric that adapts dynamically as the user meets or adjusts to the recommended objectives.

The system monitors user performance metrics in real time and when a user exceeds predefined thresholds, it triggers the assignment of milestone badges or similar achievements S604. The award of such badges serves as both a record of progress and a motivational reinforcement, enhancing user engagement by recognizing significant performance improvements. This mechanism forms a component of an integrated gamification strategy, wherein milestones obtained through surpassing set criteria are logged and visually represented within the user interface. The approach thereby enables users to receive immediate, quantifiable recognition for their efforts while driving adherence to the personalized training program.

The user's performance score is compared to anonymized data from elite athlete benchmarks giving the user a 'percentile rank' which is reflective of alignment with Olympic-level standards S606.

Figure 8:
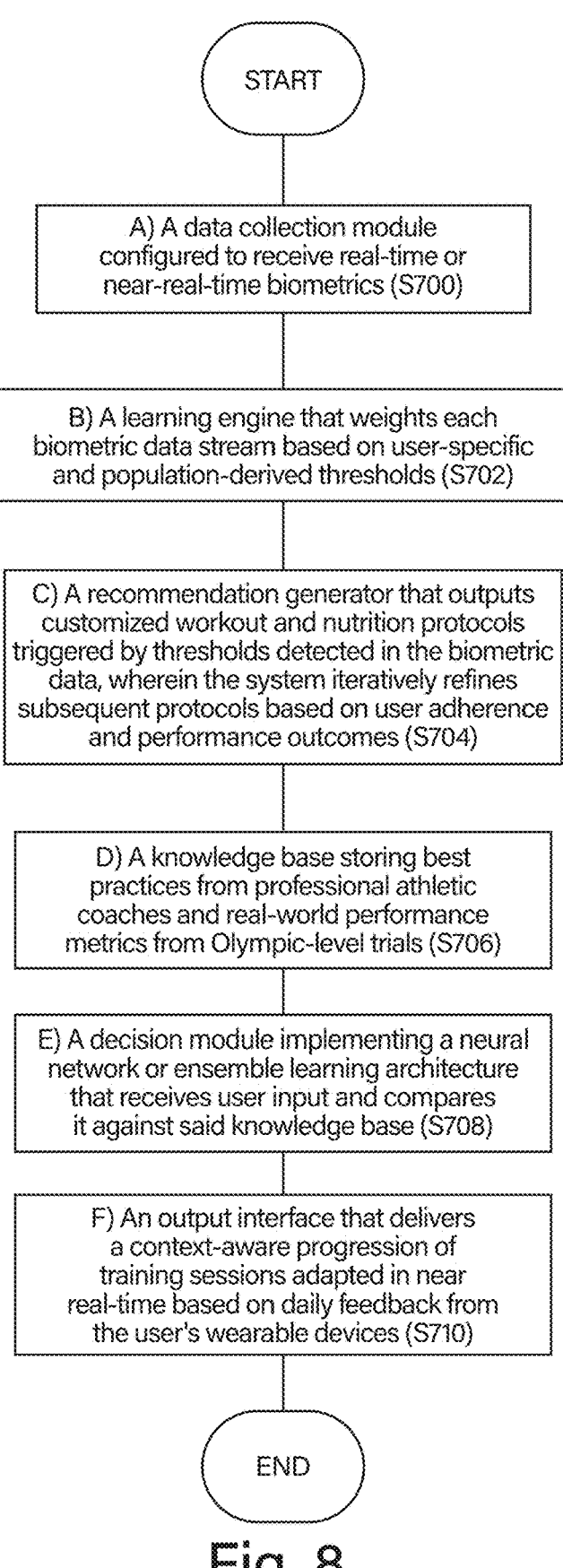
FIG. 8 illustrates an exemplary flowchart detailing a system that uses real-time biometric data to generate personalized workout and nutrition recommendations

FIG. 8 illustrates an exemplary flowchart detailing a system that uses real-time biometric data to generate personalized workout and nutrition recommendations, refining them based on user adherence and performance.

The data collection module is configured to receive real-time or near-real-time biometric data from one or more sensor networks attached to or integrated with a user's wearable devices S700. This module continuously gathers physiological parameters as they are generated, ensuring that the biometric data is captured promptly for further processing and analysis. The module is operable to interface with various sensors that detect metrics such as heart rate, activity level, and movement, among others, thereby facilitating an immediate and dynamic capture of user-specific biometric signals. Its design supports the integration of downstream system components that adjust personalized workout and nutrition protocols based on the timely acquisition of these data streams.

Furthermore, the system calculates resting metabolic rate, non-exercise activity thermogenesis, and exercise-induced calorie expenditure in order to determine total daily calorie needs and associated macronutrient ratios S702. This calculation is further adjusted based on user-defined goals and fitness levels in order to generate customized macronutrient, meal timing, and recovery strategies, thereby enhancing overall training effectiveness and supporting metabolic balance.

A recommendation generator is provided that outputs customized workout and nutrition protocols triggered by thresholds detected in the biometric data S704. The generator monitors the biometric streams and, when a predetermined threshold event is detected, produces tailored protocols based on the specific physiological state of the user. Continuous feedback from user adherence and performance outcomes is then used to iteratively refine the protocols, ensuring that the recommendations remain aligned with the user's evolving needs and responses. This approach, corresponding to reference label S704, enables the system to dynamically adjust the training and nutritional strategies over time for optimal results.

One implementation integrates a knowledge base which systematically archives premier practices sourced from professional sports coaches and empirical performance metrics drawn from Olympic-level evaluations S706. This knowledge base acts as a unified reservoir comprising rigorously verified training modules, restorative strategies, and dietary guidelines, ensuring that the system is anchored on a secure foundation of top-tier performance information. By melding these recognized methodologies, the knowledge base enables the system to set benchmarks and align user-specific outputs with proven, superior performance standards. Comprehensive factual data such as workout intensity, recuperation periods, and resultant outcomes are stored within the knowledge base to facilitate instantaneous decision making and adjustment of personal recommendations.

The decision module described in reference label S708 is configured to receive user inputs and process them through a neural network or an ensemble of learning algorithms. It compares the incoming input against a stored knowledge base that includes best practices and performance metrics, enabling the system to identify patterns and correlations. By doing so, the module refines its analysis with each iteration, ensuring that the outputs it generates are responsive to both individual user data and the broader scope of established benchmarks. This approach supports the delivery of adaptive and personalized recommendations based on continuously updated performance insights.

In one embodiment, the system comprises an output interface that is configured to deliver a context-aware progression of training sessions S710. This output interface receives daily feedback from the wearable devices associated with the user and dynamically adapts the training progression in near real-time. The interface integrates data from various performance metrics, such as heart rate, movement, and other physiological responses, to generate a training session that reflects the user's current state and recent performance trends. As feedback signals are received, the interface seamlessly recalibrates the training session parameters, ensuring that exercise routines are continuously optimized according to the user's evolving needs. This real-time adaptation facilitates immediate adjustments and helps maintain a personalized training experience, promoting both enhanced performance and effective recovery throughout the workout session.

Figure 9:
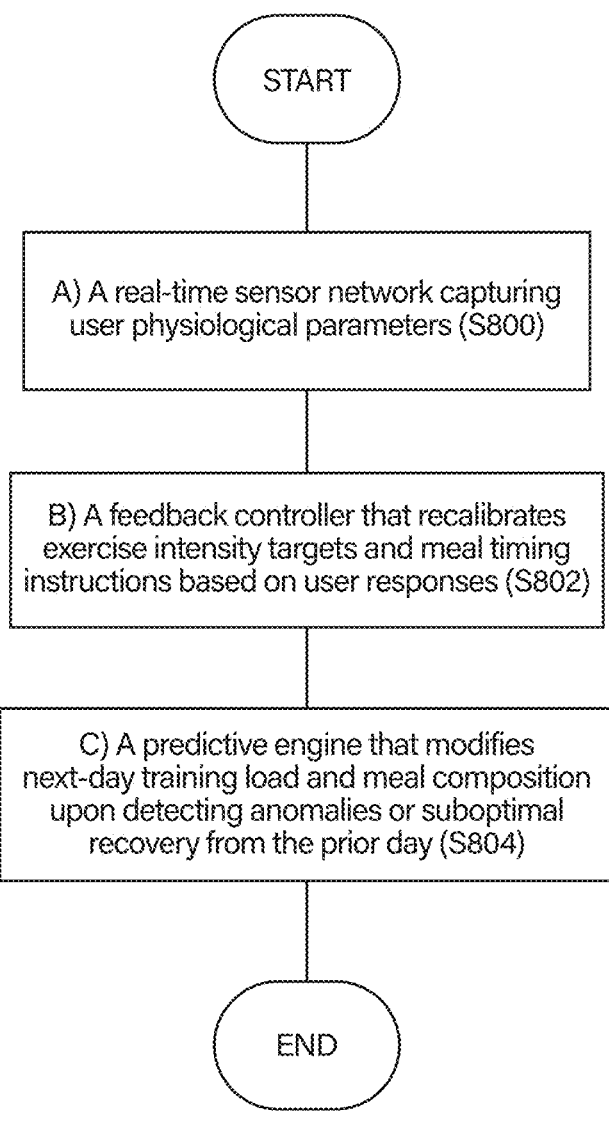
FIG. 9 shows an exemplary flowchart depicting a system that uses real-time physiological data to dynamically adjust exercise and nutrition plans for optimized adaptation and recovery.

FIG. 9 shows an exemplary flowchart depicting a system that uses real-time physiological data to dynamically adjust exercise and nutrition plans for optimized adaptation and recovery.

This system involves using a network of real-time sensors to capture the user's physiological data S800. These parameters might include heart rate, sleep data, activity levels, and other relevant biometric information. The system discloses a feedback controller that dynamically recalibrates both exercise intensity targets and meal timing instructions based on real-time user responses S802. The controller monitors input signals indicative of the user's current performance and physiological state and, in response, adjusts the prescribed intensity of workouts as well as the timing of nutritional intake. By continuously analyzing these user-specific data, the system optimizes the balance between exercise and nutritional requirements, ensuring that the training regimen and meal timing remain effectively aligned with the user's evolving recovery and performance needs.

The predictive engine S804 continuously monitors recovery data from the prior day to identify any anomalies or signs of suboptimal recovery. When such deviations are detected, the engine applies a series of adaptive algorithms to determine the necessary modifications to the next-day training load as well as the composition of meals. This modification process incorporates real-time biometrics and historical performance indices to ensure that the adjustments align with the user's overall fitness goals and recovery needs. The engine thereby facilitates a dynamic transition between recovery states by predicting potential performance deficits and proactively optimizing the subsequent day's exercise and nutritional regimen.

Figure 10:
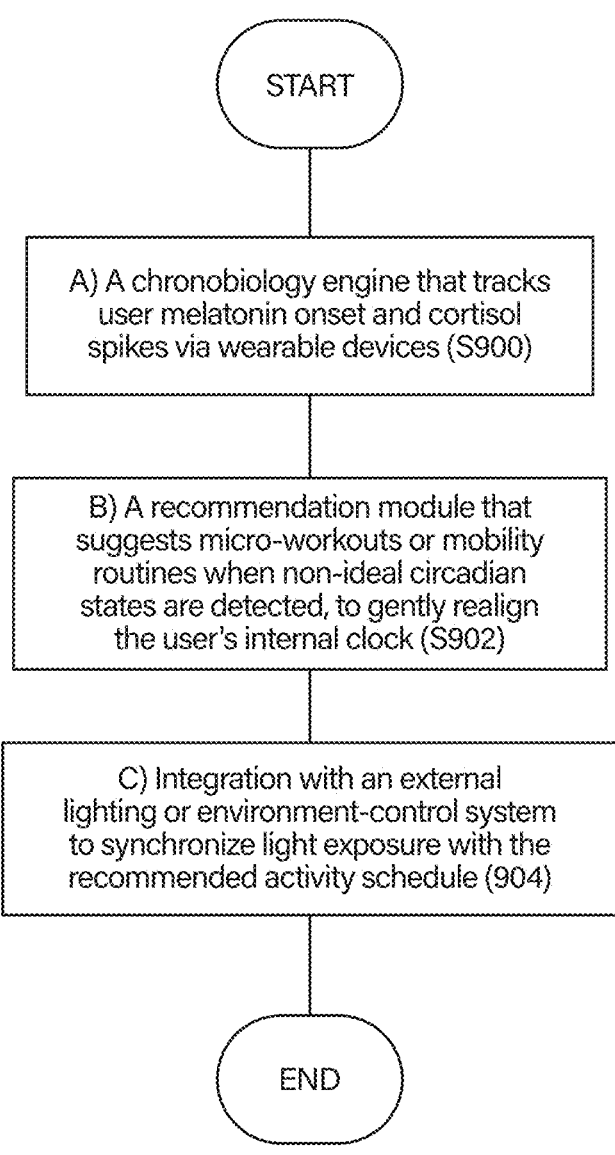
FIG. 10 shows an exemplary flowchart that illustrates a system that uses wearable device data to track a user's circadian rhythm, recommending micro-workouts and adjusting light exposure.

FIG. 10 shows an exemplary flowchart that illustrates a system that uses wearable device data to track a user's circadian rhythm, recommending micro-workouts and adjusting light exposure.

The system involves a chronobiology engine that uses data from wearable devices to track the user's melatonin onset and cortisol spikes S900. This is used to understand the user's circadian rhythm. A recommendation module suggests micro-workouts or mobility routines when non-ideal circadian states are detected, to gently realign the user's internal clock S902. In this stage, a recommendation module suggests micro-workouts or mobility routines. These suggestions are made when the system detects non-ideal circadian states, aiming to gently realign the user's internal clock. It also involves integration with an external lighting or environment-control system to synchronize light exposure with the recommended activity schedule S904. The integration with an external lighting or environment-control system synchronizes light exposure with the recommended activity schedule, which further supports circadian alignment.

Figure 11:
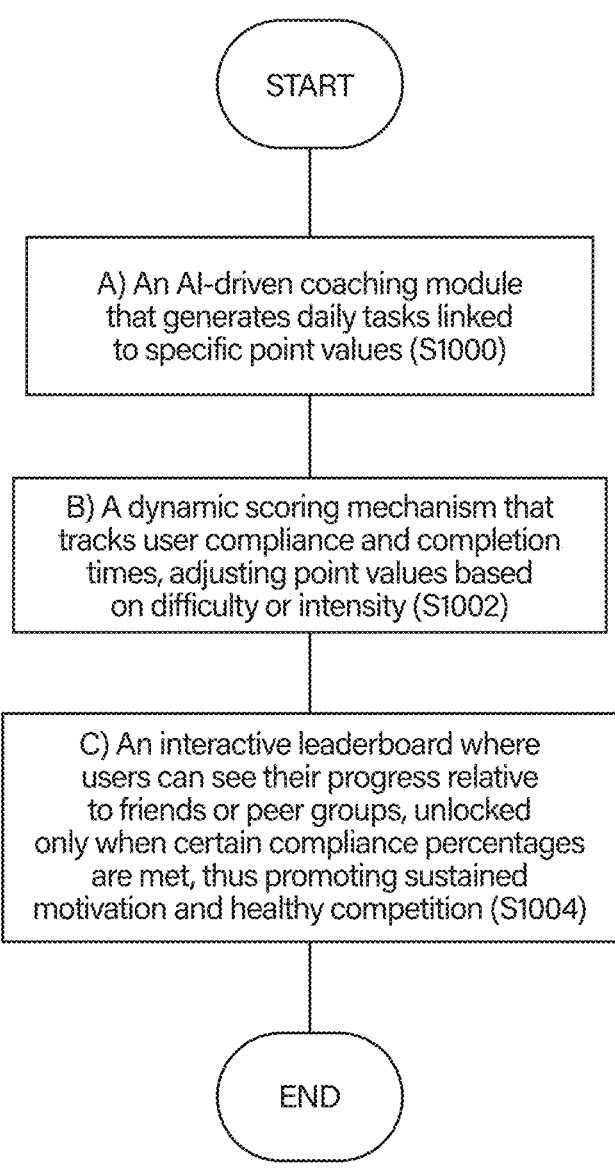
FIG. 11 shows an exemplary flowchart that outlines a system using an AI-driven coaching module.

FIG. 11 shows an exemplary flowchart that outlines a system using an AI-driven coaching module.

The AI-driven coaching module is designed to create daily tasks for users, associating each with specific point values S1000. This system motivates users by tracking their progress through assigned tasks, encouraging adherence and engagement with the program.

The system integrates a component within the system that involves a dynamic scoring mechanism S1002. This mechanism is designed to monitor user compliance and track completion times associated with various tasks. It adjusts the point values assigned to these tasks, taking into account their difficulty or intensity levels. This ensures that users are rewarded accurately based on the relative challenge of their activities. It also has an interactive leaderboard where users can see their progress relative to friends or peer groups S1004.

FIG. 12 illustrates a process for managing activity visualization on a clock-based interface.

The reference label "Showing only a bedtime indicator during day mode for sleep activities" S1102 refers to a process within the method where the system displays a bedtime indicator during the day mode. This feature is designed to present users with relevant sleep information discreetly without fully displaying the entire sleep duration, aiding in maintaining focus on daytime activities while subtly reminding the user of their upcoming sleep schedule.

The system involves displaying the full duration of sleep activities when the interface is in night mode S1104. This feature ensures users have a comprehensive view of their sleep patterns during the nighttime, allowing for better tracking and assessment of their rest quality. The mode switch facilitates easy comprehension of sleep information by adapting the display to a nighttime theme.

The method involves displaying activities on an interface designed to resemble a clock, offering users a visual representation of their schedule S1106. This representation allows for an intuitive understanding of activity times in relation to the entire day. By arranging activities around a clock face, users can easily perceive how each task fits within their daily routine, enhancing the usability of the scheduling function. It also indicates optimal and alert ranges for activity timing and duration on the clock-based interface S1108.

Figure 13:
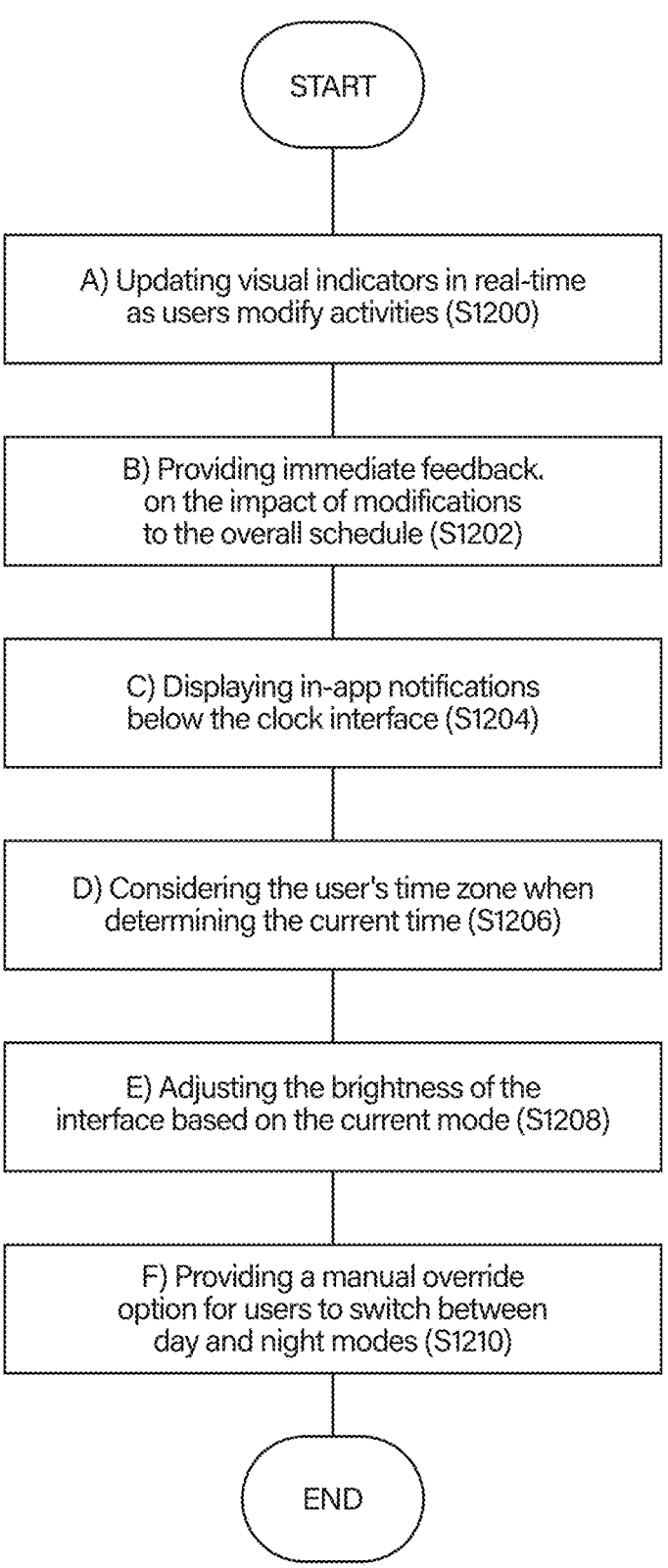
FIG. 13 shows an exemplary flowchart that outlines a process for enhancing a user interface.

FIG. 13 shows an exemplary flowchart that outlines a process for enhancing a user interface.

The method involves the real-time updating of visual indicators when users modify activities S1200. This dynamic adjustment ensures that any changes made by the user are immediately reflected in the interface, allowing for seamless tracking and management of activities. The method provides users with immediate feedback on the impacts of their alterations on their complete schedule S1202. Real-time analysis guides users in recognizing the likely outcomes of changing planned activities and equips them to make conscious decisions regarding their everyday routine. In turn, this secures optimal alignment with individualized recommendations, improving their entire experience and commitment to proposed plans or targets.

The reference label associated with "Displaying in-app notifications below the clock interface," S1204, marks a step in the method where real-time updates and feedback are provided to the user. This step involves positioning the notifications so that they appear directly beneath the clock display within the application's interface, ensuring users receive timely and relevant information without obstructing their view of other important data presented on the interface.

The method includes considering the user's time zone when determining the current time S1206. This ensures that all interfaces and functionalities accurately reflect the correct local time for the user, contributing to the seamless operation of day and night mode transitions and other time-sensitive features.

The step involves adjusting the brightness of the interface according to the current mode, ensuring that the display settings are optimal for either day or night. This adaptation enhances visibility and user experience by altering brightness levels based on the selected mode as per section S1208.

The process involves offering a manual override feature that allows users to switch between day and night modes as needed S1210. This option enables customization and flexibility in user interface settings, permitting individuals to choose their preferred visual mode regardless of the current automatic configuration.

Figure 14:
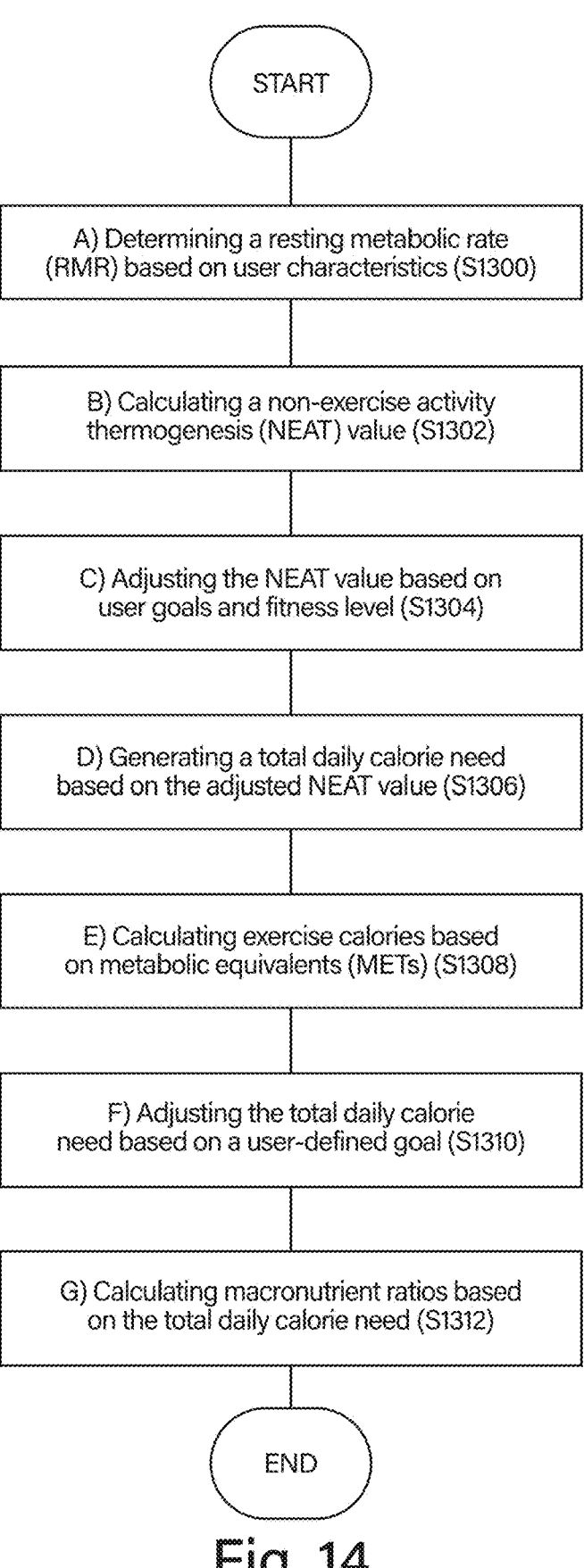
FIG. 14 shows an exemplary flowchart that outlines a process for calculating a user's daily calorie needs.

FIG. 14 shows an exemplary flowchart that outlines a process for calculating a user's daily calorie needs. In certain implementations, the system determines key metabolic metrics to further improve personalized suggestions. An imperative feature of this functionality is calculating a resting metabolic rate based on individual traits. This component, identified by reference tag S1300, functions by examining detailed user information to identify the resting metabolic rate, which stands as a starting point for additional computations. The calculated resting metabolic rate is subsequently integrated with information on non-exercise activity thermogenesis and exercise metabolic equivalents to estimate a comprehensive daily calorie requirement. Modifications are implemented taking into account personal fitness objectives and training intensities, thus making certain that macronutrient ratios and meal-oriented recommendations correspond ideally with the user's metabolic composition and performance needs.

Reference label S1302 outlines the process of determining a non-exercise activity thermogenesis (NEAT) value. In one specific embodiment, this measurement involves quantifying the energy utilization of a user during day-to-day activities not related to formal exercise, such as casual walking, standing, and other sporadic movements. The NEAT value calculated has a significant role in establishing the user's total daily calorie expenditure. Additionally, the method could include modifications based on unique user measurements or activity trends to improve the accuracy of the NEAT determination.

The method adjusts the calculated NEAT value by taking into account the specific goals and current fitness level of the user. In this approach, after determining a baseline NEAT value, the system applies a modification step wherein the user's desired training or weight management objectives, as well as their assessed level of fitness, are used to adjust the value accordingly. This adjustment refines the NEAT calculation so that it more accurately reflects the energy expenditure that is pertinent to the user's individual profile. In embodiments implementing this step S1304, the system retrieves relevant user data and applies predetermined adjustment factors based on whether the user's goal is to build muscle, maintain a balanced physique, or facilitate fat loss, and on whether the user is classified as unfit or fit. Consequently, this process generates a modified NEAT value that serves as a more precise input in determining the total daily calorie needs and subsequent nutritional and activity recommendations S1306.

In one particular embodiment, one implementation includes the calculation of exercise calories based on metabolic equivalents (METs). This aspect involves quantifying the calories expended during various activities by assigning and applying standardized MET values, thereby furnishing a precise measure of the exercise-related energy expenditure. S1308 describes a method in which the exercise calories are computed using the MET values of the performed activities, which are incorporated into the overall daily energy balance and nutritional strategy.

The reference label S1310 pertains to the step wherein the system adjusts the computed total daily calorie requirement in accordance with a user-defined goal. In this step, a base calorie need is determined by aggregating various metabolic and activity inputs, and this value is subsequently modified to align with specific user objectives, such as weight gain, weight loss, or maintenance. The adjustment process factors in the user's expressed targets to ensure that the final calorie recommendation supports their overall fitness and nutritional strategy. By incorporating user-set goals into the calculation, the system delivers customized dietary recommendations that are attuned to individual performance criteria and desired health outcomes. The method also calculates macronutrient ratios based on the total daily calorie needs S3012.

Figure 15:
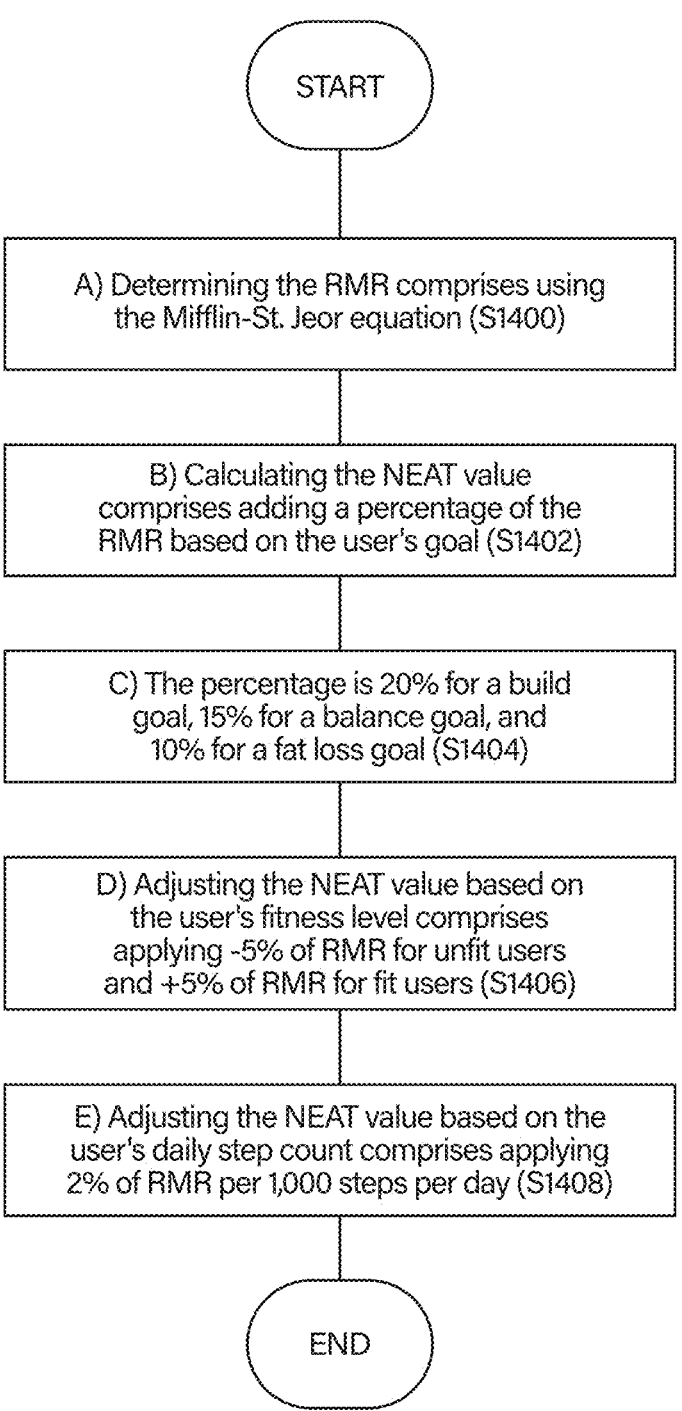
FIG. 15 shows an exemplary flowchart that outlines a process for calculating a user's daily calorie needs.

FIG. 15 shows an exemplary flowchart which outlines a process for calculating a user's daily calorie needs. The system calculates a user's resting metabolic rate by employing the Mifflin-St. Jeor equation S1400. This equation, widely recognized for its clinical relevance, uses user-specific data such as weight, height, age, and sex to generate an estimate of the user's basal energy expenditure during rest. The computed RMR serves as a foundational metric for the subsequent personalization of daily calorie needs, macronutrient distributions, and overall training and nutrition recommendations. Calculating the NEAT value comprises adding a percentage of the RMR based on the user's goal S1402.

The reference labeled S1404 is directed to an embodiment in which the adjustment of non-exercise activity thermogenesis is implemented by applying a predetermined percentage of the resting metabolic rate that varies according to the user's specific goal. In this embodiment, a build goal is supported by applying an increment of 20% of the resting metabolic rate, a balance goal is achieved by applying an increment of 15%, and a fat loss goal is facilitated by applying an increment of 10%.

One implementation adjusts the non-exercise activity thermogenesis value based on the user's fitness level S1406. In this process, if a user is determined to be unfit, the system reduces the calculated value by 5% of the user's resting metabolic rate. Conversely, if the user is determined to be fit, the system increases the value by 5% of the resting metabolic rate. This adjustment mechanism ensures that the energy expenditure estimation more accurately reflects the user's physical conditioning, thereby contributing to a personalized approach in developing tailored training and nutritional protocols.

The system adjusts the non-exercise activity thermogenesis (NEAT) value by incorporating the user's daily step count into the calculation of their overall energy expenditure S1408. In particular, for every 1,000 steps taken in a day, an amount equivalent to 2% of the user's resting metabolic rate (RMR) is added to the NEAT value. This means that if a user records additional steps, the system proportionately increases the NEAT value by the specified percentage per 1,000 steps, effectively capturing variations in daily activity levels. The adjustment facilitates a more personalized and accurate estimation of total daily calories needed by integrating the impact of routine physical movement into the overall metabolic profile.

FIG. 16 illustrates the flowchart for a personalized nutrition and fitness optimization process. This includes steps such as adjusting metabolic equivalents (METs) based on age, applying caloric restrictions, determining macronutrient needs, adjusting these based on training volume, and providing meal-specific recommendations.

The process begins with adjusting the Metabolic Equivalents (METs) in accordance with the user's age if the user is over 40 years old, as indicated by reference sign S1500. This adjustment considers the natural changes in metabolism that can occur with age, ensuring that fitness and dietary recommendations remain suitable for the individual's physiological state. This modification aims to maintain effective energy expenditure tracking and to tailor workout intensity appropriately.

The method includes applying either a 10% caloric restriction aimed at balancing performance and fat loss, or a 25% caloric restriction intended to maximize fat loss S1502. This adjustment is tailored to support the user's specific fitness objectives while ensuring efficient energy management and body composition improvement.

The process includes determining the user's protein needs by considering their body weight and specific training factors S1504. This step ensures that the protein intake is aligned with the individual's physiological requirements and activity levels, thereby optimizing muscle growth and recovery.

The process for determining carbohydrate needs involves analyzing various factors, including the user's brain usage, non-exercise activities, and exercise requirements S1506. This approach ensures that carbohydrate intake is optimized to support the user's overall cognitive and physical demands. By accounting for these diverse elements, the system can tailor carbohydrate recommendations to meet specific energy needs efficiently.

In the described method, fat needs are determined as a percentage of the total caloric intake. This process is identified in the flowchart under label S1508, highlighting its role in establishing balanced nutrition based on individual requirements. The determination of fat needs is essential for customizing dietary plans to support various fitness and health goals effectively.

The process involves adjusting calorie and macronutrient calculations based on the user's training volume S15010. This adjustment considers variations in the individual's exercise routine to ensure that energy intake aligns with specific workout intensities and frequencies, optimizing nutritional support for performance and recovery.

The system provides meal-specific macronutrient recommendations by analyzing the timing and purpose of each meal S15012. This involves adjusting nutrient intake to align with the user's daily activities and metabolic needs, ensuring that the nutrients consumed contribute optimally to the user's performance and recovery goals. By considering factors such as exercise schedules, rest periods, and metabolic rates, the system tailors macronutrient distribution across meals to enhance energy utilization and support overall health objectives.

Figure 17:
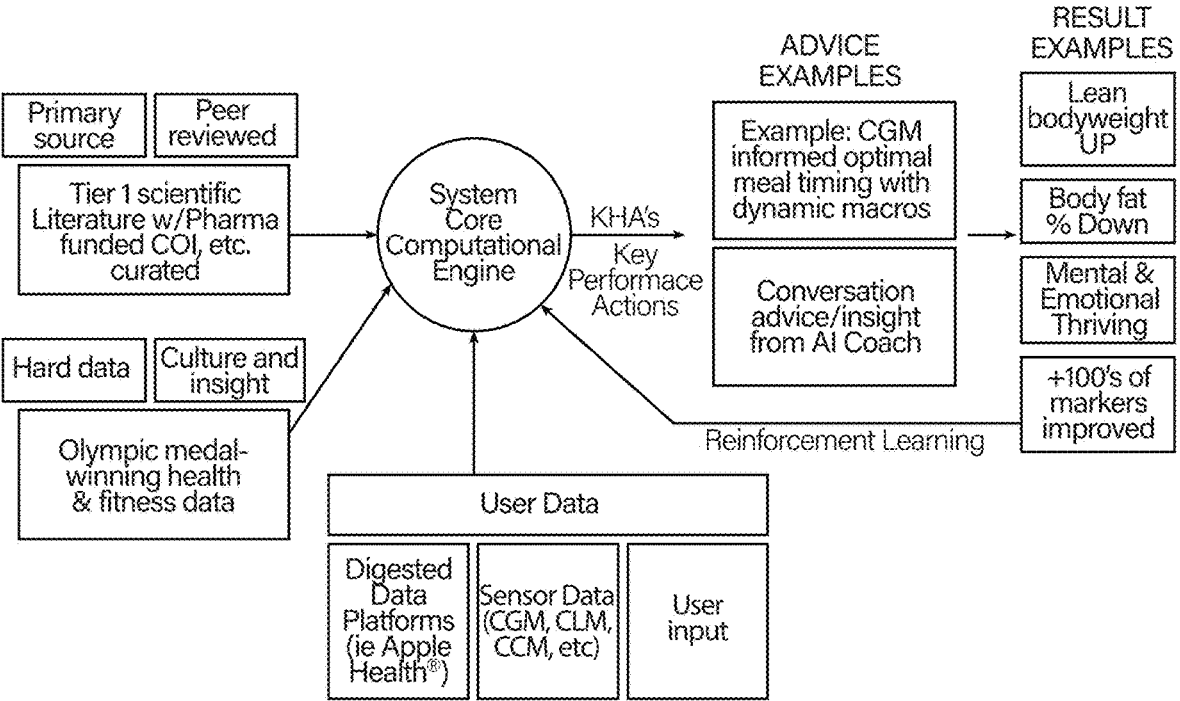
FIG. 17 illustrates the core artificial intelligence architecture that generates personalized health recommendations through multimodal data analysis.

FIG. 17 illustrates the core artificial intelligence architecture that generates personalized health recommendations through multimodal data analysis. The system employs decision trees to process user biometric data (resting heart rate, body composition), behavioral patterns (meal timing consistency, exercise frequency), and environmental factors (local timezone, daylight exposure). This model dynamically adjusts macronutrient targets, sleep window recommendations, and activity thresholds based on continuous reinforcement learning from user compliance data. The coaching engine interfaces with a temporal awareness module that synchronizes recommendations with circadian rhythm parameters derived from wearable device inputs.

Figure 18:
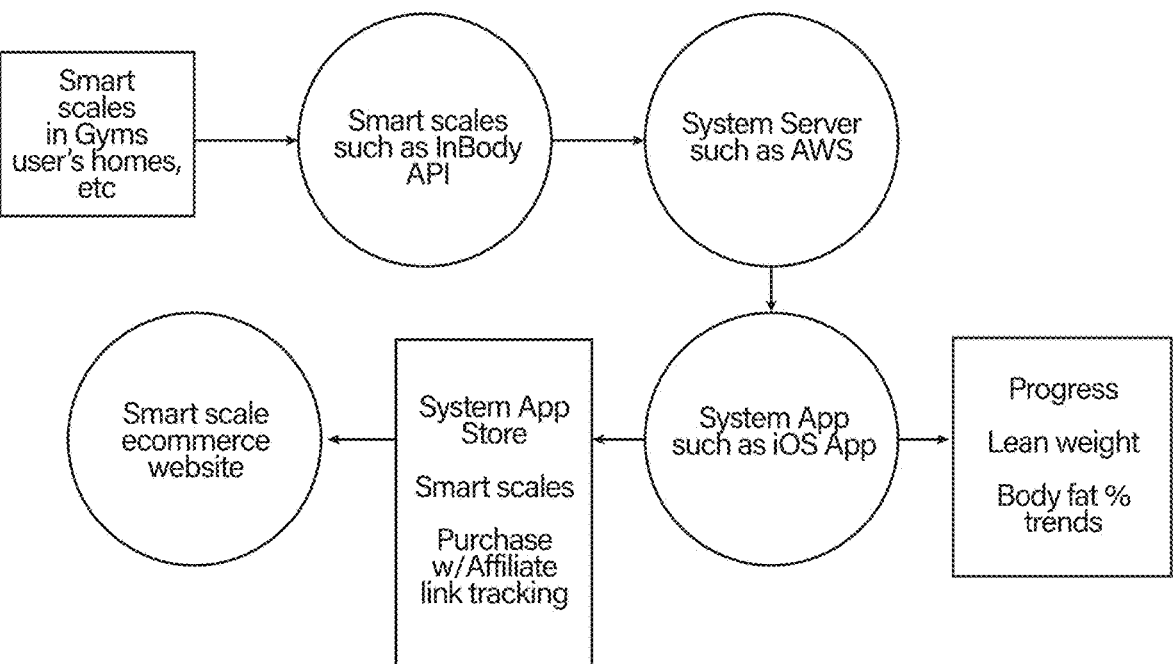
FIG. 18 details the implementation for InBody scale integration.

FIG. 18 details the implementation for InBody scale integration, showcasing the OAuth 2.0 authentication flow between mobile clients and AWS Cognito user pools. The architecture demonstrates bidirectional synchronization between locally cached scale measurements (stored in SQLite) and DynamoDB tables through API Gateway-mediated Lambda functions. Of particular note is the implementation of data integrity checks using SHA-256 hashing for biometric payloads transmitted via HTTPS POST requests, ensuring compliance with HIPAA security standards for protected health information.

Figure 19:
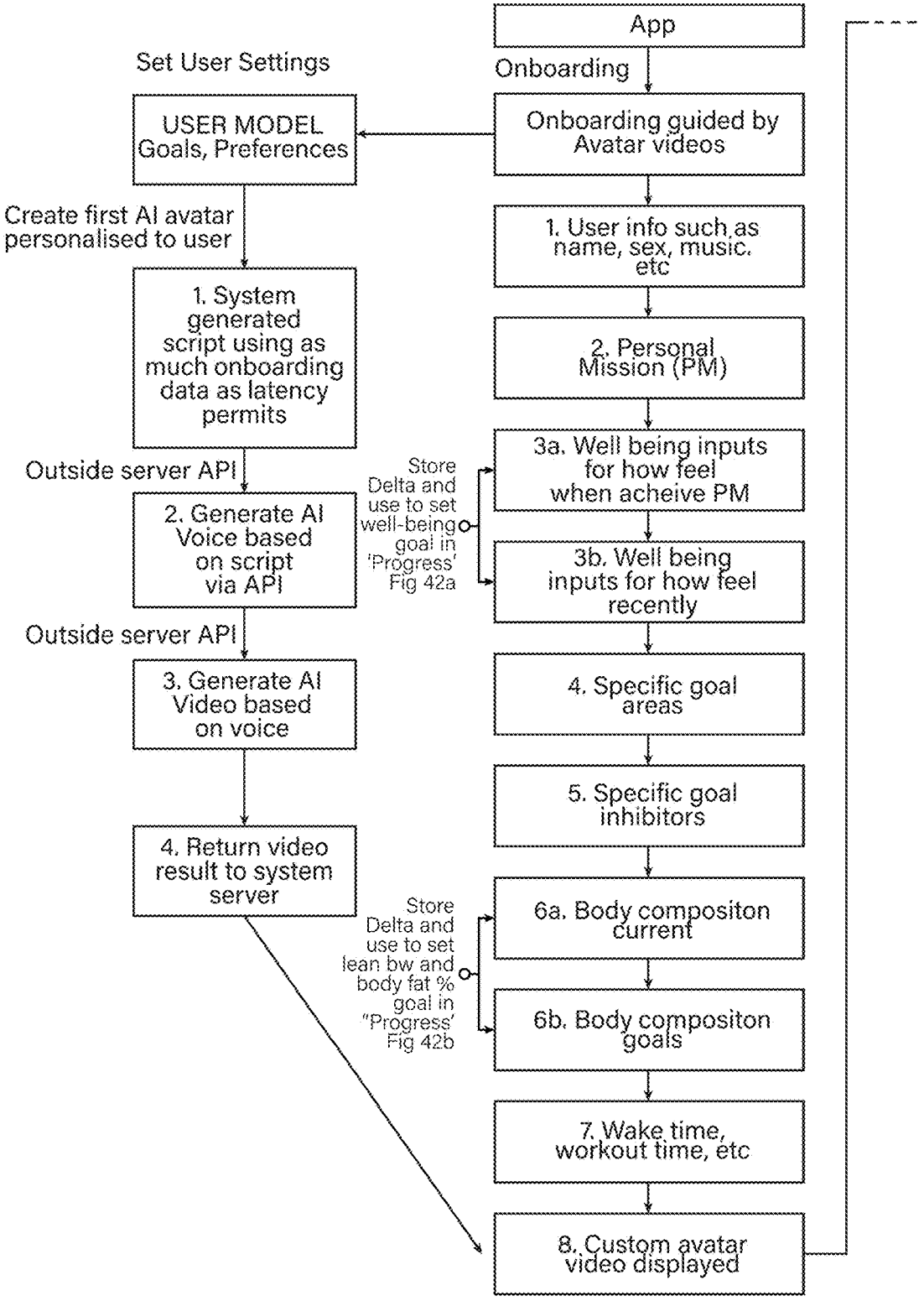
FIG. 19 illustrates primary input streams that the AI model processes to generate insights and predictions.
Figure 19:
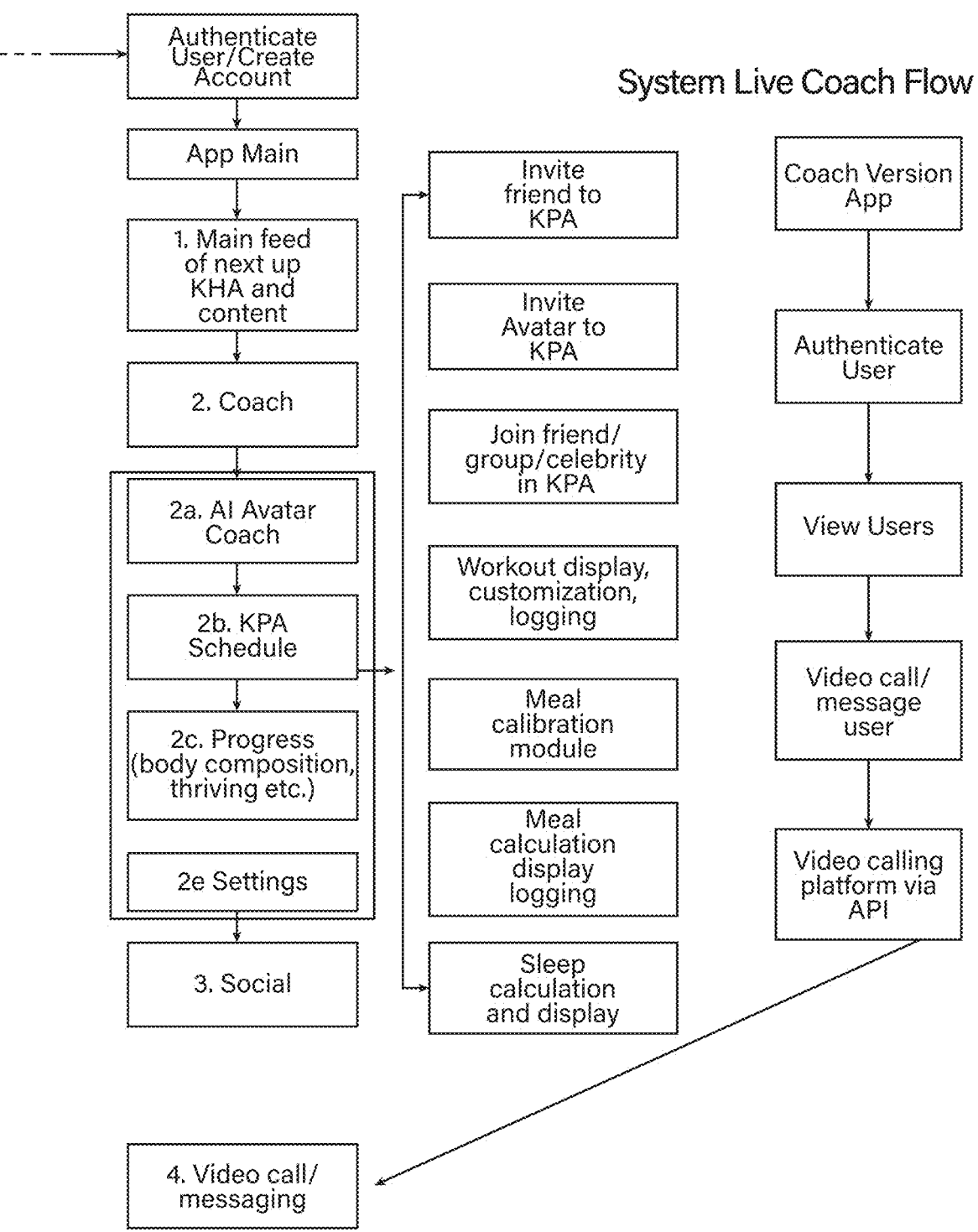

FIG. 19 illustrates seven primary input streams that the AI model processes to generate insights and predictions. The first input stream consists of continuous glucose monitoring (CGM) readings, which are sampled at 5-minute intervals to provide real-time data on glucose levels. The second stream includes heart rate variability (HRV) metrics derived from the WHOOP strap, offering insights into the user's physiological stress and recovery states. The third stream is sleep stage classification data collected from the Oura ring, which tracks the user's sleep patterns and quality. The fourth input involves manual user inputs, where individuals subjectively report their energy levels, providing a personalized context to the data. The fifth stream captures environmental context through smartphone sensors, including ambient light and GPS location, to understand the user's surroundings and activity patterns. The sixth input is historical compliance patterns extracted from app interaction logs, which help the system learn user behavior and adherence to routines over time. Lastly, the seventh stream integrates data from third-party APIs such as My Fitness Pal and Training Peaks, enabling the model to access additional health and fitness metrics like nutrition and workout details. To manage the complexity of these heterogeneous data sources, the system utilizes Apache Kafka for real-time data streaming, ensuring seamless and efficient data flow. Custom window functions are implemented to handle the temporal alignment of the diverse data streams, ensuring that the AI model can process and analyze the inputs in a synchronized and meaningful manner.

Figure 20:
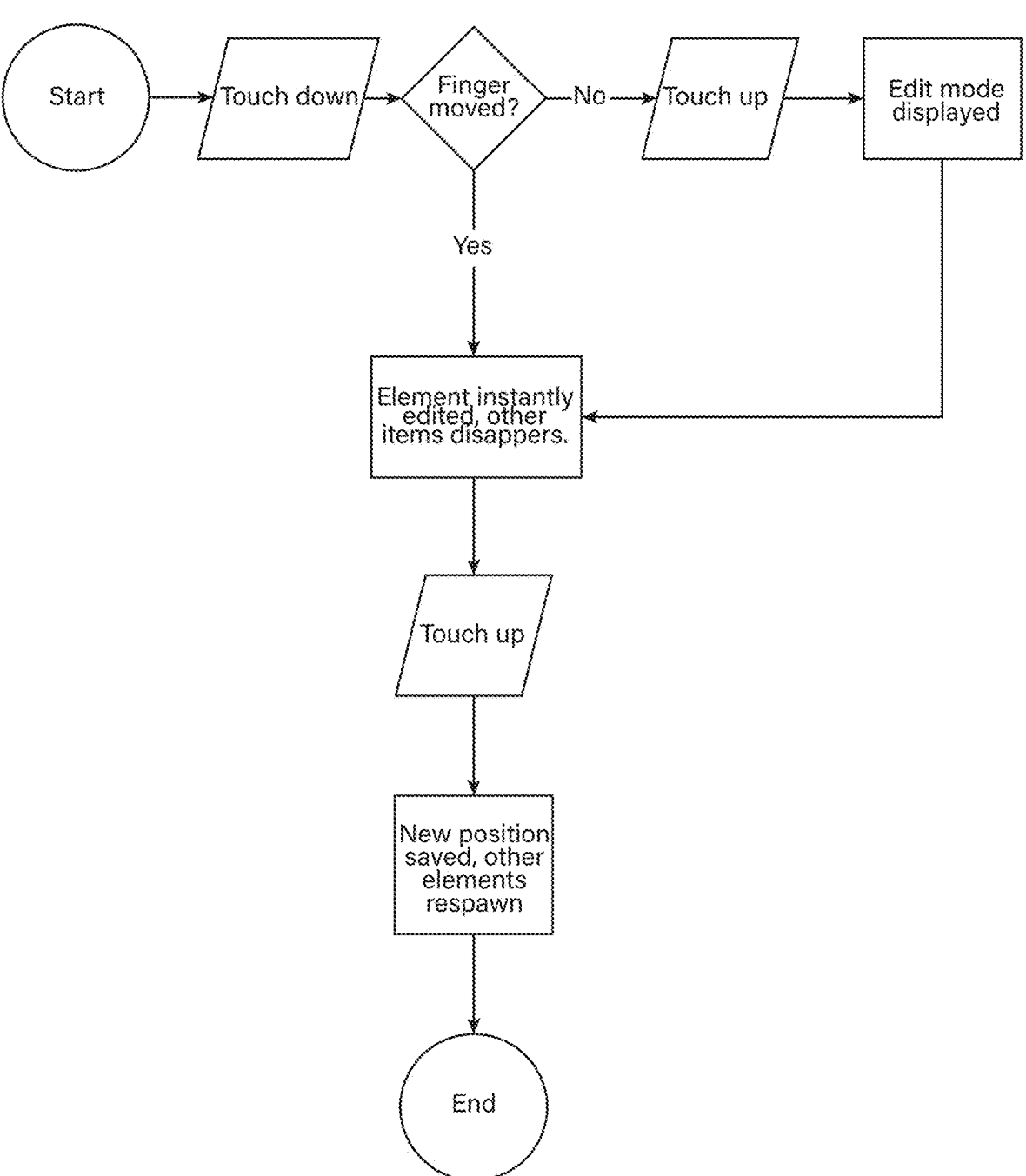
FIG. 20 illustrates the touch event handling flowchart for the circular clock interface component, detailing the sequence of actions triggered by user interactions.

FIG. 20 illustrates the touch event handling flowchart for the circular clock interface component, detailing the sequence of actions triggered by user interactions. The process begins with the "Start" step, indicating the initiation of a touch event. The next step is "Touch down," where the user's finger makes contact with the interface. The system then checks if the finger has moved by evaluating the condition "Finger moved?" If the finger has not moved, the process proceeds to "Touch up," where the user lifts their finger, and the "Edit mode displayed" step is activated, allowing the user to enter an editing state. If the finger has moved, the system immediately edits the element under the touch point, causing other items to temporarily disappear from the interface. This is followed by the "Touch up" step, where the user lifts their finger. The system then saves the new position of the edited element and re-spawns the other elements that had disappeared, restoring the interface to its complete state. The process concludes with the "End" step, signifying the completion of the touch event handling cycle. This flowchart effectively captures the dynamic and responsive nature of the circular clock interface component, ensuring a seamless user experience.

Figure 21:
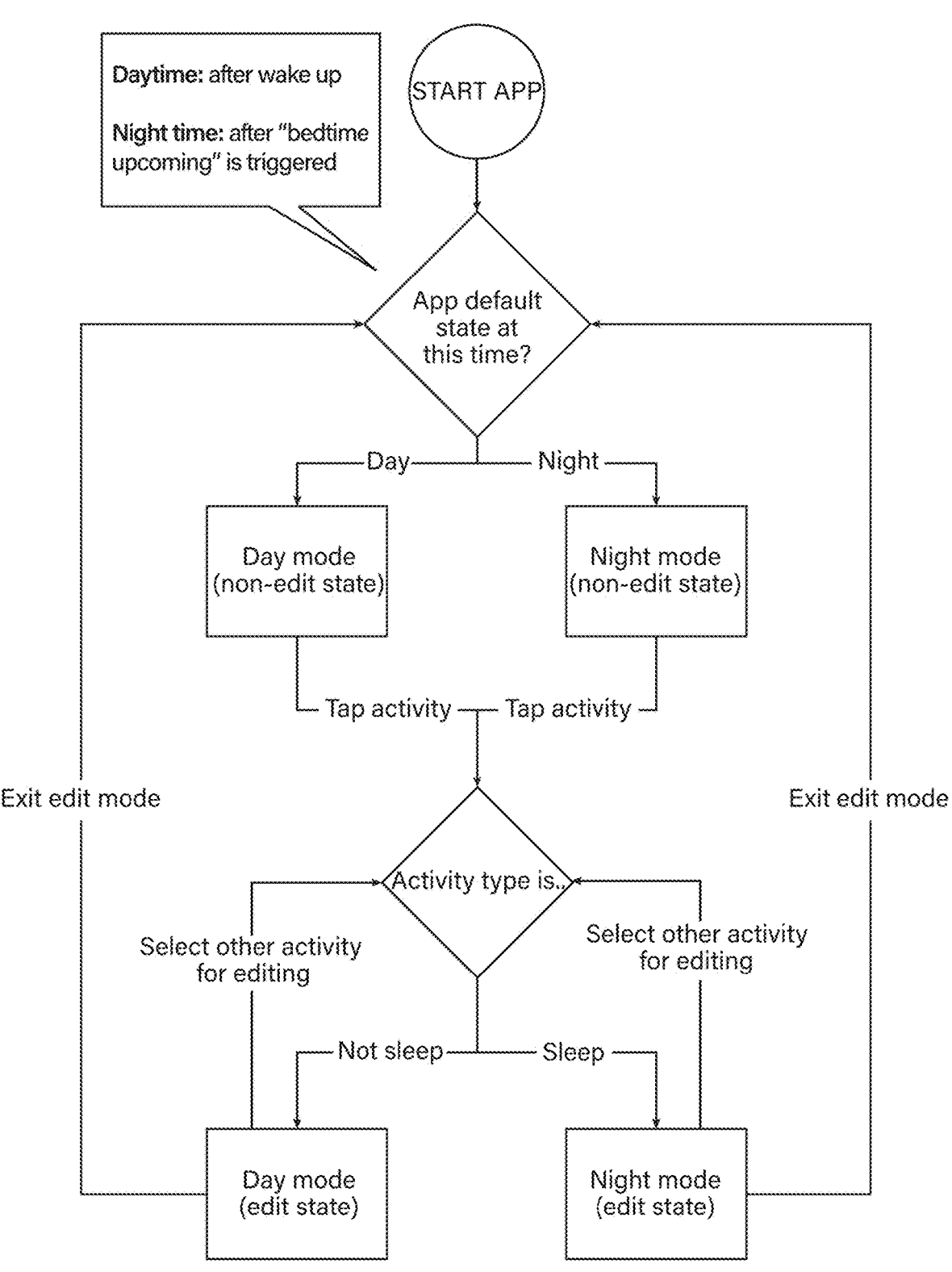
FIG. 21 demonstrates the application's state machine for switching between day and night themes.

FIG. 21 demonstrates the application's state machine for switching between day and night themes, outlining the transitions based on user interactions and time-based triggers. The process begins with the "START APP" step, where the application is launched. The system then checks the default state of the app at the current time, which can be either "Day mode (non-edit state)" or "Night mode (non-edit state)," depending on whether it is daytime after the user wakes up or nighttime after the "bedtime upcoming" trigger is activated. In both day and night modes, a "Tap activity" can occur, prompting the user to interact with the interface.

If the user selects an activity for editing, the system evaluates the "Activity type." If the activity is "Not sleep," the user can select another activity for editing. However, if the activity type is "Sleep," the system transitions to either "Day mode (edit state)" or "Night mode (edit state)" based on the current theme. This ensures that the application seamlessly switches between day and night themes while accommodating user interactions for editing activities. This design enhances user experience by providing context-aware interface adjustments and intuitive editing capabilities.

FIG. 22 discloses the priority-ordered notification schema implemented through Firebase Cloud Messaging. High-priority alerts (tier 1) trigger haptic feedback patterns and full-screen overlays for time-sensitive interventions like hydration reminders during intense activity. The system implements Markov chain-based suppression logic to prevent notification fatigue, dynamically adjusting delivery frequency based on historical user response rates stored in Redis cache clusters.

FIG. 23 shows an exemplary flowchart illustrating an AI coaching system, which utilizes Retrieval-Augmented Generation (RAG) techniques to provide personalized and context-aware coaching. The system begins by processing inputs, which can include various data sources such as user queries, documents, and contextual information. These inputs are then transformed into embedded queries using advanced models like Open AI's embedding API, which helps in understanding the semantic meaning of the queries. The embedded queries are used to retrieve relevant documents and information from a knowledge base. This retrieval process involves converting the queries into abstract representations in a high-dimensional space, considering factors like text similarity, style, and semantics. The retrieved documents are then augmented with additional context to ensure they align closely with the user's original query. The system generates responses based on the augmented information, ensuring clarity and diversity in the output. These responses are tailored to provide a personalized coaching experience, taking into account the user's specific needs and context. The flowchart also highlights the system's ability to interact with external interfaces, such as IOS and VoiceFlow, to implement an interactive approach and provide appropriate responses.

FIG. 24 shows a non-exercise activity thermogenesis (NEAT) calculation method that determines daily calorie needs based on individual factors such as hourly blood chemistry requirements, actual daily and previous days' workouts, and sleep patterns, rather than relying solely on daily totals for macronutrients. This method provides a more personalized and accurate estimation of calorie needs.

Figure 25B:
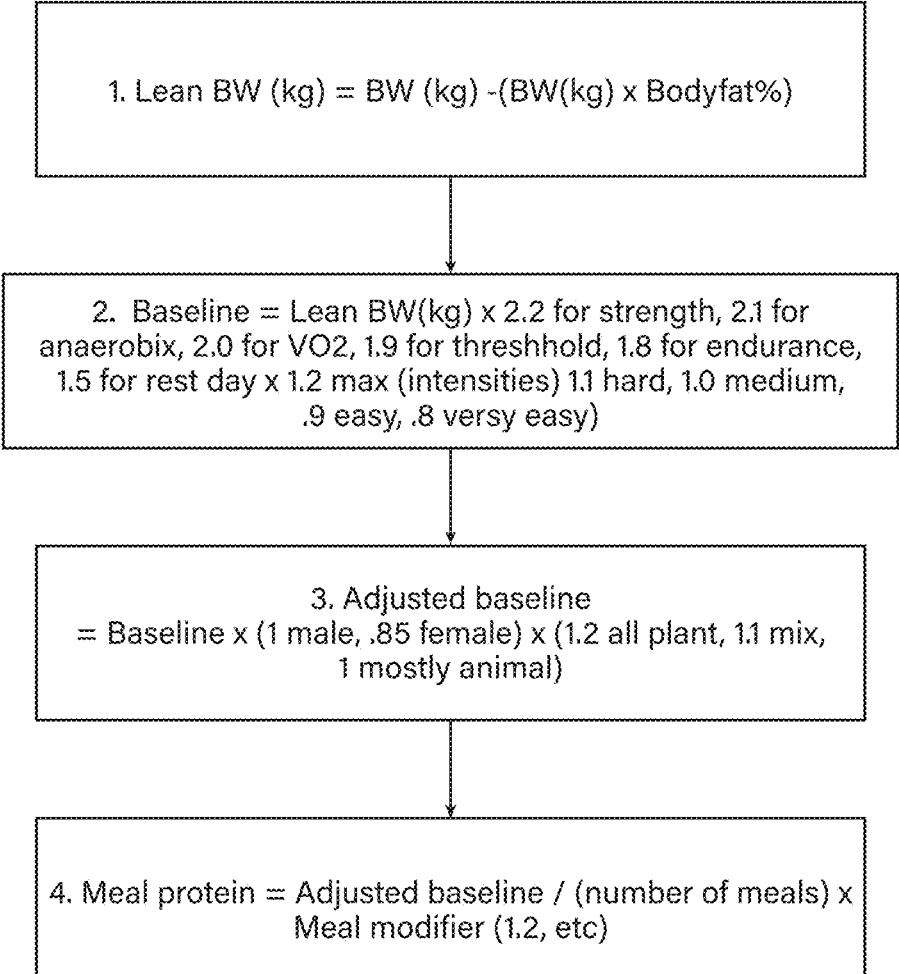

FIG. 25 details the protein requirement calculation incorporating lean body mass (derived from bioelectrical impedance analysis) multiplied by an activity-dependent coefficient (1.2-2.2 g/kg) adjusted for muscle protein synthesis rates predicted through nitrogen balance modeling.

FIG. 26 reveals the fat intake algorithm which provides a structured method for determining the appropriate amount of fat for each meal based on individual daily calorie needs and dietary goals.

Figure 27:
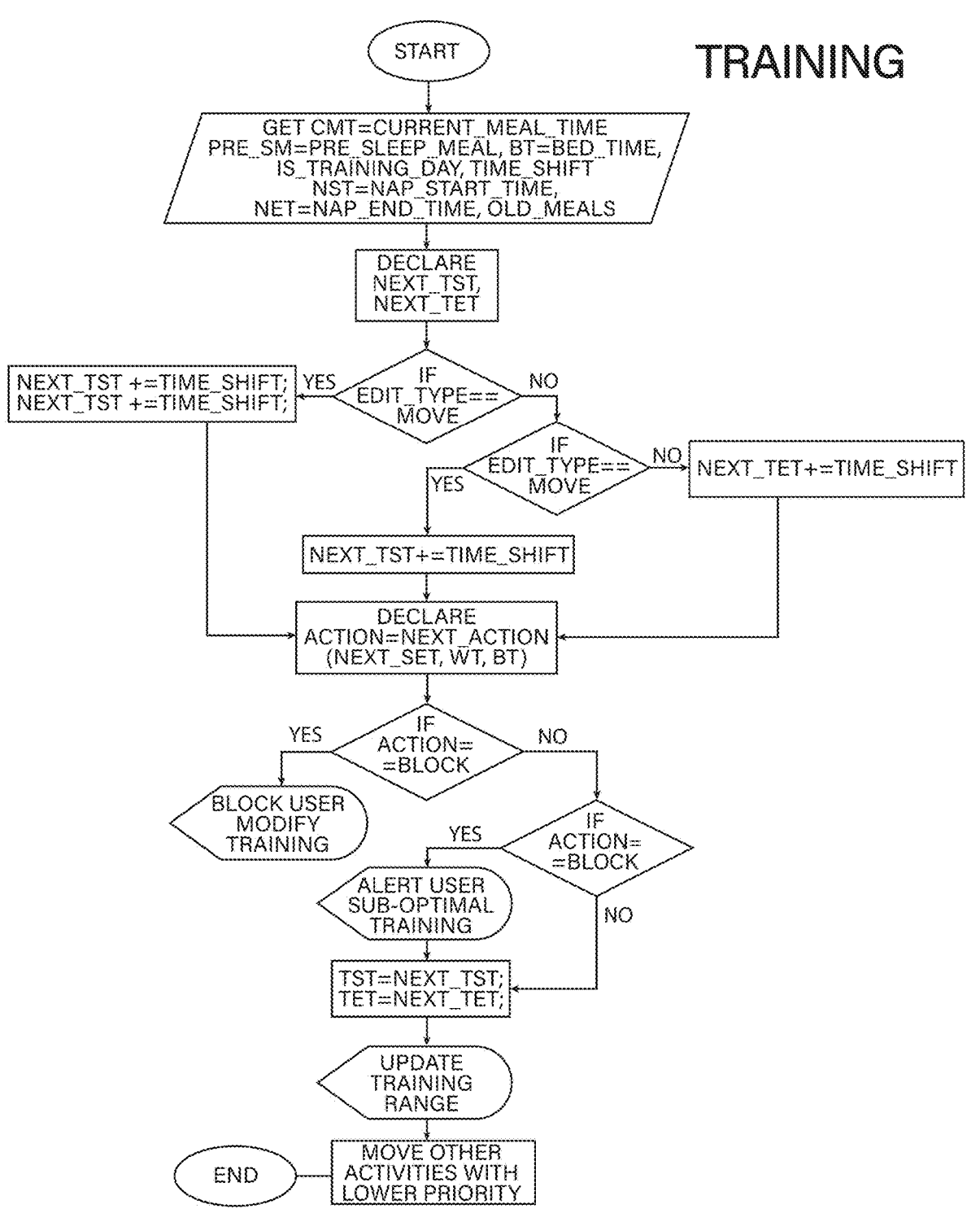
FIG. 27 shows a flowchart outlines a structured process for managing training based on meal timings, workload ratios, and user readiness.

FIG. 27 shows a flowchart outlines a structured process for managing training based on meal timings, workload ratios, and user readiness. It begins by retrieving data such as current meal time, relative meal time, and training parameters. The system checks if the next scheduled time aligns with the predefined time shift. If conditions are met, it evaluates actions like blocking or alerting the user based on acute/chronic workload ratios and readiness metrics (e.g., HRV). If the action is "BLOCK," training is modified to prevent overtraining; if "ALERT," the user is notified about suboptimal conditions. Training parameters are then updated, and lower-priority actions are processed. The flowchart also incorporates decision loops to ensure continuous monitoring and adjustment of training recommendations for optimal performance.

Figure 28A:
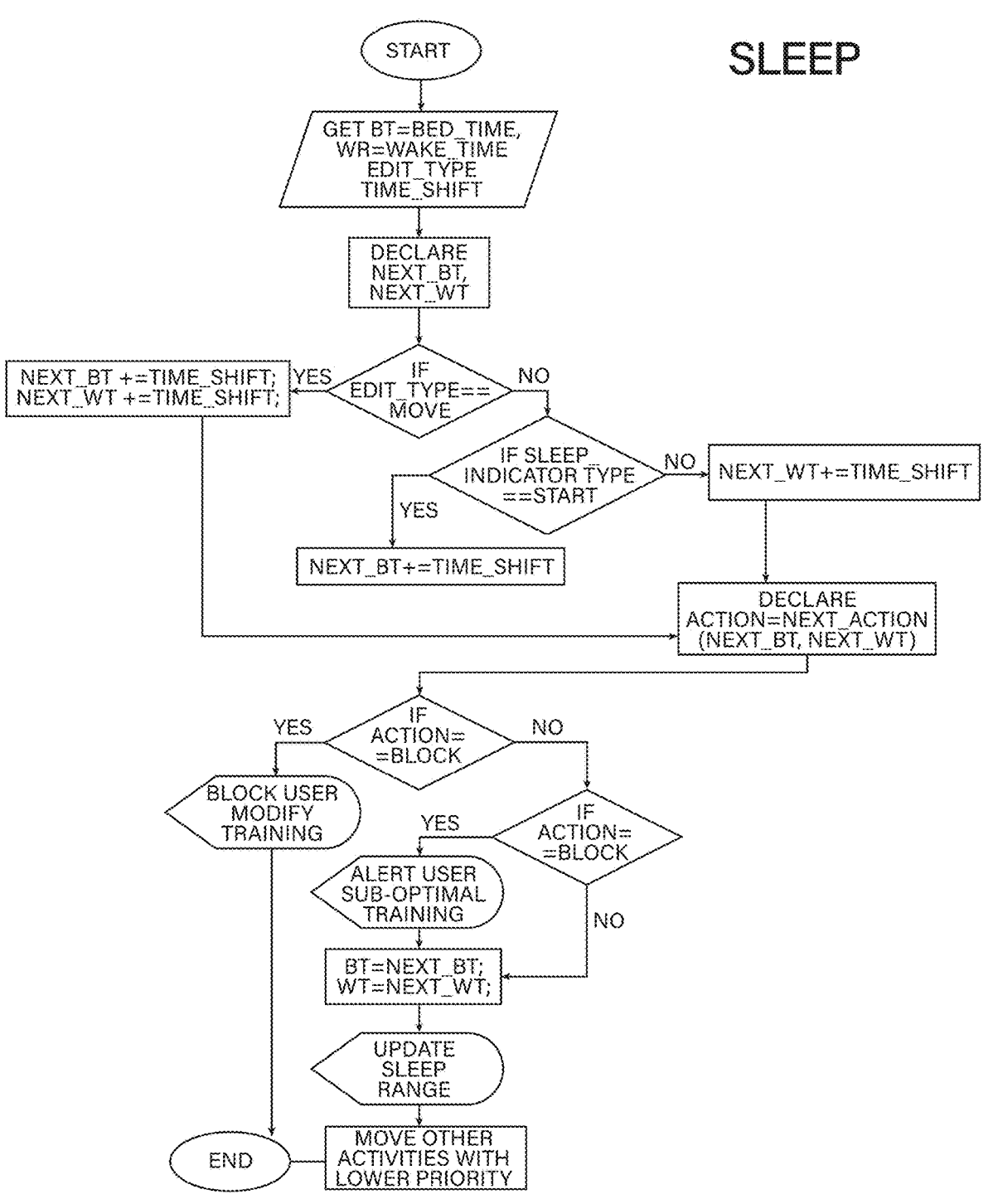
FIGS. 28A-28B show exemplary interface flowcharts of a sleep staging system to optimize sleep schedules by aligning them with circadian and ultradian rhythms.
Figure 28B:
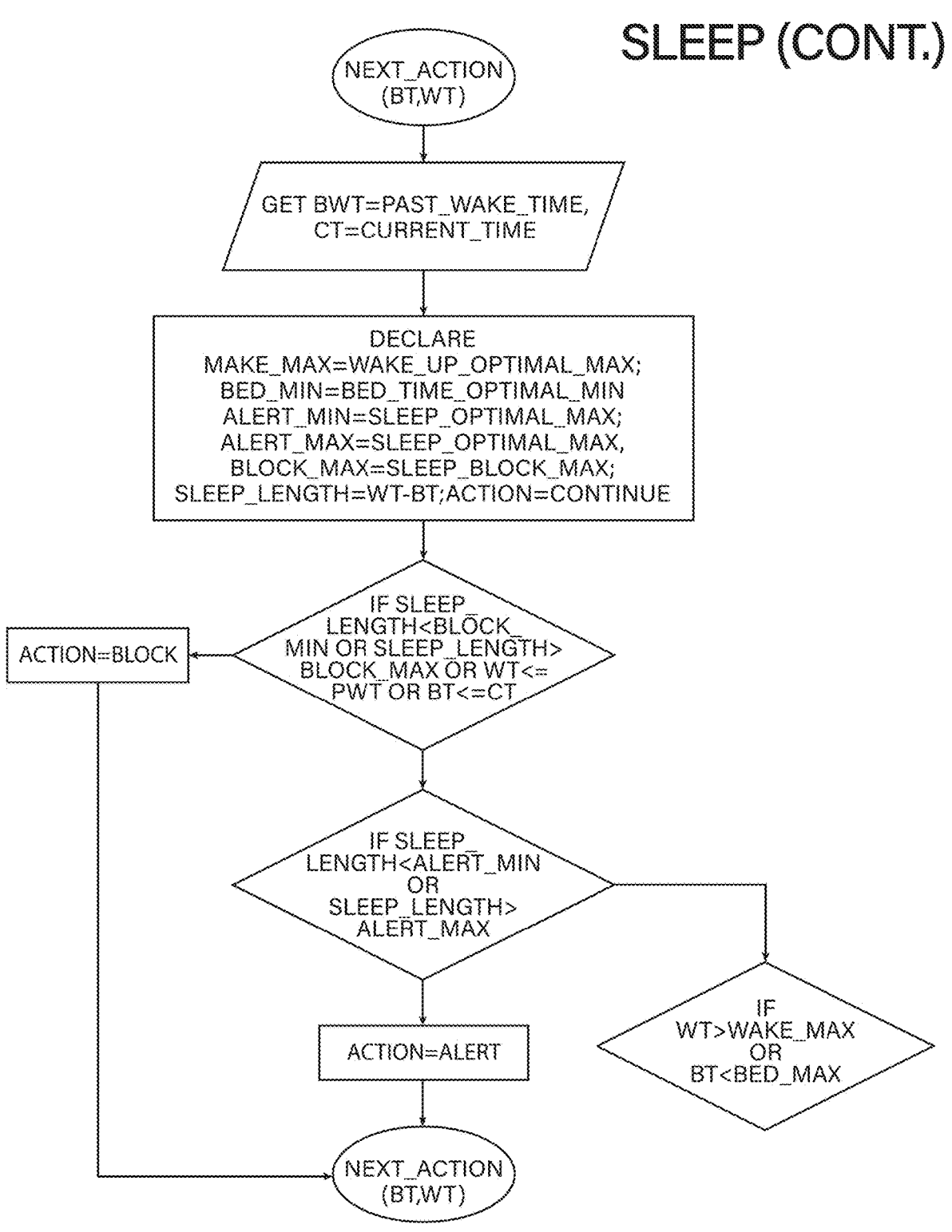

FIGS. 28A-B show exemplary interface flowcharts of a sleep staging system to optimize sleep schedules by aligning them with circadian and ultradian rhythms. FIG. 27A focuses on initial sleep scheduling, retrieving bedtime, wake time, and time shift values to define sleep intervals. It evaluates time alignment and sleep indicators to determine appropriate actions, such as blocking activities or alerting the user about suboptimal conditions, subsequently updating the sleep range and reorganizing lower-priority tasks. FIG. 27B monitors sleep stages by using past wake time and current time to evaluate sleep duration against defined thresholds, deciding whether to block activity or alert the user, and ultimately adjusting wake time or bedtime based on updated metrics. Together, these flowcharts aim to balance restorative sleep cycles with daily routines, ensuring optimal sleep quality and alignment with natural biological rhythms.

Figure 29:
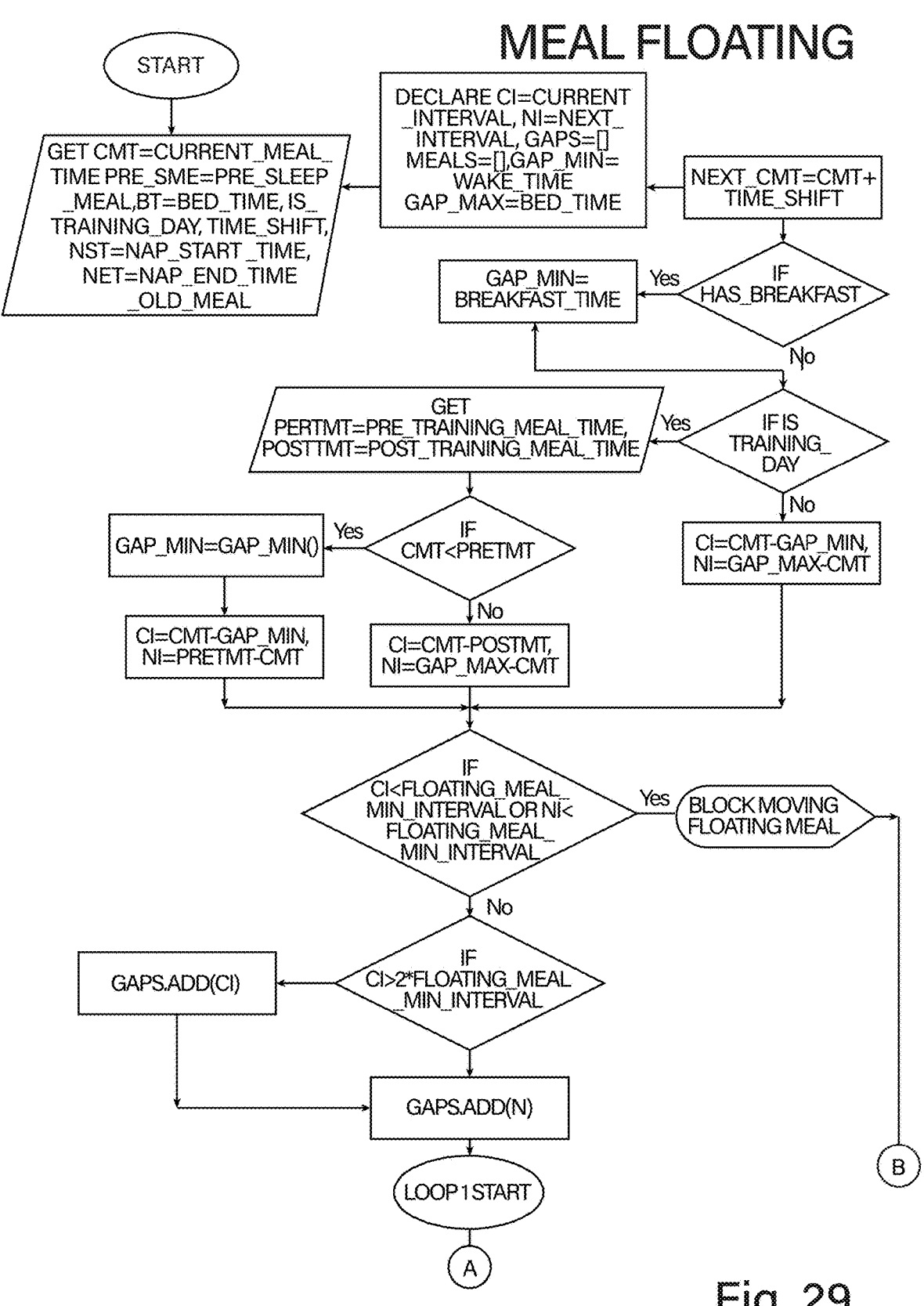
FIG. 29 shows an exemplary meal-floating interface flowchart.
Figure 29:
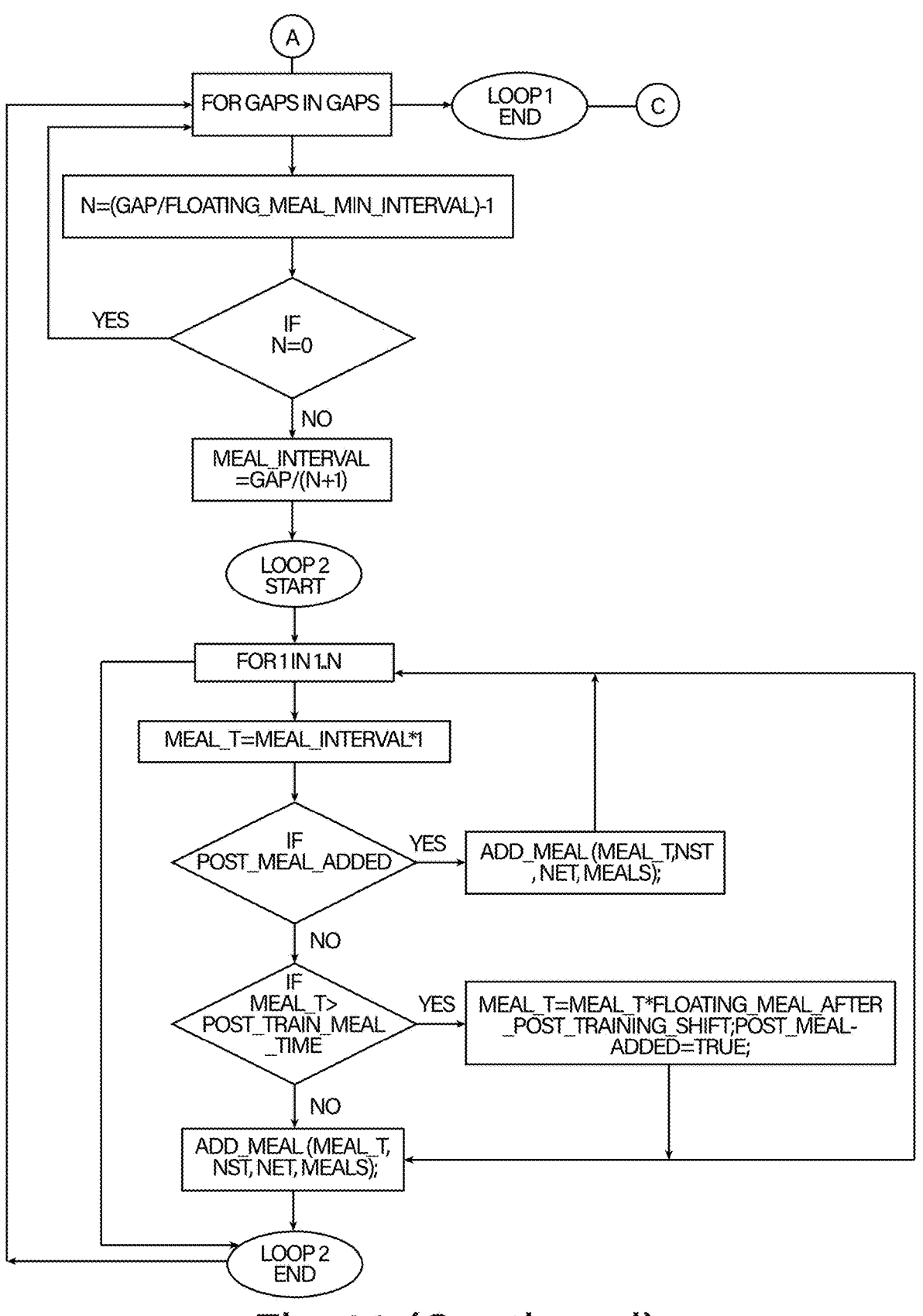
Figure 29:
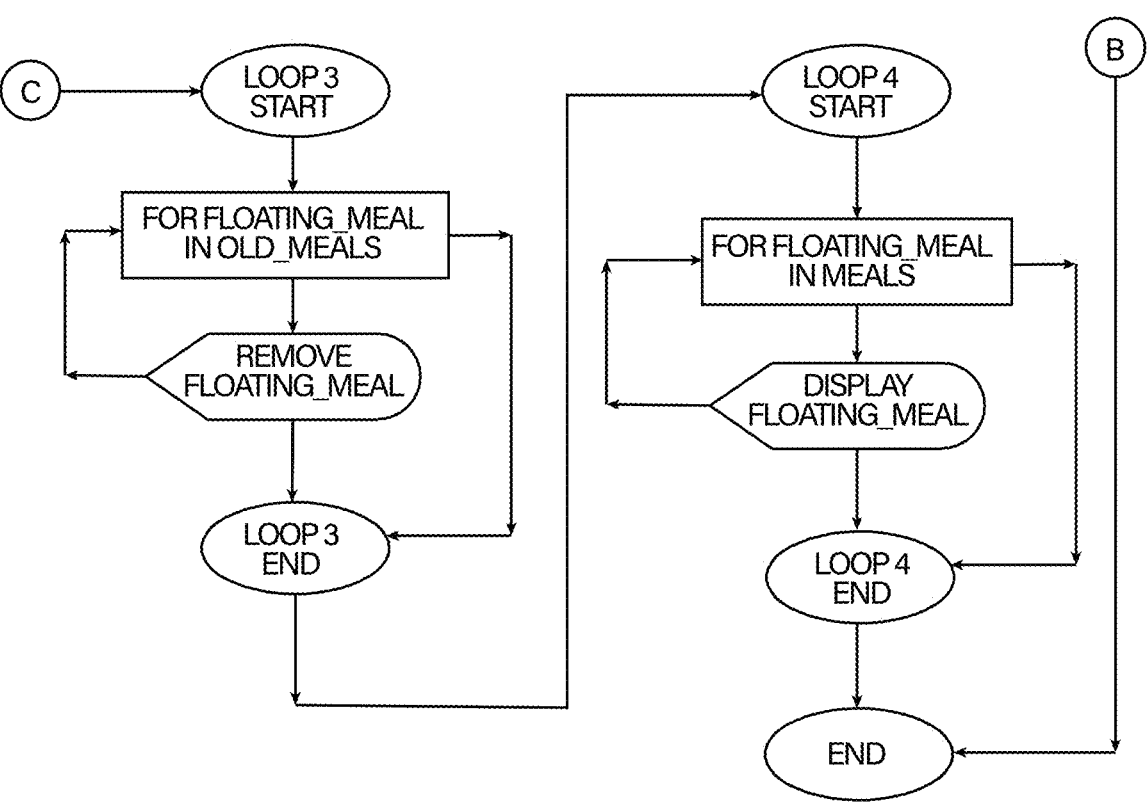
Figure 29:
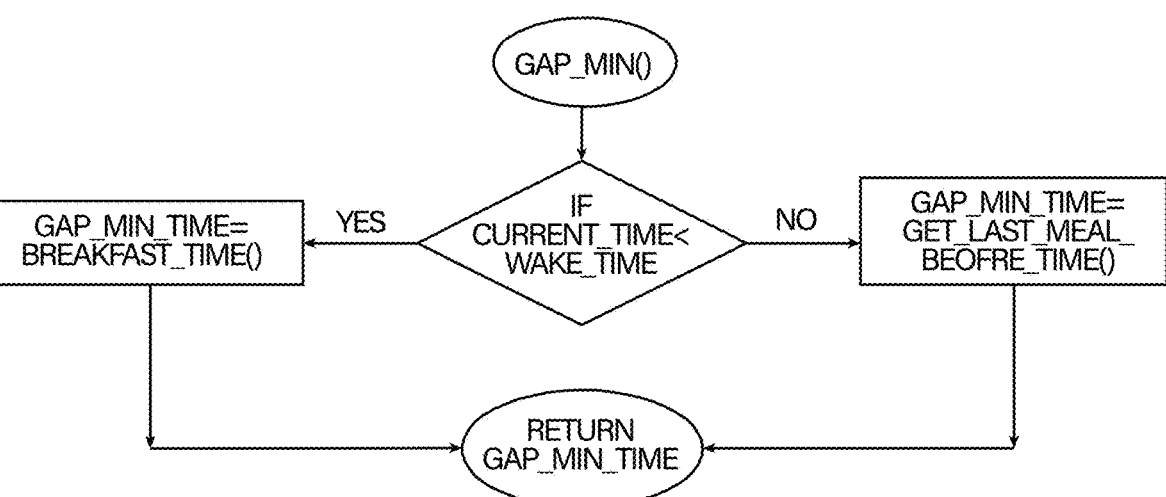

FIG. 29 shows an exemplary interface meal-floating flowchart. It initiates by retrieving essential parameters, including the current meal time, relative meal time, and any time shift values necessary for adjustments. It calculates and defines various meal-related intervals, such as breakfast time, to synchronize meal events. Next, it evaluates if the current conditions warrant a shift in meal timing based on internal parameters, possibly considering factors like alertness and readiness. If a shift is necessary, the system determines the appropriate adjustment, either blocking certain actions or alerting the user about suboptimal timing conditions. The process proceeds through multiple loops, adjusting parameters for different days and meal occurrences, continuously refining the meal schedule to align with the user's readiness and internal states. Subsequently, the flowchart evaluates parameters against defined thresholds and dynamically updates meal amounts and timing to optimize the meal schedule. The meal-floating process involves fine-tuning and looping through configurations until reaching a refined state.

Figure 30:
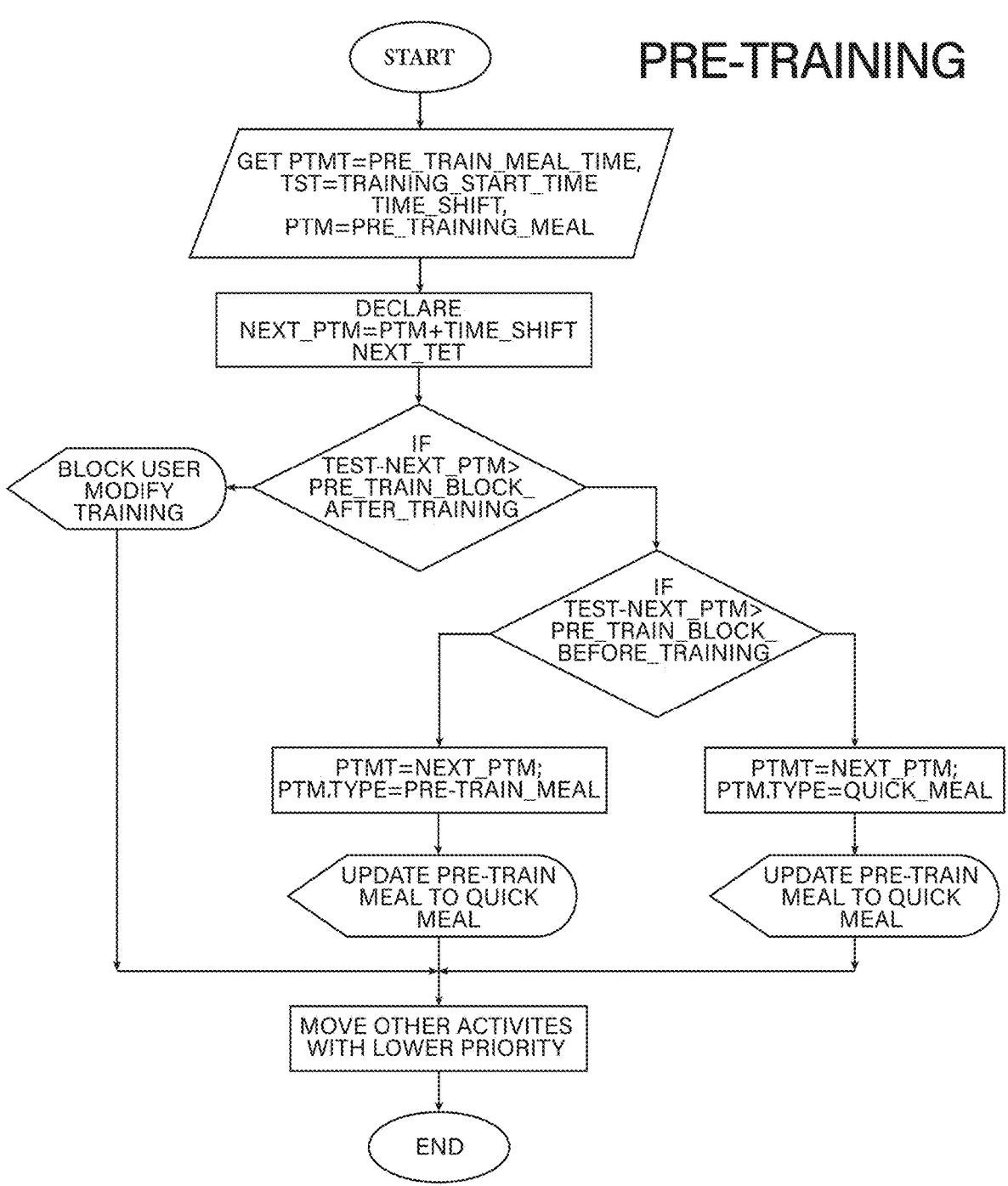
FIG. 30 shows an exemplary pre-training interface flowchart.

FIG. 30 shows an exemplary pre-training interface flowchart. It begins by gathering essential variables such as the pre-training meal time (PTMT), training start time (TST), time shift, and defining the pre-training meal itself (PTM). It then declares and calculates the next pre-training meal time (NEXT_PTM) by adding the time shift to the current pre-training meal time and calculates a next training evaluation time(NEXT TET). Next, the flowchart evaluates whether the training start time (TST) aligns with the next pre-training meal time (NEXT_PTM); if they do not align, it checks if TST is NEXT to PTM for pre-training blocking before training. If true it will update the pre-training meal to a quick meal. Once it identifies any discrepancies, the system considers blocking the user or modifying the training schedule to prevent conflicts. The process proceeds to update the pre-training meal to a quick meal, considering the adjusted circumstances. Finally, the flowchart involves moving other activities with lower priority and concludes the pre-training optimization process.

Figure 31:
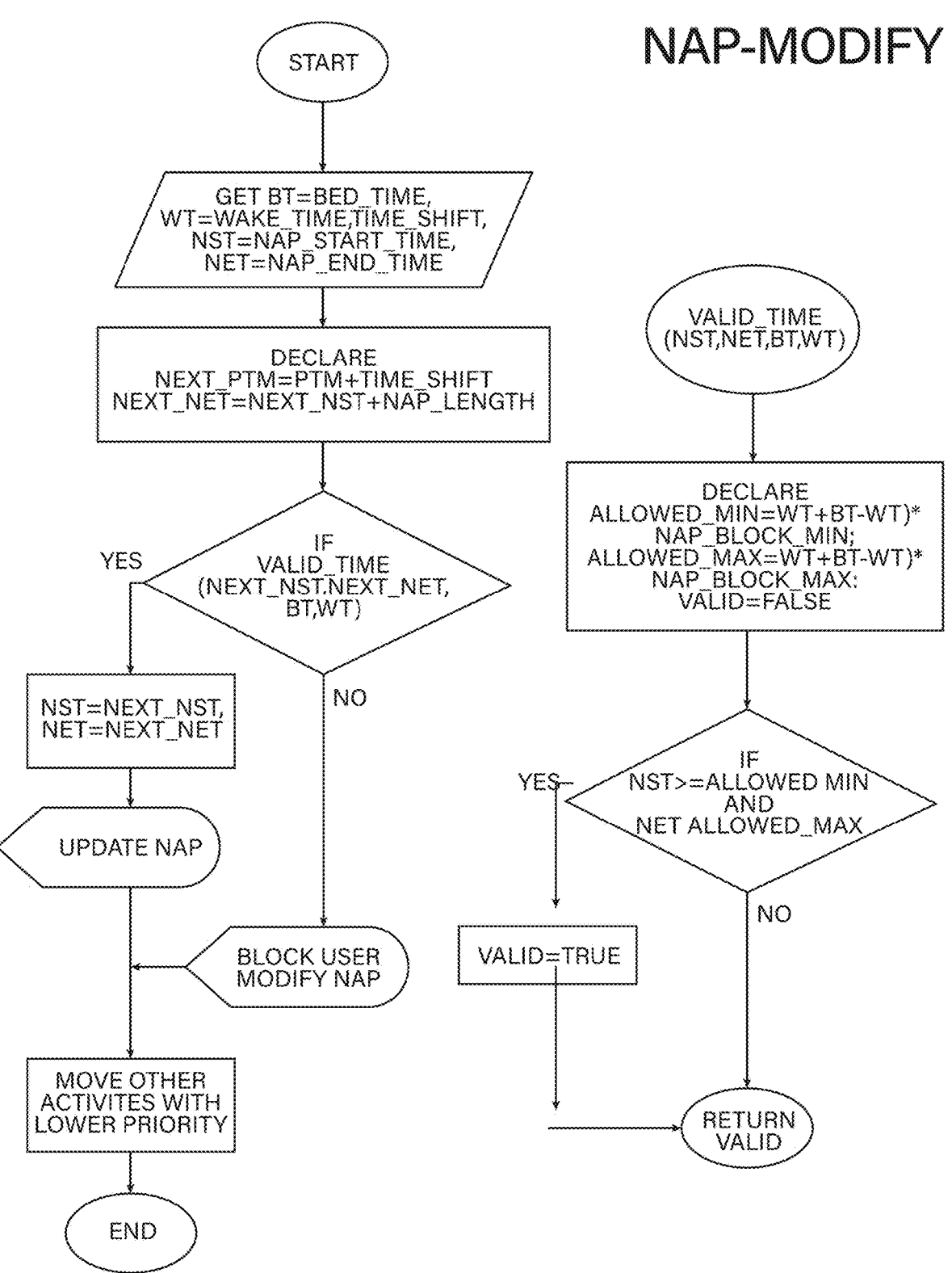
FIG. 31 shows an exemplary nap modification interface flowchart.

FIG. 31 shows an exemplary nap modification interface flowchart The first "NAP-MODIFY" flowchart starts by initializing variables such as bedtime (BT), wake time (WT), time shift, nap start time (NST), and net nap end time (NET).

It declares the next potential meal time (NEXT_PTM, unclear relation to nap) using the time shift, alongside NEXT_NET calculated by adding the nap length to NEXT_NST. The flowchart then validates whether the next nap and net times (NEXT_NST, NEXT_NET) are valid within the range of bedtime and wake time. Depending on the validation result, it updates the nap start and end times by setting NST to NEXT_NST and NET to NEXT_NET and subsequently updating the nap schedule; otherwise, the user is blocked and the nap is modified. Finally, lower-priority activities are moved to accommodate the nap schedule, and the process ends. The second "NAP-MODIFY" flowchart assesses nap validity by checking if a time (NST .NET, BT, WT) is valid. It declares allowed minimum and maximum nap times based on the difference between wake time and bedtime, multiplied by NAP_BLOCK_MIN/MAX, and sets validity initially to FALSE. If the next nap start time is greater than the allowed minimum AND the net nap end time is less than the allowed maximum, it sets the validity to TRUE. Ultimately, the flowchart returns whether the nap is considered valid or not based on these constraints.

Figure 32:
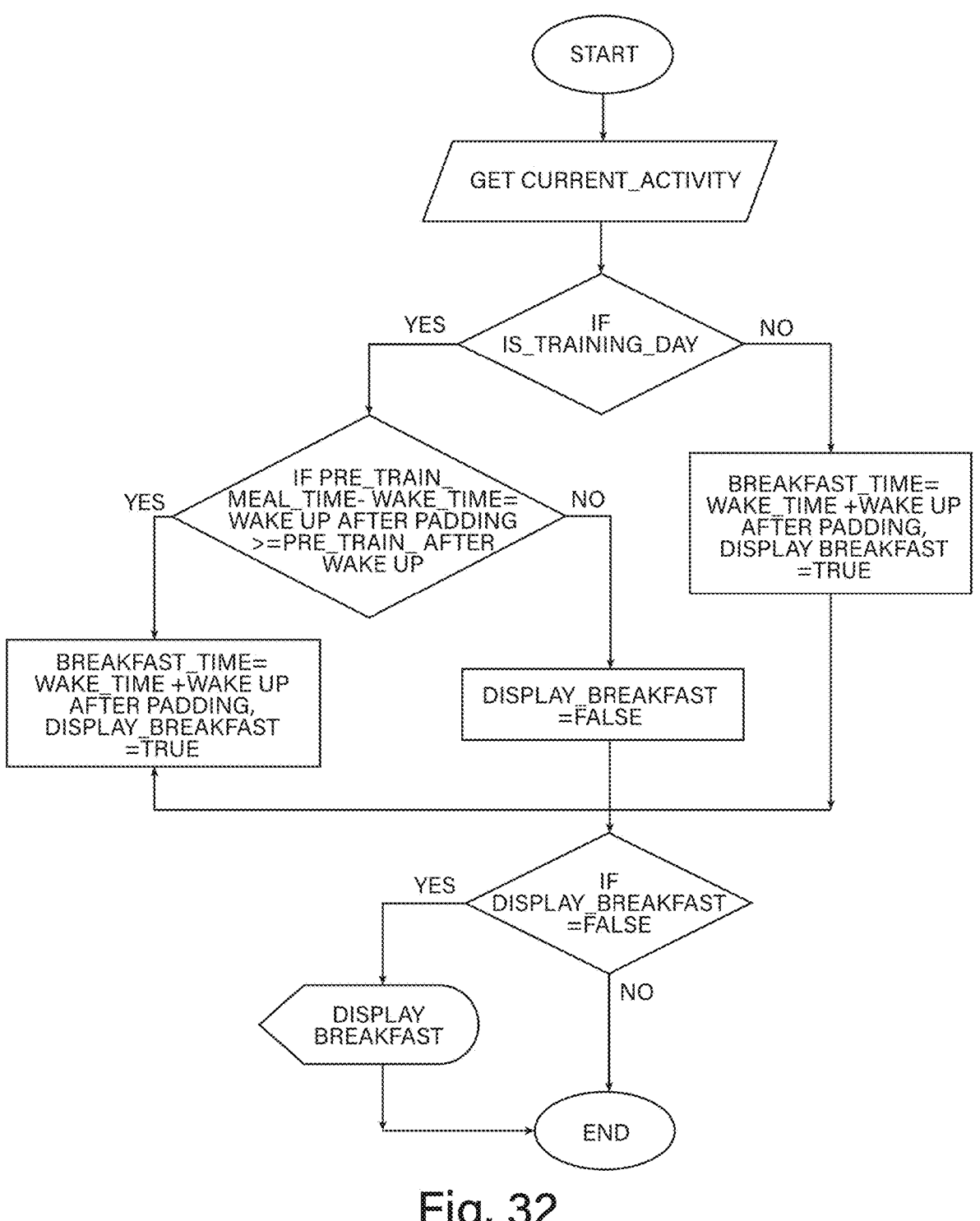
FIG. 32 shows an exemplary breakfast interface flowchart.

FIG. 32 shows an exemplary breakfast interface flowchart The breakfast flowchart begins by retrieving the current activity. A decision is made: Is it a training day? If "Yes", a comparison is made between pre-training meal time and wake time+wake up after padding against pre-training after wake-up. If the pre-training meal criteria are met, the breakfast time is set to wake time+wake up after padding, and the display breakfast flag is set to true. If it's not a training day (No), or if the pre-training meal criteria are not met (No), the breakfast time is also set to wake time+wake up after padding, and the display breakfast flag is set to true or the display breakfast flag is set to false. Finally, the flowchart checks if the "Display Breakfast" flag is false. If it is (Yes), breakfast is not displayed; if it's not (No), breakfast is displayed, and the process ends.

Figure 33:
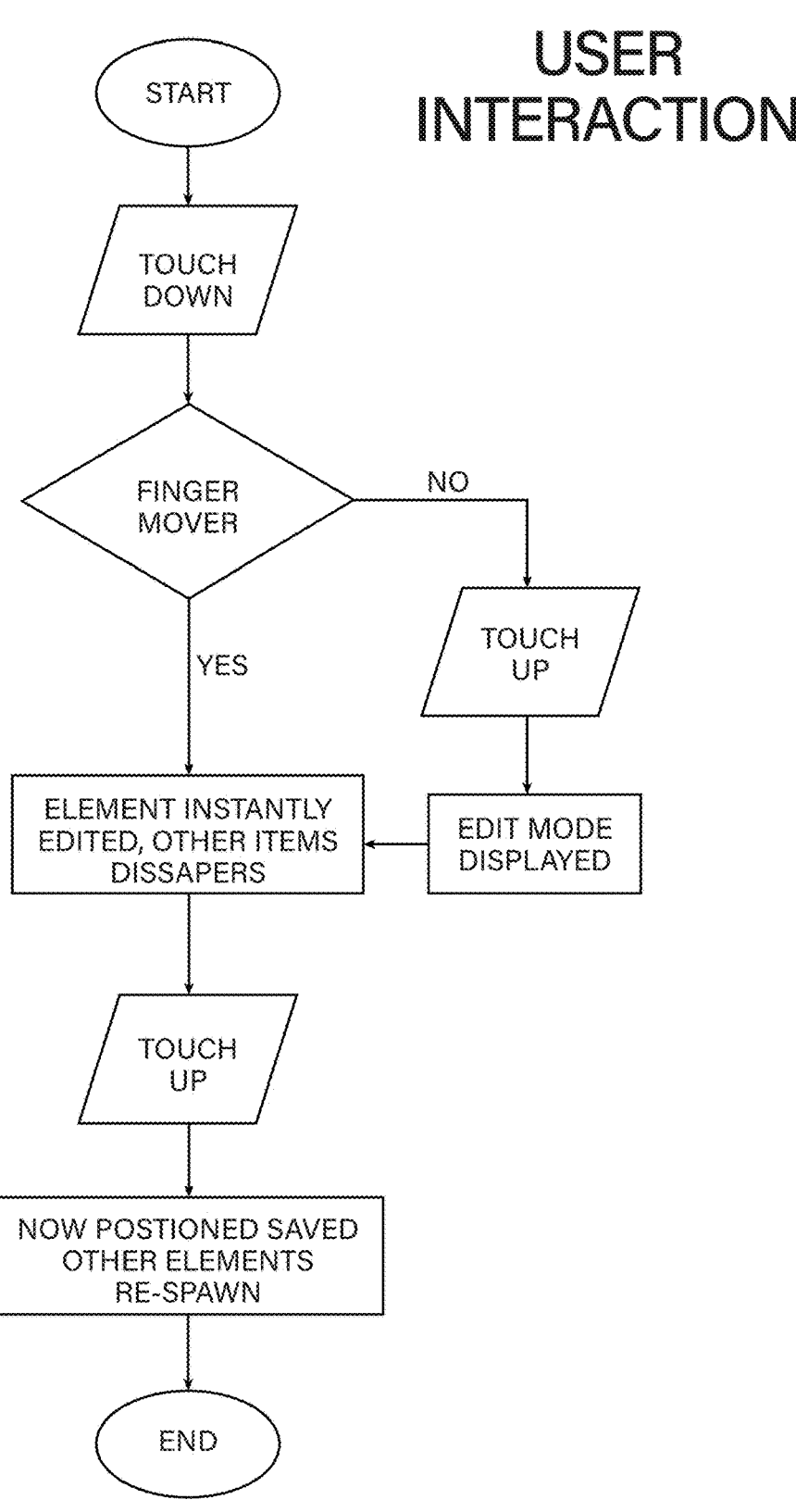
FIG. 33 shows an exemplary flowchart showing a user interaction interface flowchart.

FIG. 33 shows an exemplary flowchart showing a user interaction interface flowchart. The process initiates with a "START" point, followed by a "TOUCH DOWN" event, indicating the user's finger touching the screen. A decision point follows: "FINGER MOVED?". If the finger has not moved ("No"), the system registers a "TOUCH UP" event and displays an "EDIT MODE". If the finger has moved ("Yes"), the "ELEMENT" under the touch is instantly edited, while other items disappear from view, this is followed by the "TOUCH UP" event. Finally, the new position of the edited element is saved, and the other elements re-spawn on the screen, concluding the process with an "END" point.

Figure 34:
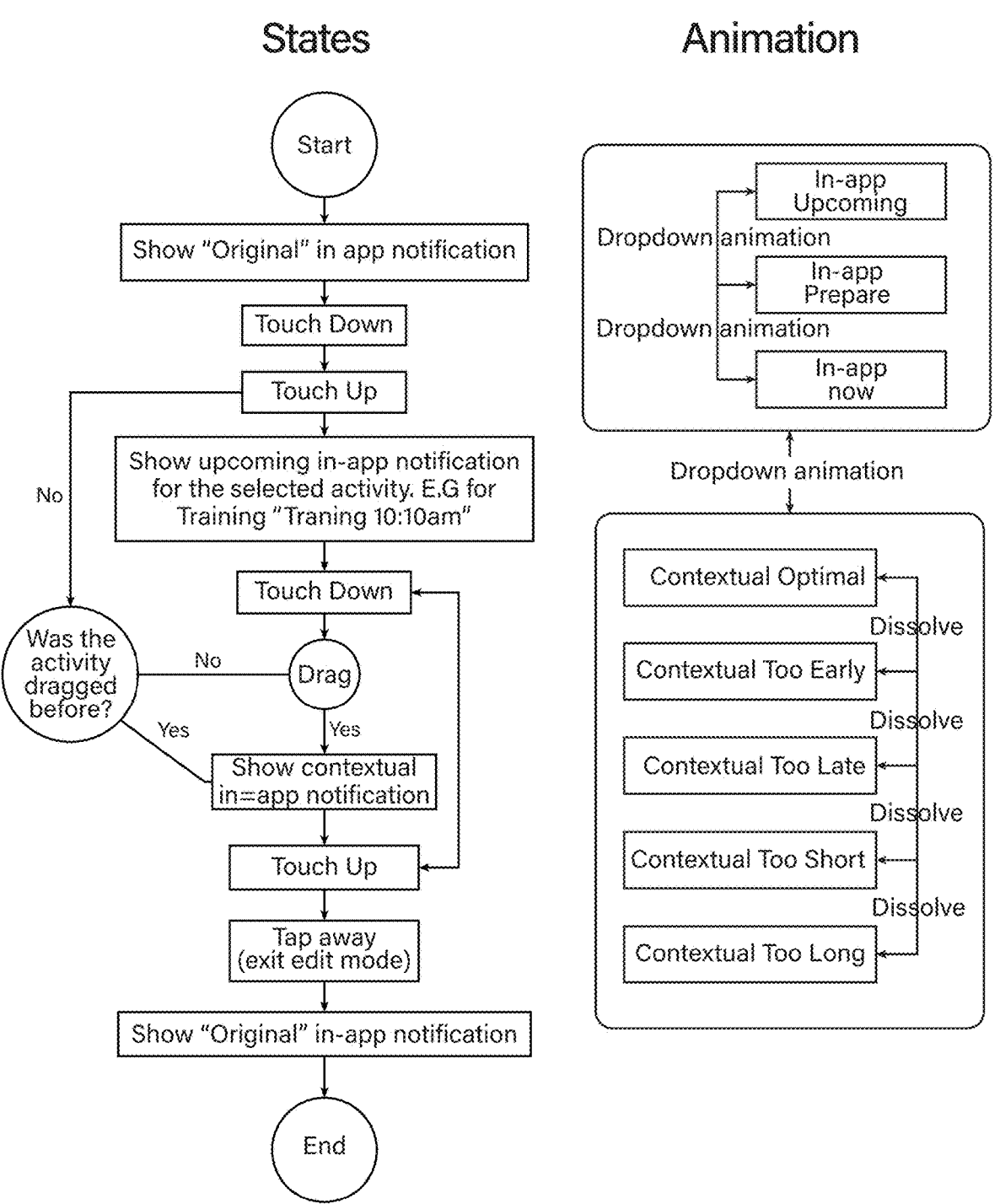
FIG. 34 outlines the interaction flow for a wearable clock device, detailing how in-app notifications respond to user actions with contextual feedback and animations to guide the user.

FIG. 34 shows the interaction flow for a wearable clock device, detailing how in-app notifications respond to user actions like tapping or dragging activities, with contextual feedback and animations to guide the user through activity selection, editing, and mode transitions "States" and "Animation" flowcharts. The "States" flowchart begins with a "START" state, which shows the "Original" in-app notification. Upon "TouchDown" and then "TouchUp," the flowchart displays an upcoming in-app notification for the selected activity (e.g., "Training 10:10 am"). Another "TouchDown" event triggers a check: "Was the activity dragged before?". If "No," the flowchart checks if the action is a "Drag". If "Yes" (activity dragged or activity tapped again), it shows a contextual in-app notification. A "TouchUp" event then leads to "Tap away (exit edit mode)", reverting to showing the "Original" in-app notification, and ending the process. If the Drag is No, the flowchart loops back to the Touch Up event. The "Animations" flowchart depicts a sequence of in-app animations. Beginning with "In-app Upcoming", a "Dropdown" animation transitions to "In-app Prepare", followed by another "Dropdown" animation leading to "In-app now". Subsequently, a "Dropdown" animation connects to a loop of contextual states: "Contextual Optimal," "Contextual Too Early," "Contextual Too Late," "Contextual Too Short," and "Contextual Too Long." Each state transitions to the next via a "Dissolve" animation, creating a cycle of contextual feedback.

Figure 35:
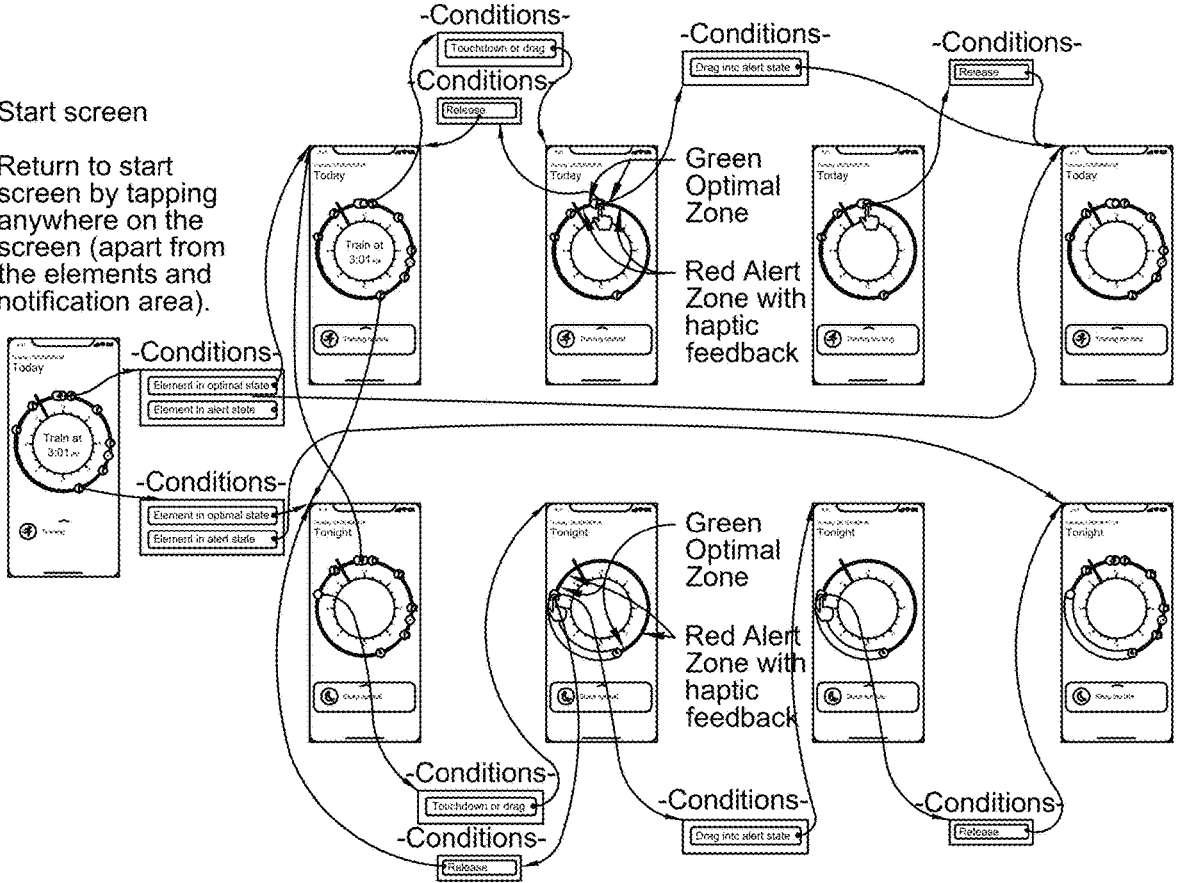
FIG. 35 illustrates an app interface designed to provide feedback based on user interactions.

FIG. 35 illustrates an app interface designed to provide feedback based on user interactions. The interface employs the Green Optimal Zone and the Red Alert Zone, which guide users in managing their activities effectively. Users can drag activities into different zones on the circular interface. Depending on where an activity is placed, the app provides feedback, such as visual cues (e.g., highlighting the zone) or tactile responses like haptic feedback. When an activity is placed in the Green Optimal Zone, the app confirms this placement with positive reinforcement, indicating that the activity aligns with optimal conditions. If an activity is dragged into the Red Alert Zone, the app issues a warning, often accompanied by haptic feedback, to alert users that this placement may lead to suboptimal outcomes. Users can return to the start screen by tapping anywhere outside of interactive elements and notifications. This ensures seamless navigation while maintaining focus on task prioritization.

Figure 36:
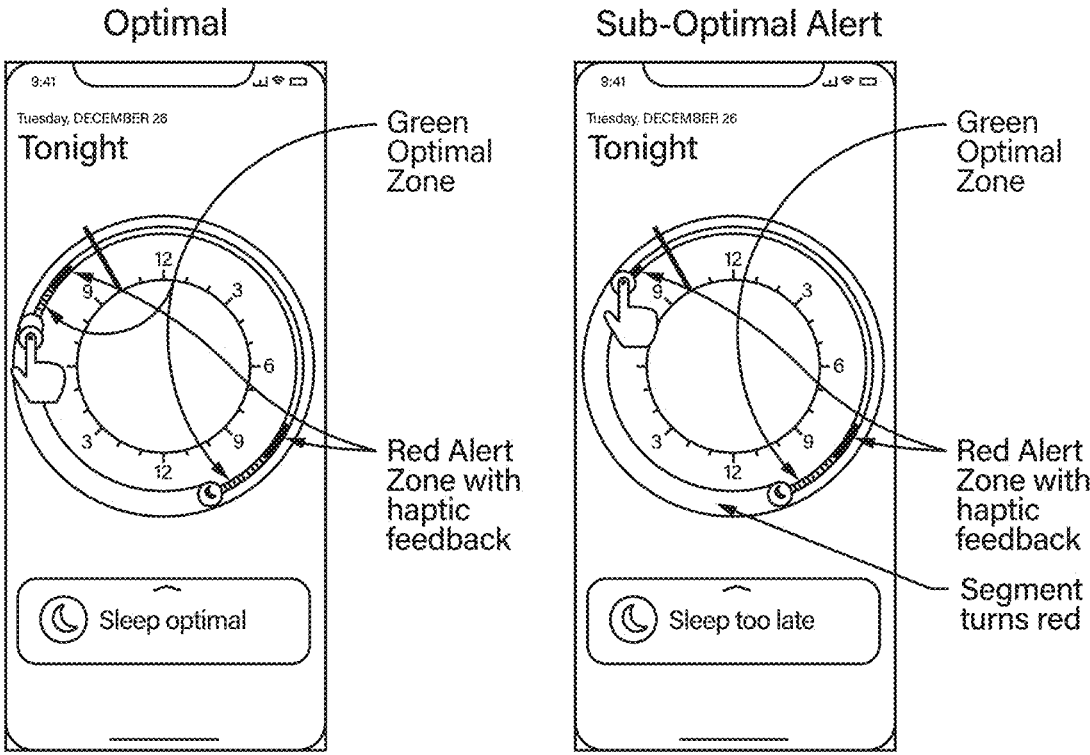
FIG. 36 shows an interface that visually represents sleep activity in the Optimal and Sub-Optimal Alert states.

FIG. 36 shows an interface that visually represents sleep activity in two distinct states: Optimal and Sub-Optimal Alert. The design uses a circular timeline to map bedtime and waketime, providing users with clear feedback on their sleep scheduling. In the Optimal state, the bedtime falls within the Green Optimal Zone, which is visually highlighted on the circular interface. The app displays a confirmation message, such as "Sleep optimal," reinforcing that the selected bedtime aligns with recommended sleep patterns. The interface remains neutral, without any alerts or warnings. When the bedtime is set too late, it moves into the Red Alert Zone which is in the sub-optimal state. This zone is visually marked with red segments on the circular timeline to indicate a deviation from optimal sleep conditions. The app provides haptic feedback to draw the user's attention to the issue and displays a warning message, such as "Sleep too late.". The red segment serves as a clear visual cue for the alert state, prompting users to reconsider their bedtime for better alignment with optimal sleep ranges.

Figure 37:
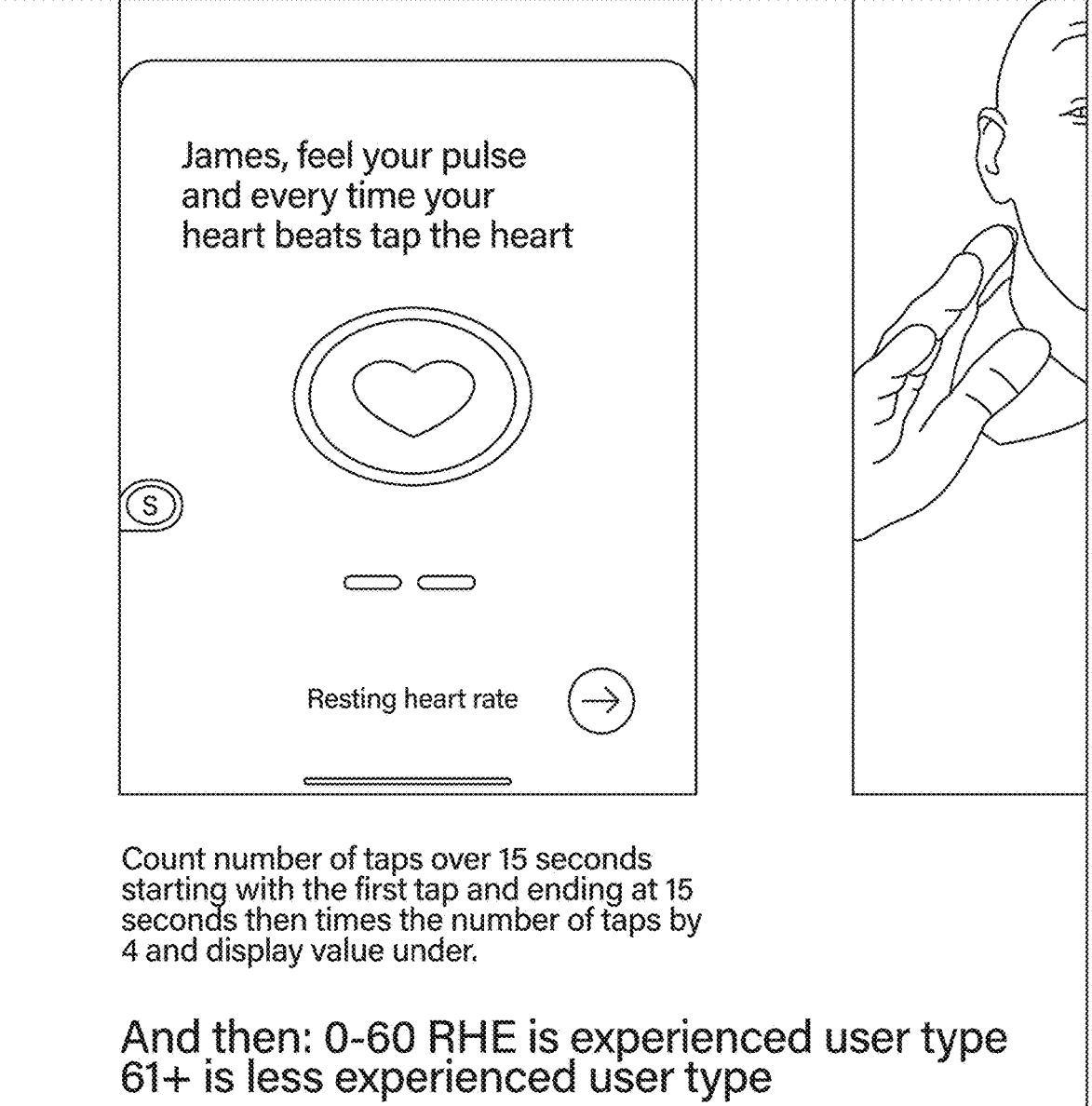
FIG. 37 shows a health dashboard interface that integrates a manual input feature for resting heart rate (RHR) alongside sensor fusion techniques.

FIG. 37 shows a health dashboard interface that integrates a manual input feature for resting heart rate (RHR) alongside sensor fusion techniques, enhancing accessibility for users without wearable devices. Users can tap a "Calculate RHR" button to input their RHR manually, which is then used to inform the goal body composition calculator. This calculator estimates the time required to achieve body composition goals, such as muscle gain or fat loss, by considering RHR as a proxy for recovery status and cardiovascular fitness. The system dynamically adjusts goal timelines based on RHR trends, extending timelines if elevated RHR indicates overtraining. The interface features a central dial displaying RHR against optimal zones, a body composition panel showing goal progress, and anomaly alerts for inconsistencies between manual RHR entries and activity logs. The one embodiment gathers data from the user which includes metrics related to exercise, sleep parameters, and nutrition information. Exercise metrics are sourced from a range of avenues like wearable sensors, mobile applications, or by manual input and comprise parameters showcasing the length, intensity, frequency and variety of physical activity undertaken by the user. Sleep data is similarly acquired through apparatus or manually entered input and could include details such as duration of sleep, quality levels of rest, different stages of sleep cycles and other relevant variables. The specifics regarding dietary intake are collected via platforms for food logging or automated systems for tracking nutritional habits, presenting insights into calorie intake, composition of meals and time markers for eating.

Figure 38:
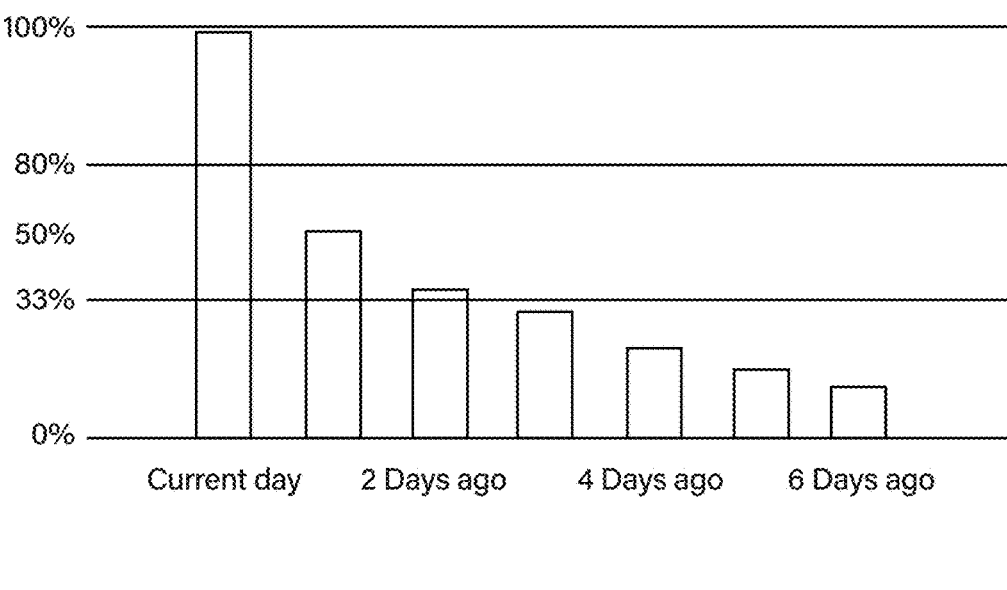
FIG. 38A shows a programmatically generated AI meal recommendation system.
FIG. 38B illustrates a daily meal and nutrient timing interface, dynamically adjusted based on user behavior and metabolic needs.
FIG. 38C illustrate the LIVE SCORE™ methodology, which employs Biological Regression Scoring (BRS™) technology.
Figure 38A:
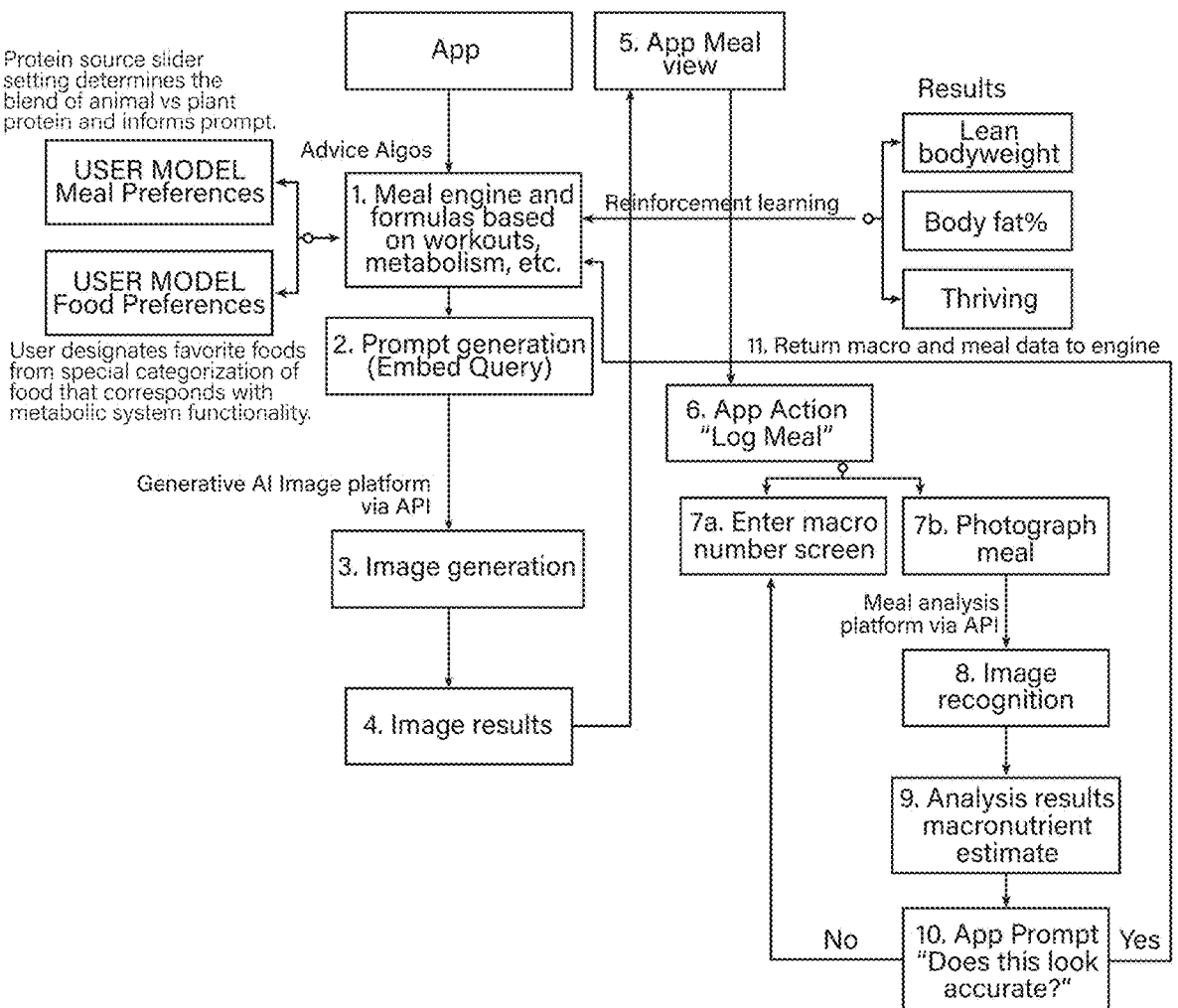

FIG. 38A illustrates a computer-implemented system for generating AI-driven visual meal recommendations based on macronutrient profiles and adaptive user feedback. The system begins by programmatically determining protein sources (animal vs. plant-based) and incorporating user food preferences, which are categorized for metabolic functionality. The User Model captures meal preferences and integrates them into Advice Algos, a set of algorithms that generate meal recommendations based on workouts, metabolism, and other health data. These algorithms create prompts for generative AI (e.g., Runway API) to produce realistic meal images that visually represent macronutrient targets (protein, carbs, fats, water, etc.). Users interact with the system through an App Meal View, where they can log meals manually or via photo uploads. The system employs AI image recognition to estimate macronutrients and prompts the user to verify accuracy. Discrepancies between recommended and actual intake feed into a Reinforcement Learning loop, refining future recommendations based on progress toward body composition goals (e.g., lean body weight, fat percentage). This closed-loop system bridges nutritional science and intuitive visual guidance, enhancing compliance and engagement.

Figure 38B:
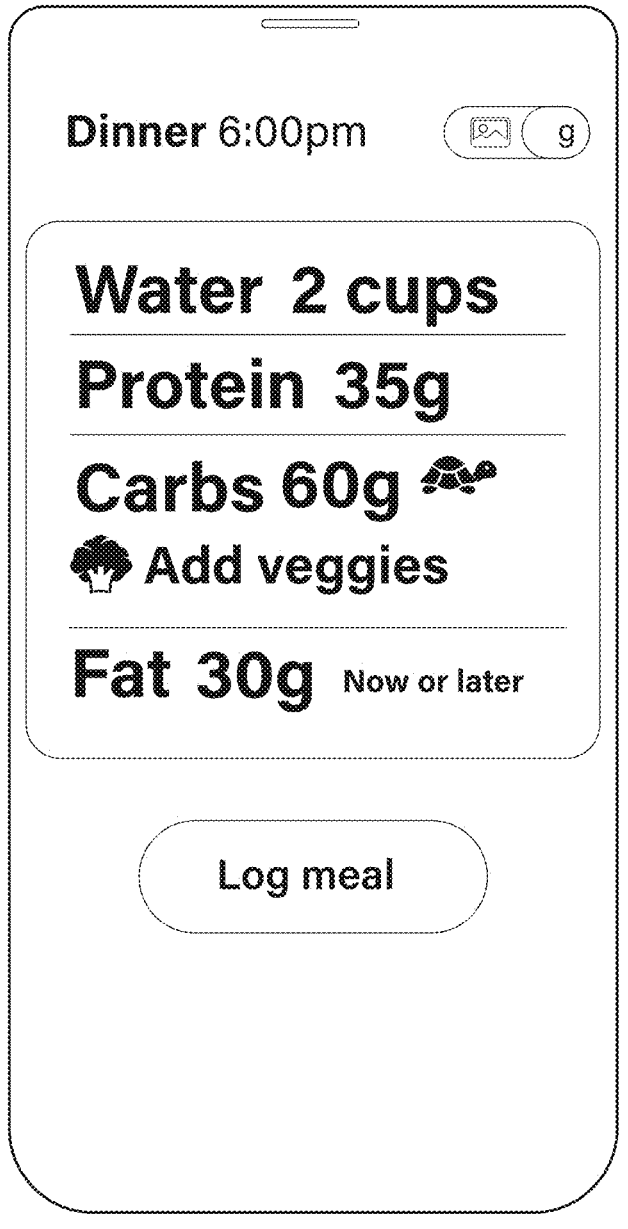

FIG. 38B demonstrates the real-time application of the meal recommendation system within a daily schedule. The interface displays timed nutritional directives (e.g., *"8:59 Protein+80 g Slower Carbs"*) and contextual prompts (e.g., "Add veggies" to modulate digestion speed). Users log meals via the "Log Meal" action, triggering either manual entry or AI-powered photo analysis. The system dynamically adjusts recommendations (e.g., fat intake timing) based on user behavior and reinforces goals like hydration ("Water 2 cups"). This FIG. highlights the seamless integration of AI-generated meal planning into a structured daily routine, emphasizing adaptability and user control.

Figure 38C:
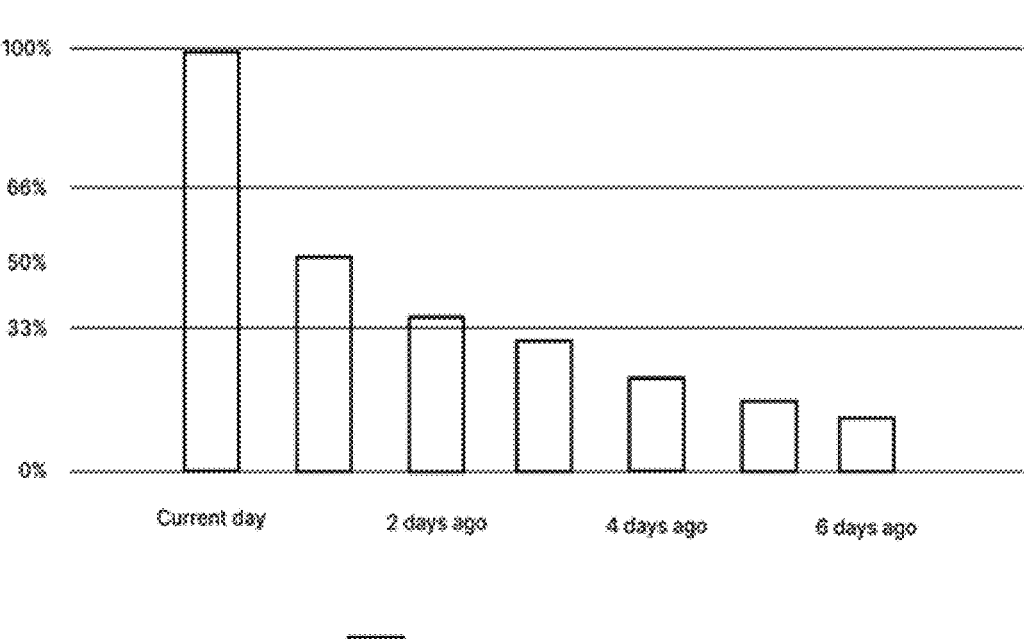

FIG. 38C illustrates the LIVE SCORE™ methodology, which employs Biological Regression Scoring (BRS™) technology. The score is based on the premise that as actions/events recede in time, they have less influence on the user current state. A method for calculating macronutrient requirements using a biological temporal regression weight is disclosed. In one embodiment, the method begins by acquiring data related to past biological stressor events. Such data include information on both the magnitude and the timing of each event. The collected data can be sourced from user inputs via an intuitive interface or from wearable devices and other sensors that monitor physical activity and potentially other stressors. Each of the identified stressor events is then associated with a biological temporal regression weight that is determined based on the recency of the event. M ore recent stressor events are assigned higher weights, while the weight decreases as the event recedes further into the past. In operation, the meal calculator updates macronutrient requirements on a daily basis. As new data is acquired and processed, the regression weights influence the recalculations of macronutrient needs without requiring direct user intervention for each update. Additionally, suggested meal plans based on these dynamically calculated macronutrient requirements are displayed to the user, thereby providing practical dietary guidance. Historical data on stressor events and the associated regression weights is stored, permitting comparative analysis over time and supporting revisions to the calculation methodology as necessary. A BTRW (biological temporal regression weight) can be used to inform the meal calculator for macronutrients based on a past affective event/stressor (like hard weight workout 2 days ago for example) then this is used to add to protein requirements to promote healing with the correct calculation.

Figure 39A:
FIG. 39A-39B are a scheduling interface integrating workouts, meals, and recovery periods, synchronized with user-specific goals and preferences.
Figure 39A:
Figure 39A:
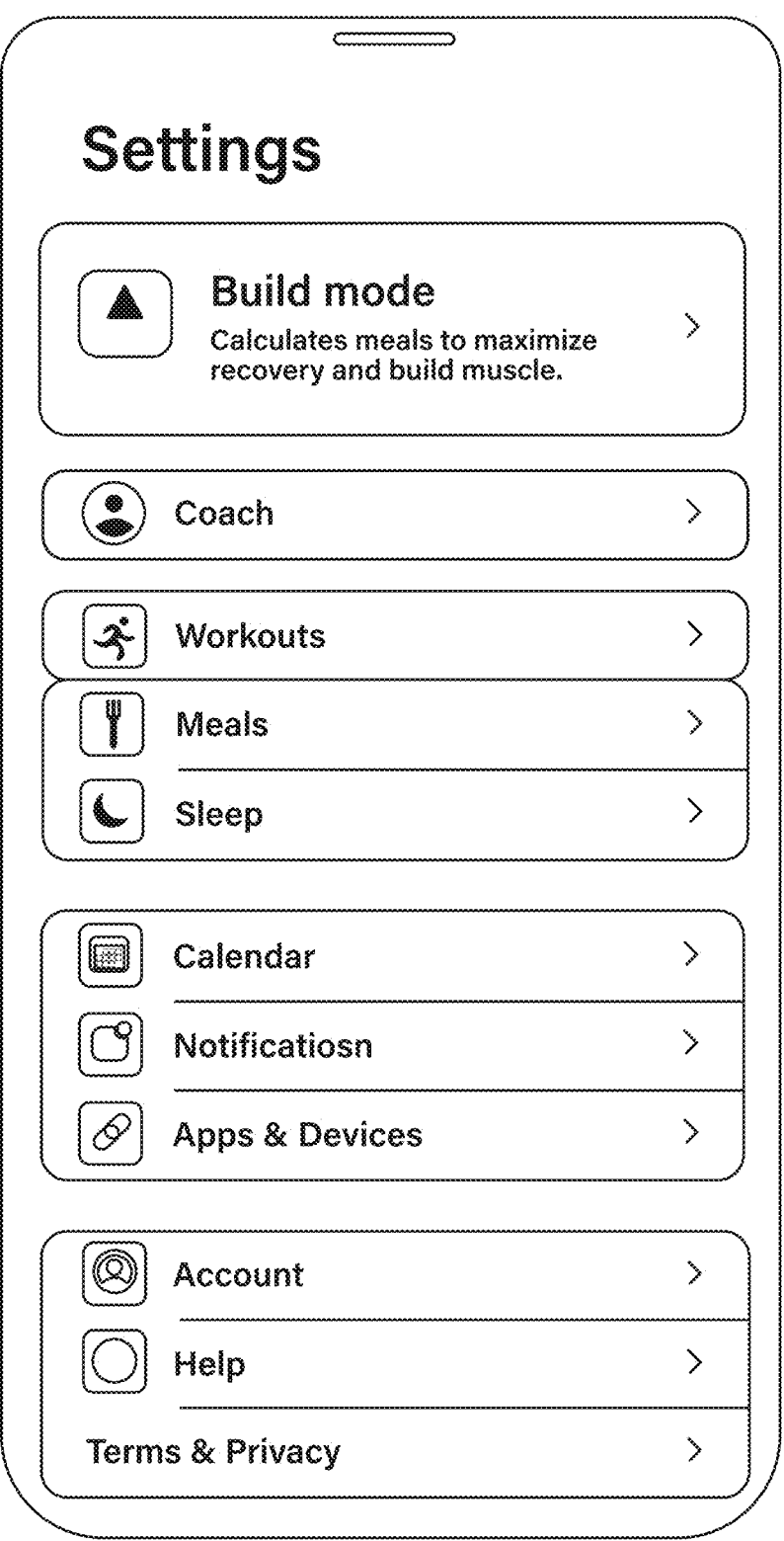
Figure 39B:
Figure 39B:
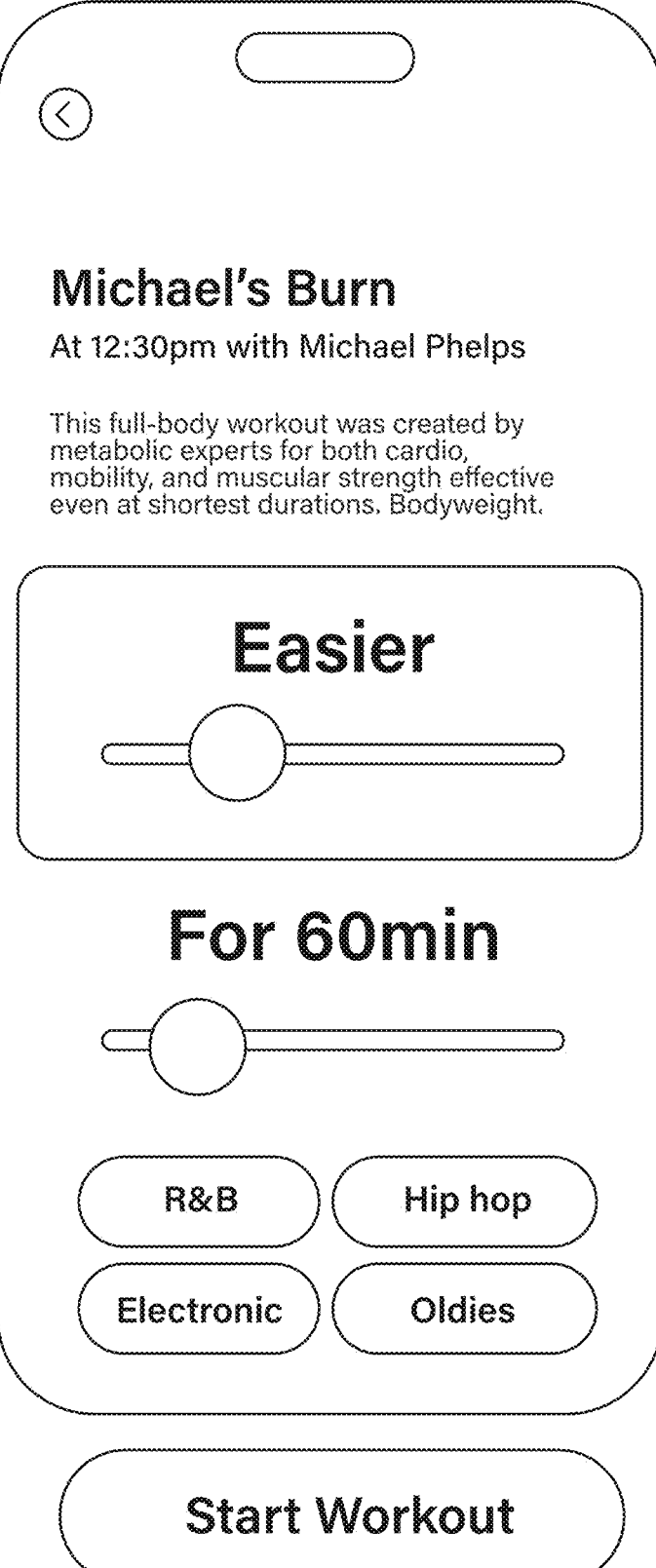

FIG. 39A and FIG. 39B showcase the system's scheduling and coaching interface, which synchronizes workouts, meals, and recovery periods. For example, "Michael's Burn"—a metabolic expert-designed workout—is paired with precise macronutrient timing (*"35 g Protein+100 g Faster Carbs"* post-exercise). The interface personalizes music preferences (e.g., R&B, Hip Hop) and adapts to user energy levels, reflecting inputs from FIG. 42 (e.g., "Energized" vs. "Fatigued"). The Coach Plan Results section tracks progress (e.g., muscle preservation, fat loss) and aligns with the body composition visualization in FIG. 43, where users see projected outcomes ("Body in 3 months").

Figure 40:
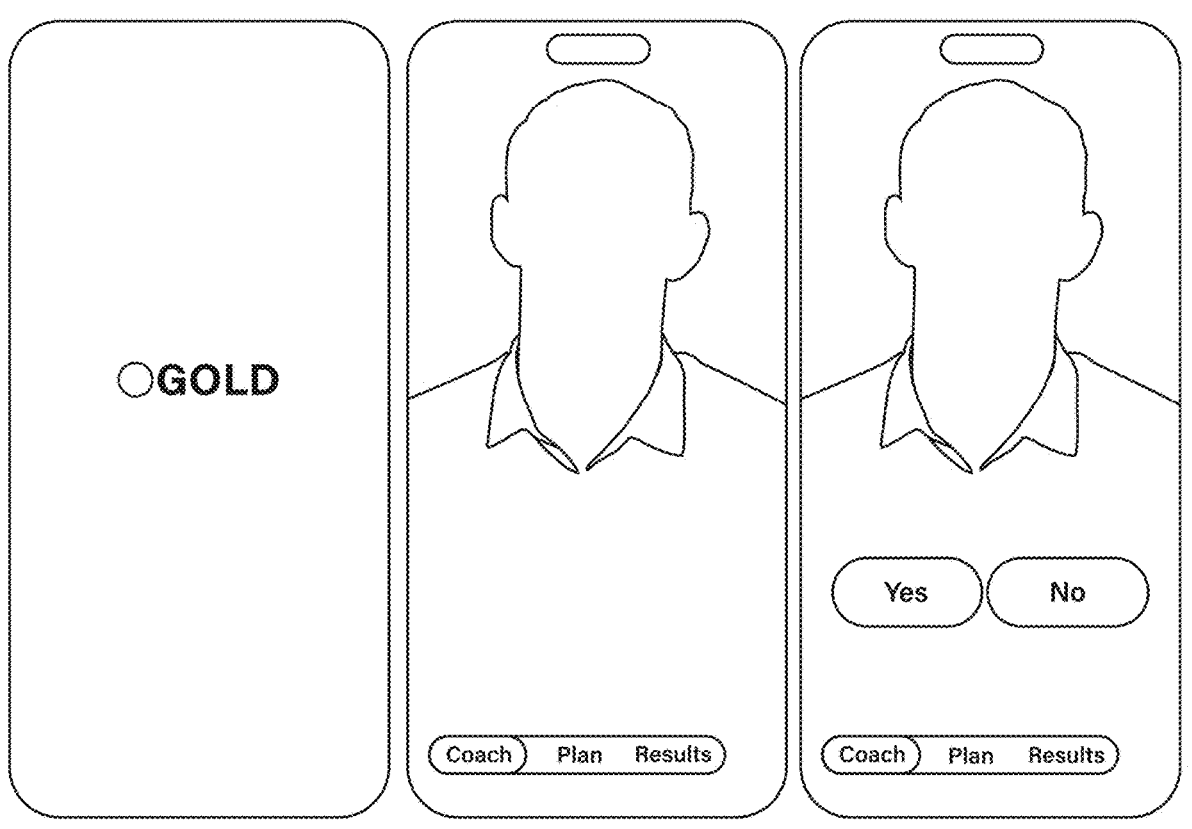
FIG. 40 depicts an emotional state tracking interface with binary choice inputs to adapt AI coaching tone and interventions.
Figure 41:
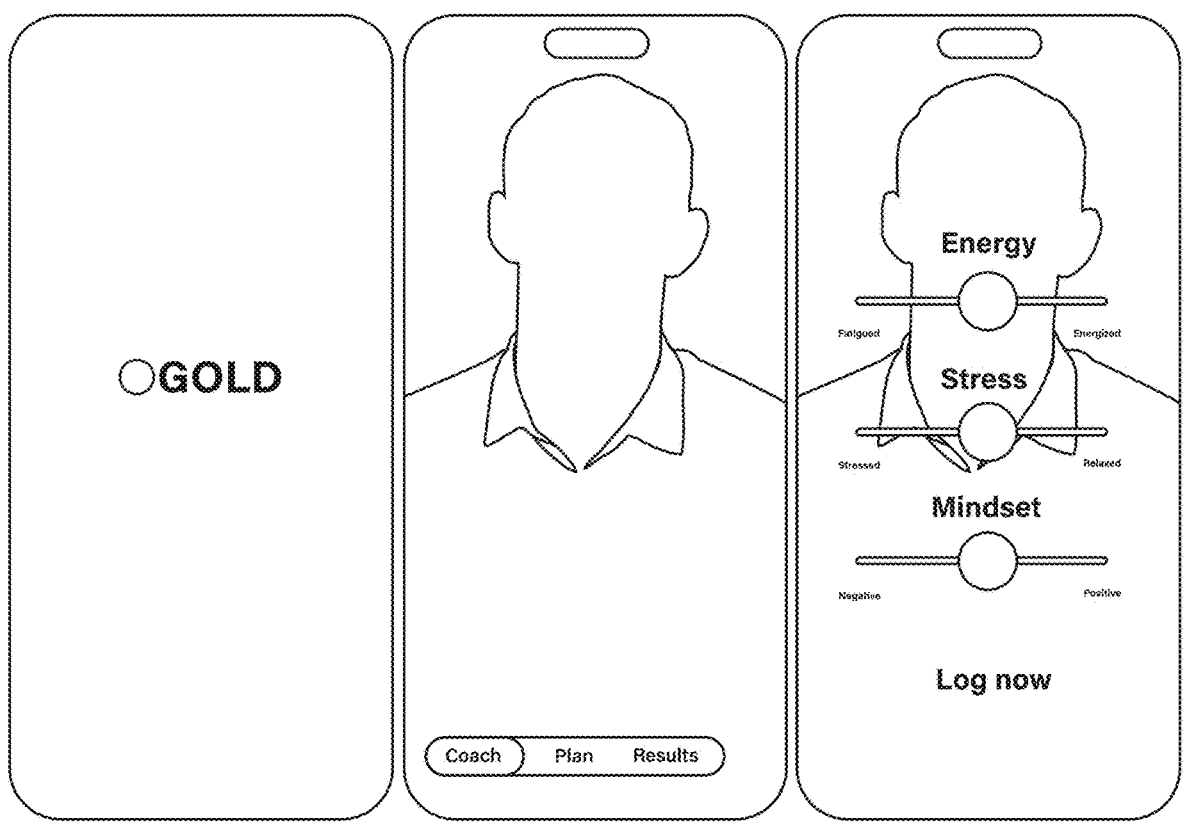
FIG. 41 expands on the emotional logging system, highlighting real-time coaching adaptations and triggers for stress or fatigue.

FIGS. 40A and 40B illustrate the emotional state tracking and motivational feedback components of the AI-powered health coaching system. The interface presents users with simple binary choices to log their current energy state (e.g., "Energized" vs. "Fatigued"), stress level ("Stressed" vs. "Relaxed"), and overall mindset ("Positive" vs. "Negative"). This emotional data collection serves multiple functions in the system. First, it allows the AI avatar to adapt its coaching tone in real-time—shifting between motivational, clinical, or casual communication styles based on the user's reported state. Second, the system uses these inputs to trigger appropriate interventions, such as suggesting stress-reduction techniques when a user reports feeling stressed or fatigued. The interface design emphasizes quick, low-friction logging (via the "Log now" prompt) to encourage regular user engagement. These emotional metrics are correlated with other health data in the system's reinforcement learning algorithms, helping the AI understand patterns between mood states, workout performance, and nutritional compliance.

Figure 42:
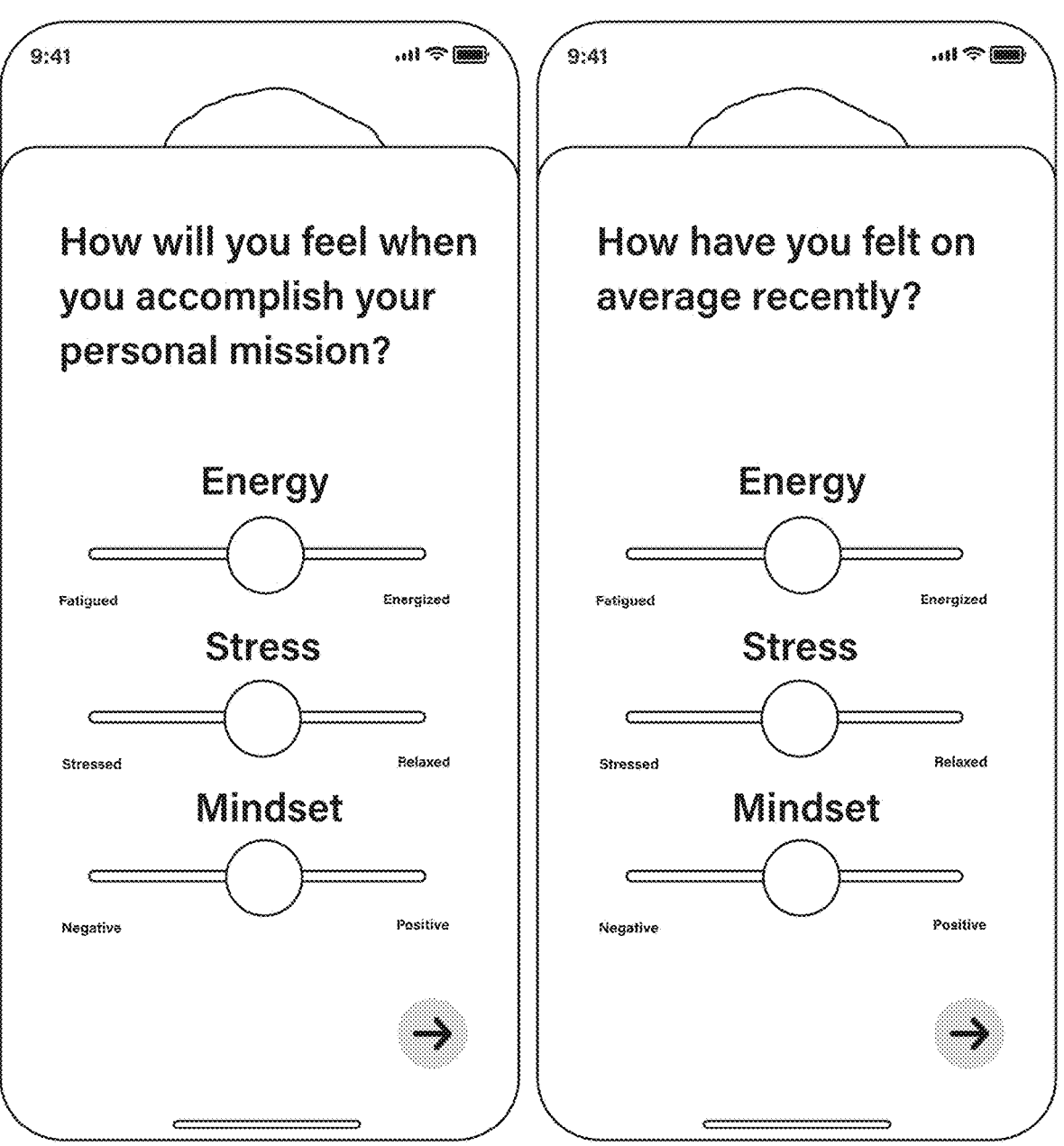
FIG. 42 demonstrates an energy and mindset tracking tool, correlating psychological states with physical progress metrics.
Figure 42:
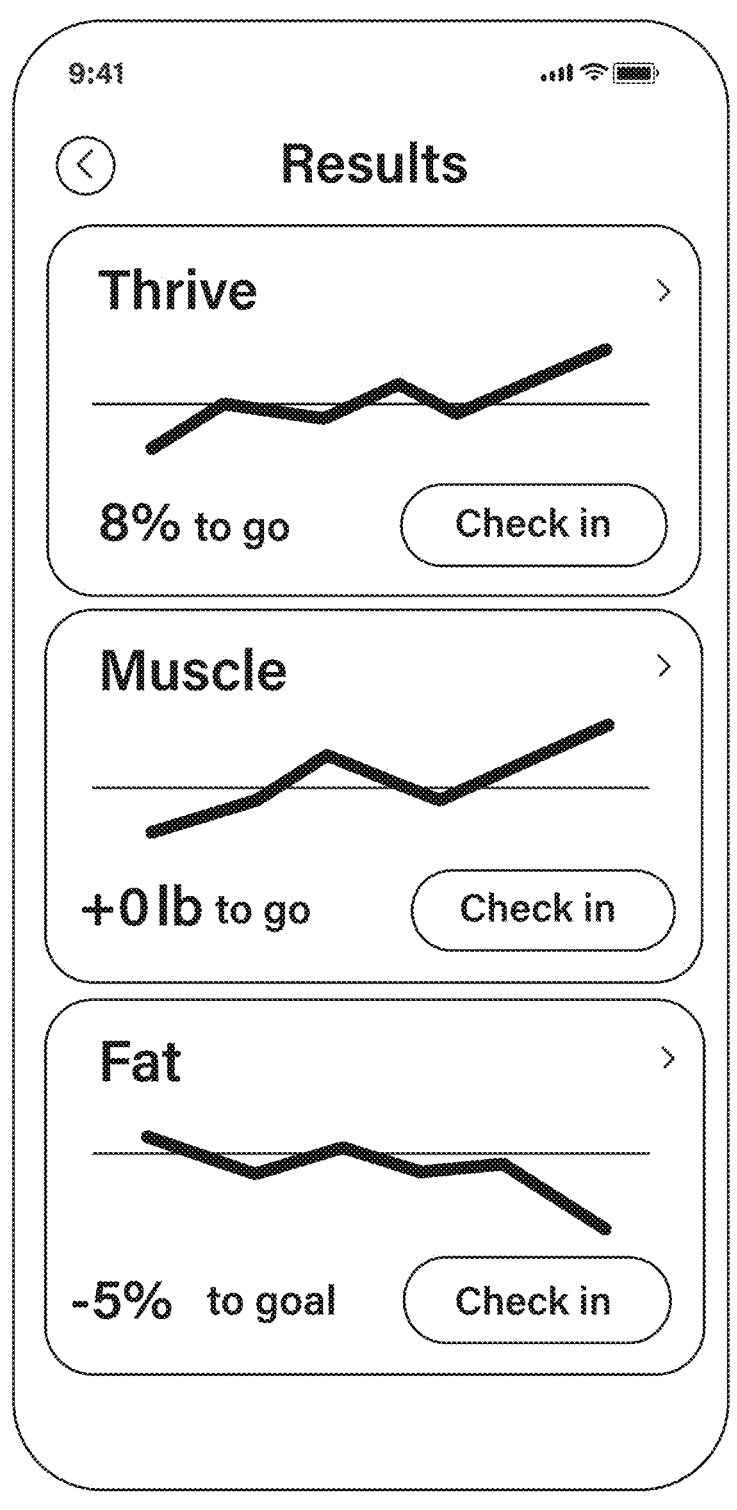

FIG. 42 presents an elegant emotional state monitoring interface that captures user wellbeing through binary choice inputs, allowing quick selection between contrasting states like "Energized/Relaxed" versus "Fatigued/Stressed" and "Positive" versus "Negative" mindset. This psychological data collection serves as critical input for the AI coaching system, enabling dynamic adaptation of workout intensity, recovery recommendations, and communication style based on the user's current mental and emotional status. The interface cleverly connects these emotional metrics to tangible health outcomes through progress tracking displays showing targets like "8% to go" for overall thriving and specific body composition goals.

Figure 43:
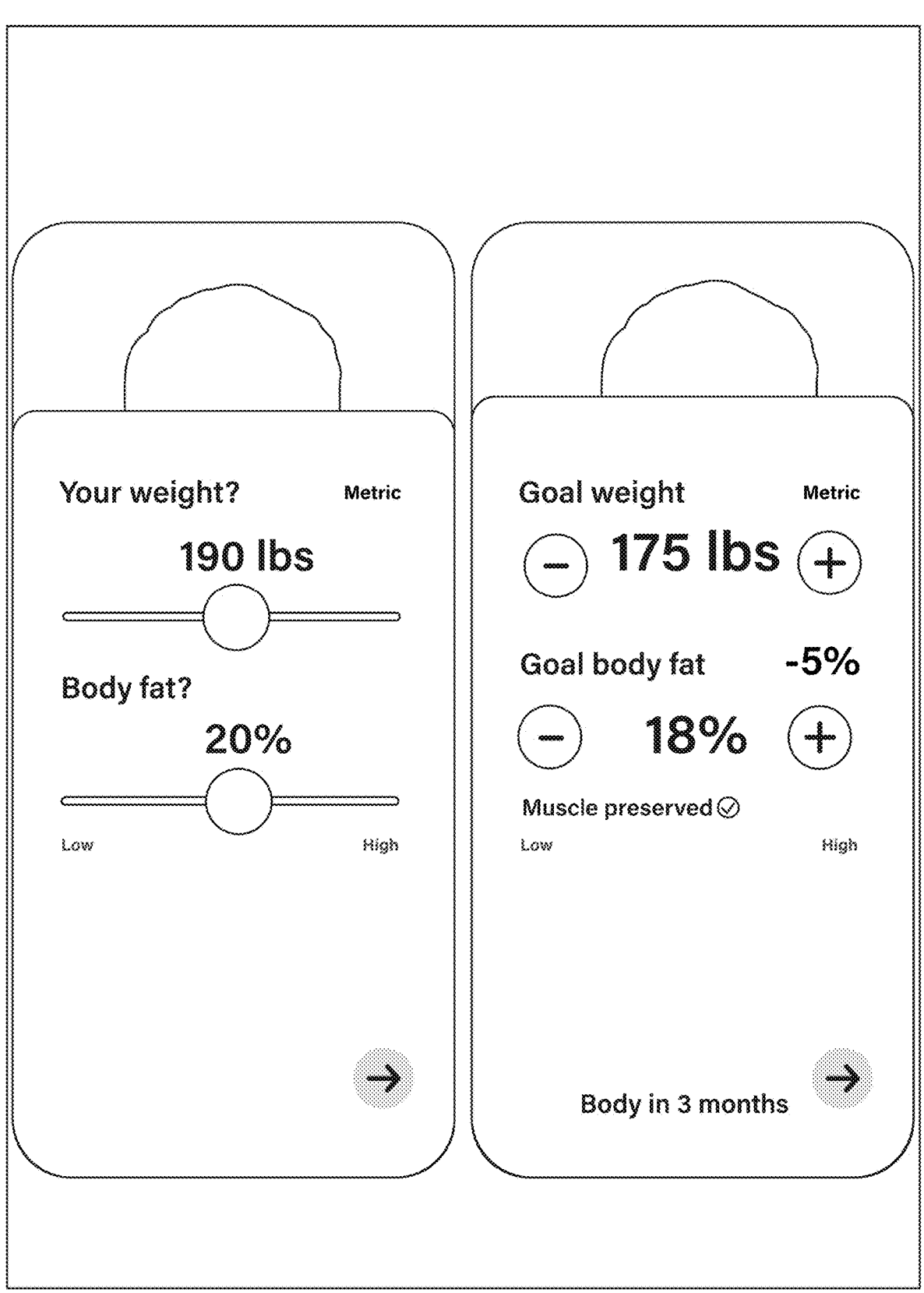
FIG. 43 visualizes body composition management, featuring AI-generated projections and non-invasive tracking of muscle/fat goals.
Figure 43:
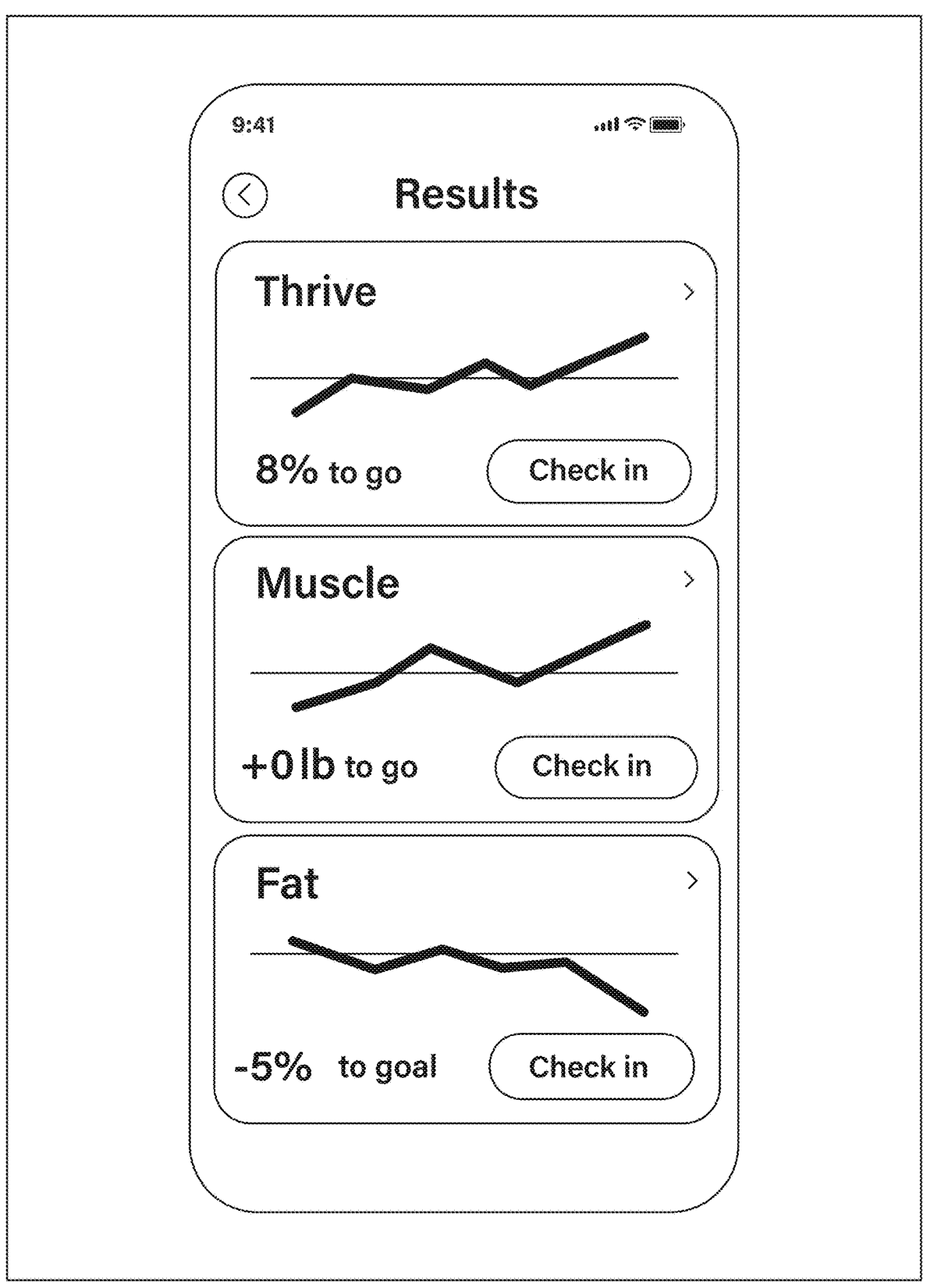

FIG. 43 provides a sophisticated body composition management interface where users input basic metrics like current weight and body fat estimation. The system then generates visual projections of potential outcomes, such as the "Body in 3 months" preview, creating motivational goalposts for users. This visualization is paired with detailed progress metrics tracking muscle preservation and fat reduction targets. The emotional state data from FIG. 42 informs how the system presents and adjusts the physical goals shown in FIG. 43, while progress toward those physical goals is used to refine the emotional support provided. Together, they create a holistic coaching ecosystem that addresses both the physical and psychological dimensions of health transformation, with all data feeding into the AI's reinforcement learning algorithms to continuously improve recommendation personalization. The interfaces exemplify the system's ability to make complex health tracking accessible through intuitive, minimal-input designs while delivering maximum personalization through sophisticated backend AI processing.

Figure 44:
FIG. 44 shows a coach and social interface with preferences for engagement.
Figure 44:
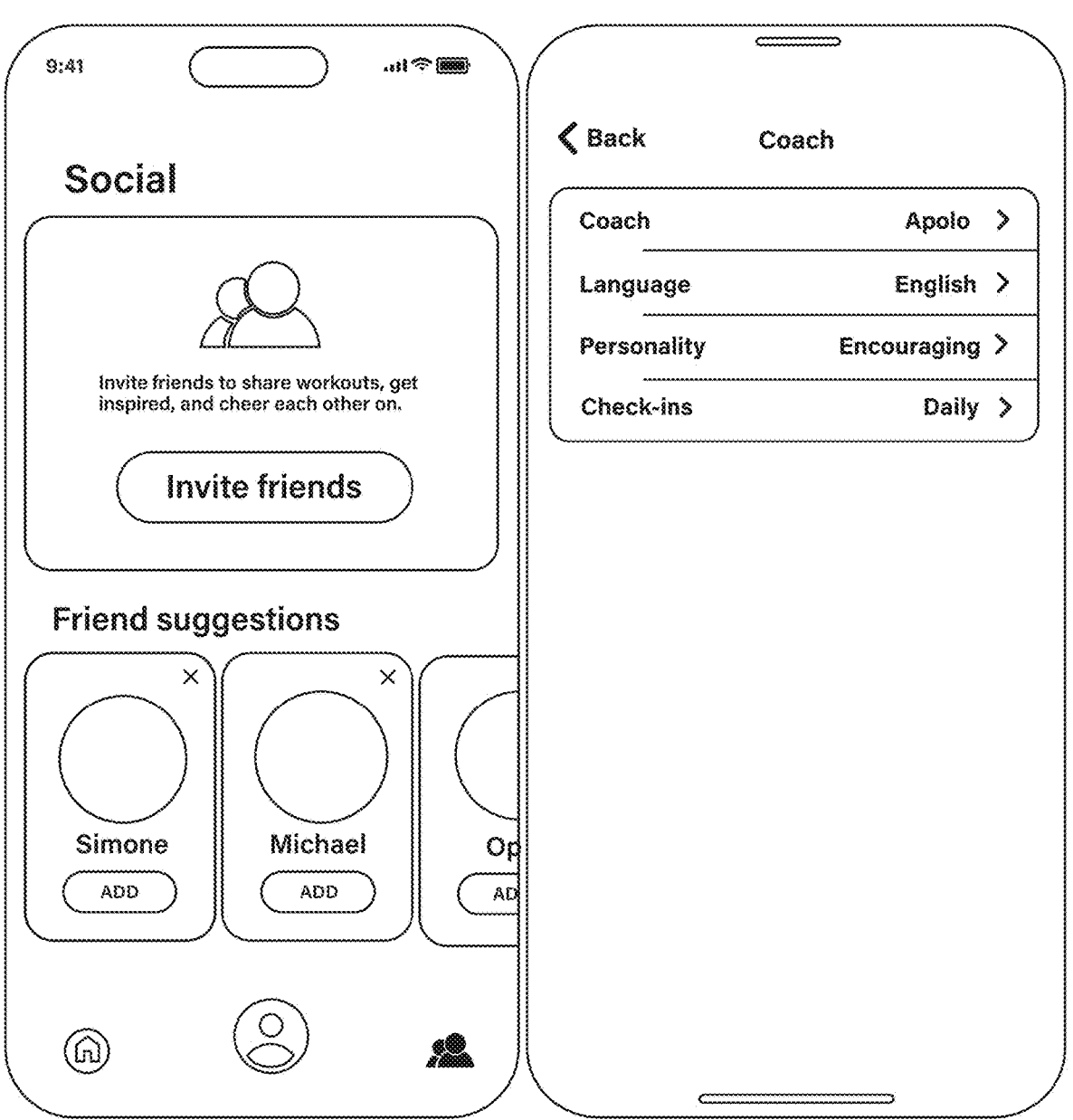

FIG. 44 showcases the user interface of a digital health and wellness platform designed for socially coordinated KHAs through AI-enhanced avatar coaching. The first screen displays the app's splash page, featuring the brand name "GOLD" against a dark background, introducing users to the platform. The second screen presents the main coaching interface, where users can view and interact with their selected avatar coach, with navigation options at the bottom for Coach, Plan, and Results. The third screen highlights the social coordination feature, allowing users to invite friends to join workouts, share inspiration, and support each other. It includes an "Invite friends" button and a horizontal list of friend suggestions, each with a profile image and an "Add" button, making it easy to build a support network. The fourth screen provides settings for customizing the avatar coach, where users can choose their preferred coach, set the language, select the coach's personality (such as "Encouraging"), and determine the frequency of check-ins (e.g., daily). Overall, the interface integrates avatar selection, language and personality customization, and social features to foster accountability, motivation, and personalized coaching, all within a visually intuitive and user-friendly environment In one embodiment, the system comprises a user onboarding module that gathers essential initial data from users, including their overarching purpose, lifestyle goals, and physiological metrics. During onboarding, the module acquires user preferences such as name, targeted health goals, tonal inclinations, personality characteristics, and language of communication. This personalized data serves as the foundation for all subsequent coaching and content generation activities.

API connectors are integrated to establish continuous data exchange with external sensor devices and health data platforms. These connectors ingest real-time biometric information—such as heart rate, blood pressure, and other physiological signals—and ensure that up-to-date health metrics are available for processing. The system also incorporates a relational mapping engine that classifies and quantifies user relationships and social influence factors based on the information provided and ancillary data sources. This mapping facilitates the consideration of social network influences that can affect the user's behavior and outcomes.

A central component of the system is the coaching recommendation engine, which leverages inputs from scientific literature, athlete data, and specific user context to generate a dynamic schedule of KHAs. These KHAs are tailored to optimize the user's health trajectory and are continuously adjusted through a real-time adjustment engine. The adjustment engine reschedules KHAs in response to missed actions or changes in user availability, ensuring that the coaching program remains flexible and responsive.

The system employs a reinforcement learning model to analyze user outcome data, correlating it with recent KHA history. This model ranks and prioritizes KHAs, identifying those actions that most significantly influence positive health outcomes. Complementing this, a biologically weighted regression model is implemented to evaluate the time-weighted influence of recent KHAs on user outcomes, allowing the system to accurately assess the temporal effectiveness of interventions.

To support sustained, drug-free optimization of various health dimensions, the system features a knowledge model that gives priority to insights from leading scientific fields. This model focuses on strategies aimed at enhancing metabolic health, preserving skeletal muscle, regulating blood sugar, reducing inflammation, and improving sleep quality. Additionally, a content generation engine personalizes the coaching experience by crafting initial scripts that incorporate individual user variables into message templates.

Subsequently, a voice synthesis module converts these scripts into audio files using advanced text-to-speech technology, ensuring natural and engaging audio output. Additionally, a video generation module constructs avatar videos by combining the AI-generated audio files with visual animation libraries, resulting in dynamic and personalized visual content. All of the personalized avatar content is managed and served by a server-based storage system, which securely stores and efficiently delivers the coaching content as needed.

The integrated operation of these modules and engines results in a comprehensive and adaptive system for personalized health coaching that dynamically aligns with user needs and preferences, continuously adjusts to real-time feedback, and effectively drives desired health outcomes.

In one embodiment, the avatar interface is designed to be fully customizable by the user, allowing modifications to voice output, personality traits, coaching tone, and the frequency of interaction. A graphical user interface provides the customization options, including selectable profiles and adjustable parameters that enable the user to tailor the interactive experience to individual preferences and situational requirements. The voice output of the avatar is altered by choosing from a variety of vocal tones, accents, and speech cadences, each optimized for clarity and user engagement. Similarly, different personality traits are assignable to the avatar—such as upbeat, empathetic, authoritative, or relaxed—thereby influencing the style and content of its verbal and non-verbal communication. The coaching tone, which ranges from a supportive and encouraging approach to a more direct and corrective mode, is calibrated to meet specific user needs based on the context of the interaction or the complexity of the task being addressed.

In addition, the adjustable interaction frequency enables the avatar to provide either persistent, real-time guidance or intermittent support based on user preferences and the evolving demands of the activity. The system is designed to monitor the user's real-time context through sensors, input devices, or software analytics to assess factors such as user engagement, performance indicators, and potential errors. Drawing on this analysis, the avatar delivers adaptive guidance that includes offering encouragement when progress is satisfactory, troubleshooting steps when issues arise, and context-sensitive instructions tailored specifically to the current situation. For instance, if the system detects a deviation from expected operational parameters or identifies user error, the avatar automatically adjusts its tone and frequency to present timely remedial advice or detailed troubleshooting information.

In embodiments of one implementation, an avatar interface is provided that incorporates culturally localized spoken language, gestural mannerisms, and affective vocal tones tailored to specific user cultural segments to enhance comprehension and emotional engagement. In some embodiments, the avatar interface employs a processing module that analyzes user profile data—including cultural background, language preferences, and behavioral patterns—to determine the optimal articulation for spoken language. This process includes adjustments in pronunciation, accent, vocabulary selection, and intonation patterns that align with the cultural norms of the particular user segment. As a result, the spoken language output is rendered in a manner that is both linguistically accurate and culturally resonant.

Furthermore, the avatar interface is designed to incorporate gestural mannerisms that align with culturally specific modes of non-verbal communication. In these embodiments, the interface integrates a gesture mapping module that correlates specific cultural contexts with predefined gesture sets. These gesture sets include variations in hand movements, facial expressions, and body postures that are recognized as appropriate or customary within the target cultural milieu. The gesture mapping module utilizes a database of culturally annotated gestures, which is dynamically referenced during interactions to ensure that the avatar's non-verbal cues reinforce the semantic content of the spoken language.

These embodiments thus ensure that the avatar interface not only communicates information in a linguistically accurate manner but also resonates with users on a cultural and emotional level, leading to enhanced overall comprehension and a more engaging user experience.

In one embodiment, reinforcement learning is used to analyze performance outcomes by receiving inputs that include body fat percentage, wellness scores, heart rate variability, and other physiological measurements. The system aggregates these metrics with recently derived KHAs into a unified data set that is then processed by one or more reinforcement learning agents. These agents observe the current state of an individual's physiological and performance data and select from a range of candidate coaching actions. Each selected action is evaluated based on a reward signal that reflects subsequent changes in performance outcomes, with the reward function designed to capture both immediate improvements and enduring health benefits.

The system incorporates techniques to balance exploration and exploitation, enabling the reinforcement learning agent to periodically test less conventional recommendations to discover potential improvements. In embodiments, the reward function includes risk-aware or uncertainty-sensitive components designed to account for variability in data quality or external factors affecting performance outcomes. By analyzing correlations between responses to coaching actions and shifts in physiological metrics, the reinforcement learning model refines its understanding of the optimal actions that lead to desirable health outcomes.

Additionally, the input to the reinforcement learning model can be enhanced with contextual factors such as age, baseline fitness levels, environmental conditions, and historical performance trends. This augmented data set increases the granularity of the system's state representation, thereby allowing for more nuanced coaching recommendations that are tailored to the individual's unique health profile and lifestyle. The iterative nature of the learning process facilitates real-time adaptation, so that as new performance outcomes and KHA s are received, the system continuously updates its policy to improve the alignment of coaching recommendations with the evolving performance data.

Overall, by leveraging reinforcement learning techniques to analyze comprehensive physiological data in conjunction with KHAs, the system offers an autonomous, data-driven approach for refining and optimizing future coaching recommendations that is responsive to the individual's real-time performance and ongoing wellness objectives.

In one embodiment, the coaching engine continuously monitors a plurality of KHAs indicative of user behavior and performance. The engine implements a correlation analysis module that receives data associated with each KHA and calculates their statistical relationship with desired outcomes such as enhanced productivity, better learning efficiency, or greater overall system performance. This analysis employs various statistical techniques, including but not limited to Pearson correlation, regression analysis, or alternative algorithms designed to identify and quantify linear or non-linear relationships. When the analysis indicates that certain KHAs exhibit a strong negative correlation with the desired outcomes, those KHAs are automatically flagged by the coaching engine. Once flagged, the system presents the identified KHAs to the user through an interface designed for subsequent review, allowing the user to assess the relevance and accuracy of the flagged data. In some embodiments, flagged KHAs are associated with recommendations for behavioral correction aimed at steering user actions toward better outcomes. The recommendations include prompts that suggest specific corrective measures or adjustments to the user's behavior to mitigate the negative impact. In other embodiments, the coaching engine automatically de-prioritizes the flagged KHAs during performance evaluation, reducing their influence on overall scoring or decision-making processes. The de-prioritization is systematically achieved by adjusting the weighting factors of these KHAs within the overall performance model, thereby permitting KHAs with positive or neutral correlations to exert a greater influence on the outcomes. In addition, the coaching engine incorporates machine learning techniques to continually refine the thresholds and criteria used for flagging KHAs as more data is accrued, adapting to changes in user behavior over time. This adaptive capability ensures that the system remains responsive to dynamic performance environments. The coaching engine further integrates a historical data repository that stores past performance data, enabling retrospective analysis and trend identification to support the flagging process. This holistic approach, encompassing real-time analysis, user interfacing, behavioral recommendations, and adaptive weighting, enables the coaching engine to effectively manage KHAs in a manner that promotes favorable outcomes while mitigating those attributes that are detrimentally correlated.

In one embodiment, nutritional recommendations are calculated on a per-meal basis using macronutrient needs determined by a multi-factor analysis that incorporates prior muscle damage data, measured circadian phase parameters, assessments of digestive efficiency, and analysis of interrelated KHAs associated with the subject's physiological state. The system processes data related to previous muscle injury or strain events, analyzing biomarkers indicative of muscle damage to determine the extent of recovery needed and to adjust subsequent protein and carbohydrate intake accordingly. Concurrently, the circadian phase is monitored through indicators such as sleep patterns, hormonal fluctuations, and measurements of ambient brightness levels; these parameters help optimize the timing and proportion of nutrient delivery to align with the body's natural metabolic rhythms. Digestive efficiency is evaluated using measures such as gastrointestinal transit time, enzyme activity levels, and nutrient absorption rates, allowing the system to tailor nutrient composition to maximize bioavailability and minimize inefficiencies in nutrient processing. Additionally, the interrelationships of surrounding KHAs—including factors like physical activity levels, stress indicators, baseline metabolic rate, and other health indices—are integrated into the algorithm to create a holistic profile of the subject's current nutritional requirements. The calculated macronutrient needs are then distributed across meals in a manner that accounts for both the timing of ingestion and the anticipated metabolic demands associated with each period of the day. This approach provides a dynamic and personalized nutritional recommendation regimen that aims to enhance recovery, optimize metabolic performance, and support overall health by adapting to real-time physiological data and situational factors.

In various embodiments, well-being is tracked through sensors and assessments that provide continuous data corresponding to multiple dimensions of a user's health. For example, physiological data is captured via wearable devices or ambient monitoring systems that measure parameters including heart rate variability, blood pressure, body temperature, and activity levels. These measurements are processed by a computing system that normalizes raw data into standardized metrics reflective of physical health. Concurrently, psychological well-being is assessed through user input, surveys, and behavioral data that provide insights into mood, stress levels, and cognitive function. Data from these assessments is normalized and evaluated over time to identify trends associated with mental health. Relational well-being is tracked using data correlated with social interactions, communication patterns, and measures of perceived social support. In some embodiments, indicators related to frequency and quality of interactions, engagement levels in social networks, and communication habits are aggregated to generate a relational well-being metric. The multidimensional scoring system then assigns specific weights to each of these axes—physiological, psychological, and relational—to generate a composite well-being score reflective of the user's overall health state. In certain implementations, these weighting factors are dynamically adjusted based on the user's profile or situational context. The system stores historical data in a secure repository, allowing for longitudinal tracking and trend analysis. The aggregated data is displayed using user-friendly interfaces that present the composite scores along with individual axis scores across selected time intervals. Moreover, machine learning algorithms are employed to identify correlations among the different axes, predict future well-being trends, and trigger alerts or recommendations for lifestyle modifications or professional interventions when significant deviations from baseline values occur. Additionally, the tracking system is designed to integrate with external data sources such as electronic health records, thereby enhancing the reliability and contextual relevance of the scores. User feedback is incorporated to iteratively recalibrate and personalize the scoring metrics, ensuring that the system remains responsive to changes in individual health status. The output of the multidimensional scoring system facilitates not only self-monitoring of health and well-being but also enables proactive health management by providing targeted recommendations and real-time alerts to users, caregivers, or health professionals as appropriate.

The vector database comprises a multidimensional data structure that integrates continually updated Olympic medal-winning strategies with real-world athlete performance data and peer-reviewed scientific literature. In one embodiment, the database is engineered to receive and process dynamic data streams that include training regimens, competitive strategies, biomechanical analysis, nutrition protocols, recovery methodologies, and psychological preparation techniques employed by Olympic-level athletes. The strategies incorporated in the database are collected from verified sources originating from official Olympic training programs, elite coaching staff, and recognized sports performance institutes, and are subsequently translated into vectorized representations that facilitate efficient retrieval and pattern recognition during the knowledge training process.

The system is designed to ingest real-world athlete data which encompasses biometric measurements, performance statistics, and longitudinal data tracking of physical and physiological parameters. This data is sourced from wearable sensors, electronic health records, and validated performance tracking systems, ensuring that the database reflects the most current and accurate representations of athlete performance and health metrics. In parallel, the database continuously integrates peer-reviewed scientific literature that is systematically prioritized based on its relevance to functional, sustainable health models in the context of athletic performance and overall well-being. The literature is parsed and analyzed using natural language processing techniques to extract key performance indicators, evidence-based training modifications, and potential health optimization strategies that are then correlated with the athlete and strategy data already stored in the database.

Data from these varied sources is normalized, vectorized, and stored in a manner that facilitates real-time updates and continuous learning. Machine learning algorithms, including supervised and unsupervised methods, are applied to the aggregated data to uncover correlations, predict trends, and refine training recommendations. The database is further equipped with a feedback mechanism that enables iterative improvement, ensuring that emerging data such as new training techniques proven effective in competitive settings are dynamically integrated. This results in a continuously evolving knowledge base that not only captures historical performance data but also adapts to the latest advancements in sports science and athletic training methodologies.

Moreover, the integration of peer-reviewed literature into the database permits the establishment of causal relationships between novel training practices and improvements in athlete performance or health outcomes. The system applies ranking algorithms to prioritize this scientific content, thereby filtering out noise and ensuring that only validated and contextually relevant information is incorporated. In doing so, the database supports decision-making processes that emphasize both performance optimization and sustainable health outcomes. This comprehensive and adaptive vector database serves as the foundational element for knowledge training systems by enabling precise extraction and application of expert-derived training strategies, continuous athlete performance monitoring, and evidence-based refinement of functional health models.

In one embodiment, the content generation engine employs a systematic process to select and sequence clips from a human-recorded content library by dynamically accounting for user goals, time-of-day, and behavioral patterns. The engine first receives one or more user-specified goals, which include preferences related to content themes, desired emotional engagement, or specific informational needs. Based on these goals, the engine accesses metadata associated with each clip—such as categorization tags, content summaries, and contextual annotations—which facilitates mapping user objectives to relevant content. Simultaneously, the engine considers the time-of-day parameter by referencing predetermined content scheduling profiles stored in its memory. For example, the engine prioritizes clips with energetic or motivational content during morning hours and selects more relaxing or reflective content during late evening periods. Additionally, time-of-day information is used to ensure that the sequencing of clips maintains continuity with circadian or situational contexts, thereby enhancing user engagement.

The system further refines content selection by analyzing recorded behavioral patterns of the user. This analysis involves tracking historical interactions such as clip view duration, frequency of engagement, user ratings, explicit feedback, and patterns of content skipping. The engine processes this behavioral data by applying algorithms that include statistical analysis techniques and machine learning models to predict content relevance and user satisfaction. The predicted outcomes serve as a weighting function that adjusts the prioritization of clips in real time. Clips that closely align with historical behavioral preferences receive higher priority in the selection process, ensuring that the user experience is continuously optimized to match evolving interests and consumption habits.

Throughout this process, the engine continually updates its profile of user behavior by capturing feedback during and after content consumption. This adaptive mechanism allows the engine to recalibrate its selection and sequencing strategies dynamically. The integration of user goals, temporal contexts, and behavioral analytics ensures that the final output is personalized and context-aware, thereby maximizing the likelihood of achieving the intended user experience.

In one embodiment, the system includes a content generation engine configured to query and retrieve pre-recorded AI video clips stored in an associated digital media repository based on predetermined criteria such as scene context, thematic relevance, and metadata attributes. The engine employs algorithms that scan the repository to identify and select video clips that best correspond to the content requirements of the composite media project. Concurrently, the engine accesses a curated AI media database that contains a collection of pre-defined transitions designed to provide seamless visual continuity between video segments. The electronic circuitry within the engine selects specific transitions from this curated database using matching parameters that consider characteristics of the preceding and subsequent video clips, such as tempo, brightness, and stylistic elements. The transition selection process includes evaluating criteria like timing, duration, and the intended visual effect to ensure that the overall generated content maintains a consistent look and feel. In addition, the system adjusts the selected transitions dynamically based on scene analysis outputs or user-defined settings to optimize the narrative flow and preserve the aesthetic coherence of the final output. The integration of these functionalities enables the content generation engine to automatically assemble a composite multimedia presentation through the strategic retrieval of pre-recorded AI video clips and the seamless insertion of contextually appropriate transitions, resulting in a cohesive and visually engaging production.

Real-time text content is generated by processing inputs related to recent user activity, biometric data, and health goals. In one embodiment, data corresponding to user activity is collected from various sources, including but not limited to application usage logs, interaction events, and sensor outputs that capture physical movements or environmental context. Biometric data is obtained through devices such as wearable sensors or mobile devices, which provide measurements of heart rate, blood pressure, skin temperature, or other physiological indicators. Health goals are entered by the user or derived from historical data concerning user preferences and medical histories, and include targets related to fitness, nutrition, or general well-being.

The collected data is aggregated and fed into a computational engine that includes a large language model configured to interpret the data in real time. The model dynamically generates customized text content intended to provide feedback, recommendations, or contextual information based on the input data. The language model, trained on a comprehensive corpus encompassing health, lifestyle, and behavioral data, incorporates recent user activity and real-time biometric readings to ensure that the output is relevant and accurately reflects the user's current state and goals.

Pre-processing steps are executed on the aggregated data to prepare it for input into the language model. These steps include normalization, filtering, and feature extraction, which standardize data formats and reduce noise. Once pre-processed, the data is integrated with the model's internal representation, enabling the language model to contextualize the information and generate coherent, context-specific text outputs. The generated text content is used to provide real-time suggestions, progress updates, or personalized narratives that align with the user's actual performance and stated health objectives.

A feedback loop is employed to continuously enhance the accuracy and relevancy of generated text. The output from the large language model is constantly monitored and, when necessary, reintegrated into the system to update performance parameters, improve prediction accuracy, and adjust subsequent text outputs. This involves further training or fine-tuning of the language model based on evolving user data and contextual factors. As a result, the system is designed to adapt over time, ensuring that the dynamic synthesis of text remains aligned with both immediate inputs and sustained user health trends.

The method further encompasses steps to ensure that the textual output is generated in a manner that is congruent with data privacy standards and that any sensitive biometric or health-related information is securely handled throughout the process. Data encryption and anonymization techniques are applied as necessary to maintain user confidentiality while still allowing the large language model to process pertinent information effectively. Thus, the system is capable of delivering real-time, personalized text content based on a holistic view of user activity, biometric status, and health goals.

In various embodiments, the avatar coaching outputs are generated by a system that continuously monitors user behavior data and contextual inputs over immediate and extended intervals. The system is configured to detect real-time events—such as deviations from expected performance patterns or momentary variations in the user's physiological or behavioral state—and to correlate these events with historical performance data stored over extended periods. Based on this dual analysis, the system dynamically generates outputs that include emotional reinforcement, praise, or habit correction suggestions tailored to the user's immediate situation and continuous progress.

For instance, when a sensor indicates inadequate posture or a momentary disruption in concentration during a real-time event, the system immediately generates an output that provides verbal or visual cues designed to elicit a positive emotional response, thereby reinforcing the desired behavior. In parallel, if historical tracking indicates a recurring trend in the user's performance, the system provides specific habit correction suggestions aimed at addressing these persistent deviations by recommending modifications or adjustments to the user's routine.

The outputs take various forms, including synthesized speech, on-screen text, or animated gestures displayed by an avatar, all designed to deliver contextually appropriate feedback. The system further refines these outputs using adaptive algorithms that adjust parameters such as timing, tone, and content of the feedback based on the observed effectiveness in promoting positive behavioral changes over successive periods.

Through this approach, immediate emotional reinforcement acknowledges and rewards favorable actions as they occur, while praise is provided in instances where both concurrent and historical analyses indicate significant progress. Conversely, habit correction suggestions are issued when the analysis identifies persistent behavior patterns that detract from the user's overall progress. This integrated feedback method ensures that the coaching outputs remain responsive to instantaneous events while aligning with the user's evolving performance and improvement objectives.

In one embodiment, the system further comprises a human-recorded content library that includes a collection of video and audio clips recorded by professional actors or coaches. Each clip is labeled with metadata that encompasses information regarding the situation depicted, the tone conveyed, or the specific topic addressed. The library is stored in a database and organized such that the labels enable efficient retrieval and categorization of the content using the attributes assigned to each recording. The labeled clips represent a range of scenarios involving communication strategies, performance coaching, role-playing, or other situational contexts. The actors or coaches record the content under standardized conditions designed to capture the nuances of human communication, ensuring that the clips accurately reflect the intended tone, situation, or topic. The labeling process is performed manually by experts in combination with automated classification techniques to provide accurate contextual information that supports subsequent filtering, searching, and use of the content during system operation. Furthermore, the system includes a categorization module that interfaces with the content library, wherein the metadata facilitates seamless integration of the human-recorded clips within the broader operational framework of one implementation. The library also stores additional metadata for each clip, such as the duration, format, and identity of the recording individual, to further enhance the organization and usability of the stored content.

In one embodiment, a timeline-based video assembly engine sequences actor-recorded, pre-generated, and real-time generated clips based on predetermined rules and artificial intelligence sequencing algorithms. The engine dynamically organizes clips within a temporal framework that corresponds to the narrative structure or storyboard requirements, thereby ensuring the final video assembly reflects a coherent sequence of events. The engine receives input from multiple sources, including files stored in local or remote databases, media captured by recording devices, and live feeds transmitted in real time. The engine includes a scheduling module that analyzes clip metadata—such as time stamps, duration, and transition cues—and subsequently sequences the clips accordingly. A rule-based system enforces predetermined conditions and constraints that dictate clip ordering, transition effects, and synchronization, thereby ensuring compliance with design specifications. Additionally, an artificial intelligence sequencing agent refines the video assembly process by employing machine learning techniques that evaluate historical data and user preferences to predict the optimal sequence for clip integration. In some embodiments, the timeline-based video assembly engine integrates with other system components, such as rendering and transcoding modules, to manage media format compatibility and resolution consistency across the assembled video. Error detection and correction algorithms are incorporated to monitor synchronization issues and address any inconsistencies encountered during the clip sequencing process. Consequently, the timeline-based video assembly engine facilitates the automatic, rule-compliant assembly of video content from a plurality of disparate media sources, thereby enhancing the efficiency and accuracy of the video creation process while meeting specific user-defined parameters and system constraints.

In one embodiment, the system further comprises a delivery engine configured to embed the final coaching video into the application interface. The delivery engine is operable to integrate the final coaching video with other application components so that the video is accessible for user playback either on demand or when notifications initiate playback. In various embodiments, the delivery engine incorporates software routines that detect the availability of the final coaching video and automatically position a video playback module within the app interface. When the final coaching video is generated, the delivery engine formats and buffers the video data to ensure compatibility with the app interface, thereby enabling seamless video streaming. The delivery engine also includes notification scheduling functionality to alert the user to the availability of the final coaching video at predetermined times or based on user-defined preferences. In one exemplary implementation, the delivery engine receives playback requests from users through the app interface and responds by retrieving the corresponding video content from a storage module. The retrieved video content is then embedded and rendered in an integrated video frame within the application interface, allowing the user to access and control video playback through familiar user interface elements. Additionally, the delivery engine is configured to monitor user interactions or system events and trigger notifications that prompt the user to view the final coaching video. In such cases, the notification service coordinates with the delivery engine to ensure that the embedded content is updated and that the notification is delivered in a timely manner. The functionality of the delivery engine thereby facilitates a streamlined user experience by providing both on-demand playback capabilities and proactive delivery of notifications to encourage user engagement with the final coaching video content.

In one embodiment, all personalization data and content generation parameters are transmitted between modules using internal RESTful APIs to facilitate a modular and scalable architecture. The personalization data, which includes user preferences, historical interaction records, demographic information, and other related details, is encapsulated into standardized data structures prior to transmission. Similarly, content generation parameters such as formatting instructions, stylistic guidelines, contextual keywords, and generation constraints are organized into predefined request payloads that ensure consistency and reliability across modules. The internal RESTful APIs are designed to operate using a stateless communication protocol that simplifies error handling and supports horizontal system scalability. Each module is programmed to consume these APIs by implementing common HTTP methods— including GET, POST, PUT, and DELETE—which promote secure and efficient data exchange. In one embodiment, the modules validate incoming data against a set of predefined schemas to ensure data integrity and prevent any unauthorized or malformed data from propagating through the system. To further enhance security, the API calls integrate authentication tokens, session keys, or cryptographic signatures, in accordance with industry standards, to ensure that both personalization data and content generation parameters are exchanged only among authorized modules. Additionally, the system is configured to utilize encryption protocols during data transmission, thereby preserving the confidentiality of sensitive user data and generation flags. In certain embodiments, the RESTful APIs support both synchronous and asynchronous communication, allowing the system architecture to be flexible in handling real-time user interactions as well as batch processing scenarios. The use of internal RESTful APIs not only simplifies communication between heterogeneous modules implemented in different programming languages or running on different hardware platforms, but also provides a clear abstraction layer that decouples the user interface and data processing functionalities from the content generation engine. This decoupling facilitates the independent evolution of system components, enabling developers to upgrade or modify specific modules with minimal impact on overall system functionality. Furthermore, the RESTful API framework supports versioning, thereby ensuring backward compatibility and permitting the incremental introduction of new functionalities over time. Consequently, the modular communication structure promoted by internal RESTful APIs contributes to a resilient data pipeline that can adapt to varying operational demands while maintaining superior performance and robust security measures.

User interaction and feedback data are captured in real time from the interface and stored in a dedicated system that records a comprehensive log of actions, responses, and behavioral metrics related to the generated video content. The stored data include, but are not limited to, metrics such as the duration of engagement with specific video segments, user-initiated actions (e.g., play, pause, or skip), and explicit feedback entries provided via rating mechanisms or comment fields. This logged feedback is subsequently processed to generate reinforcement signals that are incorporated into a reinforcement learning model. In some embodiments, the reinforcement learning model incorporates these signals into a reward function that assesses the performance of video generation output against user satisfaction metrics. The model analyzes the interaction data to detect patterns and trends, thereby determining which attributes of the video content contribute to enhanced user engagement. These insights are then used to iteratively adjust the parameters of the video generation algorithm by using established reinforcement learning techniques such as backpropagation and gradient descent within a deep neural network framework. The system retrieves the accumulated feedback data from the storage subsystem and translates the information into quantifiable rewards or penalties, which are applied during the training phase to refine the weights and biases associated with the video generation process. In alternate embodiments, the system incorporates supervised and unsupervised learning methodologies, wherein historical interaction data serve to pre-train the model and continuous real-time feedback is employed to further adjust the generated content, thereby ensuring that the output adapts to evolving user preferences and engagement patterns. The reinforcement learning model is configured to simulate potential future scenarios by integrating dynamic models of user engagement, and to automatically calibrate the video content generation process in order to optimize the delivery of personalized and contextually relevant video content. The ongoing logging of user interaction data not only facilitates the continuous development of video generation algorithms but also equips the system to predict and enhance future user experience by preemptively modifying content generation parameters based on aggregated and analyzed feedback data.

In one embodiment, an avatar is configured to interact with a user by dynamically adjusting its voice tone and language style based on real-time analysis of biometric and behavioral inputs. The system incorporates a biometric sensor module that collects physiological data from the user—including heart rate, skin conductance, and facial expressions—via a network of wearable devices or embedded sensors. This data is transmitted to a signal conditioning unit that normalizes and filters the inputs to ensure accuracy before relaying them to a mood inference module. The mood inference module utilizes statistical analysis together with machine learning techniques to determine the emotional state of the user. Concurrently, a behavioral analytics module captures data from the user's interaction history, analyzing patterns in verbal and nonverbal communication, language usage, and interaction timing. The outputs from both the biometric sensor module and the behavioral analytics module are fed into a mood-based adaptation engine, which synthesizes the data to ascertain the user's current mood state. Based on the determined mood, the engine selects appropriate parameters for voice modulation and language generation. The voice synthesis component adjusts characteristics such as pitch, inflection, cadence, and timbre in accordance with the mood state, while the language generation component alters vocabulary, sentence structure, and formality to match the user's present emotional context. For example, when the system detects indicators of stress, the voice synthesis component employs a softer, slower tone and the language generation component selects simpler, more calming language. Conversely, if indicators of excitement or happiness are observed, the avatar uses a more dynamic and enthusiastic tone paired with a correspondingly lively linguistic style. These adjustments occur in real time through the use of adaptive neural networks and rule-based algorithms designed to minimize latency, ensuring that changes in tone and language style are tightly synchronized with the user's mood shifts. In some implementations, the system further refines its accuracy by incorporating user feedback into the adaptation process, allowing the mood inference algorithms and corresponding output adjustments to be continuously updated and refined over time. The integration of biometric sensing, behavioral analytics, and adaptive processing enables the avatar to deliver a highly personalized and engaging interaction, effectively emulating human-like empathy and responsiveness across a variety of user contexts.

In one embodiment, avatars are implemented as interactive virtual agents that monitor and analyze user contributions to another's overall well-being using sensor inputs, real-time behavioral data, and historical usage patterns. The avatars correlate user actions with predefined well-being metrics and criteria, enabling the system to determine when the user's contributions meet, exceed, or fall below established thresholds. When the system identifies that the user is positively influencing another's well-being—whether through supportive communication, assistance with tasks, or other beneficial behaviors—the avatars are programmed to deliver praise. This praise is rendered through verbal expressions, visual cues such as smile animations, or auditory signals that collectively affirm the user's positive behavior.

Conversely, when the system detects that the user's actions might be inadvertently detrimental to another's well-being or otherwise insufficiently supportive, the avatars are capable of providing constructive feedback. This feedback is designed to be both corrective and supportive by suggesting alternative behaviors or improvements in communication style without discouraging the user. In certain embodiments, the process for delivering such feedback involves natural language processing routines that generate context-specific, personalized responses based on ongoing interactions and the unique characteristics of the involved parties. The avatars adjust the content and delivery of the praise or constructive feedback based on several factors, including the intensity of the behavior, historical user performance, and the sensitivity of the context in which the behavior occurs. Additionally, the avatars integrate into a broader system that includes algorithms for learning and adapting over time to refine the criteria used for evaluating user contributions. This adaptive feedback loop enables the avatars to evolve their responses in accordance with user behavior trends and feedback reception, thereby enhancing the overall efficacy of the system. In this embodiment, the avatars do not serve as passive observers but actively engage users by reinforcing positive behavior patterns and suggesting corrective measures when necessary, thereby promoting an environment where the well-being of all parties is continuously enhanced through informed and empathetic interactions.

In one embodiment, an avatar integrated within a communication interface is configured to offer an array of pre-formulated scripts or phrases designed to assist users in effectively conveying difficult emotional content to their linked user. The system includes a repository of language templates developed based on recognized communication strategies and psychological principles for addressing sensitive topics. The avatar operates by monitoring user input—either through text entry or voice recognition—and performing sentiment analysis to detect hesitancy or emotional strain. Upon determining that the user experiences difficulty articulating their feelings, the avatar retrieves a set of contextually relevant scripts from the repository. These scripts range from directly worded phrases to more subtle, suggestive language that eases the user into expressing complex emotions.

Furthermore, the system is configured to dynamically adapt as the conversation evolves. For example, if the linked user's responses indicate a misinterpretation or an emotional reaction that diverges from the user's intended message, the avatar provides additional phrasing options or suggests follow-up communication strategies. This feedback loop not only assists the user in managing immediate conversational challenges but also contributes to a continually updated repository that refines the efficacy of script offerings over time.

In some embodiments the shared activity recommendation engine is configured to analyze user data, including individual schedules, historical interactions, health status, and preferences to identify and schedule specific KHAs that both users can perform together. The engine incorporates statistical and machine learning algorithms to predict optimal times for engagement based on real-time and historical data, ensuring that scheduled activities facilitate not only physical and mental well-being but also emotional bonding between users. The engine includes a scheduling module that dynamically allocates time slots during which both users are available and receptive to engaging in the same health action simultaneously. In certain embodiments, the engine integrates with a notification system that transmits reminders or prompts to each user's connected device, thereby ensuring synchronized participation. The activity recommendation engine is further configured to select which KHAs to schedule based on user profiles, with particular emphasis on those activities previously shown to elicit positive emotional responses. Additionally, the engine gathers feedback following each shared KHA session, using input regarding user sentiment and perceived bonding as parameters for refining future recommendations. In alternate embodiments, the engine integrates a real-time monitoring component that assesses biometric or environmental data to adaptively modify the scheduled activity if sudden changes in user conditions are detected. The system also interacts with external scheduling resources or calendar applications to seamlessly integrate the shared activity with pre-existing personal or professional commitments. Furthermore, the shared activity recommendation engine maintains a comprehensive record of past KHAs, including performance metrics and user feedback, thereby supporting continuous optimization of its recommendation algorithms. Through this integrated approach, the shared activity recommendation engine not only promotes systematic engagement in health-promoting actions but also serves as a medium for enhancing emotional bonding between users by encouraging simultaneous participation in mutually beneficial activities.

User feedback is captured via an interface that presents a plurality of input mechanisms including selectable visual icons for emotion tags, one or more numerical sliders, fields for multidimensional well-being scores, and an optional journal-style entry area. For example, the emotion tags are represented by selectable icons or buttons corresponding to predefined emotional states such as happiness, sadness, anger, or anxiety. These icons allow a user to quickly and intuitively indicate the emotional context of their feedback, and the selected emotion tag is electronically associated with the user's feedback record. In alternative embodiments, the emotion tags include not only static emotional indicators but also context-sensitive icons that change in appearance based on prior user inputs or system-determined feedback trends.

The numerical sliders provide an interface element that enables the user to indicate a quantitative measure of various parameters, such as intensity of emotion, perceived energy levels, or subjective stress. These sliders are calibrated to permit the user to adjust feedback values along a continuum within preset minimum and maximum boundaries, thereby providing a fine-grained indication of the user's subjective experience.

In another aspect, the system employs multidimensional well-being scores derived from a variety of input parameters captured through the interface. These multidimensional scores comprise one or more sub-scores corresponding to different dimensions of well-being, such as physical health, mental state, or social engagement, and use algorithms that weigh and integrate inputs provided by emotion tags, numerical slider values, and supplementary data.

The interface further comprises a text entry field configured to accept journal-style entries that allow the user to elaborate on their experience or provide contextual commentary. Such journal entries include narrative descriptions, commentary on situational factors influencing the emotional state, or other relevant annotations. This journal-style entry feature supplements the structured inputs by capturing qualitative data not adequately represented by numerical or icon-based inputs.

In various embodiments, the user interface is configured to time-stamp each piece of feedback and includes additional metadata fields to capture contextual information such as the user's identity, location, or the specific conditions under which the feedback is submitted. The feedback data collected by the interface is stored in a data repository for subsequent analysis and integration into a broader system for monitoring, trend analysis, and dynamic adaptation. Data aggregation routines utilize the structured numerical slider values and well-being scores together with the qualitative aspects of journal entries to generate comprehensive user profiles. In some embodiments, these comprehensive user profiles serve to dynamically adjust system parameters or inform subsequent interactions with the user.

In one embodiment, the reinforcement learning model is configured to receive real-time data inputs derived from various sources such as sensor outputs, communication records, and historical context relating to emotional states, relational satisfaction, and previous conflict resolution scenarios. The model processes this data through interconnected layers that extract and quantify emotional cues, thereby detecting transient and evolving patterns overtime. The reinforcement learning framework incorporates a feedback mechanism in which a reward function is implemented to assess the accuracy of predicted emotional states and the effectiveness of conflict resolution, adjusting internal parameters and policy decisions based on performance outcomes. As the model encounters a diverse range of emotional events, it continuously refines its ability to interpret subtle nuances in tone, expression, and context, dynamically adjusting weightings and thresholds to accurately represent fluctuations in emotional conditions. The evolving patterns detected by the reinforcement learning algorithm consist of recurring bouts of stress, gradual improvements or declines in relational satisfaction, and specific markers indicative of potential conflict escalation. In this manner, the model not only learns to classify current emotional states but also anticipates future shifts by analyzing temporal transitions and trends within the collected data. Iterative updates to the learning algorithm ensure that the system adapts to novel data inputs, thereby improving its predictive precision over extended periods. This adaptive capability facilitates proactive interventions based on early detection of undesirable trends in emotional or relational dynamics, ultimately contributing to more effective and timely conflict resolution and relationship management strategies.

In one embodiment, feedback data provided by a user is subjected to an encryption process prior to storage to ensure that the data remains confidential and inaccessible to unauthorized parties. The encryption process employs one or more standard encryption algorithms, such as advanced encryption standard (AES) or other industry-accepted methods, thereby ensuring that the storage and handling of the feedback data complies with applicable privacy regulations and statutory data protection requirements. In such embodiments, a secure key management system is implemented to control access to the decryption keys, ensuring that only authorized parties—such as system administrators or designated processing modules—are capable of decrypting the stored data when necessary. Furthermore, the system is configured to store metadata associated with the encryption process, including the type of encryption algorithm used, the version of the encryption protocol, encryption key identifiers, and other relevant parameters required for auditing or potential future decryption events under regulated circumstances.

In addition to encrypting and securely storing the feedback data, the system further implements an anonymization procedure that removes or obscures any personally identifying information when aggregated insights are shared between users connected by established relationships. The anonymization process involves several steps, including the removal of data fields or markers that could directly reveal the identity of individual users. The process employs data aggregation techniques that combine feedback from two or more users so that individual contributions remain indistinguishable. In certain embodiments, the anonymization process includes adding random noise or replacing original user identifiers with pseudonymous identifiers, thereby ensuring that shared insights are effectively detached from the original source data.

Moreover, the system incorporates mechanisms to verify that user consent is obtained for the collection, storage, and potential sharing of feedback data. Such consent indicators are stored alongside the encrypted data and are examined by the anonymization process before any data is aggregated or shared. This verification process ensures that all data handling operations—from encryption to anonymization—comply with applicable data protection laws and industry best practices.

Overall, the described embodiments provide a robust framework for the secure and compliant handling of user feedback data. The combination of strong encryption methods, secure storage protocols, comprehensive key management practices, and a detailed anonymization process ensures both the privacy of individual users and the utility of aggregated insights for linked users, thereby fulfilling both data security and regulatory compliance objectives.

Avatar-delivered coaching is implemented through a computer-based system featuring an animated interactive character that engages a user in real-time dialogue. The system incorporates coaching techniques derived from emotional intelligence research, family counseling protocols, and evidence-based communication strategies. In certain embodiments, the avatar employs algorithms based on emotional intelligence research to evaluate the user's emotional state by analyzing affective cues and verbal indicators, then tailors responses to promote self-awareness and emotional regulation. Techniques from family counseling protocols are integrated to simulate structured therapeutic interactions, guiding the user through scenarios designed to improve interpersonal communication, resolve conflicts, and support relationship dynamics. The system also employs evidence-based communication strategies that provide systematic guidance on effective conversation techniques, including reflective listening, structured dialogue patterns, and non-verbal communication cues. Natural language processing modules interpret user input and determine appropriate coaching responses based on a database of predefined scenarios combined with adaptive feedback mechanisms. In addition, the avatar delivers multimodal feedback incorporating visual, auditory, and textual elements to reinforce positive communication behaviors and offer corrective guidance when ineffective strategies are identified. The integration of these methodologies produces personalized coaching sessions in which the avatar instructs the user to articulate emotions, suggests rephrasing of statements to reduce ambiguity, or simulates conflict resolution exercises similar to those used in family counseling sessions. Throughout the coaching interaction, the system continuously updates its response protocols based on user progress and feedback, ensuring that the coaching remains dynamic and responsive to individual needs. Data concerning user interactions and progress is securely recorded and analyzed to further refine the coaching algorithms, thereby enhancing the sustained effectiveness of the technique delivery. In certain embodiments, the system also incorporates machine learning techniques that enable the avatar to detect subtle changes in the user's communication style and emotional responses, resulting in a nuanced and adaptive coaching approach that aligns with the latest research findings in emotional intelligence, family counseling, and the efficacy of communication strategies.

In one embodiment, the avatars are engineered to detect and associate specific timeframes with periods of emotional sensitivity, utilizing contextual inputs and user data. The avatars automatically initiate check-ins during designated periods, such as following a conflict, during the menstrual phase, or throughout recovery periods after an emotionally challenging event. These check-ins are triggered by inputs from wearable sensors, calendar events, or behavioral data that indicate the occurrence of a potentially sensitive timeframe. In these embodiments, the avatars analyze collected contextual data, including physiological signals and historical user interactions, to determine the optimal timing for a proactive intervention.

The empathy-driven coaching relies on carefully curated communications intended to convey understanding, support, and guidance. The system incorporates pre-programmed modules that draw on established psychological principles and best practices to generate empathetic responses. These modules can include scripted dialogues that adjust dynamically to reflect the intensity of the emotional distress reported and the specific context of the emotionally sensitive period. For example, during the post-conflict phase, the avatar offers calming affirmations and strategies to manage residual stress, while during periods marked by physiological changes, such as the menstrual phase, the avatar suggests activities designed to promote physical comfort and emotional resilience.

In some embodiments, the avatars are further integrated with remote servers that continuously update the empathy modules based on aggregated user feedback and evolving psychological research. This integration supports a machine learning component that personalizes the content and timing of the check-ins, ensuring that the coaching remains relevant and effective over time. The system refines its responses by learning from patterns in user behavior, previous interactions, and contextual triggers, thereby continuously improving the delivery of empathy-driven support.

Additionally, the avatars include an interface that permits users to provide feedback on check-in interactions, thereby establishing an adaptive loop where the avatars adjust their prompts and coaching styles based on individual user preferences. The system then correlates the user's feedback with biometric and usage data to refine the approach for subsequent interactions within similar emotionally sensitive contexts.

In embodiments of one implementation, users are provided with the option to share menstrual cycle data through a secure interface on a mobile device or computing system configured to accept such information via manual input or automated synchronization with external data sources. The system processes the menstrual cycle data—which includes parameters such as cycle start dates, predicted ovulation periods, and associated physiological markers-using one or more processing units programmed with algorithms to determine the current physiological phase of the user. Based on the determined phase, a digital avatar is activated to provide personalized, context-aware guidance tailored to the user's present physiological condition. The avatar is programmed to deliver recommendations that address personal health management, emotional well-being, and lifestyle adjustments, and in some embodiments, it extends this guidance to include recommendations designed specifically for the user's partners. Such partner-focused recommendations include tailored advice aimed at enhancing interpersonal understanding of the user's physiological state and facilitating supportive behavior during various phases of the menstrual cycle. The digital avatar operates through an animated representation featuring interactive elements that adjust in real time to changes in the user's cycle data, thereby providing dynamic counseling and suggestions corresponding to specific phases such as the follicular, ovulatory, or luteal stages. Additionally, the system incorporates supplementary data from one or more sensors, including metrics related to sleep, stress, and physical activity, to refine the determination of the physiological phase and further customize the avatar-led guidance. Privacy measures are implemented to ensure that any menstrual cycle data shared by the user is transmitted securely over encrypted communication channels, and users can selectively control how their data is shared with partners or other designated entities. The system's architecture permits real-time updating of the digital avatar's recommendations through continuous monitoring of new cycle data, thereby enabling proactive adjustment of the guidance provided. By integrating menstrual cycle tracking with an interactive digital avatar that offers both self-directed health management advice and partner-specific recommendations, one implementation facilitates a comprehensive approach to wellness that is responsive not only to the physiological state of the user but also to the interpersonal dynamics associated with health and support.

In various embodiments, the system integrates with biosensors designed to detect physiological markers associated with emotional states, such as cortisol, endorphins, and other related biomarkers. The biosensors are implemented as wearable devices, implantable sensors, or additional detection units, and they are configured to monitor in real-time one or more physiological parameters that correlate with emotional states. The collected data is processed through signal conditioning circuits that filter out noise, calibrate sensor outputs, and derive measurable indicators representative of the subject's physiological status. In one embodiment, the biosensor outputs are transmitted via wireless or wired communication protocols to the emotional insight model, which integrates objective data inputs with behavioral and subjective inputs generated by other components of the system. Accordingly, the emotional insight model correlates physiological signals with emotional states, enhancing its ability to detect subtle variations in stress, well-being, or other affective conditions and refining the overall accuracy of the emotional analysis. The biosensor data, including continuous or periodic measurements of hormone levels and other biomarkers, is aggregated and processed with algorithms that analyze temporal and contextual patterns to generate a comprehensive emotional profile. In another embodiment, the system incorporates machine learning techniques that utilize both historical and real-time biosensor data during training and operational phases, thereby enabling the emotional insight model to adapt to individual physiological baselines and variations. The adaptation process adjusts the weighting of biosensor data relative to other inputs when determining the overall emotional state of the subject. Secure data storage and transmission protocols are employed to ensure that sensitive physiological data is protected in compliance with applicable privacy and data protection regulations. Additionally, the integration supports dynamic updating of the emotional insight model as biosensor inputs change, thereby enabling the system to provide contextually relevant responses and interventions based on objective emotional indicators.

In one embodiment, the content engine is configured to generate timeline-based avatar videos by strategically integrating three distinct types of content, namely textual narratives, audio signals, and visual elements, within a hybrid decision system. This hybrid system comprises both deterministic rule trees and artificial intelligence models, which together enable the coherent assembly of multimedia components. The deterministic rule trees consist of a series of predefined nodes that process incoming data by evaluating specific conditions, thereby establishing a structured framework for sequencing the content. Each node in the rule tree is associated with particular parameters and transition rules that ensure the proper alignment and synchronization of the textual, auditory, and visual elements along the timeline. In parallel, the artificial intelligence models contribute adaptive processing capabilities by analyzing contextual and semantic information derived from the input data. The AI models employ machine learning algorithms to interpret nuances in the content, such as emotional tone, emphasis, or visual motifs, which might not be fully captured by the rule trees alone. The output from the AI models serves to refine and adjust the sequencing determined by the deterministic rules, thereby enhancing the overall quality and coherence of the final avatar video. In practice, when a request for an avatar video is initiated, the rule trees first establish a baseline timeline by mapping out the sequence in which the different content types are introduced. Simultaneously, the AI models assess the content on a deeper level, making recommendations for adjusting timing, transitions, and the selection of specific multimedia segments based on learned patterns. The two components of the hybrid decision system then engage in an iterative process, where initial decisions from the rule trees are fine-tuned based on AI-derived insights, resulting in a polished video output that adheres to both explicit programming rules and dynamically interpreted data characteristics. This dual-layered approach not only facilitates the generation of videos that maintain narrative consistency and synchronized audiovisual representation but also provides the flexibility to incorporate feedback and adapt to varying datasets or user-specific requirements. Consequently, the system can evolve over time, integrating new types of content or implementing modified rules and learning parameters, thereby continually enhancing its ability to produce compelling and contextually appropriate timeline-based avatar videos.

The system includes a social linking module designed to enable users to designate and maintain interpersonal relationships within the application. The module facilitates the creation and management of user profiles and the establishment of relationship links by allowing users to select specific contacts, indicate the nature of these interpersonal relationships, and assign relational attributes that include family ties, friendships, professional associations, or other custom relationship types. These links serveas the basis for subsequent operations within the system, ensuring that the health coaching processes are contextually relevant to the user's social environment.

A structured feedback interface is provided to allow users to submit emotional reflections, request additional support, or articulate perceived well-being impacts associated with interactions with linked users. This interface comprises standardized input fields, selectable sentiment indicators, and guided prompts designed to capture qualitative and quantitative dimensions of the user's emotional state. By constructing a set of inputs that are both user-friendly and comprehensive, the interface ensures that the data collected reflects a range of emotional and behavioral insights related to the user's interpersonal experience. The structured nature of the feedback contributes to enhanced accuracy and consistency in the retrieval of user responses, which are subsequently processed by the system.

An emotional analysis engine is configured to process user-submitted feedback using multiple algorithmic components. The engine includes a sentiment analysis submodule that examines linguistic content to determine the overall sentiment—positive, negative, or neutral—associated with the user input. In addition, the engine applies role classification techniques to identify the specific roles of both the feedback provider and the referenced linked users, thereby facilitating a contextual evaluation of interpersonal dynamics. The engine further computes a well-being score derived from predefined metrics and behavioral parameters, including frequency of interactions, fluctuations in self-reported emotional states, and other observable behavioral trends. In combination with an analysis of behavioral context, the engine produces an assessment that reflects the current state of the user's well-being and the impact of social interactions on that state. Moreover, the emotional analysis engine adapts its analysis strategies based on historical interaction data and dynamically updated models to ensure that coaching interventions remain both relevant and timely.

The computer-implemented system seamlessly integrates these modules by ensuring that data flows efficiently between components. The social linking module provides the necessary relational data that informs the structured feedback interface which, in turn, gathers pertinent user input. The emotional analysis engine processes this feedback to generate a multi-faceted understanding of the user's emotional state and interpersonal dynamics. This analytical output is then passed to the avatar coaching module, which constructs targeted coaching interventions that are grounded in evidence-based therapeutic techniques. The overall interaction among these modules enables a robust system for delivering personalized health coaching that dynamically adapts to the user's evolving emotional and social context.

The one embodiment analyzes the collected data with a multi-layered algorithm that correlates physical activity—including its duration and intensity—with meal timing and subsequent metabolic responses. This analysis involves multiple processing stages, such as data normalization, feature extraction, and the implementation of algorithms, including but not limited to statistical models and machine learning techniques. The analysis is designed to identify key correlations between the timing of exercise and nutrient ingestion and the metabolic state of the user, enabling the system to recognize patterns associated with optimal metabolic responses during and following periods of physical exertion.

The system gathers daily data linked to physical exertion, stress, and the previous night's sleep quality by employing one or more wearable sensors and mobile device interfaces. In a particular embodiment, the system monitors physical exertion without interruption utilizing accelerometers, gyroscopes, and heart rate monitors. Stress levels can be assessed by factoring in heart rate variability or galvanic skin response. Sleep quality data is obtained during sleep intervals using evaluative measures like sleep latency, duration, efficiency, and episodes of restlessness. The amassed data is subsequently transferred to a centralized processing unit where a predictive model that has been educated on recovery curves observed in elite athletes processes the information. This predictive model applies historical performance, recouping data, and circadian rhythm patterns from elite athletes to discern an ideal sleep duration and precise sleep interval for each user. This model could also utilize machine learning algorithms which deduce associations between daily physical stressors and physiological sleep cycles while adjusting for changes in circadian rhythms and environmental impacts.

The one embodiment offers an individualized sports training system incorporates a gamification module that infuses interactivity and competition into the complete fitness routine. In this particular embodiment, this system generates a unique performance score for each user, updated instantly based on the individual's compliance with suggested exercises, timing of meals, and recuperation objectives. This immediate performance score is computed from scrutinized sensor data, assessment of adherence to scheduled tasks, and juxtaposing continual performance metrics against thresholds specific to the user. The system persistently gathers and dissects biometric data and activity data and converts these findings into a quantified performance score signifying both instantaneous exertion and sustained improvement.

In addition, the system integrates a comparison module that evaluates the user's performance score against anonymized data derived from top-tier athletes. Through juxtaposing the user's cumulated performance metrics with benchmarks set by elite athletes, the system can calculate a percentile rank or allocate a medal tier, demonstrating the user's alignment with Olympic-level performance standards. This process entails merging user-specific data with information from elite training datasets, standardizing the performance variables, and determining relative scores to justify the assigned ranking. The assigned percentile rank or medal tier serves as both an incentive and an indicator of performance progress, offering users insight into how their performance stacks up against elite athletes. This comparative analysis continually adjusts to reflect new data inputs, consequently ensuring an engaging and precise performance profile over time.

In addition to these functions, the interface is designed with a clock-based display that organizes scheduled activities around a continuous circular time representation. By mapping activities onto this clock interface, users obtain an intuitive visualization of their daily schedule. Graphical elements indicate the timing and duration of each scheduled activity, allowing for a quick assessment of how closely actual performance aligns with prescribed timings. Furthermore, the interface provides visual indicators that denote optimal versus alert ranges for activity timing and duration. These indicators are incorporated as highlighted segments or markers on the clock, where the optimal range is accentuated using specific color tones or boundary lines, and the alert range is similarly signified with contrasting colors or patterns. This arrangement enables the user to instantly recognize if an activity is scheduled within a preferred time window or if it deviates into a timing that could affect performance or recovery.

A learning engine is incorporated to process the biometric data by applying user-specific and population-derived thresholds to different data streams. The learning engine dynamically adjusts the weighting of each biometric parameter based on historical data, statistical analyses, and predictive models calibrated on large datasets. In this context, the system is designed to identify patterns, trends, and deviations from expected physiological ranges. The learning engine continuously refines its internal models by using iterative feedback from subsequent biometric readings and outcomes of previously generated interventions.

In a specific embodiment, the system additionally incorporates an instant sensor network that accumulates user physiological data during undertaking of workouts and related physical engagements. The sensor network, inclusive of numerous sensors like heart rate detectors, accelerometers, temperature detection units and various other biometric quantifying tools, is structured to transfer data instantly to the processing component of the system. This procedure of data collation permits the system to supervise fluid physiological conditions of the user with insignificant delay.

The real-time sensor network, feedback controller, and predictive engine collectively operate in an integrated manner, allowing the system to provide continuously updated and personalized exercise intensity targets, meal timing instructions, and next-day training and dietary modifications. The system is thereby capable of delivering optimized performance outcomes by adapting to the user's specific physiological responses and recovery metrics on a continual basis.

The system further comprises a reward-based coaching compliance module. The module includes an AI-driven coaching component that automatically generates daily tasks, with each task being assigned specific point values indicative of its inherent difficulty or intensity. The tasks are generated based on an analysis of the user's historical performance data and current behavioral trends and are designed to encourage progression toward defined fitness and nutrition goals. The module also comprises a dynamic scoring mechanism that tracks the user's compliance with the generated tasks, monitoring not only completion times but also the quality and consistency of task execution. This scoring mechanism is configured to adjust the assigned point values in real time, increasing or decreasing them based on the relative difficulty or intensity of the tasks and on the user's performance metrics. Furthermore, the module includes an interactive leaderboard that displays the user's progress relative to that of friends or peer groups. The leaderboard remains locked until the user achieves certain preset compliance thresholds, thereby reinforcing task adherence and sustained engagement. By combining automated task generation, adaptive scoring based on task performance, and a competitive, engagement-driven leaderboard, the reward-based coaching compliance module promotes a structured and motivating environment that supports continual improvement in athletic training and dietary adherence.

Upon identifying the R M R, the procedure continues with the computation of a non-exercise activity thermogenesis (NEAT) value. This value signifies the amount of calories utilized during normal daily activities that are not categorized as structured exercise. This stage could involve using a set proportion of the RMR or leveraging activity monitoring information to deduce the caloric expenditure related to customary movements and minor activities conducted throughout the day.

Subsequently, the sum of daily calorie need undergoes adjustment according to a user-determined target. This alteration encompasses modifying the initial total daily calorie requisite; for instance, through implementing a specific caloric deficit or surplus. In the event one pursues weight loss, a pre-decided percentage like 10% or 25% might be subtracted, whereas adding a surplus could serve muscle-building objectives. Such targets are unique to each user and are established during an initial set-up process or periodic user discussions.

Finalizing the process involves apportioning the adjusted total daily caloric need into dietary constituents such as carbohydrates, proteins, and fats in line with one or more preset ratios or algorithms. In specified embodiments, the allocation is further fine-tuned based on more user factors including workout volume, unique metabolic responses, and individual dietary preferences. The outcome comprises a collection of macronutrient targets beneficial in guiding meal preparation and meeting the overall nutrition and energy goals of the user.

In one embodiment, the method further comprises adjusting metabolic equivalent tasks (METs) based on the user's age if the user is determined to be over 40 years old, whereby the MET values are modified to account for age-related changes in metabolic efficiency and physical performance. The method further comprises applying a caloric restriction, wherein a reduction of 10% is imposed to balance overall athletic performance with fat loss requirements or, alternatively, a reduction of 25% is applied when the objective is to maximize fat loss. In addition, the method includes determining the user's protein needs based on body weight in combination with training factors such as workout intensity, duration, and frequency. The method further comprises determining carbohydrate needs by incorporating factors including cerebral energy requirements, energy expenditure from non-exercise activities, and the specific demands imposed by exercise sessions. Moreover, the method further comprises determining fat needs as a percentage of the total daily caloric intake to ensure an optimal macronutrient balance. The method further comprises adjusting the overall calorie calculations and associated macronutrient recommendations based on the user's recorded training volume, so as to dynamically tailor nutritional intake to fluctuations in physical exercise load. Finally, the method further comprises providing meal-specific macronutrient recommendations by mapping each meal to its intended timing and purpose within the daily nutritional plan, thereby optimizing the synchronization between nutrient intake and the body's metabolic and recovery phases.

Further additions to this method entail delivering developed fitness instruction and diet plan via an application on handheld gadgets monitoring physiological variables in real-time for adjustments on the fly based on present metrics acquired from wearable sensors or manually inputted feedback allowing adaptive alterations according to changes in the regime. In addition to this component, there's also incorporation of AI video messages featuring customized AI coach persona; these video messages are manifested from variable-based text-to-voice conversion APIs with resulting output channeled to generative video AI platforms for final rendering including a focus on addressing users' needs specifically along with their personal goals & constantly evolving trends Lastly, analyzing & reacting accordingly to users' behavior is achieved by reviewing indicators like humor quotient, interactive responses from both text-based content delivered by the language model and received video content for modifications to align better with the user's mindset and motivational levels. The described functionalities execute via interconnected modules on local devices or through platforms available remotely on the cloud; all providing real-time updates contributing to complete guidance and loop feedbacks of the system further refining customized health, fitness and dietary planning per ever-changing profiles of users.

In another embodiment, the method includes estimating or conveying digestion rates relying on the user's continuous glucose monitoring (CGM) data and any subsequent feedback relayed by the user. This estimation is presented graphically by representing a colored bar in a calendar interface to signal a meal "extension." By continuously tracking the user's glucose levels and associating these measurements with projected digestion efficacy, the system can evaluate the velocity of nutrient absorption. The computed digestion rate prediction then transforms into a noticeable indicator on the calendar, where a color-coded bar demonstrates whether digestion of the meal proceeds at an usual, accelerated, or delayed pace.

In another aspect, the method involves adapting meal content to regulate digestion speed. For meals that are expected to be fiber-rich, crunchy vegetables and pure fiber sources could be recommended by this system to prolong digestion rates, thereby providing persistent release of nutrients. In contrast, for meals consumed prior to workouts, components such as crunchy vegetables might see their quantity reduced and recommend elevating protein sources obtained from powder in order to ensure prompter digestion. This ensures nutritional needs are met timely in alignment with physical activity routines. Implementation of these modifications happens dynamically within the algorithm responsible for meal planning so as to improve metabolic responses and boost training outcomes holistically for users overall habits.

Furthermore, the method is enhanced by incorporating humor into the AI-generated content. This additional step leverages an analysis of user psychometric trends—which include assessments of mood, engagement, and cognitive responses derived from both wearable sensor data and in-app user interactions—to selectively integrate humorous elements into the content. The integration of humor is designed to stimulate the user's parasympathetic nervous system by promoting relaxation and reducing stress levels, thereby fostering a more positive mindset during and after workout sessions. The humorous content is manifested as witty or lighthearted commentary, amusing visual animations, or playful sound effects, all of which are contextually synchronized with the overall fitness regimen. The aim is to provide a balanced experience that maintains motivation and improves the user's psychological comfort, contributing to enhanced performance and sustained engagement with the training program.

In another embodiment, the method includes offering the user a choice to pick a particular coaching style and persona. In this embodiment, a collection of pre-trained artificial intelligence models is kept within the system. Each model is set up to mimic different coaching methodologies, encompassing stern and positive coaching styles. The user interface showcases selectable options enabling the user to determine a preferred coaching persona, influenced by predefined characteristics like tone, delivery, and behavioral reinforcement tactics.

When the user specifies their preference, the system draws the matching coaching model from the library and merges it seamlessly with the personalized training and nutrition advice platform. The style of chosen coach shapes the subsequent instructions and motivation provided, in such a manner that a rigorous coaching approach gives forthright amendment directives and intense motivational cues, while an affirmative coaching method proffers boosting reassurance and constructive feedback. This combination guarantees that user experience is customized not just based on physiological details and performance indicators but also syncs with their favoured social communication style.

In one embodiment, the method further comprises capturing user heart rate and heart rate variability (HR/HRV) data without the use of dedicated sensors by employing a phone camera and requiring the user to place a finger against the camera lens. In this configuration, the phone camera is utilized to obtain a series of optical images that reflect subtle variations in the color intensity of the user's fingertip corresponding to blood pulsations. The method includes processing these images to extract photoplethysmographic (PPG) signals, whereby the temporal fluctuations in the received optical intensity serve as an indirect measure of the user's heart rate and heart rate variability. Signal processing algorithms, including but not limited to Fourier transforms and noise filtering techniques, are applied to the extracted PPG signals to compute periodic heart rate and H R/HRV values. These computed data are then used as inputs in combination with other user data such as exercise metrics, sleep data, and dietary intake, enhancing the multi-layered algorithm's capacity to correlate physical activity, nutrient intake timing, and metabolic responses. The system further includes scheduling periodic H R/HRV check-ins, whereby the phone camera is activated at predetermined intervals or upon user initiation, enabling the generation of longitudinal data points that facilitate an insightful monitoring of fitness progression over time. The periodic check-ins allow for the dynamic updating of individual performance scores, adjustments in workout and recovery recommendations, and real-time calibration of training protocols based on detected changes in cardiovascular performance. In some embodiments, the captured HR/HRV data is further integrated into the decision module, where neural network algorithms or ensemble learning architectures weigh these parameters along with other biometric and psychometric metrics to refine the personalized fitness and nutrition plans. This sensor-less monitoring approach reduces the reliance on separate wearable devices, simplifies the user experience, and enhances the overall accuracy of fitness progression assessments by providing continuous, non-invasive cardiovascular insights.

Generating an Optimal Daily Activity Plan.

The present apparatus also provides a system for generating an optimal daily activity plan by employing a processor that is configured to prioritize various activities including sleep, training, pre-training meal, post-training meal, breakfast, nap, and floating meals. The processor utilizes predefined priorities to establish an order of importance, ensuring that higher-priority activities are scheduled and executed in a manner that maintains overall optimal daily performance. In embodiments, certain activities are classified as either dot activities or interval activities, where dot activities represent single, discrete events occurring at specific time points and interval activities denote events that span a defined period. The configuration of these time parameters is adjustable, allowing for flexibility based on user-specific requirements or external constraints.

The processor applies a set of constraints during the scheduling process to prevent any user modifications that would result in block positions containing block lengths that are not permitted by the system's design. These constraints ensure that modifications by the user do not compromise the integrity of the optimal daily activity plan. One aspect of the system involves the utilization of past wake time information to mark the start of the day. Once the day has begun, the system refrains from automatic rescheduling of activities, thereby preserving consistency in the planned activity sequence.

Moreover, the system incorporates a zoning mechanism wherein each activity type is associated with optimal, alert, and block ranges or positions. The optimal zone represents a timeframe during which the activity is ideally performed, while the alert zone indicates a period when deviations occur without significant detriment to the overall plan. The block ranges are defined intervals during which activities are restricted or blocked from being scheduled, preserving an overall balanced distribution of activities throughout the day. In one embodiment, the processor cross-references the time constraints, activity priorities, and permitted zones to dynamically adjust the daily activity plan in real time while preserving the defined optimal distribution of tasks. Integrating this zoning mechanism with the configurable dot and interval activity definitions and the strict enforcement of modification constraints ensures that the system maintains a comprehensive and robust framework for daily activity planning.

The processor is configured to execute instructions that automatically generate a default sleep recommendation during the onboarding process of the device or application. In one embodiment, the processor stores default bedtime and wake time values that correspond to 10:30 PM and 7:00 AM, respectively. When a new user initiates the onboarding procedure, the processor retrieves these preset values and presents them as the recommended sleep schedule. The instructions executed by the processor ensure that these default times are applied unless the user chooses to modify them during onboarding. For example, as the onboarding process progresses, the user interface displays the default sleep recommendation, and the user is provided with the option to adjust the suggested times in accordance with personal preference or specific sleep requirements. Should the user opt to retain the preset recommendation, the processor maintains the default values; alternatively, if the user substitutes different times, the processor updates the settings accordingly. The default recommendation is maintained within the system's memory and can be used to trigger subsequent functionality such as scheduling notifications, reminders, or analytics that monitor sleep behavior. The disclosed configuration allows the processor to seamlessly transition from onboarding to regular operation, ensuring that an initial sleep schedule is established without additional user intervention unless explicitly modified.

In one embodiment, the processor is configured to set training parameters by determining an appropriate sequence and timing for initiating training operations. Upon detecting a wake event, the processor measures or registers the system's wake time and establishes a predetermined delay such that training operations are scheduled to begin 100 minutes after the wake event. This delay period allows for necessary system initialization, ensuring that all related subsystems are fully operational before initiation of the training process.

Additionally, the processor is configured to resolve any conflicts automatically by employing a conflict resolution module that compares user-specified preferences with system-defined default values. When a user preference cannot be accommodated—for example, if the provided value falls outside of acceptable operating parameters or conflicts with another concurrent setting—the processor disregards the problematic user input. In such instances, the system automatically assigns the corresponding default value to the conflicting parameter. This automatic resolution ensures continuous operation without requiring additional user intervention and promotes system stability by adhering to predefined, optimal training parameter values.

In the "General Rules" section, when a user adjusts an element's position, the app retains this modification until an activity with equivalent or superior priority is altered. At that point, the app reschedules any activity of a diminished priority. Users are free to edit previous elements. Any changes to position or duration are rounded to the nearest value divisible by five minutes—resulting in times such as 6:05 AM, 6:10 AM, and 6:15 AM—and durations are rounded to increments like 30, 35, or 40 minutes. Importantly, users cannot move any element into blocked positions or extend its length into blocked zones. Additionally, when users modify an activity's position or duration, elements of reduced priority become hidden; these concealed activities are recalculated and reappear once the user completes the modification of the current activity.

In the section on "Past Editing," elements in the app plan can be moved both from the past into the future and vice versa. When the user moves the past wake time, all activities are cleared except for the upcoming bedtime. The app allows these activities to be freely edited according to its rules, including allowing elements to exist in the past. The system supports optimal and sub-optimal states but will automatically realign elements based on user adjustments.

The "past wake time" is utilized to denote when the last sleep session ended. This element can be repositioned and serves as a marker to indicate the start of the current day for scheduling purposes. When editing the past wake time, no tracker zones such as optimal or alert zones are shown. This is because its role is purely informative, indicating the optimal state without triggering alerts. If a user drags this marker to an earlier position, it does not prompt the addition of new activities like naps. This process is primarily concerned with adjusting a visual indicator rather than modifying the actual schedule. Additionally, edits to this element do not activate night mode or reveal other sleep-related elements within the interface.

The app restricts users from moving any element into positions designated as block positions or lengths. The bedtime for the next sleep cannot be adjusted beyond the previous wake time, and the previous wake time cannot be moved past the last bedtime, whether in a counterclockwise or clockwise manner on the clock face. Additionally, the next wake time cannot be moved backwards past the clock hand in a counterclockwise direction. If sleep is ongoing, the wake time cannot be moved into the past.

The conflict resolution module functions by first validating any user inputs against a set of predetermined criteria stored in memory. If an input meets these criteria, it is accepted and applied; otherwise, the module substitutes a default value for that parameter. This method enables the system to maintain a considerable degree of reliability, ensuring that all training parameters are configured in a manner that is both internally consistent and aligned with the overall operational objectives.

The determination of the 100 minute delay period following wake time as a default start time is based on prior empirical observations of system behavior and operational readiness. The delayed start not only provides adequate time for the activation and stabilization of necessary system components but also minimizes the risk of conflicts arising from concurrent processing activities during the initial post-wake period.

Moreover, the described functionality is implemented through a combination of hardware timers and software routines stored on a computer-readable medium. Upon execution by the processor, these routines monitor wake events, manage timing sequences, and perform the necessary checks and substitutions for user input parameters. The modular design of these routines facilitates straightforward updates and modifications, enabling adjustments to the default delay period or conflict resolution criteria as required by future system enhancements.

Thus, by setting a default start time at 100 minutes post wake time and automatically resolving conflicts through the substitution of default values when necessary, the processor ensures a robust and efficient operation of the training process, enhancing overall system performance and user experience while reducing the likelihood of errors stemming from incompatible or improperly configured parameters.

In one embodiment, the system calculates the optimal timing for consuming a pre-training meal based on both the scheduled training start time and the user's wake time. In these embodiments, the meal is planned to be eaten 100 minutes before the training begins, providing an adequate window for the absorption and metabolism of the nutrients required to support the forthcoming physical activity. In circumstances where the interval between the user's wake time and the training start time is insufficient to accommodate this 100-minute period, the system dynamically adjusts the meal timing. Specifically, if positioning the meal 100 minutes before training would leave an inadequate period following wake time, the meal is instead scheduled to occur 50 minutes before the training start time. This alternative timing ensures that the meal remains close to the user's wake period, thereby optimizing metabolic efficiency and preparing the individual for the training session. The timing adjustment mechanism minimizes the risk of reduced metabolic nutrient availability and synchronizes the pre-training meal with the user's physiological state immediately after waking.

The "Zones" section outlines optimal, alert, and block ranges for different activities within a daily plan. For sleep, the optimal length is between 7.5 and 9.5 hours, including 30 minutes of sleep latency. Alert lengths are defined as 4.5 to 7.5 hours and 9.5 to 12.5 hours, while block lengths are anything less than 4.5 hours or more than 12.5 hours. Alert positions specify that waking after 9 AM or going to bed before 9 PM is not recommended.

For training, the optimal duration ranges from 60 minutes to 2 hours. If training exceeds two hours, it is considered in the alert range, while less than 60 minutes or more than five hours falls into the block range. Training should not occur within 120 minutes of sleep.

Pre-training meals have an optimal position between 80 and 110 minutes before training starts. An alert is triggered if this meal occurs less than 80 minutes before or more than 110 minutes before training starts. Meals scheduled more than 150 minutes before training fall into the block position.

Breakfast is optimally eaten within zero to 90 minutes after waking up. It becomes an alert if it's scheduled between 90 and 120 minutes from wake time, with block positions defined as more than 120 minutes after wake time or if scheduled in the negative (before wake time).

A nap's ideal position is between 50% and 70% of the awake time during the period between one wake time and the next bedtime. Naps taken outside of this range put them in the alert category, but there is no block position specified for nap time.

Floating meals should be positioned within a gap between other meals. The alert position triggers if these meals are placed within 120 minutes of surrounding elements, and they will only fit into a block position if they collide with other surrounding elements.

To calculate meal positions, the process begins by determining the number of meals (n) to be added within a given gap length (g). Once the number of meals is established, the positions of these meals are calculated by equally distributing them within the gap, ensuring they are spaced evenly from each other and the gap edges. The distance between meals (tdist) is calculated as $tdist=g/(n+1)$, where g is the gap length and n is the number of meals. Using this distance, the position of each meal (tmeal) is determined by the formula $tmeal=tgapStart+(tdist\times m)$, where m represents the meal number (1, 2, . . . , n). However, an exception applies if the calculated meal is the first meal after a post-training meal; in this case, its position is adjusted to $tmeal=tgapStart+0.7\times(tdist\times m)$ for m=1, ensuring it is placed closer to the start of the gap. Additionally, an edge case is addressed: if a floating meal overlaps with a scheduled nap, the meal is moved to a position 45 minutes after the nap starts to avoid collision. This systematic approach ensures meals are optimally spaced, accounting for training, naps, and other constraints while maintaining balanced nutrition timing.

In one embodiment, a clock user interface is provided that enables user interaction through a series of touch-based editing flowcharts configured to trigger precise edits in the positioning of activities within a system-defined set of editable ranges. The user interface is designed to present a graphical layout where each element associated with time-dependent activities can be manipulated via touch inputs, thereby allowing the user to adjust the sequence or positioning of particular activities by interacting directly with on-screen flowcharts. When a user initiates a touch input on a designated control area associated with an activity, the system processes the input through a corresponding editing flowchart that guides the user through one or more decision steps. At each step, the flowchart displays options that are dynamically adjusted in response to the detected touch events, ensuring that the user is informed of the available interactive selections that comply with the constraints inherent in the predefined editable ranges. These ranges are set by the system to enforce scheduling integrity and ensure that any modifications remain within acceptable temporal or spatial boundaries.

As the user navigates through the editing process, the system continuously monitors the changes requested by the touch inputs and maps them to the allowed activities within the predetermined ranges. This mapping ensures that edits such as the addition, deletion, or repositioning of time segments or related activities are executed only when they fall within a permissible range. If a proposed adjustment would fall outside of this range, the system either restricts further movement or prompts the user to confirm the intent to override such limits based on additional system parameters or user permissions.

The clock user interface further integrates additional sensor data to refine the precision of touch inputs and associated commands. For example, acceleration or pressure sensors are utilized to determine the intensity or duration of touch, thereby permitting a more granular adjustment of activity positions. This sensor information is processed in coordination with predefined editable ranges to ensure that resulting modifications occur proportionally and within the limits established by the system architecture. The integration of these sensors supplies an extra degree of control, enabling both subtle and dramatic changes to the temporal layout as required by the user.

In one embodiment, a notification system is configured to generate iOS local notifications for activity reminders even when the app is not in use. The system leverages iOS frameworks, such as the UserNotifications framework, to schedule and deliver notifications independently of the app's active state. When an activity reminder is due, the notification system generates a local notification that includes elements such as an alert message, sound, badge updates, and other relevant content designed to inform the user of the pending activity. Even if the application is not running in the foreground or has been terminated, the system ensures that the operating system's notification service delivers the local notification. Upon the user tapping the local notification, the operating system initiates the launch sequence of the app. This sequence invokes application delegate methods and handles the notification's payload to load the main screen. The main screen automatically displays, providing access to the core functions and further details related to the activity reminder. In some embodiments, the notification carries contextual or user-specific data that is used to tailor the content displayed on the main screen. Alternative embodiments include additional logic that incorporates interactive elements within the notification, such as action buttons that allow users to execute secondary operations in addition to launching the main screen. Furthermore, the system implements error handling routines to address cases where the main screen cannot be loaded immediately, ensuring that users receive an appropriate message or alternative navigation path. The integration of the notification system with the app's lifecycle events ensures a seamless user experience by reliably presenting activity reminders and facilitating direct access to the application's primary interface regardless of the app's prior state.

In-app notifications are configured with now-window triggers that initiate at the moment the parent activity begins and terminate either 45 minutes thereafter or according to customizable timing parameters suited for naps. When the parent activity commences, a corresponding now-window trigger activates within the system, enabling notifications to be displayed within a defined temporal window. In one embodiment, this window is set to terminate precisely 45 minutes after the initiation of the parent activity, thereby ensuring that notifications remain limited to a predetermined duration corresponding to the typical active engagement period associated with the activity. Alternatively, the system further adapts to support customizable timing for nap periods. In such an embodiment, the end time for the now-window trigger is not fixed at 45 minutes but instead is set to a user-defined value that reflects the intended duration of a nap. This configuration allows the system to adjust dynamically to the specific timing requirements of nap-related scenarios, thereby improving the relevance and overall user experience of the notification delivery. The system includes software routines that monitor the progression of time relative to the parent activity's start, with these routines determining when the fixed 45-minute period has elapsed or when the customized nap timing threshold is reached. Moreover, the trigger configuration integrates with additional application functionalities to account for variations in user behavior, such as the potential extension or shortening of nap durations based on user preferences. This flexible approach enhances the efficiency of notification delivery by ensuring that notifications occur only during appropriate and predefined time windows, thus reducing potential disruptions and providing optimal synchronization with the user's activity patterns. The disclosed embodiments encompass both the fixed-duration trigger, terminating 45 minutes after the commencement of the parent activity, and the customizable-duration trigger designed to better accommodate nap periods, thereby providing a versatile in-app notification system responsive to varying user needs and contextual timing requirements.

In one embodiment, the system is configured to dynamically adjust its user interface in response to temporal and contextual cues by automatically switching between day and night modes. The mechanism evaluates the current system time using a clock module and compares it against predetermined thresholds to determine whether conditions correspond to typical daytime or nighttime usage. When the current time falls within a predefined daytime interval, a corresponding color scheme optimized for bright conditions is applied, whereas during intervals associated with nighttime, an alternative color scheme with darker tones is selected to reduce glare and minimize eye strain. In alternative embodiments, the system also monitors user-initiated editing of elements and assesses, based on the properties of these edited elements, whether a transition between modes is desirable. For example, when an element associated with reduced ambient brightness or with characteristics typical of nighttime editing is detected, the system overrides the current theme and automatically transitions to the night mode display. The selected color schemes are defined by distinct sets of parameters, which can include variations in contrast, brightness, saturation, and other visual attributes designed to enhance legibility and user comfort under varying environmental illumination conditions. Transitions between modes can further be implemented with gradual parameter adjustments to ensure a smooth visual experience and to avoid abrupt changes that could disrupt user interaction. In some embodiments, the system incorporates additional sensors, such as ambient illumination detectors, to supplement the time-based criteria and refined user behavior analysis, thereby providing a more robust method for determining the optimal display mode. Stored settings for each mode allow for customization by the user, and an override feature permits manual selection if the automatic configuration does not align with the user's immediate preferences. The incorporation of such an adaptive interface contributes to enhanced usability and overall user experience, as it automatically aligns display characteristics with both environmental conditions and user actions without requiring constant manual intervention.

In one embodiment, the scheduling algorithm is designed to determine an optimal nap period that constitutes approximately 60% of the total awake time. The awake time is defined as the period beginning when the user concludes their primary sleep period and ending when the next primary sleep period is initiated, with any interim awakenings accounted for as part of the overall awake duration. The algorithm calculates the target nap period based on this duration while concurrently evaluating the user's schedule to ensure that the proposed nap does not overlap with any predefined training sessions. When a conflict or collision is detected between the calculated nap period and any scheduled training session, the algorithm automatically adjusts the timing of the nap period to eliminate the overlap. Additionally, the scheduling engine assesses the temporal gaps between other scheduled activities. If the insertion of the calculated nap period would result in a gap between successive activities that exceeds a predefined allowable duration, the algorithm repositions or resizes the nap period so that the gap constraints are not violated. The system, therefore, operates by scanning the entire active period to identify intervals free of training sessions and other scheduled tasks and then determining an interval that best approximates 60% of the awake time without creating undue delays or excessively protracted interruptions between activities. In embodiments where scheduling gaps vary in length due to dynamic changes in the itinerary or modifications to training session timings, the algorithm continuously recalculates the target nap period in real time, ensuring that the final schedule reflects both the objective of optimal restorative duration and the operational constraints of adjacent activities. This approach enables a flexible yet methodical allocation of nap time that maintains overall schedule coherence while maximizing user recovery, thus demonstrating the viability and practicality of integrating automated scheduling with performance and wellness parameters.

Floating meals are dynamically adjusted within predetermined gap zones between scheduled activities. In one embodiment, when a schedule includes designated start and end gap zones, the system automatically calculates available time slots by analyzing the intervals between fixed activities such as naps and other scheduled events. The floating meals are then repositioned within these gap zones so that no overlap occurs with the fixed items in the schedule. A schedule management module continuously monitors the timing of both the floating meals and preset scheduled activities, including naps, and determines the optimal placement of the floating meals based on available time intervals. The module utilizes algorithms that evaluate the start gap zone—beginning at the conclusion of a preceding scheduled activity—and the end gap zone—extending up to the commencement of a subsequent activity. When a potential conflict between a floating meal and a scheduled nap or other activity is detected, the system automatically adjusts the timing of the floating meal to maintain complete separation from these fixed events, ensuring that the displayed floating meal timing remains entirely within the allowable gap zone. The dynamic adjustment process involves a constraint-based analysis that factors in the maximum available duration within the gap zones and recalculates the floating meal schedule accordingly. In automated embodiments, these recalculations occur in near real-time as the system receives updated schedule information, allowing floating meals to shift seamlessly without manual intervention. Alternatively, in embodiments that permit user interaction, the system will propose adjustments and display notifications to assist users in manually realigning the floating meal timing. The system also includes verification steps that cross-check the newly assigned floating meal time against all scheduled events to confirm that no overlap has been introduced, particularly with sensitive periods such as naps. If any conflict is detected, the system repeats the timing adjustment process until the floating meal is properly positioned within the gap zone. Thus, by dynamically aligning floating meals in start and end gap zones while accounting for the fixed schedule of naps and other activities, the overall scheduling apparatus maintains both flexibility and integrity within the user's timetable.

Calculating Personalized Nutritional Needs

FIG. 1 illustrates the following reference(s) that depict various aspects and embodiments of one implementation, providing visual clarification of the corresponding components discussed in the detailed description.

FIG. 2 illustrates the following reference: the unique capability to calculate based on hourly needs for blood chemistry, as well as actual daily inputs including previous days' workouts and sleep patterns, rather than relying solely on daily totals for macronutrients.

FIG. 3 illustrates the following reference: "For each meal's PROTEIN, Step 1."

FIG. 4 illustrates the following references: A table showing fitness levels with ratings categorized under very easy, medium, and max intensities.

The processor's integration capabilities extend to incorporating biometric data alongside metrics of physical activity and sleep patterns. This allows for dynamic adjustment of macronutrient recommendations on a periodic basis. By continuously monitoring and analyzing these inputs, the apparatus personalizes nutritional guidance, adapting to changes in lifestyle and physiological conditions to promote optimal health outcomes.

In another aspect, the one implementation pertains to an apparatus designed for calculating personalized nutritional needs. The apparatus features a processor specifically configured to perform a series of calculations, which collectively enable the determination and adjustment of an individual's dietary requirements. Initially, the processor calculates the resting metabolic rate (RMR) by utilizing a formula that considers user-specific variables such as weight, age, and sex. This serves as a foundational measure of the calories expended while at rest, providing a baseline for further nutritional computations.

Calculating the Resting Metabolic Rate:

RMR (Cal/day)=(10×weight in kg)+(625×176 for men, 163 for women)−(5×age)+s where Sex-Specific Constant (s)=+5 for males and −161 for females.

This formula provides a baseline estimate of the calories burned at rest.

The NEAT calculation methodology enhances traditional approaches by applying specific percentage modifications based on an individual's fitness state—build, balance, unfit, or fit. For individuals aiming to build, NEAT is augmented by adding 20% of the RMR. For those in a balanced state, the increment is 15% of the RMR. In contrast, individuals categorized as unfit experience a 5% reduction from the RMR, while those considered fit receive an additional 5% of their RMR contributing to their NEAT.

NEAT is calculated by adjusting the RMR based on fitness goals and activity levels:

NEAT=RMR+(20% of RMR for build, 15% for balance, 10% for fat loss)+(−5% of RMR for unfit, +5% for fit)+(2% of RMR per 1,000 steps per day) NEAT=RMR+(20% of R M R for build, 15% for balance, 10% for fat loss)+(−5% of RMR for unfit, +5% for fit)+(2% of RMR per 1,000 steps per day)

This adjustment accounts for the energy expended during daily activities outside of formal exercise.

Additional adjustments to NEAT take into account lifestyle factors such as daily step count, with an extra 2% of the RMR added per 1,000 steps undertaken each day. This dynamic adjustment process ensures a personalized caloric need estimation that accurately reflects an individual's current physical activity level and fitness objectives. Furthermore, the method integrates inputs from hourly metabolic requirements informed by real-time data from blood chemistry analyses and factors in daily workout intensities as well as sleep patterns. This approach provides a more precise and individualized nutritional guide instead of relying solely on cumulative daily macro data, which does not effectively capture temporal fluctuations and specific metabolic demands. The overall strategy aims to optimize nutritional intake in alignment with physiological needs, thereby supporting health maintenance and fitness achievements through precise dietary planning.

In determining the user's protein needs, the processor employs training volume factors which consider the intensity and duration of physical workouts. The calculated protein requirement is then strategically distributed over several meals throughout the day to optimize muscle recovery and growth.

Protein Needs=(0.6 to 0.8 g/day/kg)×(kg body weight)× [1+(Training Factor×2)]

Training Factor (TF) is a multiplier that adjusts protein needs based on workout intensity and volume.

The total daily protein is then divided by 20 and multiplied by the number of hours until the next meal to determine the protein portion for that meal.

Carbohydrate requirements are assessed through a dual approach: basal needs are determined to support essential physiological functions, while additional carbohydrates are allocated based on activity-derived demands. This involves computing the required intake to compensate for energy expended during physical activities, ensuring adequate supply to fuel performance and recovery.

During workout sessions, calorie requirements are determined by multiplying the METS value by the body weight (in kilograms) and by the duration of exercise (in hours), resulting in a total workout calorie value. Typically, between 50 and 100 percent of these calories are assigned toward glucose utilization. Exercise carbohydrate needs are then calculated by multiplying these workout calories by a specified percentage use factor. This process accounts for tailored carbohydrate intake requirements for objectives such as building, balancing, or fat loss, with adjustment ratios ranging from 1 to 1.7.

METS (Metabolic Equivalents): Used to estimate calorie burn during exercise. METS values are adjusted for age and for users over 35, subtract 1% from the METS range for each year over 40.

Workout Calories=METS×(body weight in kg)×hours of exercise Workout Calories=METS×(body weight in kg)×hours of exercise Exercise Carbs=(Workout Calories×Glucose Use %)×(Goal Adjustment)Exercise Carbs=(Workout Calories×Glucose Use %)×(Goal Adjustment)

Goal Adjustment: 1 for building muscle, 0.85 for balance, 0.7 for fat loss.

The computed exercise carbohydrates are refined further by considering any carbohydrates consumed during training. In instances where carbohydrates are ingested within an essential refuel window—for example, within 10 minutes post-exercise—up to 1 gram per kilogram of body weight is absorbed optimally. Carbohydrates consumed in amounts beyond this threshold are allocated to subsequent meals, ensuring proper replenishment during workouts that extend longer than one hour. Specific parameters then guide how carbohydrates should be restored to support ongoing performance, recovery efforts, and the prevention of underfueling consequences.

The system determines fat intake by utilizing a meal modifier to effectively distribute daily fat grams across multiple meals, ensuring nutritional balance aligned with the user's dietary goals. The approach begins by calculating the Non-Exercise Activity Thermogenesis (NEAT) which represents the daily calorie need. This is done by subtracting the total calories derived from protein and carbohydrates from the NEAT value, resulting in the remaining calories allocated for fat consumption. The remaining caloric value dedicated to fat is then divided by nine to convert these calories into grams of fat per day, considering that each gram of fat contains nine calories. To optimize distribution and meet specific dietary objectives, this daily total of fat grams is divided by the number of meals consumed. The process further incorporates a meal modifier, a variable multiplier that adjusts the allocation of fat grams for each meal based on factors such as meal timing, size, user activity levels, and specific dietary goals such as weight loss, maintenance, or muscle gain. This ensures that the user receives an appropriate portion of their total daily fat allowance in each meal, contributing to balanced nutrition. By doing so, the system aligns fat intake with individual health requirements and lifestyle activities, promoting adherence to personalized nutritional targets while preventing excess fat consumption and supporting overall well-being.

Remaining Calories for Fat=NEAT Daily Calorie Need−(Total Calories from Protein+Total Caloriesfrom Carbs)

Total Caloriesfrom Protein=Total protein per day×4 (since 1 g of protein=4 calories).

Total Calories from Carbs=Total carbs per day×4 (since 1 g of carbs=4 calories).

Total Fat Grams per Day=Remaining Calories for Fat/9

One implementation further comprises a user interface designed to facilitate the input and updating of personal data, including weight, age, sex, and activity levels. This interface supports precise customization and personalization of dietary and exercise recommendations based on individual characteristics and lifestyle factors. The interface is intuitive and user-friendly, enabling users to easily enter their current weight, age, and sex. It also provides options to track and update activity levels, thereby allowing the system to adjust caloric and nutritional needs accordingly. The user interface integrates seamlessly with the underlying algorithms to provide feedback and suggestions specifically tailored to the user's requirements. Data input through the interface is securely stored and processed to ensure accuracy in calculating resting metabolic rate (RMR) and non-exercise activity thermogenesis (NEAT) daily calorie needs, as outlined in previous claims. Continuous updating of this data allows for dynamic adjustments of dietary plans as changes in weight or activity levels occur, ensuring that nutritional strategies remain aligned with evolving personal goals and physiological conditions. The system also integrates with external devices or applications to automatically synchronize activity data, enhancing overall functionality and user convenience.

All in-app content such as masterclass minis are transcribed by AI and paired with the video file. A button allows users to say y37 I want to know more about this' or 'I want to incorporate this in my life/lifestyle'. The system is able to know which part of the video's script is at this timecode. The system sends this section to the LLM and asks for it to create a script for the avatar that has more in-depth info about this topic (we upload long form interviews and even more expansive written info from the avatars/key educational points), along with other prompt like Avatars language, voice, coaching style, and users current biometric/contextual data such as recent KHA's, etc. to give personalized advice in integrating this into their life. The voice is created, then the video, then avatar played to teach user more about that. Avatar can be real time interaction in the future. In meantime, chat window can bridge the gap for real-time interaction.

Once the system isolates the segment of interest, it forwards the associated text to an LLM, which generates a detailed, personalized script expanding on the topic. The LLM enriches this script by drawing from a pre-uploaded knowledge base containing long-form interviews, supplementary educational materials, and key insights from fitness and nutrition experts. Additionally, the LLM tailors the response by incorporating user-specific data, such as biometric readings (e.g., heart rate, sleep patterns), training history, nutrition logs, and psychometric trends (e.g., motivation levels, stress indicators). The system also factors in predefined coaching parameters, including the avatar's preferred language, vocal characteristics, and coaching style— whether motivational, analytical, or empathetic—to ensure the response aligns with the user's preferences and learning needs.

The next phase involves transforming the LLM —generated script into a digital avatar response. This is achieved through a multi-step process: first, the text is converted into synthetic speech using a text-to-speech (TTS) API, which is configured to emulate the coach's voice, tone, and pacing based on stored personality traits. The synthesized voice is then fed into a generative video AI platform, which animates a digital avatar—either a realistic human likeness or a stylized character—to deliver the response in a visually engaging manner. The result is a seamless audiovisual presentation that mimics a live coaching session, providing the user with deeper insights into the topic they inquired about.

To further enhance interactivity, the system includes a chat interface that allows users to ask follow-up questions in real time, bridging the gap until fully real-time avatar interactions become technologically feasible. The chat feature processes queries using the same LLM and knowledge base, ensuring continuity in the coaching dialogue. User interactions are logged and analyzed to refine future responses, creating a feedback loop that improves personalization over time. For instance, if a user frequently seeks advice on muscle-building techniques, the system will prioritize content related to strength training in subsequent interactions.

The method also accommodates varying user goals—such as fat loss, muscle gain, or general wellness—by dynamically adjusting the advice provided. For example, if a user's nutrition data indicates a calorie deficit, the avatar might emphasize recovery strategies, whereas a user in a bulking phase might receive tips on optimizing macronutrient intake. Coaching styles can also be customized; a user who prefers direct, no-nonsense advice might receive concise, action-oriented responses, while another who thrives on encouragement might get a more supportive delivery.

Underlying the entire process is a robust data infrastructure that stores and retrieves user profiles, interaction histories, and expert knowledge. This ensures that each avatar response is not only contextually relevant but also evolves with the user's progress. For example, if a user's biometric data shows improved stamina over time, the system might introduce advanced training techniques in its explanations. Similarly, psychometric trends could trigger shifts in coaching tone—e.g., more motivational cues during periods of low engagement.

The system's applications extend beyond fitness and nutrition, with potential use cases in corporate training, medical education, and language learning. By automating the synthesis of expert knowledge and personalized coaching, the system democratizes access to high-quality, adaptive education. Its integration of AI-generated content, responsive avatars, and real-time interactivity represents a significant leap forward in digital learning technologies, offering users a more immersive and tailored educational experience than static video platforms can provide.

In a system for AI-Generated Avatar Coaching Using Pre-Generated, Real-Time Generated, and Actor-Recorded Content Assembly, the system and method for delivering adaptive, emotionally intelligent coaching using an AI avatar that integrates three key content types: (1) pre-recorded human video and audio segments from actors or coaches, (2) pre-generated AI-generated voice and video segments, and (3) real-time AI-generated voice and video segments. The system is designed to produce a seamless AI avatar coaching experience that is emotionally resonant, authentic, contextually appropriate, and aligned with user goals, behaviors, and biological rhythms. The system begins with user onboarding where individual preferences such as lean body weight and body fat % goals, well-being goals, etc. are stored along with AI avatar personality preferences, tone (e.g., calm, humorous), and language. These parameters guide how the avatar content is assembled and delivered. Upon onboarding, a personalization engine generates an initial batch of avatar messages by using templates that combine text variables with user-specific inputs (e.g., "Good morning, {user_name}"). The system uses a voice generation engine to synthesize personalized speech, then feeds the resulting audio to a video generation engine which constructs a talking avatar scene using the avatar personality preferences. Both voice and video files are stored on the system's server and served upon request. The system also includes a human content library comprised of professionally recorded video and audio segments from actors or coaches (e.g., J amie Foxx, Anelise Foxx). These media assets are categorized and labeled based on context and tone (e.g., sleep.humor.bad-sleep2-jamie.m4v). These labeled assets are stored on the server and are searchable by the pipeline's rule engine to be incorporated contextually into a video stream. The avatar system also includes a real-time daily event trigger engine that uses health APIs (e.g., Apple Health), user activity, or in-app behavior (e.g., missed workouts, added meals) to initiate new coaching video creation. The system selects relevant actor-recorded clips, pre-generated AI clips, and real-time contextual insights (e.g., "your workout has been moved to 4 pm") using a decision tree logic engine. The assembled content is passed to the Video Assembly & Delivery Engine, which creates a coherent video flow by sequencing actor-recorded segments, AI-generated content, and timeline overlays using decision tree logic and LLM sequencing models. The final video is accessible within the app UI via a timeline, message thread, or coaching screen. The system also includes avatar customization settings where the user can adjust language, tone, coaching frequency, interaction mode (text, video, voice), and affective mannerisms. These inputs influence content generation models and delivery cadence.

The computer-implemented system for delivering personalized health coaching operates through an integrated architecture that combines user customization, dynamic content generation, and adaptive delivery mechanisms. At its core is a user onboarding interface that collects comprehensive preferences including the user's name, specific health goals (such as weight loss, muscle gain, or stress reduction), preferred communication tone (motivational, clinical, or casual), desired avatar personality traits (enthusiastic, calm, or authoritative), and language selection. This foundational data informs all subsequent content generation, ensuring alignment with the user's expectations and needs. The system's content generation engine then creates initial coaching scripts by intelligently inserting these user-specific variables into predefined message templates that cover various health and fitness topics. These templates are designed to be flexible enough to accommodate different coaching styles while maintaining consistency in educational quality.

The voice synthesis module plays a critical role in bringing these scripts to life by converting the text into natural-sounding audio files. This module utilizes advanced text-to-speech (TTS) technology configured with parameters that reflect the user's preferred tone and personality, such as speech rate, pitch, and emotional inflection. For instance, a user who selected an "enthusiastic" coach might receive audio with higher energy and varied intonation, while some-one preferring a "calm" approach would hear slower, more measured speech. The synthesized audio is then passed to the video generation module, which constructs the final avatar videos. This module leverages AI-driven animation libraries to synchronize lip movements, facial expressions, and body language with the audio, creating a lifelike pre-sentation. The animations can range from simple head movements to full-body gestures, depending on the context of the message and the level of dynamism requested by the user.

All personalized content is managed and served by a robust server-based storage system designed for scalability and rapid retrieval. This system organizes user profiles, generated media, and interaction histories in a structured database, enabling efficient access during content assembly. The system's architecture is further enhanced by a real-time event monitoring engine that continuously analyzes data from wearable sensors, health APIs, and in-app behaviors to determine optimal moments for generating new coaching content. For example, if a user's heart rate data indicates a stressful period, the engine might trigger the creation of a calming meditation guide. Similarly, if the user consistently logs workouts in the morning, the system could prioritize generating motivational content at that time.

To ensure high-quality and relatable coaching, the system incorporates a human-recorded content library containing labeled video and audio clips from professional actors or certified coaches. These clips are meticulously categorized by situation (e.g., post-workout recovery, meal planning), tone (e.g., celebratory, corrective), and topic (e.g., nutrition, mindfulness). The content generation engine intelligently selects and sequences these clips based on the user's current goals, time of day, and historical behavioral patterns. For instance, a user focused on marathon training might receive a sequence of clips about endurance-building techniques, while someone tracking sleep improvement could get tips on bedtime routines. When pre-recorded human content isn't available or suitable, the engine seamlessly integrates pre-generated AI video clips from a curated media database, ensuring a continuous flow of relevant advice.

For situations requiring immediate or highly personalized responses, the system employs a large language model (LLM) to generate real-time text content. This LLM syn-thesizes recent user activity data (e.g., completed workouts, logged meals), biometric trends (e.g., sleep quality fluctua-tions), and overarching health goals to produce context-aware coaching messages. These messages are then con-verted into audio and video through the same synthesis pipeline used for pre-generated content. The timeline-based video assembly engine serves as the conductor of this process, using either rule-based logic or an AI sequencing agent to combine actor-recorded segments, pre-generated AI clips, and real-time LLM outputs into cohesive video pre-sentations. This engine handles transitions, pacing, and thematic flow to maintain engagement and clarity through-out the coaching session.

The final assembled videos are delivered to users through multiple channels via a dedicated delivery engine. This component embeds coaching videos directly into the appli-cation interface for on-demand viewing or pushes them through scheduled or event-triggered notifications. For example, a user might receive a morning workout primer automatically at their usual exercise time or get a nutrition tip after logging a high-sugar meal. Behind the scenes, all personalization data and content generation parameters flow between system modules through internal RESTful APIs, ensuring secure and efficient data exchange while maintain-ing modularity for future upgrades.

Avatar customization extends beyond voice and script content to include adjustable parameters like coaching fre-quency, facial expressions during delivery, and even lan-guage localization. These settings are applied consistently across all generated outputs to maintain a coherent user experience. The system also implements a continuous improvement loop where user feedback (e.g., thumbs-up/down ratings, watch time analytics) and interaction patterns are logged and analyzed. This data feeds into a reinforce-ment learning model that progressively refines content selec-tion, scripting, and delivery timing to better match indi-vidual preferences and improve outcomes over time.

The computer-implemented method transforms user inputs into tailored coaching experiences. It begins with generating a personalized coaching plan derived from onboarding information, then proceeds to constant monitor-ing of live health data and app interactions. Content creation follows a hybrid approach, judiciously mixing pre-recorded human elements with AI-generated segments based on the most current user context. The timeline-based assembly engine then weaves these elements together with attention to narrative flow and educational effectiveness before the final presentation reaches the user through their preferred appli-cation interface. This method represents a significant advancement over static coaching systems by offering dynamic, data-driven personalization at every touchpoint while maintaining the human-like relatability that fosters user trust and adherence.

The method for creating coaching content involves a sophisticated multi-source approach that ensures both high-quality production values and real-time personalization. When generating coaching materials, the system first queries its human content library—a comprehensive database of professionally recorded video clips featuring certified coaches and actors—to select the most relevant pre-recorded segments. This selection process considers both the imme-diate context (such as whether the user just completed a workout or is preparing for sleep) and the preferred com-munication tone established during onboarding (motiva-tional, analytical, or empathetic). For example, if a user requests recovery advice after an intense training session, the system might choose a clip of a coach demonstrating stretching techniques with calm, reassuring voiceover. Simultaneously, the system retrieves appropriate pre-gener-ated AI clips from server storage, which might include standardized explanations of physiological concepts or ani-mated demonstrations of exercises. These AI-generated ele-ments fill gaps where human-recorded content isn't avail-able or needs supplementation. Most critically, the system leverages a large language model to produce real-time contextual insights that tie everything together—this com-ponent analyzes the user's most recent activity data (like yesterday's workout intensity or this morning's resting heart rate), biometric trends (such as weekly sleep quality pat-terns), and even environmental factors (like local weather conditions) to generate hyper-personalized commentary that makes generic advice feel specifically tailored.

Biometric monitoring incorporates advanced techniques like heart rate variability (HRV) tracking through the smart-phone camera using fingertip placement. This optical mea-surement method, while convenient, is enhanced with pro-prietary algorithms that account for potential artifacts and improve accuracy. The system doesn't just collect HRV data but interprets it within the context of the user's fitness journey—recognizing when decreased variability indicates overtraining and suggesting active recovery days, or detecting improved recovery capacity that might signal readiness for more intense sessions. These insights directly inform workout customization, automatically adjusting recommended exercise intensity, volume, and even exercise selection in the user's programming. For instance, a week of poor HRV readings might trigger the avatar to suggest swapping high-intensity interval training for yoga sessions until recovery metrics improve.

Nutritional guidance reaches new levels of sophistication through the system's digestion-speed-aware meal planning. Recommended meals are visually represented on a calendar timeline with color-coded bars indicating expected digestion duration—red for fast-digesting options (like white rice with lean protein, ideal pre-workout), yellow for moderate (typical balanced meals), and green for slow-digesting combinations (high-fiber, high-fat meals for sustained energy). This temporal visualization helps users intuitively understand how meal timing affects their energy levels throughout the day. The system goes beyond passive recommendations by providing active digestion modification techniques. When suggesting meals that need to sustain the user through long periods between eating opportunities, it might recommend adding crunchy vegetables like celery or carrots to mechanically slow gastric emptying. Conversely, for pre-workout nutrition, it could advise temporarily reducing high-fiber ingredients to accelerate digestion and minimize gastrointestinal discomfort during exercise. These adjustments are dynamically calculated based on the user's upcoming schedule, logged digestive comfort with previous meals, and even stress levels that might impact gut motility.

Workout content generation synthesizes multiple personalization factors into cohesive training sessions. The system cross-references the user's stated goals (e.g., marathon training), experience level (beginner/intermediate/advanced), and physiological metrics (like current strength benchmarks or mobility limitations) to create custom routines. These aren't generic exercise lists but fully produced video sessions featuring an AI-generated coach who provides real-time form cues and motivational prompts addressing the user by name. The avatar might say, "John, remember to keep your chest up during these squats—your hip mobility has improved 12% this month, so try going a little deeper today." This personal touch increases engagement and corrects form issues more effectively than static demonstration videos.

Psychological optimization occurs through carefully calibrated humor integration, where the system's analysis of psychometric trends (like declining motivation scores or increased stress markers) triggers appropriate comedic relief. The avatar might begin a session with, "I see your stress levels are up—don't worry, this workout won't judge you as harshly as your inbox does!" This isn't random joking but a strategic intervention to activate the parasympathetic nervous system, with joke timing, intensity, and subject matter all tuned to the user's personality profile and current state. The system tracks which humor styles elicit positive physiological responses (like reduced cortisol levels post-laughter) to refine future attempts.

Users select their preferred coaching style during onboarding from multiple rigorously developed personality archetypes, each grounded in distinct pedagogical methodologies. The "Drill Sergeant" option employs concise commands and high accountability, modeled after military training approaches. The "Supportive Mentor" focuses on positive reinforcement and process praise, drawing from sports psychology research. Between these extremes lie several intermediate styles, all implemented through carefully designed language patterns, vocal tones, and even avatar appearance choices that reinforce the selected methodology.

The system's interactive learning capabilities allow users to engage deeply with educational content. AI transcription enables precise navigation of video materials, and when users request clarification on specific points (by tapping "Explain This" during a nutrition science segment, for instance), the system identifies the exact topic using timecode matching. The response pipeline then generates a tailored explanation incorporating the user's knowledge level (inferred from past interactions), preferred learning style (visual/auditory/kinesthetic indicators from onboarding), and current context (are they meal prepping now? viewing this post-workout?). This explanation becomes a new micro-lesson delivered by the avatar, seamlessly extending the original content without disrupting the learning flow.

Implementation involves sophisticated technical integration. The timecode-based content addressing system hooks into the video player's API to capture precise request timing, then queries the transcript database to extract the relevant passage. This text, along with contextual metadata, feeds into the LLM prompt construction system that assembles retrieval instructions for the knowledge base, personalization parameters from the user profile, and pedagogical constraints (like maximum explanation length). The resulting script undergoes voice synthesis with careful prosody control to emphasize key points before being rendered into video with appropriate visual aids (highlighted text for important terms, animated diagrams for complex concepts). Throughout this pipeline, quality assurance checks maintain educational accuracy while allowing for the personalized delivery that makes the system uniquely effective.

This comprehensive approach to AI-driven health coaching represents a significant advancement over conventional digital training systems by combining the scalability of automated content generation with the nuance of personalized human interaction. The technical innovations in real-time biometric integration, digestion-aware nutrition planning, psychologically attuned communication, and interactive learning create a coaching experience that adapts not just to what users need to know, but to how they need to receive that information for maximum comprehension and behavior change. The system's ability to blend pre-produced quality content with dynamically generated personalization bridges the gap between the efficiency of mass-produced fitness apps and the tailored approach of one-on-one coaching, making high-quality health guidance accessible at scale.

In a System and Method for Socially Coordinated KHAs via AI-Enhanced Avatar Coaching, the system and method for enabling socially coordinated health and wellness actions—referred to as KHAs—through an integrated digital platform utilizing AI-enhanced avatar coaching, scheduling features, and real-time communication between users (or between a user and a virtual avatar). The system focuses on enabling users to coordinate KHAs with friends, family, or AI avatars in ways that foster accountability, emotional motivation, and behavioral follow-through.

The system allows a user to designate a KHA that has been planned per the systems algorithms and AI (e.g., timing and attributes of breakfast, sunlight exposure, workout, post-workout recovery meal, bedtime, etc) and invite friends (real or virtual avatars) to participate, with optional indicators for the importance of the event (e.g., essential, important, normal). These are represented by color codes (e.g., red, yellow, green) within the user interface. The system manages the sending of invitations, responses (accept, decline, propose alternative), and updates the scheduled KHA in real time.

When a KHA is accepted by another user, it becomes a Social KHA and is visually modified in the interface (e.g., a distinct color border, icon, or badge).

If one or more participants are AI avatars, the avatar videos and other content types are generated using the system's Emotionally/Culturally relevant AI Generated Avatar Content Engine (described in another patent). The avatar then offers real-time coaching, tips, and emotional encouragement before, during, and follow-up after the KHA, with problem solving if needed.

For example, a user could invite three friends (real) family members to a system generated KHA which is a dinner at 6 pm (3.5 hrs before their bedtime) with 40 g of protein, 90 g of carbs, and 20 g healthy fats through the app. Each member receives a push notification or in-app message and can view the meal plan (e.g., with recommended macronutrient targets personalized to each participant via their unique needs). Once confirmed, the KHA is tagged as a group event. Avatars may provide cooking tips, encouragement before eating, or debrief messages after the meal.

Alternatively, a user could invite a virtual avatar to the dinner since eating a healthy, properly timed dinner is something the user has been struggling with. The avatar then has content generated using the system's AI Avatar Content Assembly which includes personal greeting, jokes if relevant about dinner (for example actual pre-recorded segment by Jamie Foxx) and then a recently triggered generated video including their calculated macronutrients for that meal.

The system uses a backend rules engine and calendar API to detect scheduling conflicts and enable KHA reconfiguration. A shared chat or video call option may be enabled within the app to encourage real-time interaction. If virtual avatar, then the content is created with the system's Emotionally/Culturally relevant AI Generated Avatar Content Engine and delivered at rule based time intervals.

In a System and Method for Avatar-Mediated Emotional Support and Interpersonal Coaching via User Feedback, Multidimensional Wellbeing Inputs, and Social Relationship Analysis, the system and method for delivering AI-mediated emotional support and interpersonal coaching through avatar-based interaction. The system enables users of a health and wellness platform (such as Foxx Fit) to connect as friends, partners, or family members, submit interpersonal feedback about their emotional experiences with each other, and receive contextually sensitive coaching and support from an emotionally intelligent AI avatar.

The system supports well-being and health models that include the impact of social dynamics and connection quality as core components of overall health. In addition to user-submitted feedback, the system collects multidimensional emotional and mental well-being inputs at appropriate times in the app experience—such as after a shared activity, end of day, or weekly check-in—through short assessments, mood sliders, emotional tags, and open-ended prompts. These inputs inform the emotional modeling of each user.

Future system integration includes support for biosensing partnerships that enable continuous or periodic sensing of key emotional biomarkers such as cortisol, dopamine, serotonin, and endorphins. When available and permitted by the user, this physiological data can provide an objective layer to validate or enhance the emotional inference models.

The system enables users to establish various types of relationships within the platform-including friendships, partnerships, family connections, caregiver relationships, or workout partnerships-through linked accounts. Once connected, users can provide structured feedback about how their relationship impacts their well-being, offering insights into emotional influences (both positive and negative), requests for modified support or behaviors, and evaluations of shared KHAs. This feedback is collected through intuitive UI elements such as sentiment sliders, emotion tags, and optional written notes, which are then processed by an advanced emotional analysis engine. The engine evaluates multiple factors, including sentiment trends, relational roles, feedback frequency, and well-being metrics, to identify patterns and determine when intervention or communication support may be beneficial. Based on these insights, each user's AI avatar delivers personalized guidance, which may include affirmation or constructive feedback on their impact within the relationship, tailored scripts for navigating difficult conversations, mediation strategies for conflict resolution, and recommendations for bonding activities such as shared walks or gratitude exercises. Additionally, the avatar suggests optimized KHAs designed to reinforce emotional connections, ensuring that relationships not only support individual health goals but also foster mutual growth and understanding. This structured yet adaptive feedback system transforms interpersonal health dynamics by facilitating clearer communication, emotional awareness, and collaborative well-being improvement.

Example Use Cases: A user is feeling hurt about a comment made by their friend weeks ago but has been unsure how to bring it up. The avatar coach guides the user through emotional reflection and provides a sample script that is respectful and honest. The friend receives the message with a softening explanation by their own avatar coach and is guided in how to receive the message and offer empathy. A woman logs her menstrual cycle into the app and chooses to share it with her spouse. Both avatars are now able to offer cycle-phase-specific coaching—such as suggesting extra rest, emotional support, or dietary changes during certain phases—and provide tips for the spouse on how to be more supportive and avoid common miscommunications.

The system's avatars proactively nurture relational health by analyzing trends in user interactions and delivering timely suggestions to strengthen connections. Using privacy-preserving algorithms, the platform summarizes feedback patterns while maintaining confidentiality—only revealing anonymized insights when both users consent. This delicate balance allows for meaningful coaching without compromising personal boundaries. The computer-implemented system for facilitating emotional support establishes itsfoundation through a social linking module-thatlets users categorizetheir relationships within the app (e.g., romantic partner, workout buddy, caregiver). This classification informs how the structured feedback interface presents questions and collects responses—whether assessing how a partner's actions affect emotional states, requesting specific support from a friend, or evaluating shared KHAs. The emotional analysis engine then processes this input through multiple lenses: sentiment analysis deciphers emotional tones, role classification ensures context-aware interpretation, well-being scoring tracks holistic impacts, and behavioral context adds situational understanding—creating a multidimensional view of each relationship's health.

At the heart of the system, the avatar coaching module transforms these insights into actionable guidance using evidence-based therapeutic techniques. Drawing from cognitive behavioral therapy principles and conflict resolution research, avatars don't just offer generic advice but deliver role-specific coaching—helping romantic partners navigate difficult conversations differently than workout buddies, for instance. The avatars serve as emotional mirrors, praising users when they positively impact others' wellbeing or gently suggesting course corrections when behaviors prove counterproductive. For particularly challenging situations, the system provides carefully worded communication scripts—offering users phrases to express needs without triggering defensiveness, whether discussing a partner's inconsistent support or a friend's negative influence on health habits. These scripts adapt in real-time based on the recipient's personality profile and past responsiveness to different communication styles.

The shared activity recommendation engine acts as a relational repair tool, suggesting KHAs specifically designed to rebuild connections—perhaps a joint meditation after conflict or a cooking date to strengthen bonds. Users provide feedback through innovative interfaces combining emotion tags (selecting from nuanced feeling words), numerical sliders (rating relationship satisfaction), multidimensional well-being scores (assessing physical/emotional/social health), and optional journal entries for deeper reflection. A reinforcement learning model continuously improves the system's emotional intelligence by detecting evolving patterns—perhaps noticing that certain KHAs consistently improve moods or identifying recurring conflict triggers before they escalate.

Cultural sensitivity is baked into every interaction, with avatars adjusting their communication style based on users' backgrounds—whether that means more direct feedback for some cultures or greater emphasis on harmony for others. Privacy protections ensure all sensitive data remains encrypted, with strict controls over what insights are shared between users. The coaching incorporates techniques from multiple disciplines-emotional intelligence frameworks help users develop self-awareness, family counseling protocols guide conflict resolution, and evidence-based communication strategies foster healthier dialogue.

The system demonstrates particular sophistication in its timing of interventions. Avatars initiate check-ins during emotionally vulnerable periods—perhaps offering extra support during post-conflict reconciliation, tailoring guidance to menstrual cycle phases, or adjusting expectations during injury recovery. For users who opt-in, menstrual data enhances coaching for both the individual and their partner—suggesting cycle-appropriate activities or helping partners understand emotional fluctuations. When conflicts arise, linked avatars work in tandem—delivering coordinated but personalized coaching to each user based on their role in the relationship, creating a unified approach to resolution. Future integration with advanced biosensors will further refine the system's emotional insight, incorporating physiological data like cortisol levels to complement subjective feedback—ushering in a new era of truly holistic relational health support that bridges emotional and physical wellbeing.

The various predefined personality options are integrated into the system's overall coaching framework, ensuring that the user's coaching experience is personalized from the initial onboarding phase and continues to be tailored during ongoing interactions. This integration enables the system to deliver a customized coaching experience that aligns with the user's selected personality, thereby enhancing user engagement and optimizing the effectiveness of the coaching methodologies employed.

In one embodiment, the system is configured to provide an enhanced interactive experience by dynamically responding to a user request for additional information with respect to a current timecode in the user's media session. The system first determines the specific portion of the content by mapping the current timecode provided by the user to a corresponding segment of an associated digital media file. This mapping is achieved by correlating timestamps embedded within a content metadata database to the active playback position, thereby isolating the exact portion of content that is the subject of the additional information request.

Once the specific portion is identified, the system automatically retrieves relevant contextual data and ancillary content stored in a linked repository. It processes this information to generate a personalized script tailored to the identified content segment. The personalized script is created using a combination of pre-stored templates and real-time data insertion techniques, ensuring that additional information remains both accurate and relevant. The script generation process incorporates natural language processing and machine learning algorithms to adapt the language and detail level to the user's presumed expertise or interest.

The complete process—from identifying the relevant content segment using the current timecode, to generating and delivering a personalized script via a synthesized voiceband corresponding digital avatar—ensures that the response to the user request is both timely and contextually appropriate. By combining metadata analysis, personalized content generation techniques, superior fidelity voice synthesis, and real-time video rendering of an AI avatar, the system offers a seamless and engaging delivery of additional information that enhances the user's interactive experience with the media content.

In one embodiment, the system is configured to automatically transcribe educational content using artificial intelligence. The system receives input data representing educational material in audio, video, or live lecture formats and processes this input through a speech-to-text engine that includes one or more artificial intelligence models. These models analyze the audio or video signals to generate a text transcription that accurately reflects the spoken content. The system further integrates a natural language processing component that examines the generated transcript to identify key concepts, terminologies, and segments within the educational content which benefit from additional contextual data. Based on this analysis, the system generates interactive markers positioned at specific portions of the transcript where further information enhances understanding.

The interactive elements are implemented as selectable regions, buttons, links, or touch-sensitive markers that appear alongside or within the transcribed text. When a user interacts with an element, the system processes the request by referencing a supplementary information database or querying an integrated knowledge base that corresponds to the selected portion of the educational material. The supplementary information comprises definitions, examples, detailed explanations, related multimedia resources, and links to other educational resources that provide a broader context or additional perspectives.

In one variation, the artificial intelligence transcription module and the interactive element generation module operate in real time, enabling dynamic creation of interactive educational contents the original material is transcribed. In another variation, the transcription process is conducted in a batch mode where pre-recorded educational content is first transcribed and then annotated with interactive elements that are subsequently rendered through a web or mobile application interface for end-user access.

The system is designed to support multiple modalities of user input, including touch, voice commands, and cursor-based interactions, thereby accommodating various user preferences and accessibility requirements. Upon receiving a request for additional information, the system initiates a retrieval operation that leverages contextual relevance determined by both artificial intelligence analysis of the transcript and historical usage data obtained from previous interactions. This retrieval operation involves further processing by a machine learning module that refines the supplemental content to better match the user's inquiry.

In some embodiments, the system is deployed on a cloud-based infrastructure that enables scalable processing of educational content and adaptive streaming of interactive elements. The cloud-based system includes security features that ensure transmitted data and user interactions are encrypted and compliant with applicable privacy and data protection regulations. Additionally, a monitoring component within the system tracks user interactions with the interactive elements and provides feedback to improve the performance of both the transcription engine and the relevance of the supplementary information provided.

The integration of artificial intelligence-based transcription with interactive user request functionality provides a comprehensive approach to delivering educational content that is not only accurately transcribed but also enriched with contextual details in response to user engagement. This integration enables learners to access more detailed explanations and further resources seamlessly, thereby enhancing the overall educational experience.

A computer-implemented system for coordinating health actions among users includes several integrated modules that operate together to schedule, prioritize, invite, and update shared health activities in real time. In one embodiment, the system comprises a primary health action scheduling module configured to enable users to select and designate time-based health activities from a range of available options. The scheduling module presents a user interface that includes a calendar view, selectable time slots, and customizable event details, thereby allowing users to schedule health activities at preferred times, modify existing schedules, and view upcoming events in a coherent, organized manner.

The system further includes an invitation engine that is operatively connected to the scheduling module and is configured to send participation requests to app-connected users. This engine leverages multiple communication modalities, such as push notifications, emails, or SM S messaging, to distribute invitations. It tracks the dispatch and delivery status of each outgoing request and records acknowledgments or initial responses to ensure that scheduling conflicts are minimized and that each designated health action receives appropriate participant confirmation.

Additionally, the system features a priority assignment module that enables users to indicate the importance level of the key health action by using visual indicators. Through a graphical user interface, users can select from various visual cues, such as color codes, icons, or intensity markers, to express the relative urgency or significance of an activity. These visual indicators assist both the initiating user and invited participants in quickly discerning the priority of each scheduled action, thereby streamlining decision-making processes regarding attendance and preparation.

In addition to the scheduling, invitation, and priority modules, the system integrates a real-time acceptance engine that manages invite responses. Upon receiving a response—positive or negative—the acceptance engine immediately updates the shared schedules so that users always have access to the most current information. This real-time updating capability is essential for maintaining accurate and dynamic coordination among multiple users. The acceptance engine also includes provisions for capturing additional feedback, such as reasons for declining an invitation, which can be used to improve future scheduling and invitation strategies.

In one embodiment, the various modules are implemented as distinct software components that communicate through standardized application programming interfaces (APIs) within a cloud-based or distributed computing environment. This arrangement permits seamless integration, enabling the system to efficiently synchronize scheduling, prioritization, invitation, and response data across multiple devices and platforms. The cloud-based architecture further ensures that updates are propagated immediately to all users, reducing potential scheduling conflicts and enhancing the overall user experience.

The health action scheduling module allows for flexible planning by enabling users to either select predetermined time slots or define custom health actions with unique timing needs. In parallel, the invitation engine is designed with mechanisms to control both the volume and timing of invitations so that the network is not overloaded and response deadlines are not missed. Meanwhile, the priority assignment module uses visual indicators to offer users an intuitive grasp of the relative importance of various health actions, a feature that is especially beneficial when managing multiple concurrent activities.

In one embodiment, when a second user accepts the KHA, the system reassigns the status of the KHA from its initial state to a Social KHA. The acceptance is indicated by a user action such as tapping or clicking on a designated acceptance control. Upon detecting this action, the system updates an internal flag or attribute associated with the KHA that denotes its transition to a social status. The status update triggers a change in the visual presentation of the KHA on the user interface. For example, the system alters the color scheme, iconography, or other visual artifacts associated with the KHA to differentiate it from KHAs that have not been accepted by a second user. The change in appearance informs both the original and other users that the KHA has undergone a status transition.

In addition to the visual modifications, the system sends updated notifications regarding the status change. These notifications are generated in real time and directed to one or more users, including the original creator of the KHA, the accepting user, and additional users subscribed to updates related to that content. The notifications appear as on-screen alerts, messages within the application, or through other communication channels such as email or push notifications. The notification content typically includes information on the change, such as the fact that the KHA is now recognized as a Social KHA, and offers additional details regarding the nature of the acceptance.

The system includes a nutritional planning engine that customizes meal macronutrient targets for individual participants. The nutritional planning engine analyzes various data inputs, including user dietary preferences, health objectives, activity levels, biometric information, and other relevant user-specific data to calculate individualized macronutrient requirements. The engine utilizes existing nutritional guidelines and applies proprietary algorithms to determine optimal proportions of proteins, carbohydrates, fats, and other essential nutrients tailored to each participant's needs.

Furthermore, the engine is implemented on one or more computing systems that execute computer-readable instructions stored on a non-transitory computer-readable medium, ensuring that personalized meal planning recommendations are generated and updated efficiently in accordance with current user data and preferences.

In one embodiment, the system is configured so that users can optionally select an AI avatar to participate in the Social KHA. Upon selection, the AI avatar is activated to deliver dynamic multimedia encouragement through audio, visual, and text-based outputs that are tailored to the individual user's needs. This multimedia encouragement includes synthesized speech integrated with facial animations to convey emotional tone, as well as visual cues, such as graphical overlays or animations, that complement the coaching process. The system provides a user interface that allows users to choose from a plurality of AI avatar options based on predefined categories or customizable parameters. Once activated, the AI avatar monitors user interactions and employs adaptive algorithms to deliver follow-up coaching based on historical user data, trends in user behavior, and real-time input. The follow-up coaching is designed to motivate the user and incorporates contextually relevant suggestions, prompts, or challenges that encourage continued engagement. In some embodiments, the AI avatar uses machine learning techniques to refine its coaching strategies over time by analyzing past interactions and feedback, thereby enhancing the personalization of multimedia outputs and coaching messages. The system integrates cloud-based resources that dynamically update the avatar's content libraries with new multimedia elements, ensuring that the encouragement and coaching remain current and effective. Additionally, the AI avatar analyzes sentiment through natural language processing, which allows it to adjust the tone, timing, and style of its communications to better align with the emotional state of the user. The combination of these functionalities enables the AI avatar to serve as an interactive coach that not only delivers motivational multimedia content but also provides iterative, personalized follow-up coaching to guide the user toward achieving predetermined goals.

In one embodiment, the invitation interface is configured to present a plurality of user-selectable options including accept, decline, and reschedule to facilitate a dynamic scheduling environment. When a user selects the accept option, the system processes the confirmation by updating underlying status data and transmitting an accept signal to the associated scheduling module; as a result, the Social KHA is automatically reflowed to reflect the confirmed status of the invitation. Similarly, if the decline option is selected, the system initiates procedures to record the rejection of the invitation and to revise the corresponding social information in the Social KHA, thus effectively removing or denoting non-participation within the user interface. In the case of the reschedule option, the interface engages a scheduling service that allows the user to select an alternate time or event configuration, and upon confirmation of this new scheduling data, the Social KHA is dynamically adjusted to display the updated information. The reflow of the Social KHA involves reorganizing visual elements, reordering items within the display, or resizing interface components so that the current status and scheduling details are accurately reflected. In embodiments where multiple invitations or social events are processed concurrently, the system employs a reflow algorithm that automatically propagates updates across the entire Social KHA, ensuring that visual consistency and logical associations among events are maintained. The reflow adjustments include modifying layout parameters such as element position, order, and size based on the current invitation responses, thereby providing the user with an up-to-date and contextually relevant interface. These features are implemented through a combination of user interface controllers, scheduling modules, and layout engines that collectively ensure the Social KHA remains synchronized with user actions on the invitation interface.

In one embodiment, group-based KHAs are configured to facilitate and manage embedded shared video calling and chat features within the application interface, thereby enabling real time communication among users who are members of a predefined group. The group-based KHAs include one or more processing modules and associated memory that execute instructions to initiate video calling sessions and manage chat communications in accordance with user commands. When a designated group is formed, the KHAs automatically detect group membership and establish corresponding communication sessions by interfacing with underlying network protocols and communication servers. The KHAs coordinate the initiation, management, and termination of shared video calling sessions as well as the real time synchronization of text chat messages, ensuring all users within the group experience a consistent and reliable service. In addition, configuration parameters controlled by the KHAs dynamically adjust video quality or message delivery based on available network bandwidth and system load, thereby optimizing the user experience. The embedded features, which include both video calling and chat, are tightly integrated with the overall application interface so users can seamlessly switch between communication modalities without exiting the application environment. The system further incorporates authentication, error detection, and data encryption mechanisms within the group-based KHAs to enhance security and ensure that only authorized group members can access the shared communication functionalities. In some embodiments, the KHAs are also capable of interfacing with other modules of the application, such as notifications or content sharing components, to provide integrated collaborative functionalities that extend beyond basic video and text communication.

In one embodiment, the system is configured to generate, update, and display a unified shared KHA view that integrates each user's dietary, sleep, and exercise plans. The system collects user-specific data from a variety of sources, including nutritional logging, sleep monitoring, and fitness tracking devices, and then processes this data through algorithms that tailor individual recommendations based on the user's historical trends, current status, and goals. The unified shared KHA view presents this information in a consolidated format such that while the underlying template remains consistent across participants, the content is dynamically personalized according to each user's specific health profile. For instance, the dietary plan presented within the KHA view incorporates detailed nutritional guidelines that are adjusted based on individual metabolic rates, caloric requirements, and dietary restrictions, while the sleep plan reflects personalized recommendations derived from data on sleep duration, quality, and circadian patterns. Similarly, the exercise plan is customized based on variables such as fitness level, activity history, and physical capability, ensuring that the displayed workout regimen aligns with the user's current state and progress. The system leverages a central data management framework that continuously synchronizes individual updates with the shared interface, providing real-time adjustments to the health plans as new information is received. In addition, the system employs machine learning algorithms to analyze trends across user data, thereby enabling predictive adjustments to each plan that are then reflected in the dynamically updated KHA view. As a result, even though the KHA view is shared among users, each participant observes a uniquely configured display that emphasizes personalized dietary, sleep, and exercise information, fostering an environment in which health data is both collaboratively accessible and individually relevant.

In embodiments of one implementation, the avatar assistant is configured to analyze participant performance data collected during a knowledge handling activity (KHA) and, after the activity is completed, generate a comprehensive summary of each participant's performance. The assistant receives data from one or more sensors or input devices that capture various performance metrics such as response accuracy, task completion speed, engagement levels, and other behavior indicative of proficiency in the KHA. U sing analytics algorithms, the avatar assistant evaluates the performance data relative to predefined performance benchmarks as well as dynamically generated thresholds based on historical performance and contextual factors. Based on this analysis, the assistant creates an individualized performance summary that includes an assessment of strengths, identification of areas for improvement, and a comparative evaluation against established performance standards.

In one embodiment, the system further comprises a family grouping module configured to allow scheduling of key hierarchical activities (KHAs) across shared calendars while personalizing calendar entries according to user roles. The family grouping module identifies and manages individual user roles, such as parent and child, by accessing role-based user profiles stored in a secure database, and subsequently adjusts both the appearance and functionality of scheduled KHAs to reflect the defined roles. The module enables a parent user to input or modify a KHA event, which is synchronized across a shared calendar accessible by designated child users, with the system applying predetermined restrictions or permissions based on the role associated with each user. For example, the module automatically assigns different levels of editing rights, notification settings, and view-only status depending on whether the calendar entry is viewed by a parent or a child, ensuring that each user receives pertinent, role-specific information. Additionally, the family grouping module integrates with calendar management functionalities that include conflict resolution, event reminders, and recurring appointment scheduling.

In some embodiments, the module supports dynamic updates, whereby changes to a family member's schedule or role—such as a modification in parental control settings or a change in the family grouping—are automatically reflected throughout the shared calendar environment. The module operates by interfacing with one or more calendar synchronization protocols and employing application programming interfaces (APIs) to manage intercommunication between disparate calendar applications, thereby facilitating real-time updates across multiple devices within the family unit. Moreover, the family grouping module provides a user-friendly interface that allows users to easily transition between different views or modes of the shared calendar, enabling the display of events differentiated by role—for instance, marking activities initiated by parents distinctly from those generated or modified by children.

In one embodiment, the system collects biometric data from various sensors that monitor physiological parameters such as heart rate variability, skin conductance, and other stress-related metrics. Simultaneously, behavioral data is gathered from user interactions with software applications, movement patterns, and usage histories that indicate engagement levels as well as frequencies of social interactions. Furthermore, the system accepts user-reported data via structured questionnaires or direct input related to personal goals, emotional states, and preferences concerning social interactions. The data is then aggregated by processing components that normalize and contextualize the information to create an integrated user profile.

This profile is subsequently analyzed by machine learning algorithms that process multimodal data inputs to detect trends and correlations indicative of a user's current state, progress toward personal goals, and overall relationship quality. Based on this comprehensive user profile, the system employs recommendation engines configured to identify Social KHAs whose attributes and capabilities likely align with the user's unique needs. The recommendation process involves comparing real-time biometric indicators and historical behavioral patterns with predefined parameters associated with various Social KHAs. Additionally, the system cross-references user-reported objectives to tailor recommendations, ensuring that the selected Social KHAs not only provide suitable support for meeting personal goals but also contribute positively to enhancing the quality of interpersonal relationships.

This approach supports dynamic adjustments and continuous learning, allowing incoming data to be regularly re-evaluated to refine and optimize future Social KHA selections corresponding to emerging user circumstances and shifting priorities, thereby fostering sustained user engagement and fostering more effective relational outcomes.

The system is configured to enable users to establish, manage, and leverage interpersonal relationships for enhanced emotional support and coaching. In one embodiment, a social linking module allows users to designate and classify relationships with other application users. This module supports the entry of relationship identifiers, configurable privacy settings, and metadata that describes the nature of each connection. It is further configured so that changes in relationship status—such as friendship updates or relationship modifications—are propagated to other modules in real time.

The structured feedback interface is designed to facilitate the input of multifaceted emotional data. Users provide input that includes emotional reflections, explicit requests for support, or indications of the impact of interactions on their well-being. In some implementations, the interface guides users via structured fields and prompts that are dynamically adjusted based on prior inputs or known relationship contexts. The interface is integrated with user authentication protocols and communicates with the social linking module to ensure that feedback is properly attributed to relevant interpersonal connections within the app.

The emotional analysis engine receives input from the structured feedback interface and processes the data through several analytical submodules. A sentiment analysis component dissects user input to determine the positive, negative, or neutral emotional tone associated with the feedback. A role classification component evaluates the context of the relationships and content of the feedback to categorize the roles of linked users relative to the feedback source. In addition, a well-being scoring module is implemented to quantitatively assess the emotional state and its fluctuations over time, with this scoring incorporating metrics derived from behavioral context data. The behavioral context analysis further examines the situational factors, previous interactions, and historical patterns of communication to enhance the accuracy in understanding the user's emotional state. The outputs of these analyses are normalized and stored for subsequent use by other modules.

The avatar coaching module uses analyzed emotional data to offer personalized support, mediation, and relational advice. It is programmed according to established best practices in therapeutic communication and is enhanced by cognitive behavioral techniques. Based on the outputs of the emotional analysis engine, the module generates responses designed to address the specific emotional nuances and relationship context of the user. These responses include suggestions for interpersonal communication, recommendations for self-care practices, and prompts to engage in mediation steps with other linked users. Additionally, the module is capable of real-time iterative adjustments by using feedback loops that learn from user interactions, thereby refining the accuracy and applicability of the support provided. In one embodiment, the module supports the scheduling of follow-up sessions or reminders designed to further assist users in managing their emotional health.

Throughout its operation, the system employs secure communication protocols and data encryption methods to maintain user privacy, ensuring that personal feedback and relationship data remain confidential. The integration between the various modules is designed to support real-time processing, and the modular architecture allows for scalability and the incorporation of future enhancements based on emerging best practices in emotional support and interpersonal coaching.

In one embodiment, avatars are configured to analyze user interactions and recognize instances where a user contributes to another individual's well-being through actions or communications that are deemed beneficial. The avatars utilize algorithms incorporating natural language processing and contextual analysis to evaluate user inputs, identifying positive behaviors such as empathy, supportive language, or helpful actions. Upon detecting such behaviors, the avatars automatically deliver praise through verbal or visual cues intended to reinforce the user's actions and encourage continued positive engagement.

Furthermore, the system incorporates user-configurable settings that allow customization of the feedback process, such as adjusting the sensitivity of evaluation metrics or selecting preferred communication styles. This ensures that the avatars function in a supportive and non-intrusive manner, respecting individual differences in receiving feedback. The detailed analysis and adaptive feedback provided by the avatars not only encourage positive behaviors but also foster an environment in which users receive information regarding how their actions contribute to the overall well-being of others.

In one embodiment, the system includes an interactive avatar designed to assist users by offering a variety of scripts or phrases intended to help articulate difficult emotional content during communications with a linked user. The avatar is configured to analyze the contextual input provided by the user—such as prior conversation history, detected sentiment, or direct input regarding emotional intent—in order to generate or retrieve from a database an appropriate set of scripted phrases that are contextually relevant and emotionally considerate. In some implementations, the avatar utilizes natural language processing techniques to parse the nuances of the user's message and identifies emotional triggers or potentially sensitive topics that benefit from a moderated approach. The scripts or phrases provided by the avatar serve as a starting point for the user, offering carefully structured language that guides the user toward communicating personal feelings or complex emotional experiences in a manner that is both clear and empathetic. The scripts include, without limitation, alternative phrasing that equips the user with options tailored to various emotional intensities and relational contexts, ensuring that the language used minimizes the potential for miscommunication or unintended escalation of emotional content. Further, the avatar provides dynamic modifications to these scripts based on real-time interactions with the user, thereby allowing for personalized adjustments that reflect the ongoing conversation. In some embodiments, the system allows the user to select from a list of pre-scripted options, while in other embodiments, the avatar suggests modifications to the original scripts based on additional user feedback or changes in tone observed during the communication session. The use of such pre-defined script options intends to empower users by providing them with a guided method to address and translate challenging emotional states into constructive dialogue, particularly in moments where self-expression becomes impeded by anxiety, conflict, or other psychological barriers. Moreover, the integration of this feature within the avatar serves not only to facilitate clear communication but also to foster a more supportive communicative environment between linked users by introducing language designed to de-escalate tensions and promote mutual understanding.

The shared activity recommendation engine functions as an integrated component of the system to facilitate the scheduling and execution of KHAs that users complete together. In certain implementations, the engine continuously monitors user activity data—including historical KHA completion, current emotional state inputs, and scheduling availability—to generate tailored recommendations for collaborative activities. The engine utilizes algorithms that analyze the compatibility of users' health objectives and emotional bonding preferences, selecting KHAs that are mutually agreeable and likely to enhance interpersonal connections. Additionally, the engine incorporates a dynamic scheduling module that coordinates the timing of these shared tasks, ensuring both users receive notifications in an optimized sequence with sufficient lead time for preparation. The system further incorporates a feedback loop wherein users' performance and subjective satisfaction with completed KHAs are collected to refine future recommendations and adjust scheduling parameters. In some implementations, the shared activity recommendation engine also interfaces with a user profile repository that stores behavioral data, health metrics, and interaction history, enabling the engine to dynamically adapt its activity recommendations based on evolving user characteristics. Overall, this integration facilitates the promotion of positive health behaviors while simultaneously fostering an environment of collaborative engagement and emotional bonding between users.

In one embodiment, the system includes an interface configured to receive user feedback, wherein the interface provides multiple methods for inputting both subjective and quantifiable data. The interface allows a user to submit feedback through selecting one or more predetermined emotion tags that represent various emotional states, including a range of feelings such as happiness, sadness, anger, or anxiety, among others. These emotion tags are presented using visual formats such as icons or color-coded labels to facilitate easy selection. In addition to the emotion tags, the interface incorporates one or more numerical slider elements that enable the user to indicate the intensity, magnitude, or degree of a selected emotion or a specific well-being indicator; these sliders operate on defined scales and offer either discrete or continuous input values to allow for fine-tuned self-assessment.

Furthermore, the interface is designed to capture multi-dimensional well-being scores that reflect the user's overall state across several dimensions, such as physical, emotional, and mental well-being. These multidimensional scores are derived from aggregating various input parameters provided by the user and are computed through a combination of numerical slider adjustments and predefined weighting algorithms designed to quantify aspects of subjective well-being. The multidimensional scoring mechanism is capable of displaying the relative contribution of different well-being dimensions and adjusts dynamically based on user input gathered over time.

Additionally, the interface includes an optional journal-style entry field that permits the user to supply free-form textual feedback to elaborate on their emotional experience or to provide contextual details that are not fully represented by numerical or categorical inputs. This journal-style field facilitates narrative input, enhancing the qualitative nature of the feedback by enabling the user to detail nuances or specific experiences, while the entered content is subsequently analyzed using techniques such as natural language processing or sentiment analysis to extract further emotional or contextual insights.

The system is further configured to integrate and process data from these various input modalities—emotion tags, numerical slider values, multidimensional well-being scores, and journal-style entries—in a coherent manner so as to offer a comprehensive profile of the user's subjective state. In some embodiments, this integrated feedback is stored and analyzed using backend processing techniques that correlate discrete and continuous data points, thereby permitting time-series analysis, trend identification, and adaptive feedback loops based on changes in the user's submissions. The overall architecture ensures that the user feedback is securely captured, stored, and processed, with considerations given to both data normalization and privacy requirements.

Moreover, the interface includes additional features such as real-time visual feedback, displaying graphical representations like charts or thermometers based on the submitted scores, which help the user contextualize their input relative to past entries or an aggregate trend. The design of the interface is optimized for ease of use across multiple devices and incorporates accessibility features to accommodate users with varying needs. In embodiments that require more comprehensive data input, the system includes contextual prompts or supplementary queries to encourage elaboration when incongruities or ambiguities are detected in the primary feedback data. Through these various mechanisms, the interface provides a multifaceted and robust means for capturing user feedback, thereby enabling deeper insights into user well-being and emotional state.

In one embodiment, the system performs emotional analysis by first acquiring data indicative of a user's emotional state through various sensors and data sources. The acquired data includes audio signals, facial expressions, physiological measurements, and text input that represent both instantaneous emotional responses and prolonged behavioral patterns. The reinforcement learning model is then employed to process this data over time, detecting evolving patterns in emotional state, relational satisfaction, or conflict resolution. The model is designed to operate in a dynamic environment where the emotional data continuously updates, requiring the system to adapt to new patterns and changes in the underlying emotional dynamics by mapping the input data to a set of states and corresponding actions. These states incorporate representations of both transient emotions and aggregated historical trends that contribute to an understanding of overall relational health.

The reinforcement learning algorithm employs a reward function designed to promote patterns linked to positive relationship dynamics and effective conflict resolution strategies, while simultaneously penalizing patterns that signify escalating conflict or diminishing relational satisfaction. In particular, the reward function assigns higher values to states that exhibit increased relational satisfaction and instances where conflict resolution results in a stable or enhanced emotional state. Conversely, negative rewards are applied when data indicates worsening emotions or deteriorating relationship interactions. Through iterative updates and repeated interactions with real-time and historical data, the model learns an optimal policy.

During each iteration, the reinforcement learning model compares current emotional signals with previously acquired emotional patterns, determining whether specific actions or interventions can result in more favorable emotional states. The model is designed to incorporate exploration strategies to investigate untested responses, alongside exploitation strategies intended to reinforce demonstrated effective behavioral interventions. Additionally, the model adjusts its parameters based on continuous feedback, which refines its ability to detect subtle trends that indicate either enhancement or degradation in relationship quality. By leveraging deep neural network architectures within the reinforcement learning framework, the system facilitates the identification of complex, non-linear connections between emotional inputs and subsequent relationship outcomes.

In addition, the model includes a mechanism for forecasting future emotional states and potential areas of conflict by simulating various scenarios based on current trends. This simulation capability supports proactive measures designed to mitigate negative emotional developments or reinforce positive relational interactions. The learned policy, which is updated as new data is processed, facilitates a nuanced understanding of the interplay between individual emotions and overall relationship dynamics. Ultimately, the system provides users with actionable insights derived from its continuous assessment of evolving emotional patterns, offering tailored recommendations for enhancing relational satisfaction and managing conflict effectively over extended periods.

In some embodiments, feedback data is processed by first applying encryption algorithms compliant with recognized privacy regulations prior to any storage operations. The encryption is performed using one or more industry-standard encryption techniques, wherein the encryption keys are securely managed and stored separately from the encrypted data to ensure confidentiality. Prior to sharing any insights between linked users, the system evaluates whether the data contains any identifiable elements that could compromise user privacy; if such elements exist, they are obfuscated or removed in order to render the data effectively anonymized. In these embodiments, anonymization includes techniques such as the removal or substitution of personal identifiers, tokenization processes, and data aggregation methods that permit the derivation of useful insights without correlating the data back to any specific user. Moreover, any transmission of shared insights between linked users is performed on anonymized data sets, and the system employs safeguards that verify proper anonymization before data exchange occurs. This process further ensures that the feedback data, even when aggregated across multiple sources, does not inadvertently expose individual user identities or sensitive information. In addition, the regulatory compliance aspect is maintained throughout the data processing and storage operations by periodically updating the encryption and anonymization procedures in line with evolving privacy standards and implementing continuous auditing to detect and rectify any discrepancies. These measures collectively ensure that all feedback data is securely stored and managed, while still allowing linked users to derive beneficial aggregated insights without jeopardizing individual privacy interests.

Furthermore, the avatar-delivered coaching incorporates techniques derived from family counseling protocols that facilitate communication and conflict resolution within interpersonal relationships. In various embodiments, the system simulates interactions based on established family counseling methodologies, providing users with role-playing exercises, guided dialogue, and structured conflict management strategies. These techniques involve initiating scenario-based interactions that prompt users to consider alternative perspectives, thereby fostering a more constructive dialogue and promoting mutual understanding. The family counseling-derived protocols integrated within the system enable the avatar to offer recommendations for de-escalation, encourage the adoption of effective communication habits, and support the development of healthier relationship dynamics.

Additionally, the avatar-delivered coaching incorporates techniques based on evidence-based communication strategies that are designed to improve the clarity, persuasiveness, and overall effectiveness of the user's communication. Such strategies are informed by research findings from communication studies and involve structured activities that emphasize active listening, careful timing and sequencing of conversational inputs, and detailed feedback techniques. In some embodiments, these evidence-based communication methodologies are implemented to assist the user in restructuring both verbal and non-verbal messaging, thereby facilitating more effective exchanges during interpersonal interactions.

Avatars operate to detect and respond to periods classified as emotionally sensitive by leveraging a combination of user input, sensor data, and algorithmic assessments. In embodiments, the system monitors data related to factors such as interpersonal conflict, physiological indicators associated with menstrual phases, and signals denoting various stages of recovery, thereby establishing when a user is experiencing heightened emotional vulnerability. Once such a timeframe is detected, the avatar automatically initiates a check-in with the user. This check-in is executed either through a scheduled prompt or through real-time detection of relevant emotional or physical cues, ensuring that the timing of the intervention aligns with the user's current state.

The check-in process is designed to be nonintrusive yet supportive, with the avatar adopting a conversational style that communicates empathy and understanding. The avatar uses pre-programmed scripts, dynamic responses generated through natural language processing, and machine learning-driven adaptations to tailor its communication. The empathetic tone is maintained through careful selection of language, expressions, and even simulated nonverbal behaviors such as facial expressions or gestures, all of which contribute to a nuanced and human-like interaction.

During the check-in, the avatar initiates dialogue that includes questions aimed at gauging the user's current emotional state and offering coaching techniques. The coaching is empathy-driven, meaning that it incorporates supportive messages, reflective questioning, and suggestions for stress mitigation strategies such as mindfulness exercises, cognitive behavioral techniques, or other coping mechanisms. In some embodiments, the system is configured to adapt these responses based on historical user interactions, preferences, and feedback, thereby continuously improving the personalization and effectiveness of the coaching provided.

The system integrates external data—such as biofeedback from wearable devices or manually entered health information—to refine its understanding of when and how to engage the user. This integration enables the avatar to recognize subtle shifts in the user's condition, including those following emotionally impactful events like conflicts or during periods of physiological change associated with menstrual cycles. Additionally, the system incorporates location-based and time-specific information to ensure that check-ins occur at appropriate intervals and do not interfere with the user's routine activities.

Furthermore, when initiated during a period of increased risk, the coaching provided by the avatar can be escalated to include advice on seeking human support or even triggering alerts if the user's responses indicate severe emotional distress. This tiered approach ensures that the system offers both immediate, empathetic support through the avatar interface and, when necessary, a path to additional resources for further assistance.

In one embodiment, the system comprises a user interface that enables users to opt into sharing menstrual cycle data with a centralized processing unit. The menstrual cycle data includes information such as cycle length, bleeding duration, ovulation period, basal body temperature, and additional physiological indicators collected either manually or automatically using integrated sensors. This cyclical data is securely stored and processed to determine the current physiological phase of the user. Based on the determined phase, an avatar is algorithmically selected and customized to display guidance tailored to the user's specific stage in the menstrual cycle. The avatar-led guidance comprises personalized recommendations on wellness activities, dietary suggestions, and exercise regimens that align with the user's physiological state.

Additionally, the system provides context-sensitive recommendations for partners, where the recommendations incorporate suggested activities, communication strategies, or reminders that consider not only the physiological phase of the user but also potential preferences or behavioral trends observed in partner interactions. The recommendations for partners are generated by integrating data from historical interactions between the user and the partner as well as by referencing general behavioral patterns correlated with specific phases of the menstrual cycle. Users retain the ability to review, modify, or disregard the avatar-led guidance as desired.

In another embodiment, the system further incorporates a privacy management module that allows users to selectively share or restrict the sharing of their menstrual cycle data with third-party applications, thereby ensuring compliance with applicable data protection and privacy regulations. Data transmitted to third parties is anonymized and aggregated to preserve user confidentiality while still enabling the provision of generalized health advice.

The system architecture supports dynamic updating of the avatar-led guidance algorithms based on ongoing research or user feedback, with periodic software updates that enhance personalization accuracy over time. Furthermore, the system incorporates machine learning modules that analyze trends across multiple users to refine the timing and content of both the personalized guidance and the partner recommendations. These modules are designed to adjust to individual variability in menstrual cycle patterns, thereby confirming alignment of the avatar-led guidance with the user's unique physiological rhythms. The overall framework integrates seamlessly with existing mobile and wearable devices, enabling real-time data collection and user interaction while providing a holistic approach to personal health management.

In one embodiment, linked avatars are implemented as interactive agents residing in a computing environment that supports real-time communication and collaboration between users. The avatars are arranged to coordinate and exchange information such that each avatar monitors the dialogue between users and dynamically adjusts its responses according to the specific roles and objectives assigned to each participant. The coordination process involves capturing data related to user language, behavior, and interaction context, processing this information through an algorithmic engine designed to assess the goals and responsibilities of each user. This engine determines a set of mirrored coaching strategies that are personalized based on the identified role and goal parameters. In this manner, one avatar provides feedback aligned with the task-oriented aspects of a discussion, while a corresponding linked avatar offers reflective commentary or inquiry techniques that promote mutual understanding. The mirrored coaching strategies include, for example, prompting clarifying questions, suggesting alternative approaches, and providing real-time feedback that is harmonized between the linked avatars. The system leverages machine learning algorithms to continuously learn from user interactions, allowing these mirrored coaching strategies to become increasingly refined over time relative to the evolving profiles of user roles and objectives. Data is processed without altering the fundamental characteristics of the dialogue and is utilized solely to enhance the clarity and effectiveness of communication between users, thereby facilitating an environment in which dialogue is not only sustained but purposefully directed toward mutual understanding and collaborative success. The described technique ensures that adjustments in coaching strategies occur automatically in response to shifts in user engagement or context, thus maintaining a balanced and supportive interaction optimized for achieving the desired outcomes of each participant.

The present disclosure further contemplates a system architecture in which the methods and apparatus are configured to integrate future biosensors capable of detecting physiological markers correlated with an individual's emotional state. For example, the system includes one or more sensors configured to detect concentrations of cortisol, endorphins, or other relevant biochemical compounds. The biosensor module is operatively coupled to the emotional insight model so that it receives and processes objective data inputs indicative of the user's physiological state. In one implementation, the system continuously monitors physiological signals via these biosensors and transmits raw and processed data to a processing unit where these data are combined with inputs from user interactions or external stimuli. The integration of biosensor data enables the emotional insight model to refine its determinations by grounding them in objective biological metrics. In addition, the system incorporates algorithms that correlate various biosensor data points with known patterns of emotional responses, thereby enhancing the predictive accuracy and reliability of the emotional insight model. Calibration routines execute during initial setup or intermittently during use to ensure that sensor outputs remain consistent with expected variations in biomarker levels, compensating for sensor drift or environmental interference. The disclosed integration also encompasses data fusion techniques that merge computed metrics from traditional digital inputs, such as user selections or behavioral observations, with direct physiological measurements provided by the biosensors. This hybrid approach enables robust and comprehensive analysis of emotional state, supporting applications requiring precise monitoring and evaluation of user emotions in real time.

During the presentation of the video, a user can decide to request additional information on a portion of the video content. When the user request is received, a user interface module collects the request and determines a current timecode associated with the portion of the video that is being viewed. In one exemplary embodiment, the timecode is extracted automatically from the video playback module in real time. The system then employs a selection module that maps the current timecode with the synchronized text transcript to identify the specific portion of the video content for which the user requires additional information.

Following the identification of the specific portion of interest, a generation module, which is configured to employ a large language model, accesses the synchronized transcript corresponding to the identified timecode. The large language model processes the transcript and additional contextual data relevant to the subject matter, such as previous user interactions or predefined educational guidelines, to generate a personalized script. The personalized script is designed to provide supplementary educational information on the identified subject matter, potentially including detailed explanations, further instructions, and clarifying examples tailored to the user's context.

In an additional aspect, a personalized script is provided to a digital avatar module. In one embodiment, this module generates a video response featuring a coach avatar created through a generative video algorithm. The module converts the personalized script into synthetic speech using text-to-speech processes, where synthetic voice generation techniques produce a voice output in a selected accent, tone, and style. The synthetic voice is synchronized with the coach avatar's movements so that the visual output appears as a natural and coherent explanation delivered by the avatar.

The final step in the method involves presenting the digital avatar response to the user. The system delivers the avatar video with a synchronized synthetic voice in a way that enables the user to view and interact with additional information. In some embodiments, the response is seamlessly integrated within the ongoing video content to preserve an uninterrupted and personalized educational experience. The method further includes feedback mechanisms that allow the user to indicate the usefulness of the response, which is used by the system to continuously improve content personalization.

Throughout these processes, efficiency and timeliness are emphasized. The transcription, timecode identification, script generation, and avatar creation are designed to occur in real time or near real time to ensure that the personalized educational content remains closely aligned with the user's current focus and needs. Various algorithms are implemented to ensure that latency is minimized and that the personalized response is delivered promptly following the user's request.

In one embodiment, the system is implemented as a combination of software modules executed in a computing device or distributed across a network of computing devices. The computing device includes a processor, memory, and input/output interfaces configured to capture user requests, process video content, and generate digital avatar responses. The system further includes network interfaces that enable synchronization of content across remote servers, which supports the storage, retrieval, and processing of video files, transcripts, and user interaction data.

Thus, the disclosed method provides an integrated approach for delivering personalized educational content in a fitness and nutrition application by combining video content presentation, real-time transcription of content, user-driven content augmentation, natural language processing via large language model technologies, and the synthesis of digital avatar responses.

In one embodiment, generating the personalized script comprises incorporating user-specific data including biometric data, training history, nutrition data, and psychometric trends. Biometric data includes physiological metrics such as heart rate, blood pressure, oxygen saturation, and body temperature, collected using wearable sensors or other monitoring devices. Additional biometric parameters include information derived from motion sensors, such as gait analysis and posture details, allowing the system to refine the personalized script based on the user's physical state. Training history encompasses records of previous exercise sessions detailing the type, duration, intensity, and frequency of workouts, as well as associated performance metrics such as distance covered, calories expended, or repetition counts. This historical data assists in identifying trends or patterns in the user's physical activity and informs adjustments to the personalized script for optimizing training progression. Nutrition data involves details regarding daily caloric intake, macronutrient composition, meal timing, and dietary preferences or restrictions. The nutritional profile, entered manually by the user or automatically imported from integrated digital platforms, helps the system tailor recommendations that align with the user's nutritional requirements and fitness goals. Psychometric trends include self-reported mood assessments, stress levels, cognitive performance indicators, and other mental wellness metrics collected through surveys, mobile applications, or wearable technology capable of monitoring psychological states. The system analyzes these psychometric indicators over time to detect shifts in the user's mental health or emotional well-being, thereby adapting the personalized script to incorporate activities or interventions that support both mental and physical health. The generation of the personalized script involves aggregating and analyzing these diverse data sets using one or more computational algorithms, such as machine learning models, to establish correlations and predict optimal adjustments. The resulting script includes recommendations for exercise regimens, recovery protocols, nutritional adjustments, and mindfulness practices that update dynamically based on continuous data input. By integrating these varied categories of user-specific data, the system provides a comprehensive, holistic approach that addresses both the physiological and psychological aspects of the user's overall health, ensuring that the personalized script adapts to ongoing changes in the user's condition and goals.

In one embodiment, generating a personalized script comprises retrieving expanded information from a knowledge base that includes detailed data associated with topics recognized in the video content. The knowledge base stores expanded information in formats such as textual descriptions, metadata, multimedia data, and contextual annotations that enhance the understanding of the topics presented. In this context, accessing the knowledge base involves executing one or more queries generated based on extracted topic identifiers, keywords, or other relevant metadata derived from the video content. The process further includes analyzing the video content using speech recognition, image processing, or natural language processing techniques to identify and tag topics for which additional information is available. The system then utilizes these tags or identifiers as search parameters to retrieve corresponding detailed information stored in the knowledge base. The stored information includes historical data, technical background, definitions, or related multimedia content that provides a richer context to the topics. In some implementations, the knowledge base is dynamically updated to include new information relevant to emerging topics or changes in user interests, thereby ensuring that the personalized script reflects the most current and comprehensive data available. Furthermore, the retrieval operation is enhanced by ranking results based on relevance and user-defined parameters, such that the most pertinent information is prioritized in the subsequent personalized script. Once the expanded information is obtained, the system processes and integrates it into the personalized script, generating a script that not only corresponds to the video content but also provides additional context and elaboration to enhance user understanding. This integration process involves text normalization, aggregation of data from multiple sources, and formatting the information into a coherent narrative suited to the user's preferences and the overall informational objectives of the video content presentation. The apparatus further includes modules that manage the storage and caching of expanded information locally or via cloud-based services, enabling rapid access and optimized performance during the personalized script generation process. In one embodiment, the system further comprises a chat interface configured to facilitate real-time interaction between the user and the digital coach avatar. The chat interface is implemented using various software and hardware components operating on a computing device and is designed to receive and display text, voice, or multimedia inputs from the user. In these embodiments, the chat interface includes one or more input fields for capturing user commands and queries and one or more output areas for rendering responses generated by the digital coach avatar. The interface utilizes technologies such as speech recognition to interpret voice inputs and text-to-speech conversion to provide spoken output, thereby supporting a multimodal interaction experience. The digital coach avatar, rendered in either two-dimensional or three-dimensional graphics and dynamically animated for realism, continuously monitors the chat interface for incoming inputs. Upon detection of a user input, the digital coach avatar processes the input using one or more natural language processing algorithms that analyze the content of the input to determine an appropriate response. The generated response is displayed as text, voice, or a combination thereof and includes interactive multimedia elements to enhance user engagement.

In one embodiment, the user request is initiated through a user interface element displayed concurrently with playback of the video content. The user interface element is configured as an overlay that appears on top of the video stream and incorporates various interactive features designed to capture and process user input. For example, the overlay includes one or more selectable icons, buttons, or text entries that become visible during key moments of the video, allowing a viewer to actively engage with contextual features or supplemental information while the video is playing. The control unit dynamically generates the interface element and synchronizes its appearance with the playback timeline of the video content, ensuring that the element remains contextually relevant to the displayed content. In some embodiments, the control unit monitors playback parameters such as the current timestamp or scene metadata to determine optimal insertion points for the interface element. The display characteristics of the user interface element, including its size, position, opacity, and duration of appearance, are adjusted based on predetermined conditions or user preferences. Additionally, the element is designed with the capacity to initiate specific software routines or trigger a backend service request upon user interaction, thus enabling functionality such as content annotation retrieval, additional media presentation, or the initiation of communication with remote servers for further processing. In alternate embodiments, the interface element is configured to respond to various types of user input, including mouse clicks, touch gestures, or keyboard entries. This responsiveness is enhanced through the use of gesture recognition algorithms or adaptive interface designs that tailor the interactive experience to the device on which the video content is displayed. The display and operation of the user interface element are managed to ensure seamless integration with the video content, preventing undue interference with the viewing experience while still providing an accessible mechanism for the user to trigger interactive commands during content playback.

In one embodiment, the system includes a module configured to select a coaching style for a digital avatar response based on user preferences stored in a user profile. In this embodiment, the user profile includes various types of information, such as historical interaction data, explicitly entered user preferences, and behavioral data that indicate a preference for specific coaching modalities. At the time of generating a response, the system retrieves the relevant user profile data and analyzes it to determine which coaching style best suits the user's needs. For example, the profile might reveal that a user favors a supportive coaching style over a more directive approach, leading the system to generate a response that employs encouraging language and gradual guidance. Alternatively, if the profile indicates a preference for an analytical coaching style, the digital avatar offers responses that incorporate detailed information, structured problem analysis, or data-driven suggestions. The selection mechanism includes decision logic implemented in one or more processors executing instructions stored on a non-transitory computer-readable medium. The instructions incorporate algorithms for parsing profile data, comparing available coaching styles, and selecting the optimum style based on current contextual factors in addition to stored preferences. In another embodiment, the system further refines the selected coaching style by integrating real-time contextual input such as current user activities, recent performance metrics, or situational factors. This dynamic adjustment enables the digital avatar response to be tailored not only to static user preferences but also to the immediate needs of the user. The process of selecting the coaching style benefits from enhancements provided by machine learning techniques that continuously update and improve the alignment between user preferences and coaching responses. For instance, the system analyzes historical outcomes and user feedback to adjust the weighting of different coaching style factors, thereby optimizing future interactions. The digital avatar is then programmed to deliver its response in a manner consistent with the selected coaching style, which might include variations in tone, language complexity, pacing, and the inclusion of motivational cues or analytical insights, depending on the user's stored preferences and the current context.

In some embodiments, the system further comprises a data storage module configured to record user interactions with the digital avatar, wherein the recorded interactions include, but are not limited to, input commands, dialog history, response selections, and feedback provided by the user during engagement with educational content. The stored data is used for analyzing patterns in user behavior and refining subsequent personalization algorithms to deliver educational content that is better aligned with the unique learning style, pace, and interests of the user. The digital avatar is adapted to capture real-time interaction events during user sessions and transmit them to a central processing unit, which employs one or more machine learning algorithms to assess the data and update a user-specific profile maintained in the data storage module. This profile is used to tailor future interactions by dynamically adjusting the content, tone, and structure of educational material based on historical user performance, preferences, and interaction frequency. In embodiments where adaptive learning pathways are implemented, the system leverages the stored interaction data to predict potential learning gaps and proactively suggest supplemental resources or modifications to the instructional content. Furthermore, the system incorporates feedback loops wherein analysis of aggregated user interaction data across multiple sessions and users informs ongoing refinements of both the digital avatar's response strategies and the overall educational curriculum. The data storage module is configured to ensure the security and integrity of the user interaction records by implementing encryption and access control measures, thereby maintaining confidentiality and compliance with applicable data protection regulations. Overall, the integration of the storage of user interactions with the digital avatar response facilitates an iterative process whereby the educational experience is continuously optimized to enhance user engagement, learning outcomes, and the overall effectiveness of the digital avatar as an educational tool.

The video content comprises masterclass presentations featuring fitness and nutrition experts delivering detailed instructions, demonstrations, and discussions on proper exercise techniques, dietary planning, and healthy living principles. In various embodiments, the masterclass content consists of recorded video segments in which the experts offer comprehensive guidance on multiple aspects of physical fitness and nutritional wellness through instructional lectures, practical examples, and step-by-step methodologies. Concurrently, a digital avatar operates within the system to provide personalized implementation strategies that are directly derived from and tailored to the expert content. The digital avatar is configured to analyze the content presented by the fitness and nutrition professionals and to utilize a combination of algorithms, user input, and contextual data to generate customized recommendations that facilitate the practical application of the information conveyed in the masterclass. These personalized strategies include customized exercise routines, dietary modification plans, and lifestyle adjustments that are dynamically adjusted based on individual user profiles, progress metrics, and preferences. In certain embodiments, the system further integrates biometric data, historical usage information, and user feedback to refine the digital avatar's responses, thereby ensuring that the guidance remains relevant and specifically targeted to the user's evolving needs. The digital avatar communicates these recommendations through an interactive interface, providing visual cues, auditory instructions, or a blend of both, and can prompt the user to undertake specific actions or adjustments that reinforce the expert advice. Overall, the integration of masterclass content with digital avatar-driven personalization creates a cohesive platform where professional expertise is seamlessly translated into actionable, individualized wellness strategies.

A computer-implemented system for delivering health coaching comprises a user onboarding interface that collects user preferences including, but not limited to, a name, goals, tone, personality, and language. The interface is designed to capture these data points and transmit them to subsequent modules within the system. The system further comprises a content generation engine that creates initial scripts based on the collected user variables; the engine utilizes predefined message templates and substitutes variables corresponding to the user's name, goals, tone, personality, and language to generate personalized text-based coaching messages. In one embodiment, the content generation engine incorporates algorithms for natural language processing and dynamic content adjustments to ensure that the generated scripts satisfy coaching guidelines and reflect the specific needs and preferences of the user.

A server-based storage system is operably coupled with the aforementioned modules for managing and serving personalized avatar content; this storage system maintains a repository of generated scripts, audio files, avatar animation sequences, and final video outputs, ensuring that the personalized content can be efficiently retrieved and delivered to user devices. The various modules are interconnected such that the user onboarding interface collects the input data, the content generation engine uses this data to generate customized messages, the voice synthesis module converts these messages into audio outputs, and the video generation module produces coordinated avatar videos, with the server-based storage system facilitating seamless delivery of the personalized coaching experience.

In one embodiment, the system further comprises a real-time event monitoring engine that leverages sensor data from one or more devices along with in-app activity data to determine when new coaching content should be generated. The real-time event monitoring engine continuously receives data streams from various sensors—such as accelerometers, gyroscopes, GPS units, heart rate monitors, and environmental sensors—which collectively provide contextual and physiological information related to the user's current state. In parallel, the engine processes in-app data including user interactions, usage patterns, and historical feedback associated with previously delivered coaching content. The engine applies predetermined thresholds and pattern recognition algorithms to the aggregated sensor and in-app data to detect specific events or changes in user behavior that warrant the generation of tailored coaching advice. When the monitored data indicate that a significant deviation from expected behavior thresholds or a notable change in the user's activity metrics has occurred, the real-time event monitoring engine initiates a trigger for the generation of new coaching content. In certain embodiments, the engine utilizes machine learning models to continuously refine its criteria for event detection based on feedback from user engagement and effectiveness assessment.

ments of the previously provided coaching content. As a result, the system adapts to variations in user performance and environmental conditions in real time, thereby ensuring that coaching content is both timely and contextually relevant. The integration of diverse data sources into the event monitoring process enhances the reliability of event detection and supports the dynamic and responsive delivery of coaching content aimed at optimizing user performance and overall user experience.

A further embodiment comprises a human-recorded content library that includes labeled video and audio clips from actors or coaches, with each clip stored and categorized by situation, tone, or topic. The content library is maintained in a digital storage medium and organized into various segments that facilitate rapid search and retrieval based on metadata associated with each clip. In one implementation, content experts perform the labeling manually, assigning descriptive tags corresponding to the situational context, emotional tone, or subject matter of the recorded material. Alternatively, the labeling process is automated using algorithms designed to analyze visual and auditory features and determine appropriate descriptors. The categorized clips are subsequently stored in an indexed database where each entry is linked with its respective classification, thereby enabling the system to select proper clips to match user interactions, training scenarios, or other application-specific requirements. The content library is employed during system operation to provide tailored outputs—including prompts, examples, or guided interactions—based on dynamically received input regarding the user's context, desired tone, or situational criteria. Its organized structure permits seamless integration into the larger system framework, with content automatically retrieved and presented to the user in real time based on contextual triggers and pre-established mappings. Additionally, the library is designed to be expandable, incorporating provisions for adding new clips and updating categorization schemes when additional content becomes available or as user needs evolve.

The content generation engine is designed to analyze diverse input parameters—including user goals, time-of-day, and behavioral patterns—to enable dynamic selection and sequencing of clips from a human-recorded content library. The engine continuously evaluates stored user preferences and contextual information to determine the most appropriate clip selections for any given moment. For instance, user goals derive from explicit inputs or are inferred through historical interaction data, which allows the engine to identify thematic or purpose-driven content segments. The time-of-day factor is incorporated through built-in scheduling heuristics that correlate certain content types with specific periods, enhancing the relevance and timeliness of the displayed clips. Behavioral patterns are assessed by monitoring user interactions such as viewing duration, frequency, and engagement metrics, enabling the engine to adjust content sequencing in real time based on observed responses. In some embodiments, the engine employs rule-based algorithms or machine learning models to predict an optimal sequence that results in a coherent and contextually relevant presentation. The human-recorded content library further includes metadata associated with each clip—such as genre, sentiment, and temporal markers—that is cross-referenced during the selection process to ensure consistency with user goals and current context. Moreover, the content generation engine dynamically updates its selection criteria by incorporating feedback loops that continuously learn from newly observed user behaviors and environmental factors, resulting in a personalized and adaptive content experience. This systematic approach ensures that the sequence of clips not only aligns with the user's current objectives but also adapts to variations in daily rhythms and evolving preferences.

The content generation engine is configured to access an integrated media repository that comprises a plurality of pre-recorded AI video clips along with a separate curated AI media database housing various transition effects. The engine retrieves one or more pre-recorded video clips based on predetermined criteria, which include metadata annotations, user input signals, environmental conditions, or content-specific attributes. After retrieving the video clips, the engine analyzes both the visual and contextual properties of the selected clips to determine an appropriate sequence and timing for transitions. It then interfaces with the curated AI media database, which stores a wide range of transition effects characterized by attributes such as duration, style, motion parameters, and aesthetic qualities. This design enables dynamic matching between clip content and transitional effects.

The selection process employs algorithms that evaluate the compatibility of a given transition with adjacent video segments, ensuring smooth visual continuity and stylistic consistency. It considers factors like color grading, resolution, and synchronization with common audio cues when present. In embodiments where enhanced user experience is desired, the engine implements machine learning techniques that iteratively refine transition selections based on historical user engagement data or feedback, thus adapting the transition effects to align more closely with evolving user preferences and content themes.

Additionally, the engine can adjust playback speed and modify the temporal aspects of both video clips and transitions, ensuring that the composite video output maintains a coherent narrative structure and visual fluidity. The retrieval and selection process also takes system performance parameters into account, optimizing processing speed and resource utilization during real-time content generation.

In one embodiment, realtime text content is generated using a large language model integrated with modules for processing recent user activity, biometric data, and health goals. The system receives input from sensors and user interfaces configured to detect and collect realtime data associated with user actions, physiological parameters, or defined health-related objectives. The large language model, trained on a diverse corpus that includes medical literature, motivational texts, and historical user interactions, processes these inputs to produce tailored text content. The model evaluates the current data against stored historical information and predefined user health criteria to generate notifications, recommendations, or status reports that are coherent with the user's immediate context. In embodiments wherein biometric data such as heart rate, body temperature, or activity levels are captured via wearable devices, the system analyzes this data in combination with recent user-generated input. The analysis identifies trends or sudden changes that warrant user feedback, and the large language model accordingly adapts its output to provide timely, context-aware messages. In further embodiments, the system includes a data aggregation module that collates inputs from remote sensors, mobile devices, and cloud-based repositories, ensuring that the generated text reflects the most current and relevant information. The large language model utilizes algorithms based on machine learning techniques, such as reinforcement learning and continual learning frameworks, to refine its output based on user interactions and the accuracy of prior generated content. Additionally, secure data processing protocols are employed to protect biometric and health goal information while still enabling the generation of output that responds to this data. The realtime text content is delivered through various interfaces, including mobile applications, web platforms, or integrated device screens, which facilitates immediate user engagement. The system also supports user feedback mechanisms wherein corrections or preferences can be input by the user, thereby enabling the model to iteratively improve its output by adjusting parameters and updating internal models. In certain embodiments, the generated text is used to provide educational content, alert the user to necessary actions related to health improvements, or simply communicate the current status of the user's biometric readings in a clear and actionable manner. The described system implementation ensures that the large language model not only processes varied inputs in realtime but also delivers customized, context-sensitive text content that continuously adapts to the evolving characteristics of user activity, biometric information, and health goals.

The system further comprises a timeline-based video assembly engine that sequences actor-recorded, pre-generated, and real-time generated clips. In one embodiment, the engine accepts multiple input streams originating from diverse sources and coordinates their incorporation into a unified timeline. The engine is configured to operate using either a rule-based sequencing engine or an AI sequencing agent. When functioning in rule-based mode, the engine applies a predetermined set of rules to establish the correct temporal order of the clips, ensuring that each clip is placed according to predefined criteria such as duration, transition sequences, and narrative emphasis. The rules are based on temporal constraints, metadata attributes, and logical dependencies between clips, ensuring that the final video composition maintains narrative coherence and continuity.

Alternatively, when utilizing the AI sequencing agent, the engine leverages machine learning algorithms to analyze clip metadata, user input, and contextual cues to derive optimal sequencing arrangements. The agent is trained on historical sequencing data to identify common patterns and preferences, thereby providing dynamic and adaptive sequencing that adjusts to varying conditions during real-time video generation. The AI agent assesses factors such as scene relevance, pacing, visual continuity, and audio synchronization, recommending modifications or automatically adjusting the timeline to enhance the overall quality of the video output.

The engine further facilitates dynamic editing capabilities that enable real-time review, adjustment, and fine-tuning of the timeline. It supports features such as trimming, rearrangement, and overlay of clips, including options to insert transitions, effects, or additional content as dictated by the sequencing rules or AI recommendations. In embodiments where both sequencing approaches are implemented, the system can provide a hybrid mode that initially applies rule-based logic and then refines the sequence with AI-driven adjustments to better align with user preferences or evolving narrative requirements.

Additionally, the timeline-based video assembly engine incorporates error detection and synchronization mechanisms designed to monitor the interleaving of disparate clip sources. These mechanisms identify potential discontinuities or misalignments within the timeline and trigger corrective procedures either through predefined rules or via AI intervention. The engine also interfaces with external data sources to retrieve supplementary metadata, which can inform adjustments in sequencing parameters and further optimize the final assembly.

In one embodiment, the system further comprises a delivery engine configured to embed the final coaching video directly into the application interface for user playback either on demand or via notifications. In this embodiment, the delivery engine operates by integrating a video embedding module that retrieves the final coaching video from a secure data store or streaming server and seamlessly embeds it within the application's user interface. The delivery engine is further configured to monitor user interactions, scheduled events, or system-triggered notifications, thereby determining appropriate moments to prompt the user to view the final coaching video. When a user initiates a playback request or when a notification is issued, the delivery engine activates the embedded video player that supports standard playback functions such as play, pause, seek, and stop.

In some embodiments, the delivery engine further includes a metadata processing unit that extracts and utilizes metadata associated with the final coaching video, such as version information, time stamps, or user-specific data. This metadata is used to ensure that the correct version of the final coaching video is embedded and that updates or revisions to the video content are automatically propagated to the application interface without disrupting the user experience. The delivery engine is also implemented to support dynamic content updates, wherein the embedded video content is refreshed in real time based on updates from the content server or upon detection of network connectivity.

This architecture allows for seamless delivery and efficient management of the final coaching video, ensuring that users can access the content at their convenience either through an on-demand playback mechanism or via proactive notifications issued by the delivery engine.

In one embodiment, personalization data and content generation parameters are transmitted between various system modules using internal RESTful APIs. The use of internal RESTful A Pls enables seamless communication between modules by standardizing the format and procedure for transmitting data. In this embodiment, each module is equipped with an interface designed to send and receive HTTP-based requests, such as GET and POST, thereby ensuring that data exchanges are carried out in a uniform and predictable manner. The personalization data, which can include user preferences, behavioral indicators, and other user-specific identifiers, is encapsulated within structured message bodies that are transmitted to content generation modules. Similarly, content generation parameters, which define variables such as tone, style, format, and content structure, are included in these transactions to enable dynamic generation of output tailored to the end recipient.

In an exemplary implementation, the internal RESTful APIs are implemented in such a way that each request and response is subject to strict validation and error-handling procedures. Upon receiving a request, a module first verifies that the incoming data conforms to pre-established schemas and security protocols, thereby ensuring data integrity and consistency across the system. This validation process serves to mitigate potential errors related to incorrect or malformed data, thus enhancing the overall reliability of the content generation process. In addition, the APIs are designed to operate within a secured network environment, employing authentication and encryption mechanisms to protect sensitive user data during its transmission between modules.

The communication structure provided by these internal RESTful APIs facilitates the decoupling of system components, allowing each module to operate independently while still maintaining synchronization with the overall system architecture. This modularity enables easier maintenance and scalability of the system since individual modules can be updated or replaced without necessitating changes to the underlying communication framework. Moreover, by using a standardized protocol such as REST, the system benefits from a well-established technology ecosystem that supports interoperability with a variety of tools and platforms commonly used in software development.

In the context of scheduled processing routines or real-time content generation, the internal RESTful APIs handle the dynamic flow of information by coordinating the distribution of personalization data and content generation parameters across dedicated processing pipelines. These pipelines ensure that data is available to content generation algorithms precisely when and where it is needed. Furthermore, the system architecture supports logging and monitoring of all RESTful API transactions, which facilitates auditing of data flows, performance tuning, and error tracking. The inclusion of such monitoring capabilities contributes to continuous improvement in system performance and can be used to enhance the security and efficiency of data transmission.

In one embodiment, the system comprises avatar customization settings configured to modify tone, coaching frequency, animation expressions, and language across all generated outputs. The avatar customization settings include a series of parameter values stored in memory that determine the qualitative attributes of the output, wherein tone adjusts to reflect a formal, casual, or humorous style. The tone parameter is controlled by predefined profiles or is adapted dynamically based on contextual analysis of user interaction history or specific user preferences. The coaching frequency setting determines the interval or repetition rate of coaching messages, hints, or guidance prompts delivered to the user. This setting is implemented via a timing mechanism or algorithmic scheduler that responds to user engagement metrics and predefined thresholds, thereby enabling a tailored coaching experience that varies from rare to recurring interventions. The customization of animation expressions involves modifications to the visual representations of the avatar, including facial expressions, body language, and gesture animations. These animations are selected from a library of pre-programmed or dynamically generated movements and expressions, with selection criteria based on both the overall tone setting and the immediate conversational context. In one embodiment, the system uses sensor inputs or feedback from previous interactions to algorithmically determine the most appropriate animation expression that correlates with the intended emotional state or communicative nuance. The language setting provides the selection and modification of language attributes such as vocabulary, syntactic style, and dialect, thereby influencing the linguistic structure of all generated outputs. The language customization supports multiple languages and incorporates regional variations, and it adjusts dynamically based on detected user language proficiency or explicit user selection. The avatar customization settings are managed by a central customization engine that receives input from user preferences, contextual analysis modules, and system diagnostics, and then applies the corresponding modifications to the output generation process. In this manner, the applied settings ensure that tone, coaching frequency, animation expressions, and language are cohesively integrated into the generated outputs. The integrated adjustment mechanism further allows for real-time modifications; for example, a change in any one setting automatically prompts recalibration of the associated elements without requiring a complete regeneration of the output template. Additionally, the customization engine supports the storage of user-defined presets that encapsulate combinations of tone, coaching frequency, animation expressions, and language settings, thereby enabling rapid reconfiguration of output characteristics in subsequent interactions. This modular approach permits scalable customization while maintaining consistency in output quality and user experience across different contexts and user profiles.

In one embodiment, user feedback and interaction data are logged and used to refine future video generation through a reinforcement learning model. In this embodiment, the system captures detailed information regarding user engagement with generated video content, including explicit inputs such as ratings, selections, or comments, as well as implicit signals such as viewing duration, click-through behavior, scrolling patterns, and other interaction events. This data is stored and aggregated over multiple sessions and across various user profiles to create a comprehensive dataset reflecting user preferences and behavior patterns. The reinforcement learning model utilizes the logged data to adjust and optimize its decision-making policy. Specifically, the model assigns reward values based on the analyzed feedback metrics, where higher rewards are associated with video generation outcomes that result in increased user engagement and satisfaction, and diminished rewards correspond to outcomes yielding reduced user interaction or negative feedback. Through an iterative process, the reinforcement learning module dynamically updates its parameters by evaluating both successful and unsuccessful generation sequences in relation to the recorded feedback. As the system is exposed to continuous streams of fresh data, it refines its strategies for content generation by learning to predict and favor video sequences that are more likely to align with evolving user tastes and preferences. This refinement process involves adjustments to various parameters within the video generation pipeline, such as the selection of visual elements, pacing of sequence transitions, narrative flow, and incorporation of graphic overlays or audio cues, all tailored to maximize overall engagement. The system is designed to support adaptive learning, leveraging techniques such as policy gradients, deep Q-learning, or other reinforcement learning methodologies to iteratively improve the generation process. Additionally, the logged feedback data is segmented based on factors like geographic location, device type, or time zone to provide a more granular analysis of user interaction patterns, thereby enabling the model to further customize the video generation process for different user demographics or contexts. This technique ensures that the reinforcement learning model not only captures real-time user responses but also adapts to sustained trends in user behavior, making the overall video generation system more robust and responsive. The continuous feedback loop created by the logging and analysis of user interactions serves to optimize the reward function guiding the model, resulting in a progressive improvement in the relevance, quality, and personalization of the generated video content over time.

The AI avatar system incorporates a module that generates a personalized coaching plan based on onboarding information received from the user. This onboarding information includes the user's health goals, preferences regarding the personality of the avatar, and additional data relevant to tailoring a customized plan. Upon receiving this information, the system processes the data to create a coaching plan that recommends specific activities, dietary guidelines, exercise routines, and mindfulness practices, with adjustments made according to the user's stated health objectives and personality preferences.

The system continuously monitors user biometric data and activity patterns through integrated health APIs and application interactions. This monitoring can include data such as heart rate, sleep quality, steps, or movement patterns collected via wearable devices or mobile sensors, as well as user behavior within the application interface. The collected information is analyzed to assess the user's current state relative to the personalized coaching plan and to provide real-time feedback for further content generation.

Based on the monitored biometric data and observed activity patterns, the system creates coaching content by selectively combining various multimedia segments. The content creation module is configured to draw from a library of pre-recorded human video segments, pre-generated AI voice and video segments, and real-time AI-generated content. Algorithms within the system determine which segments to select and how to integrate them based on the user's current biometric measurements and engagement patterns, ensuring that the resultant coaching content is both timely and appropriate for the user's needs.

The selected cinematic components are then communicated to a timeline-based video assembly engine that methodically arranges the content into a coherent video presentation. This engine aligns audio, video, transitions, and any supplementary graphical overlays to produce a seamless and engaging visual narrative. The assembly process takes into consideration the sequence and timing of content segments to effectively deliver the coaching plan in a user-friendly format.

Finally, the assembled video presentation is delivered to the user through an application interface. The delivery mechanism is built as part of a mobile or web-based application that supports interactive viewing, encourages further user engagement, and offers the option to provide feedback on the content received. The system also logs user responses to adjust the personalized coaching plan over time, thereby establishing an adaptive coaching environment that continuously refines its recommendations based on ongoing health data and in-app behavior analytics.

Additional embodiments include integration with cloud-based computing resources to manage and process large volumes of biometric data and to support sophisticated machine learning algorithms. Such integration facilitates robust data analytics and secure data storage in compliance with industry standards, ensuring that user privacy is maintained while the system adapts to changing health parameters. In this way, the AI avatar system offers a scalable and dynamic approach to personalized coaching by leveraging advanced monitoring, content selection, and video assembly technologies.

In one embodiment, creating coaching content comprises selecting relevant actor-recorded clips from a human content library based on context and tone. The human content library includes a plurality of actor-recorded video or audio clips, each annotated with metadata such as keywords, emotional tone indicators, context descriptors, and timestamps. This metadata is processed by a selection engine that applies algorithms to match the context and tone requirements of a particular coaching scenario to the corresponding recorded content. The selection involves filtering based on factors including, but not limited to, the subject matter of the clip, the actor's demeanor, and the intended emotional impact on the user.

In another aspect, the method includes retrieving pre-generated AI clips from a server-based storage system. The storage system houses a diverse repository of AI-generated clips that have been previously synthesized and indexed according to relevant variables such as coaching themes, motivational messaging, and situational context. The retrieval step involves establishing a communication link with the server-based storage, executing a query based on coaching criteria, and downloading or streaming the selected AI-generated clip. The system employs additional filtering parameters such as timestamp, file format, or resolution to ensure that the retrieved clip meets the performance and quality specifications required for integration into the overall coaching content.

Further, the method includes generating real-time contextual insights using a large language model based on recent user activity and biometric data. The model processes input data collected from user interactions, including recent in-application activity, as well as biometric data sourced from sensors or wearable devices. In this context, biometric inputs include indicators such as heart rate variability, galvanic skin response, facial expressions, or other physiological signals that provide insight into the user's current state. By correlating this data with historical user behavior and contextual cues, the large language model produces dynamic coaching insights intended to augment the selected actor-recorded clips and AI clips. These contextual insights provide tailored feedback, suggest adaptive strategies, or propose adjustments in real time to optimize the coaching experience.

The integration of these steps-selecting human-sourced clips, retrieving AI-generated clips, and generating contextual insights-enables the creation of a personalized coaching content package that is dynamically responsive to the user's current context and emotional state. The method is implemented within a server-based environment where a processor coordinates the selection, retrieval, and insight generation steps, ensuring that the coaching content delivered to the user remains both relevant and timely. The system also includes a user interface that seamlessly displays the curated clips alongside the contextual insights, thereby enabling an interactive and adaptive coaching session that evolves based on continuous monitoring of user input and physiological data.

In some embodiments, monitoring user biometric data involves tracking heart rate variability (HRV) using a phone camera paired with a finger placement technique in which the user covers the camera lens, optionally aligning the finger with the flash, to capture optical signals generated by variations in blood flow through the finger's capillaries. The mobile device records a sequence of image frames that show fluctuations in absorption corresponding to the pulsatile blood flow, and these frames are processed to extract pulse waveforms. Digital signal processing techniques, such as filtering to remove noise and artifacts, are applied to the recorded images to isolate the pulsatile components, and algorithms like peak detection and time-domain analysis are used to determine the intervals between successive heartbeats. These intervals are used to calculate HRV metrics that include statistical measures such as the standard deviation of inter-beat intervals and frequency-domain parameters.

The calculated HRV is utilized to evaluate fitness progression by comparing current HRV data with stored historical biometric profiles of the user, thereby enabling the system to identify trends over time. In one embodiment, the mobile device evaluates these HRV metrics against predetermined thresholds or adaptive baselines that reflect the user's fitness level, thus guiding the customization of workout routines. If the HRV indicates that the user is experiencing recovery or stress, the system is configured to recommend a decreased intensity workout, or conversely, to suggest a higher intensity session when the metrics fall within an optimal range.

The technique's implementation involves software routines that guide the user in positioning their finger correctly on the camera lens to optimize signal quality, ensuring that the flash provides adequate illumination for optimal signal capture. The acquired pulse waveform data undergo further processing through time-frequency conversion methods, such as Fourier transform-based analysis, to facilitate a comprehensive evaluation of the HRV spectrum. These computed parameters are then encapsulated within a fitness profile that is monitored in real-time, offering immediate feedback on the user's current state and serving as an input to adaptive workout algorithms.

In one embodiment, techniques are provided to modify meal digestion speed by incorporating recommendations that adjust meal composition based on the energy needs and activity state of a user. For meals designed to sustain the user for extended periods, one implementation recommends the addition of crunchy vegetables. The inclusion of these vegetables requires increased mastication and a prolonged mechanical breakdown process, which in turn results in delayed gastric emptying and a gradual release of nutrients throughout the digestive tract. This slower digestion proves beneficial in meeting sustained energy requirements by delivering a continuous nutrient flow. The recommendation is derived from algorithms that assess the user's activity profile, nutritional status, and desired duration of energy release, thereby suggesting specific varieties and quantities of crunchy vegetables that best extend digestion time.

In another embodiment, when rapid digestion is desired—for example, in preparation for, during, or following workouts—one implementation advises reducing the fiber content of meals. A meal composition with decreased fiber facilitates faster transit of food from the stomach through the intestine, thereby accelerating nutrient absorption. This approach involves identifying ingredients known for abundant fiber, which can be substituted with alternative ingredients offering minimal fiber levels, formulating meals with controlled fiber quantities, or scheduling meals strategically around workout sessions to maximize performance and recovery. In both embodiments, the techniques for modifying digestion speed are integrated into a larger nutritional management system that adjusts meal composition based on real-time data related to the user's energy expenditure, metabolic rate, and specific performance goals. The described techniques offer a customizable approach to dietary planning, allowing for the modulation of digestion speed through adjustable meal formulations tailored to various physiological and activity-based demands.

In various embodiments, a personalized coaching plan comprises a comprehensive module for meal recommendations that integrates digestion speed information. The meal recommendations rely on user-specific physiological data, dietary habits, and individualized nutrition goals. In one exemplary embodiment, the system analyzes relevant user data to determine predicted digestion speeds for recommended meals, categorizing those speeds into distinct ranges. The digestion speed ranges are illustrated on a calendar timeline by colored bars, with each color corresponding to a specific rate of digestion. For example, a first color indicates rapid digestion, a second color designates moderate digestion, and a third color represents slow digestion. The colored bars extend across the calendar timeline such that each bar aligns with the scheduled meal time, offering an at-a-glance summary of expected digestive performance over a designated period. The length, position, and color intensity of the bars reflect factors such as predicted digestion duration, meal composition, and the interval between corresponding meals. In particular embodiments, the visualization dynamically updates when the colored bars adjust in response to real-time sensor inputs or user-reported data, ensuring refined predictions and personalized adjustments to the coaching plan. An interactive interface permits users to tap or click on a colored bar to access detailed information regarding a specific meal recommendation, including nutritional breakdown, digestion analysis, and relevant coaching tips. This integration of digestion speed data with meal recommendations on a calendar timeline facilitates proactive meal planning and dietary adjustments, ultimately assisting users in managing digestive health and optimizing nutritional outcomes.

In one embodiment, the system further comprises a custom workout content generation module that receives user-specific inputs indicative of fitness goals, experience level, and physiological metrics. The module processes the received inputs to determine the optimal set of exercises, workout durations, and intensities tailored to the individual user. For example, if the user has a goal of improving endurance while possessing an intermediate level of experience, the module adjusts exercise selections, timings, and rest intervals accordingly. Additionally, the module incorporates physiological metrics, such as heart rate, blood pressure, or other biometrically derived parameters, to ensure that the workout content remains within effective and appropriate ranges for the individual user. This processing is performed using machine learning algorithms that factor in historical exercise data along with real-time measurements from wearable sensors.

The generated workout content includes AI-generated video segments that visually demonstrate the exercises while providing an engaging and interactive experience. The video generation component employs deep neural networks to synthesize video content that illustrates proper exercise form, technique, and pacing. Moreover, the video content is supplemented by personalized verbal cues that address the user by name, thereby creating a uniquely tailored experience. The personalized verbal cues are synthesized using text-to-speech technologies, where the system interleaves the user's name and motivational phrases with contextual instructions throughout the workout session. The AI module ensures that these cues correspond with the specific sequence and timing of the exercises displayed within the video.

The workflow includes a feedback mechanism that stores user performance data and workout session outcomes, enabling the custom workout content generation module to enhance its recommendations over time. By analyzing trends in user performance and adjusting for individual learning curves, the system gradually improves the personalization of both the exercise program and the sequence of AI-generated video content. This feedback-driven enhancement reinforces the utility and responsiveness of the workout content generation module, ensuring that each subsequent workout session is increasingly tailored to the evolving needs and capabilities of the user.

In embodiments, the system further comprises incorporating humor into the AI avatar's communication based on user psychometric trends to stimulate the parasympathetic nervous system during periods of detected stress. The system monitors, collects, and analyzes user psychometric data, which consists of, though is not limited to, facial expressions, voice intonations, text inputs, and physiological indicators retrieved from sensors, to determine stress levels. When the analysis indicates that the user is experiencing stress, the control module activates a humor generation engine. This engine selects and/or generates humorous content tailored to the detected mood, user preferences, and communication history. The humorous content includes jokes, puns, playful remarks, or situation-appropriate banter that is dynamically integrated into the AI avatar's regular communication.

In one embodiment, the system includes a user onboarding process where the onboarding information comprises the selection of a coaching style from a set of predefined personality options. The predefined personality options incorporate distinct coaching methodologies implemented by training the system on various datasets and algorithms reflective of different coaching approaches. For example, one predefined personality option is configured to provide coaching in a strict, disciplinarian manner, with the system's feedback, instructions, and motivational content delivered in a firm tone that enforces clear rules and expectations designed to promote accountability. In contrast, another predefined personality option integrates principles of positive encouragement, whereby the system employs a supportive tone with an emphasis on affirmations, positive reinforcement, and motivational language intended to foster confidence and gradual improvement. In certain embodiments, additional personality options are provided that exhibit intermediate or hybrid characteristics, combining elements of both disciplinarian and encouraging approaches to suit a wider range of user preferences and coaching contexts.

The system further refines the coaching experience by correlating the selected coaching personality with a set of trained machine learning models, each designed to interpret and generate content according to the established characteristics of the chosen style. This mapping supports dynamic adaptation to a user's evolving requirements while maintaining the integrity of the selected coaching methodology. In certain embodiments, the system also includes the option for users to alter their coaching style in response to changing personal goals or feedback, with the interface permitting modification of the stored personality preference and reconfiguration of the underlying coaching algorithms.

The various predefined personality options are integrated into the system's overall coaching framework, ensuring that the user's coaching experience is personalized from the initial onboarding phase and continues to be tailored during ongoing interactions. This integration enables the system to deliver a customized coaching experience that aligns with the user's selected personality, thereby enhancing user engagement and optimizing the effectiveness of the coaching methodologies employed.

In one embodiment, the system is configured to provide an enhanced interactive experience by dynamically responding to a user request for additional information with respect to a current timecode in the user's media session. The system first determines the specific portion of the content by mapping the current timecode provided by the user to a corresponding segment of an associated digital media file. This mapping is achieved by correlating timestamps embedded within a content metadata database to the active playback position, thereby isolating the exact portion of content that is the subject of the additional information request.

Once the specific portion is identified, the system automatically retrieves relevant contextual data and ancillary content stored in a linked repository. It processes this information to generate a personalized script tailored to the identified content segment. The personalized script is created using a combination of pre-stored templates and real-time data insertion techniques, ensuring that additional information remains both accurate and relevant. The script generation process incorporates natural language processing and machine learning algorithms to adapt the language and detail level to the user's presumed expertise or interest.

The complete process—from identifying the relevant content segment using the current timecode, to generating and delivering a personalized script via a synthesized voice and corresponding digital avatar—ensures that the response to the user request is both timely and contextually appropriate. By combining metadata analysis, personalized content generation techniques, superior fidelity voice synthesis, and real-time video rendering of an AI avatar, the system offers a seamless and engaging delivery of additional information that enhances the user's interactive experience with the media content.

In one embodiment, the system is configured to automatically transcribe educational content using artificial intelligence. The system receives input data representing educational material in audio, video, or live lecture formats and processes this input through a speech-to-text engine that includes one or more artificial intelligence models. These models analyze the audio or video signals to generate a text transcription that accurately reflects the spoken content. The system further integrates a natural language processing component that examines the generated transcript to identify key concepts, terminologies, and segments within the educational content which benefit from additional contextual data. Based on this analysis, the system generates interactive markers positioned at specific portions of the transcript where further information enhances understanding.

The interactive elements are implemented as selectable regions, buttons, links, or touch-sensitive markers that appear alongside or within the transcribed text. When a user interacts with an element, the system processes the request by referencing a supplementary information database or querying an integrated knowledge base that corresponds to the selected portion of the educational material. The supplementary information comprises definitions, examples, detailed explanations, related multimedia resources, and links to other educational resources that provide a broader context or additional perspectives.

In one variation, the artificial intelligence transcription module and the interactive element generation module operate in real time, enabling dynamic creation of interactive educational content as the original material is transcribed. In another variation, the transcription process is conducted in a batch mode where pre-recorded educational content is first transcribed and then annotated with interactive elements that are subsequently rendered through a web or mobile application interface for end-user access.

The system is designed to support multiple modalities of user input, including touch, voice commands, and cursor-based interactions, thereby accommodating various user preferences and accessibility requirements. Upon receiving a request for additional information, the system initiates a retrieval operation that leverages contextual relevance determined by both artificial intelligence analysis of the transcript and historical usage data obtained from previous interactions. This retrieval operation involves further processing by a machine learning module that refines the supplemental content to better match the user's inquiry.

In some embodiments, the system is deployed on a cloud-based infrastructure that enables scalable processing of educational content and adaptive streaming of interactive elements. The cloud-based system includes security features that ensure transmitted data and user interactions are encrypted and compliant with applicable privacy and data protection regulations. Additionally, a monitoring component within the system tracks user interactions with the interactive elements and provides feedback to improve the performance of both the transcription engine and the relevance of the supplementary information provided.

The integration of artificial intelligence-based transcription with interactive user request functionality provides a comprehensive approach to delivering educational content that is not only accurately transcribed but also enriched with contextual details in response to user engagement. This integration enables learners to access more detailed explanations and further resources seamlessly, thereby enhancing the overall educational experience.

A computer-implemented system for coordinating health actions among users includes several integrated modules that operate together to schedule, prioritize, invite, and update shared health activities in real time. In one embodiment, the system comprises a primary health action scheduling module configured to enable users to select and designate time-based health activities from a range of available options. The scheduling module presents a user interface that includes a calendar view, selectable time slots, and customizable event details, thereby allowing users to schedule health activities at preferred times, modify existing schedules, and view upcoming events in a coherent, organized manner.

The system further includes an invitation engine that is operatively connected to the scheduling module and is configured to send participation requests to app-connected users. This engine leverages multiple communication modalities, such as push notifications, emails, or SM S messaging, to distribute invitations. It tracks the dispatch and delivery status of each outgoing request and records acknowledgments or initial responses to ensure that scheduling conflicts are minimized and that each designated health action receives appropriate participant confirmation.

Additionally, the system features a priority assignment module that enables users to indicate the importance level of the key health action by using visual indicators. Through a graphical user interface, users can select from various visual cues, such as color codes, icons, or intensity markers, to express the relative urgency or significance of an activity. These visual indicators assist both the initiating user and invited participants in quickly discerning the priority of each scheduled action, thereby streamlining decision-making processes regarding attendance and preparation.

In addition to the scheduling, invitation, and priority modules, the system integrates a real-time acceptance engine that manages invite responses. Upon receiving a response—positive or negative—the acceptance engine immediately updates the shared schedules so that users always have access to the most current information. This real-time updating capability is essential for maintaining accurate and dynamic coordination among multiple users. The acceptance engine also includes provisions for capturing additional feedback, such as reasons for declining an invitation, which can be used to improve future scheduling and invitation strategies.

In one embodiment, the various modules are implemented as distinct software components that communicate through standardized application programming interfaces (APIs)

within a cloud-based or distributed computing environment. This arrangement permits seamless integration, enabling the system to efficiently synchronize scheduling, prioritization, invitation, and response data across multiple devices and platforms. The cloud-based architecture further ensures that updates are propagated immediately to all users, reducing potential scheduling conflicts and enhancing the overall user experience.

The health action scheduling module allows for flexible planning by enabling users to either select predetermined time slots or define custom health actions with unique timing needs. In parallel, the invitation engine is designed with mechanisms to control both the volume and timing of invitations so that the network is not overloaded and response deadlines are not missed. Meanwhile, the priority assignment module uses visual indicators to offer users an intuitive grasp of the relative importance of various health actions, a feature that is especially beneficial when managing multiple concurrent activities.

In one embodiment, when a second user accepts the KHA, the system reassigns the status of the KHA from its initial state to a Social KHA. The acceptance is indicated by a user action such as tapping or clicking on a designated acceptance control. Upon detecting this action, the system updates an internal flag or attribute associated with the KHA that denotes its transition to a social status. The status update triggers a change in the visual presentation of the KHA on the user interface. For example, the system alters the color scheme, iconography, or other visual artifacts associated with the KHA to differentiate it from KHAs that have not been accepted by a second user. The change in appearance informs both the original and other users that the KHA has undergone a status transition.

In addition to the visual modifications, the system sends updated notifications regarding the status change. These notifications are generated in real time and directed to one or more users, including the original creator of the KHA, the accepting user, and additional users subscribed to updates related to that content. The notifications appear as on-screen alerts, messages within the application, or through other communication channels such as email or push notifications. The notification content typically includes information on the change, such as the fact that the KHA is now recognized as a Social KHA, and offers additional details regarding the nature of the acceptance.

The system includes a nutritional planning engine that customizes meal macronutrient targets for individual participants. The nutritional planning engine analyzes various data inputs, including user dietary preferences, health objectives, activity levels, biometric information, and other relevant user-specific data to calculate individualized macronutrient requirements. The engine utilizes existing nutritional guidelines and applies proprietary algorithms to determine optimal proportions of proteins, carbohydrates, fats, and other essential nutrients tailored to each participant's needs.

Furthermore, the engine is implemented on one or more computing systems that execute computer-readable instructions stored on a non-transitory computer-readable medium, ensuring that personalized meal planning recommendations are generated and updated efficiently in accordance with current user data and preferences.

In one embodiment, the system is configured so that users can optionally select an AI avatar to participate in the Social KHA. Upon selection, the AI avatar is activated to deliver dynamic multimedia encouragement through audio, visual, and text-based outputs that are tailored to the individual user's needs. This multimedia encouragement includes synthesized speech integrated with facial animations to convey emotional tone, as well as visual cues, such as graphical overlays or animations, that complement the coaching process. The system provides a user interface that allows users to choose from a plurality of AI avatar options based on predefined categories or customizable parameters. Once activated, the AI avatar monitors user interactions and employs adaptive algorithms to deliver follow-up coaching based on historical user data, trends in user behavior, and real-time input. The follow-up coaching is designed to motivate the user and incorporates contextually relevant suggestions, prompts, or challenges that encourage continued engagement. In some embodiments, the AI avatar uses machine learning techniques to refine its coaching strategies over time by analyzing past interactions and feedback, thereby enhancing the personalization of multimedia outputs and coaching messages. The system integrates cloud-based resources that dynamically update the avatar's content libraries with new multimedia elements, ensuring that the encouragement and coaching remain current and effective. Additionally, the AI avatar analyzes sentiment through natural language processing, which allows it to adjust the tone, timing, and style of its communications to better align with the emotional state of the user. The combination of these functionalities enables the AI avatar to serve as an interactive coach that not only delivers motivational multimedia content but also provides iterative, personalized follow-up coaching to guide the user toward achieving predetermined goals.

In one embodiment, the invitation interface is configured to present a plurality of user-selectable options including accept, decline, and reschedule to facilitate a dynamic scheduling environment. When a user selects the accept option, the system processes the confirmation by updating underlying status data and transmitting an accept signal to the associated scheduling module; as a result, the Social KHA is automatically reflowed to reflect the confirmed status of the invitation. Similarly, if the decline option is selected, the system initiates procedures to record the rejection of the invitation and to revise the corresponding social information in the Social KHA, thus effectively removing or denoting non-participation within the user interface. In the case of the reschedule option, the interface engages a scheduling service that allows the user to select an alternate time or event configuration, and upon confirmation of this new scheduling data, the Social KHA is dynamically adjusted to display the updated information. The reflow of the Social KHA involves reorganizing visual elements, reordering items within the display, or resizing interface components so that the current status and scheduling details are accurately reflected. In embodiments where multiple invitations or social events are processed concurrently, the system employs a reflow algorithm that automatically propagates updates across the entire Social KHA, ensuring that visual consistency and logical associations among events are maintained. The reflow adjustments include modifying layout parameters such as element position, order, and size based on the current invitation responses, thereby providing the user with an up-to-date and contextually relevant interface. These features are implemented through a combination of user interface controllers, scheduling modules, and layout engines that collectively ensure the Social KHA remains synchronized with user actions on the invitation interface.

In one embodiment, group-based KHAs are configured to facilitate and manage embedded shared video calling and chat features within the application interface, thereby enabling real time communication among users who are members of a predefined group. The group-based KHAs include one or more processing modules and associated memory that execute instructions to initiate video calling sessions and manage chat communications in accordance with user commands. When a designated group is formed, the KHAs automatically detect group membership and establish corresponding communication sessions by interfacing with underlying network protocols and communication servers. The KHAs coordinate the initiation, management, and termination of shared video calling sessions as well as the real time synchronization of text chat messages, ensuring all users within the group experience a consistent and reliable service. In addition, configuration parameters controlled by the KHAs dynamically adjust video quality or message delivery based on available network bandwidth and system load, thereby optimizing the user experience. The embedded features, which include both video calling and chat, are tightly integrated with the overall application interface so users can seamlessly switch between communication modalities without exiting the application environment. The system further incorporates authentication, error detection, and data encryption mechanisms within the group-based KHAs to enhance security and ensure that only authorized group members can access the shared communication functionalities. In some embodiments, the KHAs are also capable of interfacing with other modules of the application, such as notifications or content sharing components, to provide integrated collaborative functionalities that extend beyond basic video and text communication.

In one embodiment, the system is configured to generate, update, and display a unified shared KHA view that integrates each user's dietary, sleep, and exercise plans. The system collects user-specific data from a variety of sources, including nutritional logging, sleep monitoring, and fitness tracking devices, and then processes this data through algorithms that tailor individual recommendations based on the user's historical trends, current status, and goals. The unified shared KHA view presents this information in a consolidated format such that while the underlying template remains consistent across participants, the content is dynamically personalized according to each user's specific health profile. For instance, the dietary plan presented within the KHA view incorporates detailed nutritional guidelines that are adjusted based on individual metabolic rates, caloric requirements, and dietary restrictions, while the sleep plan reflects personalized recommendations derived from data on sleep duration, quality, and circadian patterns. Similarly, the exercise plan is customized based on variables such as fitness level, activity history, and physical capability, ensuring that the displayed workout regimen aligns with the user's current state and progress. The system leverages a central data management framework that continuously synchronizes individual updates with the shared interface, providing real-time adjustments to the health plans as new information is received. In addition, the system employs machine learning algorithms to analyze trends across user data, thereby enabling predictive adjustments to each plan that are then reflected in the dynamically updated KHA view. As a result, even though the KHA view is shared among users, each participant observes a uniquely configured display that emphasizes personalized dietary, sleep, and exercise information, fostering an environment in which health data is both collaboratively accessible and individually relevant.

In embodiments of one implementation, the avatar assistant is configured to analyze participant performance data collected during a knowledge handling activity (KHA) and, after the activity is completed, generate a comprehensive summary of each participant's performance. The assistant receives data from one or more sensors or input devices that capture various performance metrics such as response accuracy, task completion speed, engagement levels, and other behavior indicative of proficiency in the KHA. U sing analytics algorithms, the avatar assistant evaluates the performance data relative to predefined performance benchmarks as well as dynamically generated thresholds based on historical performance and contextual factors. Based on this analysis, the assistant creates an individualized performance summary that includes an assessment of strengths, identification of areas for improvement, and a comparative evaluation against established performance standards.

In one embodiment, the system further comprises a family grouping module configured to allow scheduling of key hierarchical activities (KHAs) across shared calendars while personalizing calendar entries according to user roles. The family grouping module identifies and manages individual user roles, such as parent and child, by accessing role-based user profiles stored in a secure database, and subsequently adjusts both the appearance and functionality of scheduled KHA s to reflect the defined roles. The module enables a parent user to input or modify a KHA event, which is synchronized across a shared calendar accessible by designated child users, with the system applying predetermined restrictions or permissions based on the role associated with each user. For example, the module automatically assigns different levels of editing rights, notification settings, and view-only status depending on whether the calendar entry is viewed by a parent or a child, ensuring that each user receives pertinent, role-specific information. Additionally, the family grouping module integrates with calendar management functionalities that include conflict resolution, event reminders, and recurring appointment scheduling.

In some embodiments, the module supports dynamic updates, whereby changes to a family member's schedule or role—such as a modification in parental control settings or a change in the family grouping—are automatically reflected throughout the shared calendar environment. The module operates by interfacing with one or more calendar synchronization protocols and employing application programming interfaces (APIs) to manage intercommunication between disparate calendar applications, thereby facilitating real-time updates across multiple devices within the family unit. Moreover, the family grouping module provides a user-friendly interface that allows users to easily transition between different views or modes of the shared calendar, enabling the display of events differentiated by role—for instance, marking activities initiated by parents distinctly from those generated or modified by children.

In one embodiment, the system collects biometric data from various sensors that monitor physiological parameters such as heart rate variability, skin conductance, and other stress-related metrics. Simultaneously, behavioral data is gathered from user interactions with software applications, movement patterns, and usage histories that indicate engagement levels as well as frequencies of social interactions. Furthermore, the system accepts user-reported data via structured questionnaires or direct input related to personal goals, emotional states, and preferences concerning social interactions. The data is then aggregated by processing components that normalize and contextualize the information to create an integrated user profile.

This profile is subsequently analyzed by machine learning algorithms that process multimodal data inputs to detect trends and correlations indicative of a user's current state, progress toward personal goals, and overall relationship quality. Based on this comprehensive user profile, the system employs recommendation engines configured to identify Social KHAs whose attributes and capabilities likely align with the user's unique needs. The recommendation process involves comparing real-time biometric indicators and historical behavioral patterns with predefined parameters associated with various Social KHAs. Additionally, the system cross-references user-reported objectives to tailor recommendations, ensuring that the selected Social KHAs not only provide suitable support for meeting personal goals but also contribute positively to enhancing the quality of interpersonal relationships.

This approach supports dynamic adjustments and continuous learning, allowing incoming data to be regularly re-evaluated to refine and optimize future Social KHA selections corresponding to emerging user circumstances and shifting priorities, thereby fostering sustained user engagement and fostering more effective relational outcomes.

The system is configured to enable users to establish, manage, and leverage interpersonal relationships for enhanced emotional support and coaching. In one embodiment, a social linking module allows users to designate and classify relationships with other application users. This module supports the entry of relationship identifiers, configurable privacy settings, and metadata that describes the nature of each connection. It is further configured so that changes in relationship status—such as friendship updates or relationship modifications—are propagated to other modules in real time.

The structured feedback interface is designed to facilitate the input of multifaceted emotional data. Users provide input that includes emotional reflections, explicit requests for support, or indications of the impact of interactions on their well-being. In some implementations, the interface guides users via structured fields and prompts that are dynamically adjusted based on prior inputs or known relationship contexts. The interface is integrated with user authentication protocols and communicates with the social linking module to ensure that feedback is properly attributed to relevant interpersonal connections within the app.

The emotional analysis engine receives input from the structured feedback interface and processes the data through several analytical submodules. A sentiment analysis component dissects user input to determine the positive, negative, or neutral emotional tone associated with the feedback. A role classification component evaluates the context of the relationships and content of the feedback to categorize the roles of linked users relative to the feedback source. In addition, a well-being scoring module is implemented to quantitatively assess the emotional state and its fluctuations over time, with this scoring incorporating metrics derived from behavioral context data. The behavioral context analysis further examines the situational factors, previous interactions, and historical patterns of communication to enhance the accuracy in understanding the user's emotional state. The outputs of these analyses are normalized and stored for subsequent use by other modules.

The avatar coaching module uses analyzed emotional data to offer personalized support, mediation, and relational advice. It is programmed according to established best practices in therapeutic communication and is enhanced by cognitive behavioral techniques. Based on the outputs of the emotional analysis engine, the module generates responses designed to address the specific emotional nuances and relationship context of the user. These responses include suggestions for interpersonal communication, recommendations for self-care practices, and prompts to engage in mediation steps with other linked users. Additionally, the module is capable of real-time iterative adjustments by using feedback loops that learn from user interactions, thereby refining the accuracy and applicability of the support provided. In one embodiment, the module supports the scheduling of follow-up sessions or reminders designed to further assist users in managing their emotional health.

Throughout its operation, the system employs secure communication protocols and data encryption methods to maintain user privacy, ensuring that personal feedback and relationship data remain confidential. The integration between the various modules is designed to support real-time processing, and the modular architecture allows for scalability and the incorporation of future enhancements based on emerging best practices in emotional support and interpersonal coaching.

In one embodiment, avatars are configured to analyze user interactions and recognize instances where a user contributes to another individual's well-being through actions or communications that are deemed beneficial. The avatars utilize algorithms incorporating natural language processing and contextual analysis to evaluate user inputs, identifying positive behaviors such as empathy, supportive language, or helpful actions. Upon detecting such behaviors, the avatars automatically deliver praise through verbal or visual cues intended to reinforce the user's actions and encourage continued positive engagement.

Furthermore, the system incorporates user-configurable settings that allow customization of the feedback process, such as adjusting the sensitivity of evaluation metrics or selecting preferred communication styles. This ensures that the avatars function in a supportive and non-intrusive manner, respecting individual differences in receiving feedback. The detailed analysis and adaptive feedback provided by the avatars not only encourage positive behaviors but also foster an environment in which users receive information regarding how their actions contribute to the overall well-being of others.

In one embodiment, the system includes an interactive avatar designed to assist users by offering a variety of scripts or phrases intended to help articulate difficult emotional content during communications with a linked user. The avatar is configured to analyze the contextual input provided by the user—such as prior conversation history, detected sentiment, or direct input regarding emotional intent—in order to generate or retrieve from a database an appropriate set of scripted phrases that are contextually relevant and emotionally considerate. In some implementations, the avatar utilizes natural language processing techniques to parse the nuances of the user's message and identifies emotional triggers or potentially sensitive topics that benefit from a moderated approach. The scripts or phrases provided by the avatar serve as a starting point for the user, offering carefully structured language that guides the user toward communicating personal feelings or complex emotional experiences in a manner that is both clear and empathetic. The scripts include, without limitation, alternative phrasing that equips the user with options tailored to various emotional intensities and relational contexts, ensuring that the language used minimizes the potential for miscommunication or unintended escalation of emotional content. Further, the avatar provides dynamic modifications to these scripts based on real-time interactions with the user, thereby allowing for personalized adjustments that reflect the ongoing conversation. In some embodiments, the system allows the user to select from a list of pre-scripted options, while in other embodiments, the avatar suggests modifications to the original scripts based on additional user feedback or changes in tone observed during the communication session. The use of such pre-defined script options intends to empower users by providing them with a guided method to address and translate challenging emotional states into constructive dialogue, particularly in moments where self-expression becomes impeded by anxiety, conflict, or other psychological barriers. Moreover, the integration of this feature within the avatar serves not only to facilitate clear communication but also to foster a more supportive communicative environment between linked users by introducing language designed to de-escalate tensions and promote mutual understanding.

The shared activity recommendation engine functions as an integrated component of the system to facilitate the scheduling and execution of KHAs that users complete together. In certain implementations, the engine continuously monitors user activity data—including historical KHA completion, current emotional state inputs, and scheduling availability—to generate tailored recommendations for collaborative activities. The engine utilizes algorithms that analyze the compatibility of users' health objectives and emotional bonding preferences, selecting KHAs that are mutually agreeable and likely to enhance interpersonal connections. Additionally, the engine incorporates a dynamic scheduling module that coordinates the timing of these shared tasks, ensuring both users receive notifications in an optimized sequence with sufficient lead time for preparation. The system further incorporates a feedback loop wherein users' performance and subjective satisfaction with completed KHAs are collected to refine future recommendations and adjust scheduling parameters. In some implementations, the shared activity recommendation engine also interfaces with a user profile repository that stores behavioral data, health metrics, and interaction history, enabling the engine to dynamically adapt its activity recommendations based on evolving user characteristics. Overall, this integration facilitates the promotion of positive health behaviors while simultaneously fostering an environment of collaborative engagement and emotional bonding between users.

In one embodiment, the system includes an interface configured to receive user feedback, wherein the interface provides multiple methods for inputting both subjective and quantifiable data. The interface allows a user to submit feedback through selecting one or more predetermined emotion tags that represent various emotional states, including a range of feelings such as happiness, sadness, anger, or anxiety, among others. These emotion tags are presented using visual formats such as icons or color-coded labels to facilitate easy selection. In addition to the emotion tags, the interface incorporates one or more numerical slider elements that enable the user to indicate the intensity, magnitude, or degree of a selected emotion or a specific well-being indicator; these sliders operate on defined scales and offer either discrete or continuous input values to allow for fine-tuned self-assessment.

Furthermore, the interface is designed to capture multidimensional well-being scores that reflect the user's overall state across several dimensions, such as physical, emotional, and mental well-being. These multidimensional scores are derived from aggregating various input parameters provided by the user and are computed through a combination of numerical slider adjustments and predefined weighting algorithms designed to quantify aspects of subjective well-being. The multidimensional scoring mechanism is capable of displaying the relative contribution of different well-being dimensions and adjusts dynamically based on user input gathered overtime.

Additionally, the interface includes an optional journal-style entry field that permits the user to supply free-form textual feedback to elaborate on their emotional experience or to provide contextual details that are not fully represented by numerical or categorical inputs. This journal-style field facilitates narrative input, enhancing the qualitative nature of the feedback by enabling the user to detail nuances or specific experiences, while the entered content is subsequently analyzed using techniques such as natural language processing or sentiment analysis to extract further emotional or contextual insights.

The system is further configured to integrate and process data from these various input modalities—emotion tags, numerical slider values, multidimensional well-being scores, and journal-style entries—in a coherent manner so as to offer a comprehensive profile of the user's subjective state. In some embodiments, this integrated feedback is stored and analyzed using backend processing techniques that correlate discrete and continuous data points, thereby permitting time-series analysis, trend identification, and adaptive feedback loops based on changes in the user's submissions. The overall architecture ensures that the user feedback is securely captured, stored, and processed, with considerations given to both data normalization and privacy requirements.

Moreover, the interface includes additional features such as real-time visual feedback, displaying graphical representations like charts or thermometers based on the submitted scores, which help the user contextualize their input relative to past entries or an aggregate trend. The design of the interface is optimized for ease of use across multiple devices and incorporates accessibility features to accommodate users with varying needs. In embodiments that require more comprehensive data input, the system includes contextual prompts or supplementary queries to encourage elaboration when incongruities or ambiguities are detected in the primary feedback data. Through these various mechanisms, the interface provides a multifaceted and robust means for capturing user feedback, thereby enabling deeper insights into user well-being and emotional state.

In one embodiment, the system performs emotional analysis by first acquiring data indicative of a user's emotional state through various sensors and data sources. The acquired data includes audio signals, facial expressions, physiological measurements, and text input that represent both instantaneous emotional responses and prolonged behavioral patterns. The reinforcement learning model is then employed to process this data over time, detecting evolving patterns in emotional state, relational satisfaction, or conflict resolution. The model is designed to operate in a dynamic environment where the emotional data continuously updates, requiring the system to adapt to new patterns and changes in the underlying emotional dynamics by mapping the input data to a set of states and corresponding actions. These states incorporate representations of both transient emotions and aggregated historical trends that contribute to an understanding of overall relational health.

The reinforcement learning algorithm employs a reward function designed to promote patterns linked to positive relationship dynamics and effective conflict resolution strategies, while simultaneously penalizing patterns that signify escalating conflict or diminishing relational satisfaction. In particular, the reward function assigns higher values to states that exhibit increased relational satisfaction and instances where conflict resolution results in a stable or enhanced emotional state. Conversely, negative rewards are applied when data indicates worsening emotions or deteriorating relationship interactions. Through iterative updates and repeated interactions with real-time and historical data, the model learns an optimal policy.

During each iteration, the reinforcement learning model compares current emotional signals with previously acquired emotional patterns, determining whether specific actions or interventions can result in more favorable emotional states. The model is designed to incorporate exploration strategies to investigate untested responses, alongside exploitation strategies intended to reinforce demonstrated effective behavioral interventions. Additionally, the model adjusts its parameters based on continuous feedback, which refines its ability to detect subtle trends that indicate either enhancement or degradation in relationship quality. By leveraging deep neural network architectures within the reinforcement learning framework, the system facilitates the identification of complex, non-linear connections between emotional inputs and subsequent relationship outcomes.

In addition, the model includes a mechanism for forecasting future emotional states and potential areas of conflict by simulating various scenarios based on current trends. This simulation capability supports proactive measures designed to mitigate negative emotional developments or reinforce positive relational interactions. The learned policy, which is updated as new data is processed, facilitates a nuanced understanding of the interplay between individual emotions and overall relationship dynamics. Ultimately, the system provides users with actionable insights derived from its continuous assessment of evolving emotional patterns, offering tailored recommendations for enhancing relational satisfaction and managing conflict effectively over extended periods.

In some embodiments, feedback data is processed by first applying encryption algorithms compliant with recognized privacy regulations prior to any storage operations. The encryption is performed using one or more industry-standard encryption techniques, wherein the encryption keys are securely managed and stored separately from the encrypted data to ensure confidentiality. Prior to sharing any insights between linked users, the system evaluates whether the data contains any identifiable elements that could compromise user privacy; if such elements exist, they are obfuscated or removed in order to render the data effectively anonymized. In these embodiments, anonymization includes techniques such as the removal or substitution of personal identifiers, tokenization processes, and data aggregation methods that permit the derivation of useful insights without correlating the data back to any specific user. Moreover, any transmission of shared insights between linked users is performed on anonymized data sets, and the system employs safeguards that verify proper anonymization before data exchange occurs. This process further ensures that the feedback data, even when aggregated across multiple sources, does not inadvertently expose individual user identities or sensitive information. In addition, the regulatory compliance aspect is maintained throughout the data processing and storage operations by periodically updating the encryption and anonymization procedures in line with evolving privacy standards and implementing continuous auditing to detect and rectify any discrepancies. These measures collectively ensure that all feedback data is securely stored and managed, while still allowing linked users to derive beneficial aggregated insights without jeopardizing individual privacy interests.

Furthermore, the avatar-delivered coaching incorporates techniques derived from family counseling protocols that facilitate communication and conflict resolution within interpersonal relationships. In various embodiments, the system simulates interactions based on established family counseling methodologies, providing users with role-playing exercises, guided dialogue, and structured conflict management strategies. These techniques involve initiating scenario-based interactions that prompt users to consider alternative perspectives, thereby fostering a more constructive dialogue and promoting mutual understanding. The family counseling-derived protocols integrated within the system enable the avatar to offer recommendations for de-escalation, encourage the adoption of effective communication habits, and support the development of healthier relationship dynamics.

Additionally, the avatar-delivered coaching incorporates techniques based on evidence-based communication strategies that are designed to improve the clarity, persuasiveness, and overall effectiveness of the user's communication. Such strategies are informed by research findings from communication studies and involve structured activities that emphasize active listening, careful timing and sequencing of conversational inputs, and detailed feedback techniques. In some embodiments, these evidence-based communication methodologies are implemented to assist the user in restructuring both verbal and non-verbal messaging, thereby facilitating more effective exchanges during interpersonal interactions.

Avatars operate to detect and respond to periods classified as emotionally sensitive by leveraging a combination of user input, sensor data, and algorithmic assessments. In embodiments, the system monitors data related to factors such as interpersonal conflict, physiological indicators associated with menstrual phases, and signals denoting various stages of recovery, thereby establishing when a user is experiencing heightened emotional vulnerability. Once such a timeframe is detected, the avatar automatically initiates a check-in with the user. This check-in is executed either through a scheduled prompt or through real-time detection of relevant emotional or physical cues, ensuring that the timing of the intervention aligns with the user's current state.

The check-in process is designed to be nonintrusive yet supportive, with the avatar adopting a conversational style that communicates empathy and understanding. The avatar uses pre-programmed scripts, dynamic responses generated through natural language processing, and machine learning-driven adaptations to tailor its communication. The empathetic tone is maintained through careful selection of language, expressions, and even simulated nonverbal behaviors such as facial expressions or gestures, all of which contribute to a nuanced and human-like interaction.

During the check-in, the avatar initiates dialogue that includes questions aimed at gauging the user's current emotional state and offering coaching techniques. The coaching is empathy-driven, meaning that it incorporates supportive messages, reflective questioning, and suggestions for stress mitigation strategies such as mindfulness exercises, cognitive behavioral techniques, or other coping mechanisms. In some embodiments, the system is configured to adapt these responses based on historical user interactions, preferences, and feedback, thereby continuously improving the personalization and effectiveness of the coaching provided.

The system integrates external data—such as biofeedback from wearable devices or manually entered health information—to refine its understanding of when and how to engage the user. This integration enables the avatar to recognize subtle shifts in the user's condition, including those following emotionally impactful events like conflicts or during periods of physiological change associated with menstrual cycles. Additionally, the system incorporates location-based and time-specific information to ensure that check-ins occur at appropriate intervals and do not interfere with the user's routine activities.

Furthermore, when initiated during a period of increased risk, the coaching provided by the avatar can be escalated to include advice on seeking human support or even triggering alerts if the user's responses indicate severe emotional distress. This tiered approach ensures that the system offers both immediate, empathetic support through the avatar interface and, when necessary, a path to additional resources for further assistance.

In one embodiment, the system comprises a user interface that enables users to opt into sharing menstrual cycle data with a centralized processing unit. The menstrual cycle data includes information such as cycle length, bleeding duration, ovulation period, basal body temperature, and additional physiological indicators collected either manually or automatically using integrated sensors. This cyclical data is securely stored and processed to determine the current physiological phase of the user. Based on the determined phase, an avatar is algorithmically selected and customized to display guidance tailored to the user's specific stage in the menstrual cycle. The avatar-led guidance comprises personalized recommendations on wellness activities, dietary suggestions, and exercise regimens that align with the user's physiological state.

Additionally, the system provides context-sensitive recommendations for partners, where the recommendations incorporate suggested activities, communication strategies, or reminders that consider not only the physiological phase of the user but also potential preferences or behavioral trends observed in partner interactions. The recommendations for partners are generated by integrating data from historical interactions between the user and the partner as well as by referencing general behavioral patterns correlated with specific phases of the menstrual cycle. Users retain the ability to review, modify, or disregard the avatar-led guidance as desired.

In another embodiment, the system further incorporates a privacy management module that allows users to selectively share or restrict the sharing of their menstrual cycle data with third-party applications, thereby ensuring compliance with applicable data protection and privacy regulations. Data transmitted to third parties is anonymized and aggregated to preserve user confidentiality while still enabling the provision of generalized health advice.

The system architecture supports dynamic updating of the avatar-led guidance algorithms based on ongoing research or user feedback, with periodic software updates that enhance personalization accuracy over time. Furthermore, the system incorporates machine learning modules that analyze trends across multiple users to refine the timing and content of both the personalized guidance and the partner recommendations. These modules are designed to adjust or individual variability in menstrual cycle patterns, thereby confirming alignment of the avatar-led guidance with the user's unique physiological rhythms. The overall framework integrates seamlessly with existing mobile and wearable devices, enabling real-time data collection and user interaction while providing a holistic approach to personal health management.

In one embodiment, linked avatars are implemented as interactive agents residing in a computing environment that supports real-time communication and collaboration between users. The avatars are arranged to coordinate and exchange information such that each avatar monitors the dialogue between users and dynamically adjusts its responses according to the specific roles and objectives assigned to each participant. The coordination process involves capturing data related to user language, behavior, and interaction context, processing this information through an algorithmic engine designed to assess the goals and responsibilities of each user. This engine determines a set of mirrored coaching strategies that are personalized based on the identified role and goal parameters. In this manner, one avatar provides feedback aligned with the task-oriented aspects of a discussion, while a corresponding linked avatar offers reflective commentary or inquiry techniques that promote mutual understanding. The mirrored coaching strategies include, for example, prompting clarifying questions, suggesting alternative approaches, and providing real-time feedback that is harmonized between the linked avatars. The system leverages machine learning algorithms to continuously learn from user interactions, allowing these mirrored coaching strategies to become increasingly refined over time relative to the evolving profiles of user roles and objectives. Data is processed without altering the fundamental characteristics of the dialogue and is utilized solely to enhance the clarity and effectiveness of communication between users, thereby facilitating an environment in which dialogue is not only sustained but purposefully directed toward mutual understanding and collaborative success. The described technique ensures that adjustments in coaching strategies occur automatically in response to shifts in user engagement or context, thus maintaining a balanced and supportive interaction optimized for achieving the desired outcomes of each participant. The programmatically generated AI avatar serves as the embodied interface between the user and a highly advanced health optimization engine, providing users with a trusted, human-like guide that delivers personalized coaching to improve their health, well-being, and longevity. Each avatar includes a customizable personality and appearance module, allowing for coaching personas—ranging from archetypal roles to branded or celebrity-style guides. This embodiment builds trust, emotional connection, and long-term engagement. Functionally, the avatar is powered by a dynamic computational "mind": an AI system that delivers forward-prescribed KHAs based on continuously updated, multi-modal health data. These KHAs are synthesized using machine learning (ML), large language models (LLMs), and biometric modeling to process and act on real-time inputs such as sleep, nutrition, emotional state, glucose patterns, activity, and social dynamics. At its core, the system is designed to identify and correct underlying metabolic dysfunction—the root cause of many modern chronic conditions—by guiding behavior in precise, timely, and personalized ways. Unlike human coaches—who cannot cognitively or logistically integrate and respond to these data streams in real time—this system provides context-aware, behaviorally prioritized, and dynamically rescheduled actions, creating a closed feedback loop that evolves with the user. First validated in Olympic athletes, it contributed directly to improvements in metabolic function, glucose regulation, sleep quality, and performance readiness, leading to medal-winning outcomes. Far more than a digital assistant, this system constitutes a scalable, emotionally intelligent decision engine, uniquely positioned to guide human health.

In aspect 1, a method of providing personalized educational content in a fitness and nutrition application includes: presenting video content to a user and transcribing the video content using artificial intelligence to create a synchronized text transcript; receiving a user request for additional information about a specific portion of the video content; identifying the specific portion of the video content based on a current timecode when the user request is received; generating, using a large language model, a personalized script containing additional information about the specific portion; creating a digital avatar response by generating synthetic voice based on the personalized script and applying the synthetic voice to a generative video of a coach avatar; and presenting the digital avatar response to the user. The method of aspect 1, wherein generating the personalized script comprises incorporating user-specific data including at least one of: biometric data, training history, nutrition data, and psychometric trends. The method includes generating the personalized script comprises accessing a knowledge base containing expanded information about topics presented in the video content. The method includes providing a chat interface for real-time interaction between the user and the digital coach avatar. The creating the digital avatar response comprises: generating the synthetic voice by calling a text-to-voice API with parameters defining coach personality characteristics; feeding the synthetic voice output to a generative video AI platform to create the digital avatar response. The user request is initiated through a user interface element displayed during playback of the video content. The method includes selecting a coaching style for the digital avatar response based on user preferences stored in a user profile. The method includes adapting the personalized script based on the user's specified goals, including at least one of: building muscle, maintaining balance, or losing fat. The method includes storing user interactions with the digital avatar response to improve future personalization of educational content. The video content comprises masterclass content featuring fitness and nutrition experts, and wherein the digital avatar response provides personalized implementation strategies based on the expert content.

11. A system of delivering health coaching includes a user onboarding interface that collects preferences including name, goals, tone, personality, and language; a content generation engine that creates initial scripts using user variables inserted into message templates; a voice synthesis module configured to generate audio files from said scripts; a video generation module that constructs avatar videos using AI-generated audio files and visual animation libraries; and a server-based storage system for managing and serving personalized avatar content.

The system of aspect 11 includes a real-time event monitoring engine that uses sensor and in-app data to determine when new coaching content should be generated. A human-recorded content library containing labeled video and audio clips from actors or coaches, stored and categorized by situation, tone, or topic. The content generation engine selects and sequences clips from the human-recorded content library based on user goals, time-of-day, and behavioral patterns. The content generation engine retrieves pre-recorded AI video clips and selects transitions from a curated AI media database. Real-time text content is generated using a large language model based on recent user activity, biometric data, or health goals. A timeline-based video assembly engine that sequences actor-recorded, pre-generated, and real-time generated clips using a rule-based engine or AI sequencing agent. A delivery engine that embeds the final coaching video into the app interface for user playback on demand or via notifications. Personalization data and content generation parameters are transmitted between modules using internal RESTful APIs. 20. The system of aspect 11 wherein avatar customization settings modify tone, coaching frequency, animation expressions, and language across all generated outputs. 21. The system of aspect 11 wherein user feedback and interaction data are logged and used to refine future video generation through a reinforcement learning model.

In aspect 22, a method for AI avatar includes: generating a personalized coaching plan based on user onboarding information including health goals and avatar personality preferences; monitoring user biometric data, activity patterns, and in-app behaviors through health APIs and application interactions; creating coaching content by selectively combining pre-recorded human video segments, pre-generated AI voice and video segments, and real-time AI-generated content based on the monitored data; assembling the selected content into a coherent video presentation using a timeline-based video assembly engine; and delivering the assembled video presentation to the user through an application interface. The method of aspect 22, wherein creating coaching content comprises: selecting relevant actor-recorded clips from a human content library based on context and tone; retrieving pre-generated AI clips from a server-based storage system; generating real-time contextual insights using a large language model based on recent user activity and biometric data. The monitoring user biometric data includes tracking heart rate variability (HRV) using a phone camera and finger placement technique to assess fitness progression and inform workout customization. The method includes providing techniques to modify meal digestion speed by: recommending the addition of crunchy vegetables to slow digestion for meals that need to sustain the user for longer periods; recommending the reduction of fiber content for faster digestion before, during, and after workouts. The personalized coaching plan includes meal recommendations that incorporate digestion speed information, visually represented by colored bars extending across a calendar timeline. The method includes generating custom workout content based on user goals, experience level, and physiological metrics, wherein the workout content includes AI-generated video with personalized verbal cues addressing the user by name. The method includes incorporating humor into the AI avatar's communication based on user psychometric trends to stimulate the parasympathetic nervous system during periods of detected stress. The user onboarding information includes selection of a coaching style from multiple predefined personality options, each trained on different coaching methodologies ranging from strict disciplinarian approaches to positive encouragement techniques. The responding to user requests for additional information comprises: identifying the specific portion of content based on a current timecode; generating a personalized script containing additional information about the specific portion; creating a digital avatar response by generating synthetic voice based on the personalized script; applying the synthetic voice to a generative video of the AI avatar for presentation to the user. The method includes transcribing educational content using artificial intelligence and enabling users to request additional information about specific portions of the content through interactive elements.

In aspect 32, a system for coordinating health actions among users includes a Key Health Action (KHA) scheduling module allowing users to select time-based health activities; an invitation engine configured to send participation requests to app-connected users; and a priority assignment module enabling users to indicate the importance level of the KHA using visual indicators; a real-time acceptance engine for managing invite responses and updating shared schedules.

The system of aspect 32 includes the KHA becomes a Social KHA upon acceptance by a second user, triggering a visual interface change and updated user notifications. A nutritional planning engine that customizes meal macronutrient targets for each participant and delivers those values to each user via the shared interface. Users can optionally select an AI avatar to participate in the Social KHA, delivering multimedia encouragement and follow-up coaching. The invitation interface supports accept, decline, and reschedule options, and reflows the Social KHA accordingly. The group-based KHAs support shared video calling and chat features embedded within the app interface. Each user's dietary, sleep, or exercise plan is reflected in a unified shared KHA view, personalized per individual participant. The avatar assistant can summarize how each participant performed in a KHA and provide adaptive coaching or praise post-activity. A family grouping module allowing KHAs to be scheduled across shared calendars and personalized according to user roles (e.g., parent, child). The system utilizes biometric, behavioral, and user-reported data to recommend Social KHAs likely to support each user's goals and relationship quality.

In aspect 42, a system for facilitating emotional support and interpersonal coaching includes a social linking module that enables users to designate interpersonal relationships in the app; a structured feedback interface allowing users to submit emotional reflections, requests, or well-being impacts related to linked users; an emotional analysis engine that processes said feedback using sentiment analysis, role classification, well-being scoring, and behavioral context; and an avatar coaching module that provides personalized support, mediation, and relational advice using best practices in therapy and cognitive behavior techniques.

The system of aspect 42 includes avatars capable of delivering praise or constructive feedback based on how the user is contributing to another's well-being. The avatar offers scripts or phrases to help users communicate difficult emotional content with their linked user. A shared activity recommendation engine that schedules Key Health Actions (KHAs) for both users to complete together as a means of emotional bonding. User feedback is submitted via an interface including emotion tags, numerical sliders, multidimensional well-being scores, and optional journal-style entries. Emotional analysis uses a reinforcement learning model to detect evolving patterns in emotional state, relational satisfaction, or conflict resolution over time. Avatars adapt communication style, tone, and language based on the cultural segment and emotional preferences of the user. The feedback data is encrypted and stored in compliance with privacy regulations, with anonymization of shared insights between linked users where appropriate. The avatar-delivered coaching includes techniques derived from emotional intelligence research, family counseling protocols, and evidence-based communication strategies. Avatars initiate check-ins and offer empathy-driven coaching during emotionally sensitive timeframes (e.g., post-conflict, menstrual phases, recovery periods). Users can opt to share menstrual cycle data and receive avatar-led guidance tailored to their physiological phase, including recommendations for partners. Linked avatars coordinate to facilitate dialogue and mutual understanding between users using mirrored coaching strategies personalized to each user's role and goals. The integration with future biosensors that detect physiological markers of emotional state, such as cortisol or endorphins, to enhance the emotional insight model through objective data inputs.

In another aspect 1, a method of delivering personalized health coaching through an AI avatar system includes: generating the AI avatar with customizable personality and appearance characteristics; collecting multi-domain user data including sleep patterns, nutritional behavior, physical activity, emotional state, and social dynamics; processing the collected data through a contextual health engine to generate personalized coaching decisions; determining prioritized Key Health Actions (KHAs) based on the processed data; delivering the KHAs to the user through the avatar using photo-realistic video and voice interaction; and adapting coaching strategies over time using reinforcement learning based on user responses and progress metrics.

The method of aspect 1 includes evaluating user progress through a Thriving Index derived from proxy data including estimated changes in body composition, sleep quality, nutritional patterns, emotional well-being, and social support metrics. The KHA s include glucose-stabilizing walks, heart rate variability-adjusted exercise routines, and timed nutrient intake for recovery or performance. The method includes generating Social KHAs that coordinate health actions between the user and other individuals or instances of HERA acting as supportive peers. The method includes customizing the HERA avatar's appearance, communication style, and cultural adaptation based on user preferences. 6. The method of aspect 1, further comprising detecting user-specific metabolic dysfunction using contextual biometric and behavioral patterns and delivering precision interventions prioritizing sleep enhancement, nutrient timing, physical activity, and stress regulation. 7. The method of aspect 1, wherein adapting coaching strategies includes analyzing correlations between specific interventions and changes in the user's composite health metrics. 8. The method of aspect 1, further comprising generating AI-customized workout content that adapts in real-time to accommodate user constraints and pairing it with personalized AI-generated music that aligns with the energy and tempo of the session. 9. The method of aspect 1, further comprising enabling close contacts to contribute data about one another through mutual consent, including emotional impressions, mood check-ins, or expression of emotional needs. 10. The method of aspect 1, wherein the HERA avatar leverages archetypal roles including warrior, nurturer, mentor, or guide to create coaching interactions that resonate with innate human relational patterns and emotional memory.

In another aspect 1, a system for delivering personalized health coaching includes a generative AI avatar interface that builds emotional rapport with the user and adapts based on coaching style preferences; a user onboarding module configured to collect high-level purpose, lifestyle goals, and physiological metrics, including preferences such as name, goals, tone, personality, and language; API connectors for ingesting real-time biometric data from sensor devices and health data platforms; a coaching recommendation engine that generates and dynamically adjusts a schedule of Key Health Actions (KHAs) based on scientific literature, athlete data, and user context; a real-time adjustment engine for rescheduling future KHA s in response to missed actions or updated user availability; a reinforcement learning model for analyzing user outcome data in conjunction with recent KHA history to rank and prioritize KHA s contributing to desired outcomes; a biologically weighted regression model for determining time-weighted influence of recent KHAs on user outcomes; a knowledge model prioritizing high-level, functional scientific fields for long-term, drug-free optimization of metabolic health, skeletal muscle preservation, blood sugar regulation, inflammation reduction, and sleep quality; a content generation engine that creates initial scripts using user variables inserted into message templates; a voice synthesis module configured to generate audio files from said scripts; a video generation module that constructs avatar videos using AI-generated audio files and visual animation libraries; and a server-based storage system for managing and serving personalized avatar content.

2. The system of aspect 1, wherein the avatar interface is customizable by the user in terms of voice, personality traits, coaching tone, and interaction frequency, and provides encouragement, troubleshooting, and adaptive guidance based on real-time context. The avatar interface includes cultural localization of spoken language, gestural mannerisms, and affective vocal tones tailored to user-specific cultural segments to enhance comprehension and emotional engagement. Reinforcement learning is used to analyze performance outcomes such as body fat percentage, wellness scores, and other physiological metrics in conjunction with recent KHAs to refine future coaching recommendations. The coaching engine flags KHAs with strong negative correlation to desired outcomes for user review, behavioral correction, or de-prioritization. The nutritional recommendations are calculated based on per-meal macronutrient needs derived from prior muscle damage, circadian phase, digestive efficiency, and the interrelationship of surrounding KHAs. User well-being is tracked through a multidimensional scoring system including physiological, psychological, and relational axes. The coaching recommendation engine continuously re-optimizes the user's short-term and multi-day schedule of KHAs to reflect evolving goals, missed actions, and real-time updates in biometric and contextual inputs.

The system of aspect 1, wherein the vector database used for knowledge training incorporates continually updated Olympic medal-winning strategies, real-world athlete data, and peer-reviewed scientific literature prioritized toward functional, sustainable health models. The content generation engine selects and sequences clips from the human-recorded content library based on user goals, time-of-day, and behavioral patterns.

In the system of aspect 9, the content generation engine retrieves pre-recorded AI video clips and selects transitions from a curated AI media database. Real-time text content is generated using a large language model based on recent user activity, biometric data, or health goals. Avatar coaching outputs include emotional reinforcement, praise, or habit correction suggestions based on both real-time events and long-term progress alignment. A real-time event monitoring engine that uses sensor and in-app data to determine when new coaching content should be generated. A human-recorded content library containing labeled video and audio clips from actors or coaches, stored and categorized by situation, tone, or topic. A timeline-based video assembly engine that sequences actor-recorded, pre-generated, and real-time generated clips using a rule-based engine or AI sequencing agent. A delivery engine that embeds the final coaching video into the app interface for user playback on demand or via notifications. Personalization data and content generation parameters are transmitted between modules using internal RESTful APIs. Avatar customization settings modify tone, coaching frequency, animation expressions, and language across all generated outputs. User feedback and interaction data are logged and used to refine future video generation through a reinforcement learning model.

Avatar interactions include mood-based adaptation, where voice tone and language style adjust in real-time to biometric and behavioral trends. Avatars are capable of delivering praise or constructive feedback based on how the user is contributing to another's well-being. 23. The avatar offers scripts or phrases to help users communicate difficult emotional content with their linked user. A shared activity recommendation engine that schedules Key Health Actions (KHAs) for both users to complete together as a means of emotional bonding. User feedback is submitted via an interface including emotion tags, numerical sliders, multidimensional well-being scores, and optional journal-style entries. Emotional analysis uses a reinforcement learning model to detect evolving patterns in emotional state, relational satisfaction, or conflict resolution overtime. Avatars adapt communication style, tone, and language based on the cultural segment and emotional preferences of the user. Feedback data is encrypted and stored in compliance with privacy regulations, with anonymization of shared insights between linked users where appropriate. Avatar-delivered coaching includes techniques derived from emotional intelligence research, family counseling protocols, and evidence-based communication strategies. Avatars initiate check-ins and offer empathy-driven coaching during emotionally sensitive timeframes (e.g., post-conflict, menstrual phases, recovery periods). Users can opt to share menstrual cycle data and receive avatar-led guidance tailored to their physiological phase, including recommendations for partners. The linked avatars coordinate to facilitate dialogue and mutual understanding between users using mirrored coaching strategies personalized to each user's role and goals. The system can integrate with future biosensors that detect physiological markers of emotional state, such as cortisol or endorphins, to enhance the emotional insight model through objective data inputs. The content engine uses a hybrid decision system incorporating deterministic rule trees and AI models to compose timeline-based avatar videos from the three content types.

In another aspect, a system for delivering health coaching comprising a social linking module that enables users to designate interpersonal relationships in the app; a structured feedback interface allowing users to submit emotional reflections, requests, or well-being impacts related to linked users; an emotional analysis engine that processes said feedback using sentiment analysis, role classification, well-being scoring, and behavioral context; and an avatar coaching module that provides personalized support, mediation, and relational advice using best practices in therapy and cognitive behavior techniques. In aspect 36, a method of optimizing a user's daily routine includes: generating an optimal plan for a user's activities based on prioritized activity categories; displaying the optimal plan on a clock-based user interface; receiving user modifications to the optimal plan; dynamically adjusting lower priority activities in response to user modifications of higher priority activities.

In the method of aspect 36, the prioritized activity categories include sleep, training, pre-training meal, post-training meal, breakfast, nap, and floating meals. 38. The method of aspect 36, wherein generating the optimal plan comprises assigning optimal, alert, and block ranges for each activity's timing and duration. The method includes displaying the optimal plan comprises showing visual indicators for optimal and alert ranges on the clock-based interface. The method includes categorizing activities as either dot activities or interval activities. The dot activities are single time-point events and interval activities have a configurable duration. The method includes providing in-app notifications for upcoming activities. The in-app notifications include now-notifications, prepare-notifications, and upcoming-notifications. The method includes generating local device notifications when the application is not in use. The displaying contextual notifications with additional information when an activity is selected. The clock-based user interface includes day and night modes. The method includes automatically switching between day and night color schemes based on the current time. The method includes hiding lower priority activities during modification of a higher priority activity. The method includes recalculating and redisplaying affected activities after a modification is complete. The method includes collecting user information during an onboarding process to generate initial activity schedules. The user information includes training frequency and preferred wake-up time. The method includes learning from user modifications to improve future activity recommendations. The dynamically adjusting lower priority activities comprises rescheduling meals and naps based on changes to sleep and training times. The method includes allowing modification of past activities and recalculating future activities accordingly. The method includes rounding modified activity times to values divisible by 5 minutes.

In aspect 56, a method of managing sleep recommendations in a daily routine optimization application includes: determining a default sleep duration and start time; displaying the sleep recommendation on a clock interface; allowing user modification of sleep duration and start time within predefined ranges; automatically adjusting subsequent activities based on changes to the sleep recommendation.

For aspect 56, the default sleep duration can be 8.5 hours. The predefined ranges include an optimal range of 7.5-9.5 hours and an alert range of 4.5-7.5 hours and 9.5-12.5 hours. The method includes blocking sleep durations less than 4.5 hours or greater than 12.5 hours. The automatically adjusting subsequent activities comprises rescheduling training, meals, and naps. The method includes g displaying a visual indicator for optimal and alert sleep ranges on the clock interface. The method includes providing an in-app notification for upcoming bedtime. The in-app notification for bedtime is triggered 120 minutes before the recommended bedtime. The method includes generating a local device notification for bedtime when the application is not in use. The method includes displaying a wake-up time notification minutes after the recommended wake-up time. The allowing user modification includes constraining the next sleep's bedtime to be after the last sleep's wake time. The allowing user modification includes constraining the previous sleep's wake time to be before the last sleep's bedtime. The switching to a night mode display when editing sleep times. The providing contextual notifications with sleep quality information when sleep activity is selected. The automatically adjusting subsequent activities includes maintaining a minimum gap between sleep and training activities. The method includes learning from user modifications to sleep times to improve future sleep recommendations. The method includes g allowing modification of past wake times and recalculating the day's schedule accordingly. The displaying the sleep recommendation includes showing only a bedtime indicator during day mode. The method includes providing alert notifications when sleep duration or timing falls outside the optimal range. The automatically adjusting subsequent activities includes redistributing floating meals based on new wake and sleep times.

76. A method of scheduling training activities in a daily routine optimization application includes: determining if a current day is a training day based on user preferences; calculating an optimal training duration and start time; adjusting the training schedule to avoid conflicts with sleep periods; inserting pre-training and post-training meals at optimal times relative to the training activity.

For aspect 76, the optimal training duration can be between 60 minutes and 2 hours. 78. The method includes setting an alert for training durations exceeding 2 hours. The method includes blocking training durations less than 60 minutes or greater than 5 hours. The calculating the optimal training start time comprises setting it 100 minutes after wake time by default. The method includes adjusting the training start time if it conflicts with sleep, maintaining at least 120 minutes between training and sleep. The method includes inserting the pre-training meal comprises placing it 80-110 minutes before training start. The inserting the post-training meal comprises placing it 0-30 minutes after training end. The method includes providing an in-app notification 30 minutes before training start. 85. The method includes generating a local device notification for training when the application is not in use. The method includes displaying a visual indicator for optimal and alert training duration ranges on a clock interface. The method includes allowing user modification of training duration and start time within predefined ranges. The allowing user modification includes constraining training to avoid overlap with sleep periods. The method includes automatically adjusting floating meal times based on changes to the training schedule. The method includes providing contextual notifications with training preparation information when the training activity is selected. The method includes determining if a current day is a training day is based on user-selected training frequency during an onboarding process. The method includes learning from user modifications to training times to improve future training recommendations. The method includes adjusting nap placement based on the training schedule. The inserting pre-training and post-training meals includes providing alert notifications if meal timing falls outside optimal ranges. 95. The method of aspect 76, further comprising rounding modified training times to values divisible by 5 minutes.

In aspect 96, a method of managing meal schedules in a daily routine optimization application includes: identifying gaps between fixed activities in a user's daily plan; calculating optimal positions for floating meals within the identified gaps; distributing a variable number of meals based on gap duration; adjusting meal positions in response to user modifications of other activities.

For aspect 96, the fixed activities include sleep, training, and breakfast. The calculating optimal positions for floating meals comprises equally distributing meals within each gap. The distributing a variable number of meals comprises adding one meal for gaps of 5 hours or more, and an additional meal for every 2 hours thereafter. The method includes inserting a pre-training meal-110 minutes before training start. The method includes inserting a post-training meal-30 minutes after training end. The method includes inserting breakfast-90 minutes after wake time. The method includes providing in-app notifications for upcoming meals. The method includes generating local device notifications for meals when the application is not in use. The adjusting meal positions includes maintaining at least 120 minutes between meals and surrounding activities. The method includes displaying visual indicators for optimal and alert meal timing ranges on a clock interface. The method includes allowing user modification of meal times within predefined ranges. The allowing user modification includes constraining meals to avoid overlap with sleep and training periods. The method includes providing contextual notifications with meal preparation information when a meal activity is selected. The distributing meals includes adjusting the first meal after post-training to be closer to the gap start. The method includes learning from user modifications to meal times to improve future meal recommendations. The method includes adjusting meal schedules when a nap is inserted into the daily plan. The adjusting meal positions includes providing alert notifications if meal timing falls outside optimal ranges. The method includes rounding modified meal times to values divisible by 5 minutes. The identifying gaps includes considering the time between the last meal of the day and the next day's breakfast.

In aspect 116, a method of handling user interactions with a schedule interface in a daily routine optimization application includes: detecting user selection of an activity on a clock-based interface; allowing modification of the selected activity's timing or duration; hiding lower priority activities during the modification process; recalculating and redisplaying affected activities after the modification is complete.

For aspect 116, the method includes constraining modifications to prevent overlap with higher priority activities. The allowing modification includes displaying optimal and alert ranges for the selected activity. The method includes providing haptic feedback during activity modification. The recalculating affected activities includes adjusting meal and nap schedules. The method includes displaying contextual information about the selected activity during modification. The hiding lower priority activities includes fading them out gradually. The method includes animating the transition of activities to new positions after recalculation. The allowing modification includes enabling drag-and-drop functionality on the clock interface. The method includes providing undo and redo options for activity modifications. The recalculating activities includes maintaining minimum time gaps between activities. The method includes providing visual feedback during activity modification to indicate optimal and alert ranges. The allowing modification includes enabling pinch-to-zoom functionality to adjust activity duration. The method includes displaying a summary of changes after modification is complete. The hiding lower priority activities includes gradually fading them out based on their priority level. The method includes providing audio feedback to indicate when an activity enters or exits optimal ranges during modification. The recalculating and redisplaying affected activities includes adjusting the day-night mode display if necessary. The method includes allowing users to set custom constraints for specific activities. The detecting user selection includes recognizing long-press gestures to initiate activity modification. The method includes synchronizing modified schedules across multiple devices associated with the user's account.

136. A method of implementing a day-night mode interface in a daily routine optimization application includes: determining the current time; switching between day and night color schemes based on the current time; adjusting the display of sleep activities based on the current mode; temporarily overriding the current mode when editing specific activities.

For aspect 136, the switching between day and night color schemes occurs automatically at predetermined times. The adjusting the display of sleep activities comprises showing only a bedtime indicator during day mode. The adjusting the display of sleep activities comprises showing full sleep duration during night mode. The method includes displaying activities on a clock-based interface. The method includes indicating optimal and alert ranges for activity timing and duration on the clock-based interface. The temporarily overriding the current mode includes switching to night mode when editing sleep activities. The method includes updating visual indicators in real-time as users modify activities. The method includes providing immediate feedback on the impact of modifications to the overall schedule. The method includes displaying in-app notifications below the clock interface. The determining the current time includes considering the user's time zone. The method includes adjusting the brightness of the interface based on the current mode. The method includes providing a manual override option for users to switch between day and night modes. The adjusting the display includes changing icon designs for day and night modes. The method includes animating transitions between day and night modes. The method includes adjusting text contrast to ensure readability in both modes. The temporarily overriding the current mode includes reverting to the appropriate mode after exiting edit state. The method includes displaying a visual indicator of the current mode. The adjusting the display includes modifying the appearance of activity trackers in different modes. The method includes synchronizing the day-night mode with the device's system-wide dark mode settings.

156. A method of providing adaptive notifications in a daily routine optimization application includes: generating in-app notifications for upcoming activities; creating local device notifications for activities when the application is not in use; displaying contextual notifications with additional information when an activity is selected; dynamically updating notification content based on activity state changes. For aspect 156, the generating in-app notifications comprises creating now-notifications, prepare-notifications, and upcoming-notifications. The now-notifications are displayed from the activity start time to 45 minutes after start. The prepare-notifications are displayed for a specified time before the activity start. The upcoming-notifications are displayed from the preceding activity start to the current activity start. The creating local device notifications includes triggering notifications for sleep, training, and meal activities. The displaying contextual notifications includes showing different content for optimal and alert states of an activity. The method includes hiding notifications during activity modification. The method includes recalculating and refreshing notifications after user exits edit mode. The dynamically updating notification content includes changing notification state when an activity moves between optimal and alert ranges. The method includes providing expandable views for in-app and contextual notifications. The expanded notifications remain static until manually collapsed by the user. The method includes customizing notification icons for day and night modes. The generating in-app notifications includes prioritizing notifications when multiple activities overlap. The method includes integrating with a remote configuration service to update notification content and timing. The creating local device notifications includes ensuring notifications work even when the application is not running in the background. The method includes animating transitions between different notification states. The displaying contextual notifications includes showing different content for "too early," "too late," "too long," and "too short" states. The method includes collapsing expanded notifications when navigating to another screen or putting the app in the background. The dynamically updating notification content includes adjusting notifications based on real-time changes to the user's schedule.

176. A method of personalizing a daily routine optimization application includes: collecting user information during an onboarding process; determining initial activity schedules based on the collected information; generating default sleep and training recommendations; creating an initial optimized daily plan based on the user information and default recommendations.

For aspect 176, the collecting user information includes obtaining the user's preferred wake-up time. The collecting user information includes determining the user's training frequency. The training frequency options include training every weekday for Olympic/Pro athletes and Amateur athletes. The determining initial activity schedules includes calculating an initial sleep schedule based on the user's preferred wake-up time. The calculating the initial sleep schedule uses a default sleep duration of 8.5 hours. The method includes allowing users to modify the initial optimized daily plan. The method includes providing explanations for each step of the onboarding process. The generating default sleep recommendations includes setting optimal and alert ranges for sleep duration. The generating default training recommendations includes setting optimal and alert ranges for training duration. The method includes adapting the onboarding process based on the user's athlete category. The method includes allowing users to skip certain onboarding steps and use default values. The method includes providing visual representations of how user inputs affect the daily plan during onboarding. The method includes offering a guided tour of the application's features after completing the onboarding process. The creating the initial optimized daily plan includes scheduling meals at recommended intervals. The method includes allowing users to import data from other fitness or health applications during onboarding. 192 The method includes providing personalized tips based on the collected user information. The determining initial activity schedules includes considering the user's time zone. The method includes allowing users to set initial goals during the onboarding process. 1 The method includes providing an option to reset the onboarding process and start over if desired.

In aspect 196, a method of calculating daily calorie needs for a user includes: determining a resting metabolic rate (RMR) based on user characteristics; calculating a non-exercise activity thermogenesis (NEAT) value; adjusting the NEAT value based on user goals and fitness level; generating a total daily calorie need based on the adjusted NEAT value.

For aspect 196, the determining the RMR can be using the Mifflin-St. Jeor equation. The calculating the NEAT value comprises adding a percentage of the RMR based on the user's goal. The percentage is 20% for a build goal, 15% for a balance goal, and 10% for a fat loss goal. The method includes adjusting the NEAT value based on the user's fitness level. The adjustment is −5% of RMR for unfit users and +5% of RMR for fit users. The method includes adjusting the NEAT value based on the user's daily step count. The adjustment is 2% of RMR per 1,000 steps per day. 204 The method includes calculating exercise calories based on metabolic equivalents (METs). 205. The METs are adjusted based on the user's age if over 40 years old. The method includes adjusting the total daily calorie need based on a user-defined goal. The adjustment is a 10% caloric restriction for balancing performance and fat loss. The adjustment is a 25% caloric restriction for maximizing fat loss. The method includes calculating macronutrient ratios based on the total daily calorie need. The calculating macronutrient ratios comprises determining protein needs based on body weight and training factors. The calculating macronutrient ratios comprises determining carbohydrate needs based on brain usage, non-exercise activity, and exercise requirements. The calculating macronutrient ratios comprises determining fat needs as a percentage of total calories. The method includes adjusting calorie and macronutrient calculations based on the user's training volume. The training volume is calculated using a training volume factor (TF) based on different types and intensities of exercise. The method includes providing meal-specific macronutrient recommendations based on the timing and purpose of each meal.

In aspect 216, a method of calculating protein needs for a user in a nutrition planning application includes: determining a baseline protein requirement based on the user's body weight; calculating a training volume factor based on the user's exercise intensity and duration; adjusting the baseline protein requirement using the training volume factor; generating protein recommendations for individual meals based on the adjusted protein requirement.

For aspect 216, the determining the baseline protein requirement comprises multiplying the user's body weight in kilograms by 0.6 grams. 218. The method of aspect 216, wherein calculating the training volume factor comprises categorizing exercises into aerobic, threshold, VO2max, interval, and strength/power types. The method includes assigning intensity levels of low, medium, high, and very high to each exercise type. The calculating the training volume factor comprises dividing the user's training hours by a maximum training limit for each exercise type and intensity. The adjusting the baseline protein requirement comprises multiplying the baseline by [1+(Training Factor× 2)]. The method includes calculating an overreaching factor based on the training volume factor. The overreaching factor is calculated as (TF−1), where TF is the training volume factor. The method includes estimating the time before overreaching is likely based on the overreaching factor. The generating protein recommendations for individual meals comprises dividing the daily protein need by 20 to determine hourly protein needs. The method includes multiplying the hourly protein need by the number of hours until the next meal to determine the protein content for a specific meal. The method includes adjusting protein recommendations based on the user's goal of building muscle, maintaining balance, or losing fat. The method includes calculating inherent protein in meals from non-protein food sources. The calculating inherent protein comprises estimating 10% of the calorie count of all feedings as usable protein. The method includes adjusting protein recommendations based on the timing of meals relative to training sessions. The protein recommendations are increased for pre-training and post-training meals. The method includes providing recommendations for protein food sources based on the digestion time needed until the next meal. The method includes adjusting protein recommendations based on the user's age, with increased recommendations for users over 40 years old. The method includes g calculating and displaying the caloric contribution of protein to the total daily calorie intake. The method includes integrating the protein calculations with carbohydrate and fat calculations to provide a comprehensive macronutrient plan.

236. A method of calculating carbohydrate needs for a user in a nutrition planning application includes: determining a baseline carbohydrate requirement for brain function; calculating non-exercise activity thermogenesis (NEAT) carbohydrate needs; estimating exercise-induced carbohydrate requirements based on workout intensity and duration;

generating carbohydrate recommendations for individual meals based on the calculated needs.

For aspect 236, the determining the baseline carbohydrate requirement comprises setting a minimum of 60 grams per day for brain function. The calculating NEAT carbohydrate needs comprises considering the user's weight and daily step count. The NEAT carbohydrate needs are calculated as 60 g+(weight in kg×0.03×(step count per day/1,000)). The estimating exercise-induced carbohydrate requirements comprises using metabolic equivalents (METs) based on the user's fitness level and exercise intensity. The method includes adjusting MET values for users over 40 years old by subtracting 1% for each year over 40. The estimating exercise-induced carbohydrate requirements comprises calculating workout calories as (METs×body weight in kg×exercise duration in hours). The method includes determining the percentage of workout calories derived from glucose based on the type of exercise. The method includes adjusting carbohydrate recommendations based on the user's goal of building muscle, maintaining balance, or losing fat. The adjustment is 100% of calculated needs for building, 85% for balance, and 70% for fat loss. The method includes comprising limiting carbohydrate under-fueling to 10% of RMR for fat loss goals. The method includes deducting carbohydrates consumed during training from post-exercise carbohydrate recommendations. The carbohydrates consumed during training are limited to 1 g per kg of body weight within 10 minutes of exercise completion. The method includes providing recommendations for carbohydrate timing and sources based on the glycemic index. The method includes adjusting carbohydrate recommendations based on the timing of meals relative to training sessions. The carbohydrate recommendations are increased for pre-training and post-training meals. The method includes calculating and displaying the caloric contribution of carbohydrates to the total daily calorie intake. The method includes integrating carbohydrate calculations with protein and fat calculations to provide a comprehensive macronutrient plan. The method includes adjusting carbohydrate recommendations based on the user's training volume factor. The generating carbohydrate recommendations for individual meals comprises considering the number of hours until the next meal and the meal's purpose (e.g., pre-training, post-training, or general sustenance).

In aspect 256, a method of calculating fat needs for a user in a nutrition planning application includes: determining total daily calorie needs; subtracting calories allocated to protein and carbohydrates; calculating remaining calories for fat consumption; converting remaining calories to fat grams; distributing fat recommendations across individual meals.

For aspect 256, the determining total daily calorie needs comprises using the previously calculated NEAT (Non-ExerciseActivity Thermogenesis) value. The subtracting calories allocated to protein comprises multiplying total protein grams by 4 calories per gram. The subtracting calories allocated to carbohydrates comprises multiplying total carbohydrate grams by 4 calories per gram. The converting remaining calories to fat grams comprises dividing the remaining calories by 9 calories per gram of fat. The distributing fat recommendations across individual meals comprises dividing the total fat grams by the number of meals. The method includes applying a meal modifier to adjust fat content for specific meals. The adjusting fat recommendations based on the user's goal of building muscle, maintaining balance, or losing fat. The adjustment is 0% reduction for building, 15% reduction for balance, and 30% reduction for fat loss. The method includes ensuring a minimum intake of essential fatty acids, including omega-3, omega-6, and omega-9. The method includes adjusting fat recommendations based on the timing of meals relative to training sessions. The fat recommendations are decreased for pre-training meals and increased for post-training meals. The method includes providing recommendations for fat sources based on the meal's purpose and timing. The method includes calculating and displaying the caloric contribution of fat to the total daily calorie intake. The method includes integrating fat calculations with protein and carbohydrate calculations to provide a comprehensive macronutrient plan. The method includes adjusting fat recommendations based on the user's training volume factor. The distributing fat recommendations across individual meals comprises considering the number of hours until the next meal. The method includes providing recommendations for the ratio of saturated, monounsaturated, and polyunsaturated fats. The method includes adjusting fat recommendations based on the user's age and gender. The method includes allowing manual adjustments to fat intake within predetermined safe ranges based on the user's preferences and tolerances.

In aspect 276, a method of calculating meal-specific macronutrient recommendations in a nutrition planning application includes: determining the timing and purpose of each meal; calculating base macronutrient needs for the meal; and; applying meal-specific modifiers to the base macronutrient needs; adjusting recommendations based on the time until the next meal; generating final macronutrient recommendations for the meal.

277. The method of aspect 276, wherein determining the timing and purpose of each meal comprises categorizing meals as breakfast, pre-training, post-training, or general sustenance. The calculating base macronutrient needs comprises dividing daily protein, carbohydrate, and fat requirements by the number of planned meals. The applying meal-specific modifiers for protein comprises increasing protein for pre-training and post-training meals. The applying meal-specific modifiers for carbohydrates comprises increasing carbohydrates for pre-training meals and post-training meals. The applying meal-specific modifiers for fats comprises decreasing fats for pre-training meals and increasing fats for general sustenance meals. The adjusting recommendations based on the time until the next meal comprises increasing protein and fat for meals that need to sustain the user for longer periods. The method includes recommending the inclusion of coarse vegetables in meals to slow digestion when appropriate.

In aspect 284, a method of calculating training volume for a user in a fitness and nutrition planning application includes: categorizing exercises into types including aerobic, threshold, VO2max, intervals, and strength/power; assigning intensity levels to each exercise type; determining training hours for each exercise type and intensity; calculating a training volume factor based on the ratio of training hours to maximum training limits; using the training volume factor to adjust nutrition and recovery recommendations.

For aspect 284, the categorizing exercises comprises defining aerobic exercises as those lasting more than 2 hours. The categorizing exercises comprises defining threshold exercises as those performed at lactate threshold pace for 30-90 minutes. The categorizing exercises comprises defining VO2max exercises as those performed at or near maximum oxygen uptake for 6-12 minutes. The categorizing exercises comprises defining interval exercises as those lasting 1-3 minutes at high intensity. The categorizing exercises comprises defining strength/power exercises as resistance training or plyometric movements. The assigning intensity levels comprises using categories of low, medium, high, and very high for each exercise type. The determining training hours comprises recording the duration of each exercise session performed by the user. The calculating the training volume factor comprises dividing the user's training hours by a predefined maximum training limit for each exercise type and intensity. The maximum training limits are based on research-backed guidelines for preventing overtraining. The method includes calculating an overreaching factor by subtracting 1 from the training volume factor. The method includes estimating the time before overreaching is likely based on the overreaching factor. The using the training volume factor to adjust nutrition recommendations comprises increasing protein intake as the factor increases. The training volume factor to adjust nutrition recommendations comprises increasing carbohydrate intake as the factor increases. The using the training volume factor to adjust recovery recommendations comprises suggesting longer rest periods as the factor increases. The method includes comprising adjusting the training volume calculations based on the user's age, with reduced capacities for users over 40 years old. The method includes providing warnings to the user when the training volume factor approaches or exceeds 1.0, indicating increased risk of overtraining. The method includes using the training volume factor to adjust the distribution of macronutrients in meal recommendations. The method includes integrating the training volume calculations with sleep quality and duration data to provide comprehensive recovery recommendations. The method includes allowing manual adjustments to the training volume factor based on the user's perceived exertion and recovery status.

In aspect 304, a method for calculating macronutrient requirements using biological temporal regression weight comprising acquiring data related to past biological stressor events identifying the magnitude and timing of each stressor event applying a biological temporal regression weight to each stressor event based on its recency adjusting macronutrient calculations according to the weighted stressor events primarily altering protein requirements to optimize healing and recovery.

For aspect 269 the the biological stressor event includes physical activities such as exercise. The method includes overlaying multiple regression weights for different types of stressors. The regression weight decreases as the stressor event recedes further into the past. The meal calculator updates macronutrient requirements daily. The method includes displaying suggested meal plans based on calculated macronutrient requirements. Data related to stressor events is input via a user interface; macronutrient calculations are adjusted automatically without user intervention; storing historical data on stressor events and associated regression weights; provides feedback on macronutrient adjustments to the user. Machine learning algorithms are employed to refine regression.

The present disclosure further contemplates a system architecture in which the methods and apparatus are configured to integrate future biosensors capable of detecting physiological markers correlated with an individual's emotional state. For example, the system includes one or more sensors configured to detect concentrations of cortisol, endorphins, or other relevant biochemical compounds. The biosensor module is operatively coupled to the emotional insight model so that it receives and processes objective data inputs indicative of the user's physiological state. In one implementation, the system continuously monitors physiological signals via these biosensors and transmits raw and processed data to a processing unit where these data are combined with inputs from user interactions or external stimuli. The integration of biosensor data enables the emotional insight model to refine its determinations by grounding them in objective biological metrics. In addition, the system incorporates algorithms that correlate various biosensor data points with known patterns of emotional responses, thereby enhancing the predictive accuracy and reliability of the emotional insight model. Calibration routines execute during initial setup or intermittently during use to ensure that sensor outputs remain consistent with expected variations in biomarker levels, compensating for sensor drift or environmental interference. The disclosed integration also encompasses data fusion techniques that merge computed metrics from traditional digital inputs, such as user selections or behavioral observations, with direct physiological measurements provided by the biosensors. This hybrid approach enables robust and comprehensive analysis of emotional state, supporting applications requiring precise monitoring and evaluation of user emotions in real time. In sum, the computer-implemented system delivers personalized health coaching by integrating a generative AI avatar interface, adaptive coaching engines, and dynamic content generation to provide tailored, real-time guidance. The system collects user goals, physiological metrics, and interpersonal preferences through a dedicated onboarding module while using API connectors to ingest biometric and health data from various sensors and platforms. A relational mapping engine classifies user relationships to gauge social influence, and multiple coaching engines—including reinforcement learning and biologically weighted regression models—dynamically adjust KHAs based on scientific literature, athlete data, and contextual factors. Additionally, the system features modules for voice synthesis, video generation, and timeline-based assembly of AI-generated and human-recorded content, ensuring personalized interactions through customizable avatars that adapt in tone, language, and emotional expression. Furthermore, modules supporting cultural localization, real-time event monitoring, detailed feedback logging, and emotion-driven coaching strategies work together to optimize physical, cognitive, and relational well-being using bespoke, science-based health optimization protocols. Further, while athletes usage of the system has been detailed, the inventors contemplate that the above trial data is applicable to non-athletes as well.

The invention claimed is:

1. A method of delivering personalized health coaching through an artificial intelligence (AI) avatar system, comprising:

generating the AI avatar with customizable personality and appearance characteristics;

collecting multi-domain user data including sleep patterns, nutritional behavior, physical activity, emotional state, and social dynamics;

processing the collected data through a contextual health engine to generate personalized coaching decisions;

determining prioritized Key Health Actions (KHAs) based on the processed data;

delivering the KHAs to the user through the avatar using photo-realistic video and voice interaction; and adapting coaching strategies over time using reinforcement learning based on user responses and progress metrics wherein the AI avatar interface is programmatically configured to serve as an emotionally adaptive, human-like coaching entity that:

receives, synthesizes, and analyzes multi-modal user data including physiological metrics, behavioral patterns, emotional state, schedule, and social context via sensors, wearable devices, and user input;

dynamically selects and delivers personalized KHAs, coaching interventions, and feedback with machine learning, large language models, and time-weighted regression to prioritize current and recent events most relevant to user wellbeing;

adaptively generates and presents avatar-guided coaching through multiple media formats including text, synthesized voice, and AI-generated video, wherein the avatar's communication style, coaching frequency, and visual expressions are customized in real time according to detected user context, profile preferences, and cultural background;

modulates content and delivery of motivational, clinical, or casual messages responsive to real-time and longitudinal user data, to provide emotional rapport, optimizing engagement, and building trust over repeated interactions; and employs a feedback loop wherein each coaching interaction is logged and analyzed using reinforcement learning to refine avatar decision-making and recommendation personalization.

2. The method of claim 1, further comprising evaluating user progress through a Thriving Index derived from proxy data including estimated changes in body composition, sleep quality, nutritional patterns, emotional well-being, and social support metrics.

3. The method of claim 1, wherein the KHAs include glucose-stabilizing walks, heart rate variability-adjusted exercise routines, and timed nutrient intake for recovery or performance.

4. The method of claim 1, further comprising generating Social KHAs that coordinate health actions between the user and other individuals or instances of Health Enhancing Relational Avatar (HERA) acting as supportive peers.

5. The method of claim 1, further comprising customizing the HERA avatar's appearance, communication style, and cultural adaptation based on user preferences.

6. The method of claim 1, further comprising detecting user-specific metabolic dysfunction using contextual biometric and behavioral patterns and delivering precision interventions prioritizing sleep enhancement, nutrient timing, physical activity, and stress regulation.

7. The method of claim 1, wherein adapting coaching strategies includes analyzing correlations between specific interventions and changes in the user's composite health metrics.

8. The method of claim 1, further comprising generating AI-customized workout content that adapts in real-time to accommodate user constraints and pairing it with personalized AI-generated music that aligns with the energy and tempo of the session.

9. The method of claim 1, further comprising enabling close contacts to contribute data about one another through mutual consent, including emotional impressions, mood check-ins, or expression of emotional needs.

10. The method of claim 1, wherein the HERA avatar leverages archetypal roles including warrior, nurturer, mentor, or guide to create coaching interactions that resonate with innate human relational patterns and emotional memory.

11. The method of claim 1, comprising:

calculating macronutrient requirements using biological temporal regression weight (BTRW) determined where recent stressor events are assigned higher weights, while the BTRW decreases as the event recedes into the past;

acquiring data related to past biological stressor events identifying the magnitude and timing of each stressor event; and overlaying a plurality of BTRWs corresponding to different biological stressors;

applying the BTRW to each stressor event based on its recency adjusting macronutrient calculations according to the weighted stressor events primarily altering protein requirements to optimize healing and recovery.

12. The method of claim 1, wherein the biological stressor event comprises a physical activity, including exercise.

13. The method of claim 1, wherein a machine learning algorithm is employed to refine the biological temporal regression weights over time.

14. The method of claim 1, further comprising receiving, via an emotional state monitoring interface, user inputs indicating a current energy state, a stress level, and an overall mindset, each selected between respective contrasting binary options, wherein the received emotional state data is processed by the AI-powered health coaching system to: adapt a coaching communication style in real time by selecting among motivational, clinical, or casual tone profiles, trigger targeted behavioral interventions including stress-reduction recommendations when a user indicates a stressed or fatigued state, and generate correlations between the emotional state data and other health metrics for storage and analysis within a reinforcement learning algorithm to improve personalization over time.

15. The method of claim 1, further comprising displaying a progress tracking interface that correlates logged emotional state inputs with physical health metrics including at least current weight, estimated body fat percentage, and projected body composition outcomes, wherein the system dynamically adjusts workout intensity recommendations, nutritional guidance, and body composition targets responsive to the detected emotional state trends, progress indicators are displayed in a goal-oriented format including percentage-to-go metrics toward predefined objectives such as overall wellbeing scores or muscle preservation thresholds, and progress toward the physical health goals is utilized to refine the nature, frequency, and style of motivational feedback and emotional support messages provided to the user by the AI avatar.

16. The method of claim 1, wherein the reinforcement learning model receives as inputs physiological and performance data comprising at least body fat percentage, wellness score, heart rate variability, and additional biometric measurements, and further aggregates said inputs with recent key health actions (KHAs) to generate a unified state representation used for selecting candidate coaching actions.

17. The method of claim 1, wherein the reinforcement learning model implements an exploration—exploitation strategy configured to periodically select unconventional coaching actions for discovering potentially improved outcomes while maintaining a bias toward actions demonstrated to produce desired results.

18. The method of claim 1, wherein the reinforcement learning model applies a reward function comprising risk-aware and uncertainty-sensitive components, said components adjusting estimates in response to variability in data quality or external factors affecting anticipated performance outcomes.

19. The method of claim 1, wherein the reinforcement learning model refines its policy by analyzing correlations between measured changes in physiological metrics and user responses to previously delivered coaching actions.

20. The method of claim 1, wherein the inputs to the reinforcement learning model are augmented with contextual factors comprising user age, baseline fitness level, environmental conditions, and historical performance trends, such that the resulting policy produces coaching recommendations tailored to the user's unique health profile and lifestyle.

\* \* \* \* \*